United States Patent
Rabbitts et al.

(10) Patent No.: US 12,024,506 B2
(45) Date of Patent: Jul. 2, 2024

(54) COMPOUNDS

(71) Applicant: Oxford University Innovation Limited, Oxford (GB)

(72) Inventors: Terrence Rabbitts, Oxford (GB); Camilo Quevedo, Oxford (GB); Abimael Cruz, Oxford (GB); Simon Phillips, Oxford (GB); Philip Spencer Fallon, Saffron Walden (GB); Jonathan Neil Dunn, Saffron Walden (GB); Joshua Robert Freem, Saffron Walden (GB); Lydia Yuen-Wah Lee, Saffron Walden (GB); Tenin Traore, Saffron Walden (GB); Sophie Caroline Williams, Saffron Walden (GB)

(73) Assignee: THE INSTITUTE OF CANCER RESEARCH: ROYAL CANCER HOSPITAL, London (GB)

(*) Notice: Subject to any disclaimer, the term of this patent is extended or adjusted under 35 U.S.C. 154(b) by 179 days.

(21) Appl. No.: 16/963,564

(22) PCT Filed: Jan. 23, 2019

(86) PCT No.: PCT/GB2019/050198
§ 371 (c)(1),
(2) Date: Jul. 21, 2020

(87) PCT Pub. No.: WO2019/145718
PCT Pub. Date: Aug. 1, 2019

(65) Prior Publication Data
US 2021/0009576 A1    Jan. 14, 2021

(30) Foreign Application Priority Data

Jan. 24, 2018 (GB) .................................... 1801128.8

(51) Int. Cl.
| | | |
|---|---|---|
| C07D 413/14 | (2006.01) |
| C07D 319/18 | (2006.01) |
| C07D 319/20 | (2006.01) |
| C07D 405/04 | (2006.01) |
| C07D 405/12 | (2006.01) |
| C07D 405/14 | (2006.01) |
| C07D 471/10 | (2006.01) |

(52) U.S. Cl.
CPC ......... *C07D 413/14* (2013.01); *C07D 319/18* (2013.01); *C07D 319/20* (2013.01); *C07D 405/04* (2013.01); *C07D 405/12* (2013.01); *C07D 405/14* (2013.01); *C07D 471/10* (2013.01)

(58) Field of Classification Search
None
See application file for complete search history.

(56) References Cited

U.S. PATENT DOCUMENTS

| 2006/0122175 A1 | 6/2006 | Hes et al. |
| 2006/0241172 A1* | 10/2006 | Zhou ........................ A61P 3/04 514/452 |
| 2014/0094456 A1 | 4/2014 | Buckman et al. |

FOREIGN PATENT DOCUMENTS

| WO | 98/22455 A1 | 5/1998 |
| WO | 99/40068 A2 | 8/1999 |
| WO | 00/58301 A1 | 10/2000 |
| WO | 2006/116136 A1 | 11/2006 |
| WO | 2006/116158 A1 | 11/2006 |
| WO | 2007/052123 A2 | 5/2007 |
| WO | 2007/123942 A2 | 11/2007 |
| WO | 2007/128694 A1 | 11/2007 |
| WO | 2008/052086 A1 | 5/2008 |
| WO | 2014/164767 A1 | 10/2014 |
| WO | 2016/044772 A1 | 3/2016 |
| WO | 2018/049214 A1 | 3/2018 |
| WO | 2018/113584 A1 | 6/2018 |

OTHER PUBLICATIONS

Database Registry Chemical Abstracts Service, Columbus, Ohio, Accession No. RN 2006582-41-6. Entered STN: Oct. 6, 2016.*
Database Registry Chemical Abstracts Service, Columbus, Ohio, Accession No. RN 2025385-71-9. Entered STN: Nov. 6, 2016.*
Database Registry Chemical Abstracts Service, Columbus, Ohio, Accession No. RN 2028002-95-9. Entered STN: Nov. 9, 2016.*

(Continued)

*Primary Examiner* — Samantha L Shterengarts
(74) *Attorney, Agent, or Firm* — Thomas|Horstemeyer, LLP

(57) ABSTRACT

The present invention relates to compounds of Formula I as defined herein, and salts and solvates thereof. (I) The present invention also relates to pharmaceutical compositions comprising compounds of Formula (I), and to compounds of Formula (I) for use in the treatment of proliferative disorders, such as cancer, as well as other diseases or conditions in which inhibition of a RAS-effector protein-protein interaction is implicated.

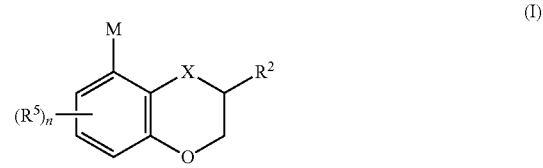

16 Claims, 2 Drawing Sheets

(56) References Cited

OTHER PUBLICATIONS

International Search Report & Written Opinion for WO2019/145718 (PCT/GB2019/050198), dated Mar. 6, 2019, pp. 1-11.
JK Search Report for GB1801128.8, dated Dec. 15, 2017, pp. 1-22.
Camilo E. Quevedo et al.: "Small molecule inhibitors of RAS effector protein interactions derived using an Intracellular antibody fragment", Nature Communications, vol. 9, No. 1. Aug. 9, 2018 (Aug. 9, 2018).
Bioorganic & Medicinal Chemistry Letters, vol. 8, No. 18, 1998, pp. 2457-2462, Van Steen et al. "Functional characteristics of a series of N4-substituted 1-(2,3-dihydro-i ,4-benzodioxin-5-yl)piperazines as 5-HT 1 A receptor ligands".

* cited by examiner

Abd-2 (Ref):

COMPOUNDS

CROSS-REFERENCE TO RELATED APPLICATIONS

This application is the National Stage of International Application No. PCT/GB2019/050198, filed Jan. 23, 2019, which claims priority to GB 1801128.8, filed Jan. 24, 2018, which are entirely incorporated herein by reference.

INTRODUCTION

This application relates to compounds of Formula I as defined herein and salts or solvates thereof.

The compounds of Formula I and their salts have the capability to inhibit protein-protein interactions, in particular interactions between RAS and effector proteins (such as RAF and PI3K) and may be used to treat diseases or conditions mediated, at least in part, by mutant RAS, such as cancer.

The present application further provides pharmaceutical compositions comprising a compound of Formula I, or a pharmaceutically acceptable salt or solvate thereof, and an pharmaceutically acceptable excipient.

The present application also provides methods of treating a proliferative disorder, such as cancer, in a subject in need thereof comprising administering to the subject a compound of Formula I or a pharmaceutically acceptable salt or solvate thereof.

BACKGROUND OF THE INVENTION

The aetiology of many human diseases such as cancer, neural degeneration and inflammation involves abnormal proteins participating in macromolecular complexes to elicit a biologically relevant effect. As such, protein-protein interactions represent a major potential drug target for manifold human disease indications.

The RAS proteins are guanine nucleotide binding molecules that play key roles in signal transduction as molecular switches, mediated through two switch regions displaying conformational differences between active (GTP bound) and inactive (GDP bound) states (Vetter and Wittinghofer, 2001). Most of the RAS effectors bind to these RAS switch regions (Downward, 2003). RAS is the most important target in cell transformation, being involved in cell proliferation and differentiation through the RAF-MEK-ERK cascade (Marshall, 1995; Kolch, 2005) and cell survival through activation of PI3K (Downward, 2003). The RAS effector, RAL-GDS, is also involved in RAS-dependent tumorigenesis in vivo (Gonzalez-Garcia et al, 2005) and cell transformation in human cells (Rangarajan et al, 2004).

Activating RAS gene mutations are found in as many as 30% of humans, with the highest frequencies in pancreas, colon and lung adenocarcinoma. Mutations of the RAS proteins (K, H or NRAS) create constitutively activated GTP-bound forms that promote cell transformation in a signal-independent manner (Adjei, 2001). In addition, secondary RAS-associated aberrations such as mutation or overexpression of receptor tyrosine kinases (e.g. EGFR, ERBB2) have been indicated in many cancers that lack RAS mutation (Mendelsohn and Baselga, 2000).

Thus, inhibiting aberrant RAS function has been an exciting possible mode of human cancer therapy. This notion has been supported by observations in mouse models in which oncogenic RAS has been shown to be essential for early onset of tumours and necessary for maintenance of tumour viability (Johnson et al, 2001), as tumours harbouring mutant RAS can regress when mutant RAS expression is stopped (Chin et al, 1999; Fisher et al, 2001).

These facts highlight activated RAS proteins as attractive targets for cancer therapy. Despite this, anti-RAS therapies have not yet been particularly effective (Friday and Adjei, 2005). Farnesyltransferase inhibitors (FTIs) can inhibit membrane localisation of RAS proteins by preventing post-translational modification, and thus blocking downstream RAS signalling. However, the antitumour activity of FTIs may only partly be due to targeting RAS and may also affect farnesylation of other proteins (Friday and Adjei, 2005).

An ideal RAS-based anticancer therapy would involve reagents that can specifically inhibit oncogenic RAS. Antibodies have such qualities of specificity and affinity that can easily be manipulated. However, most oncogenic proteins, including RAS, are located inside cells and not available for antibody-mediated targeting.

Over the last decade, antibody engineering has led to development of fragments that can be expressed intracellularly (intrabodies) (Cattaneo and Biocca, 1997), but there are still few intrabodies that work efficiently in the reducing environment of cells due to the usual need for disulphide bonds for correct folding. To overcome this limitation, intracellular antibody capture (IAC) has been developed, based on in vivo yeast two-hybrid screening (Visintin et al, 1999; Tse et al, 2002; Tanaka and Rabbitts, 2003), and it has been shown that single variable region (V) domains (iDabs) are highly efficient as intrabodies (Tanaka et al, 2003).

A single domain VH intrabody binding specifically to activated GTP-bound RAS with high affinity has been shown to neutralise oncogenicity in cancerous cells harbouring a RAS mutation (Tanaka et al., 2007). The crystal structure of the intrabody bound to mutant RAS, solved to 2 Å, shows that the intrabody specifically recognises the conformational structure of oncogenic RAS and inhibits RAS-effector protein interactions with RAS.

Nonetheless, there are currently few small-molecule drugs in clinical trials that are capable of impeding protein interactions, since these generally require clefts in a protein into which a small molecule can fit (Blundell et al, 2006).

There is a need in the art for the development of novel approaches to target protein-protein interactions. In particular, there is a need in the art for the provision of molecules capable of penetrating cells and which can bind to RAS and inhibit protein-protein interactions, in particular aberrant RAS-effector interactions, with high affinity and/or specificity. Such molecules represent promising treatments for proliferative disorders such as cancer.

The BRET ratio corresponds to the light emitted by the GFP2 acceptor constructs (515 nm±30) upon addition of Coelenterazine 400a divided by the light emitted by the RLuc8 donor constructs (410 nm±80). The normalized BRET ratio is the BRET ratio normalized to the DMSO negative and calculated as follows: (BRETcompound/BRETDMSO)×100, where BRETcompound corresponds to the BRET ratio for the compound-treated cells, BRETDMSO to the DMSO-treated cells. Each experiment was repeated at least three times. Statistical analyses were performed using a one-way ANOVA followed by Dunnett's post-tests (*P<0.05, P<0.01, *P<0.001, ****P<0.0001). Where error bars are presented, they correspond to mean values±SD of biological repeats (a-c).

Figure 2:
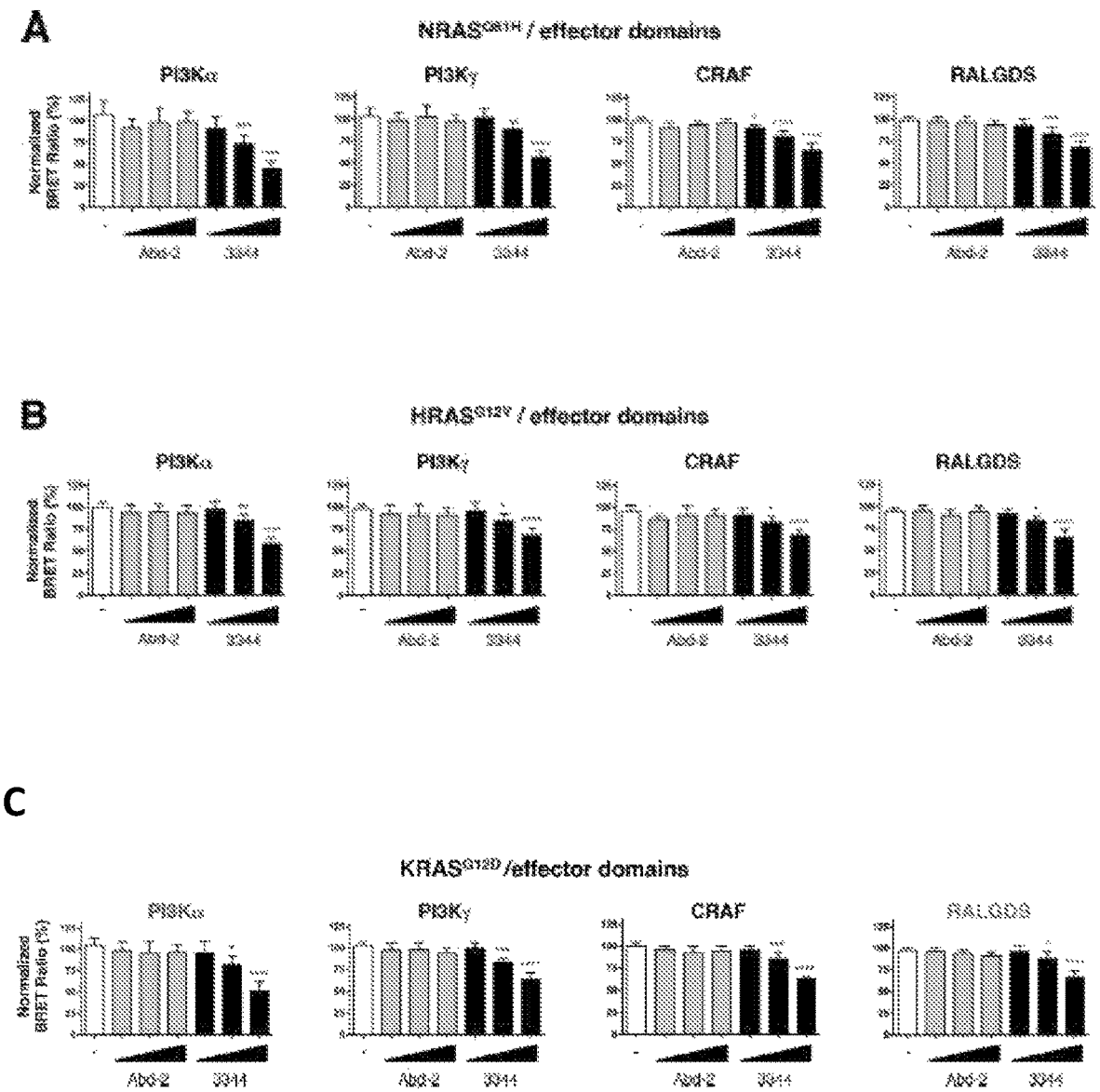

FIG. 2 shows that compound 72 (labelled 3344) inhibits NRAS-(see FIG. 2A) and HRAS-(see FIG. 2B) effector BRET-based biosensors. HEK293T cells were transfected 24 hr with plasmids expressing the NRAS Q61H Tools and resources Cancer Biology and HRAS G12V (B, D) biosensors together with the indicated RBDs of PI3K, CRAF and RALGDS (A, B) or full-length CRAF. These were treated with 5, 10 and 20 mM of Abd-2 (grey bars) or 3344 (black bars) compounds for 20 hr. DMSO (white bar) was used as the negative control. Statistical analyses were performed using a one-way ANOVA followed by Dunnett's post-tests (*p<0.05, p<0.01, *p<0.001, ****p<0.0001). Each experiment was repeated at least four times. Where error bars are presented, they correspond to mean values±SD of biological repeats.

FIG. 2C shows that compound 72 (labelled 3344) (black bars) decreases KRAS G12D/effector domain interactions in a dose-dependent manner showing its broad range of inhibition. Cells were treated with 5, 10 and 20 mM of 3344 (black bars), Abd-2 (grey bars) or DMSO alone (white bars) as the negative control. Statistical analysis was performed with a one-way ANOVA followed by Dunnett's post-hoc tests (*p<0.05, *p<0.001, **p<0.0001). Each experiment was repeated four times. Where error bars are presented, these correspond to mean values±SD of biological repeats.

SUMMARY OF THE INVENTION

In one aspect, the present invention provides a compound as defined herein, and/or a salt or solvate thereof.

In another aspect, the present invention provides a pharmaceutical composition which comprises a compound as defined herein, or a pharmaceutically acceptable salt or solvate thereof, and one or more pharmaceutically acceptable excipients.

In another aspect, the present invention provides a compound as defined herein, or a pharmaceutically acceptable salt or solvate thereof, or a pharmaceutical composition as defined herein, for use in therapy.

In another aspect, the present invention provides a compound as defined herein, or a pharmaceutically acceptable salt or solvate thereof, or a pharmaceutical composition as defined herein, for use in the treatment of a proliferative condition.

In another aspect, the present invention provides a compound as defined herein, or a pharmaceutically acceptable salt or solvate thereof, or a pharmaceutical composition as defined herein, for use in the treatment of cancer.

In another aspect, the present invention provides a compound as defined herein, or a pharmaceutically acceptable salt or solvate thereof, or a pharmaceutical composition as defined herein, for use in inhibiting a RAS-effector protein-protein interaction.

In another aspect, the present invention provides the use of a compound as defined herein, or a pharmaceutically acceptable salt or solvate thereof, in the manufacture of a medicament for use in the treatment of a proliferative condition.

In another aspect, the present invention provides the use of a compound as defined herein, or a pharmaceutically acceptable salt or solvate thereof, in the manufacture of a medicament for use in the treatment of cancer.

In another aspect, the present invention provides the use of a compound as defined herein, or a pharmaceutically acceptable salt or solvate thereof, in the manufacture of a medicament for use in inhibiting a RAS-effector protein-protein interaction.

In another aspect, the present invention provides a method of inhibiting a RAS-effector protein-protein interaction in vitro or in vivo, said method comprising contacting a cell with an effective amount of a compound as defined herein, or a pharmaceutically acceptable salt or solvate thereof.

In another aspect, the present invention provides a method of inhibiting cell proliferation in vitro or in vivo, said method comprising contacting a cell with an effective amount of a compound as defined herein, or a pharmaceutically acceptable salt or solvate thereof.

In another aspect, the present invention provides a method of treating a proliferative disorder in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating cancer in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a combination comprising a compound, or a pharmaceutically acceptable salt or solvate thereof, as defined herein, with one or more additional therapeutic agents.

Preferred, suitable, and optional features of any one particular aspect of the present invention are also preferred, suitable, and optional features of any other aspect.

DETAILED DESCRIPTION OF THE INVENTION

Definitions

The compounds and intermediates described herein may be named according to either the IUPAC (International Union for Pure and Applied Chemistry) or CAS (Chemical Abstracts Service) nomenclature systems. It should be understood that unless expressly stated to the contrary, the terms "compounds of Formula I", "compounds of Formula Ia", "compounds of Formula Ic", "compounds of Formula Id" and the more general term "compounds" refer to and include any and all compounds described by and/or with reference to Formula I, Ia, Ic and Id respectively. It should also be understood that these terms encompasses all stereoisomers, i.e. cis and trans isomers, as well as optical isomers, i.e. R and S enantiomers, of such compounds and all salts thereof, in substantially pure form and/or any mixtures of the foregoing in any ratio. This understanding extends to pharmaceutical compositions and methods of treatment that employ or comprise one or more compounds of the Formula I, Ia, Ic and Id, either by themselves or in combination with additional agents. In one embodiment, a compound of formula I, Ia, Ic or Id, where it possesses a stereocentre on the benzodioxan ring, is the R-stereoisomer. In another embodiment, a compound of formula I, Ia, Ic or Id, where it possesses a stereocentre on the benzodioxan ring, is the S-stereoisomer. The various hydrocarbon-containing moieties provided herein may be described using a prefix designating the minimum and maximum number of carbon atoms in the moiety, e.g. "$(C_a-C_b)$". For example, $(C_a-C_b)$ alkyl indicates an alkyl moiety having the integer "a" to the integer "b" number of carbon atoms, inclusive. Certain moieties may also be described according to the minimum and maximum number of members with or without specific reference to a particular atom or overall structure. For example, the terms "a to b membered ring" or "having between a to b members" refer to a moiety having the integer "a" to the integer "b" number of atoms, inclusive.

"About" when used herein in conjunction with a measurable value such as, for example, an amount or a period of time and the like, is meant to encompass reasonable variations of the value, for instance, to allow for experimental error in the measurement of said value.

As used herein by themselves or in conjunction with another term or terms, "alkyl" and "alkyl group" refer to a branched or unbranched saturated hydrocarbon chain. Unless specified otherwise, alkyl groups typically contain 1-10 carbon atoms, such as 1-6 carbon atoms or 1-4 carbon atoms or 1-3 carbon atoms, and can be substituted or unsubstituted. Representative examples include, but are not limited to, methyl, ethyl, n-propyl, i-propyl, n-butyl, i-butyl, s-butyl, t-butyl, n-pentyl, n-hexyl, n-heptyl, n-octyl, n-nonyl, n-decyl, isopropyl, tert-butyl, isobutyl, etc.

As used herein by themselves or in conjunction with another term or terms, "alkylene" and "alkylene group" refer to a branched or unbranched saturated hydrocarbon chain. Unless specified otherwise, alkylene groups typically contain 1-10 carbon atoms, such as 1-6 carbon atoms or 1-3 carbon atoms, and can be substituted or unsubstituted. Representative examples include, but are not limited to, methylene ($—CH_2—$), the ethylene isomers ($—CH(CH_3)—$ and $—CH_2CH_2—$), the propylene isomers ($—CH(CH_3)CH_2—$, $—CH(CH_2CH_3)—$, $—C(CH_3)_2—$, and $—CH_2CH_2CH_2—$), etc.

As used herein by themselves or in conjunction with another term or terms, "alkenyl" and "alkenyl group" refer to a branched or unbranched hydrocarbon chain containing at least one double bond. Unless specified otherwise, alkenyl groups typically contain 2-10 carbon atoms, such as 2-6 carbon atoms or 2-4 carbon atoms, and can be substituted or unsubstituted. Representative examples include, but are not limited to, ethenyl, 3-buten-1-yl, 2-ethenylbutyl, and 3-hexen-1-yl.

As used herein by themselves or in conjunction with another term or terms, "alkynyl" and "alkynyl group" refer to a branched or unbranched hydrocarbon chain containing at least one triple bond. Unless specified otherwise, alkynyl groups typically contain 2-10 carbon atoms, such as 2-6 carbon atoms or 2-4 carbon atoms, and can be substituted or unsubstituted. Representative examples include, but are not limited to, ethynyl, 3-butyn-1-yl, propynyl, 2-butyn-1-yl, and 3-pentyn-1-yl.

As used herein by itself or in conjunction with another term or terms, "aromatic" refers to monocyclic and polycyclic ring systems containing 4n+2 pi electrons, where n is an integer. Aromatic should be understood as referring to and including ring systems that contain only carbon atoms (i.e. "aryl") as well as ring systems that contain at least one heteroatom selected from N, O or S (i.e. "heteroaromatic" or "heteroaryl"). An aromatic ring system can be substituted or unsubstituted.

As used herein by itself or in conjunction with another term or terms, "non-aromatic" refers to a monocyclic or polycyclic ring system having at least one double bond that is not part of an extended conjugated pi system. As used herein, non-aromatic refers to and includes ring systems that contain only carbon atoms as well as ring systems that contain at least one heteroatom selected from N, O or S. A non-aromatic ring system can be substituted or unsubstituted.

As used herein by themselves or in conjunction with another term or terms, "aryl" and "aryl group" refer to phenyl and 7-15 membered bicyclic or tricyclic hydrocarbon ring systems, including bridged, spiro, and/or fused ring systems, in which at least one of the rings is aromatic. Aryl groups can be substituted or unsubstituted. Unless specified otherwise, an aryl group may contain 6 ring atoms (i.e., phenyl) or a ring system containing 9 to 15 atoms, such as 9 to 11 ring atoms, or 9 or 10 ring atoms. Representative examples include, but are not limited to, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl. Suitably an aryl group is phenyl.

As used herein by themselves or in conjunction with another term or terms, "arylene" and "arylene group" refer to a phenylene ($—C_6H_4—$) or to 7 to 15 membered bicyclic or tricyclic hydrocarbon ring systems, including bridged, spiro, and/or fused ring systems, in which at least one of the rings is aromatic. Arylene groups can be substituted or unsubstituted. In some embodiments, an arylene group may contain 6 (i.e., phenylene) ring atoms or be a ring system containing 9 to 15 atoms; such as 9 to 11 ring atoms; or 9 or 10 ring atoms. Arylene groups can be substituted or unsubstituted.

As used herein by themselves or in conjunction with another term or terms, "alkylaryl" and "alkylaryl group" refer to an alkyl group in which a hydrogen atom is replaced by an aryl group, wherein alkyl group and aryl group are as previously defined, such as, for example, benzyl ($C_6H_5CH_2—$). Alkylaryl groups can be substituted or unsubstituted.

As used herein by themselves or in conjunction with another term or terms, "carbocyclic group" and "carbocycle" refer to monocyclic and polycyclic ring systems that contain only carbon atoms in the ring(s), i.e., hydrocarbon ring systems, without regard or reference to aromaticity or degree of unsaturation. Thus, carbocyclic group should be understood as referring to and including ring systems that are fully saturated (such as, for example, a cyclohexyl group), ring systems that are aromatic (such as, for example, a phenyl group), as well as ring systems having fully saturated, aromatic and/or unsaturated portions (such as, for example, cyclohexenyl, 2,3-dihydro-indenyl, and 1,2,3,4-tetrahydronaphthalenyl). The terms carbocyclic and carbocycle further include bridged, fused, and spirocyclic ring systems.

As used herein by themselves or in conjunction with another term or terms, "cycloalkyl" and "cycloalkyl group" refer to a non-aromatic carbocyclic ring system, that may be monocyclic, bicyclic, or tricyclic, saturated or unsaturated, and may be bridged, spiro, and/or fused. A cycloalkyl group may be substituted or unsubstituted. Unless specified otherwise, a cycloalkyl group typically contains from 3 to 12 ring atoms. In some instances a cycloalkyl group may contain 4 to 10 ring atoms (e.g., 4 ring atoms, 5 ring atoms, 6 ring atoms, 7 ring atoms, etc.). Representative examples include, but are not limited to, cyclopropyl, cyclopropenyl, cyclobutyl, cyclobutenyl, cyclopentyl, cyclopentenyl, cyclohexyl, cyclohexenyl, norbornyl, norbornenyl, bicyclo[2.2.1] hexane, bicyclo[2.2.1]heptane, bicyclo[2.2.1]heptene, bicyclo[3.1.1]heptane, bicyclo[3.2.1]octane, bicyclo[2.2.2] octane, bicyclo[3.2.2]nonane, bicyclo[3.3.1]nonane, and bicyclo[3.3.2]decane.

As used herein by themselves or in conjunction with another term or terms, "alkylcycloalkyl" and "alkylcycloalkyl group" refer to an alkyl group in which a hydrogen atom is replaced by a cycloalkyl group, wherein alkyl group and cycloalkyl group are as previously defined, such as, for example, cyclohexylmethyl ($C_6H_{11}CH_2$—). Alkylcycloalkyl groups can be substituted or unsubstituted.

As used herein by themselves or in conjunction with another term or terms, "haloalkyl" and "haloalkyl group" refer to alkyl groups in which one or more hydrogen atoms are replaced by halogen atoms. Haloalkyl includes both saturated alkyl groups as well as unsaturated alkenyl and alkynyl groups. Representative examples include, but are not limited to, —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —$CF=CF_2$, —$CCl=CH_2$, —$CBr=CH_2$, —$Cl=CH_2$, —$C=C-CF_3$, —$CHFCH_2CH_3$ and —$CHFCH_2CF_3$. Haloalkyl groups can be substituted or unsubstituted.

As used herein by themselves or in conjunction with another term or terms, "halo" and "halogen" include fluorine, chlorine, bromine and iodine atoms and substituents.

As used herein by themselves or in conjunction with another term or terms, "heteroaryl" and "heteroaryl group" refer to (a) 5 and 6 membered monocyclic aromatic rings, which contain, in addition to carbon atom(s), at least one heteroatom, such as nitrogen, oxygen or sulfur, and (b) 7 to 15 membered bicyclic and tricyclic rings, which contain, in addition to carbon atom(s), at least one heteroatom, such as nitrogen, oxygen or sulfur, and in which at least one of the rings is aromatic. In some instances, a heteroaryl group can contain two or more heteroatoms, which may be the same or different. Heteroaryl groups can be substituted or unsubstituted, and may be bridged, spiro, and/or fused. In some instances, a heteroaryl group may contain 5, 6, or 8 to 15 ring atoms. In other instances, a heteroaryl group may contain 5 to 10 ring atoms, such as 5, 6, 9, or 10 ring atoms. Representative examples include, but are not limited to, 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl, triazolyl, pyridin-2-yl, pyridin-4-yl, pyrimidin-2-yl, pyridazin-4-yl, pyrazin-2-yl, naphthyridinyl, pteridinyl, phthalazinyl, purinyl, alloxazinyl, benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, isoquinolinyl, 10-aza-tricyclo[6.3.1.02.7]dodeca-2(7),3,5-trienyl, 12-oxa-10-aza-tricyclo[6.3.1.02.7]dodeca-2(7),3,5-trienyl, 12-aza-tricyclo[7.2.1.02.7]dodeca-2 (7),3,5-trienyl, 10-aza-tricyclo[6.3.2.02.7]trideca-2(7),3,5-trienyl, 2,3,4,5-tetrahydro-1H-benzo[d]azepinyl, 1,3,4,5-tetrahydro-benzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro-7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl. Suitably, a heteroaryl is a 5- or 6-membered heteroaryl ring comprising one, two or three heteroatoms selected from N, O or S.

As used herein by themselves or in conjunction with another term or terms, "alkylheteroaryl" and "alkylheteroaryl group" refer to an alkyl group in which a hydrogen atom is replaced by a heteroaryl group, wherein alkyl group and heteroaryl group are as previously defined. Alkylheteroaryl groups can be substituted or unsubstituted. Suitably, an alkyl heteroaryl group comprises is a 5- or 6-membered heteroaryl ring comprising one, two or three heteroatoms selected from N, O or S and a alkyl moiety selected from methyl, ethyl or propyl.

As used herein by themselves or in conjunction with another term or terms, "heterocyclic group" and "heterocycle" refer to monocyclic and polycyclic ring systems that contain carbon atoms and at least one heteroatom selected from nitrogen, oxygen, sulfur or phosphorus in the ring(s), without regard or reference to aromaticity or degree of unsaturation. Thus, a heterocyclic group should be understood as referring to and including ring systems that are fully saturated (such as, for example, a piperidinyl group), ring systems that are aromatic (such as, for example, a pyrindinyl group), as well as ring systems having fully saturated, aromatic and/or unsaturated portions (such as, for example, 1,2,3,6-tetrahydropyridinyl and 6,8-dihydro-5H-[1,2,4]triazolo[4,3-a]pyrizinyl). The terms heterocyclic and heterocycle further include bridged, fused, and spirocyclic ring systems.

As used herein by themselves or in conjunction with another term or terms, "heterocycloalkyl" and "heterocycloalkyl group" refer to 3 to 15 membered monocyclic, bicyclic, and tricyclic non-aromatic ring systems, which contain, in addition to carbon atom(s), at least one heteroatom, such as nitrogen, oxygen, sulfur or phosphorus. Heterocycloalkyl groups may be fully saturated or contain unsaturated portions and may be bridged, spiro, and/or fused ring systems. In some instances a heterocycloalkyl group may contain at least two or heteroatoms, which may be the same or different. Heterocycloalkyl groups can be substituted or unsubstituted. In some instances a heterocycloalkyl group may contain from 3 to 10 ring atoms or from 3 to 7 ring atoms or from 5 to 7 ring atoms, such as 5 ring atoms, 6 ring atoms, or 7 ring atoms. Representative examples include, but are not limited to, tetrahydrofuranyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, thiomorpholinyl, homomorpholinyl, homopiperidyl, homopiperazinyl, thiomorpholinyl-5-oxide, thiomorpholinyl-S,S-dioxide, pyrrolidinyl, tetrahydropyranyl, piperidinyl, tetrahydrothienyl, homopiperidinyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-5-oxide, tetrahydrothienyl-S,S-dioxide, homothiomorpholinyl-5-oxide, quinuclidinyl, 2-oxa-5-azabicyclo

[2.2.1]heptanyl, 8-oxa-3-aza-bicyclo[3.2.1]octanyl, 3,8-diaza-bicyclo[3.2.1]octanyl, 2,5-diaza-bicyclo[2.2.1]heptanyl, 3,8-diaza-bicyclo[3.2.1]octanyl, 3,9-diaza-bicyclo[4.2.1]nonanyl, 2,6-diaza-bicyclo[3.2.2]nonanyl, [1,4]oxaphosphinanyl-4-oxide, [1,4]azaphosphinanyl-4-oxide, [1,2]oxaphospholanyl-2-oxide, phosphinanyl-1-oxide, [1,3]azaphospholidinynl-3-oxide, [1,3]oxaphospholanyl-3-oxide, 7-oxabicyclo[2.2.1]heptanyl, 6,8-dihydro-5H-[1,2,4]triazolo[4,3-a]pyrazin-7-yl, 6,8-dihydro-5H-imidazo[1,5-a]pyrazin-7-yl, 6,8-dihydro-5H-imidazo[1,2-a]pyrazin-7-yl, 5,6,8,9-tetrahydro-[1,2,4]triazolo[4,3-d][1,4]diazepin-7-yl and 6,8-dihydro-5H-[1,2,4]triazolo[4,3-a]pyrazin-7-yl. Suitably, a heterocyclylalkyl group as defined herein is a monocyclic, bicyclic or spiro heterocyclyl group comprising one, two or three heteroatoms selected from N, O or S.

As used herein by themselves or in conjunction with another term or terms, "heterocycloalkylene" and "heterocycloalkylene group" refer to 3 to 15 membered monocyclic, bicyclic, or tricyclic non-aromatic ring systems, which contain, in addition to carbon atom(s), at least one heteroatom, such as nitrogen, oxygen, sulfur or phosphorus. Heterocycloalkylene groups may be fully saturated or contain unsaturated portions and may be bridged, spiro, and/or fused. Heterocycloalkylene groups can be substituted or unsubstituted. In some instances, a heterocycloalkylene group may contain from 3 to 10 ring atoms; such as from 3 to 7 ring atoms. In other instances a heterocycloalkylene group may contain from 5 to 7 ring atoms, such as 5 ring atoms, 6 ring atoms, or 7 ring atoms.

As used herein by themselves or in conjunction with another term or terms, "alkylheterocycloalkyl" and "alkylheterocycloalkyl group" refer to an alkyl group in which a hydrogen atom is replaced by a heterocycloalkyl group, wherein alkyl group and heterocycloalkyl group are as previously defined, such as, for example, pyrrolidinylmethyl ($C_4H_8NCH_2$—). Alkylheteroycloalkyl groups can be substituted or unsubstituted.

As used herein by itself or in conjunction with another term or terms, "pharmaceutically acceptable" refers to materials that are generally chemically and/or physically compatible with other ingredients (such as, for example, with reference to a formulation), and/or is generally physiologically compatible with the recipient (such as, for example, a subject) thereof.

As used herein by itself or in conjunction with another term or terms, "pharmaceutical composition" refers to a composition that can be used to treat a disease, condition, or disorder in a subject, including a human.

As used herein by itself or in conjunction with another term or terms, "pseudohalogen" refers to —OCN, —SCN, —CF$_3$, and —CN.

As used herein by themselves or in conjunction with another term or terms, "stable" and "chemically stable" refer to a compound that is sufficiently robust to be isolated from a reaction mixture with a useful degree of purity. The present application is directed solely to the preparation of stable compounds. When lists of alternative substituents include members which, owing to valency requirements, chemical stability, or other reasons, cannot be used to substitute a particular group, the list is intended to be read in context to include those members of the list that are suitable for substituting the particular group. For example, when considering the degree of optional substitution of a particular moiety, it should be understood that the number of substituents does not exceed the valency appropriate for that moiety. For example, if $R^1$ is a methyl group (—CH$_3$), it can be optionally substituted by 1 to 3 $R^5$.

As used herein by themselves or in conjunction with another term or terms, "subject(s)" and "patient(s)", refer to animals (e.g. mammals), particularly humans. Suitably, the "subject(s)" and "patient(s)" may be a non-human animal (e.g. livestock and domestic pets) or a human.

As used herein by itself or in conjunction with another term or terms, "substituted" indicates that a hydrogen atom on a molecule has been replaced with a different atom or group of atoms and the atom or group of atoms replacing the hydrogen atom is a "substituent." It should be understood that the terms "substituent", "substituents", "moiety", "moieties", "group", or "groups" refer to substituent(s).

As used herein by themselves or in conjunction with another term or terms, "therapeutic" and "therapeutically effective amount" refer to an amount a compound, composition or medicament that (a) inhibits or causes an improvement in a particular disease, condition or disorder; (b) attenuates, ameliorates or eliminates one or more symptoms of a particular disease, condition or disorder; (c) or delays the onset of one or more symptoms of a particular disease, condition or disorder described herein. It should be understood that the terms "therapeutic" and "therapeutically effective" encompass any one of the aforementioned effects (a)-(c), either alone or in combination with any of the others (a)-(c). It should be understood that in, for example, a human or other mammal, a therapeutically effective amount can be determined experimentally in a laboratory or clinical setting, or a therapeutically effective amount may be the amount required by the guidelines of the United States Food and Drug Administration (FDA) or equivalent foreign regulatory body, for the particular disease and subject being treated. It should be appreciated that determination of proper dosage forms, dosage amounts, and routes of administration is within the level of ordinary skill in the pharmaceutical and medical arts.

As used herein whether by themselves or in conjunction with another term or terms, "treating", "treated" and "treatment", refer to and include prophylactic, ameliorative, palliative, and curative uses and results. In some embodiments, the terms "treating", "treated", and "treatment" refer to curative uses and results as well as uses and results that diminish or reduce the severity of a particular condition, characteristic, symptom, disorder, or disease described herein. For example, treatment can include diminishment of several symptoms of a condition or disorder or complete eradication of said condition or disorder. It should be understood that the term "prophylactic" as used herein is not absolute but rather refers to uses and results where the administration of a compound or composition diminishes the likelihood or seriousness of a condition, symptom, or disease state, and/or delays the onset of a condition, symptom, or disease state for a period of time.

As used herein, a "therapeutically active agent", whether used alone or in conjunction with another term or terms, refers to any compound, i.e. a drug, that has been found to be useful in the treatment of a disease, disorder or condition and is not described by Formula I. It should be understood that a therapeutically active agent may not be approved by the FDA or an equivalent foreign regulatory body.

A "therapeutically effective amount" means the amount of a compound that, when administered to a subject or patient for treating a disease, is sufficient to effect such treatment for the disease. The "therapeutically effective amount" will vary depending on the compound, the disease and its severity and the age, weight, etc., of the subject or patient to be treated.

As used herein, the term direct bond means that the two adjacent groups (e.g. in the case of $J^{1a}$, $(CR^eR^f)_a$ and $(CR^gR^h)^b$) are directly linked, (i.e. $(CReRf)_a$—$(CR^gR^h)_b$).

As used herein, the term "RAS-effector protein-protein interaction" refers to the interaction between RAS and a RAS effector.

As used herein, the term "RAS effector" refers to proteins which interact with the active GTP-bound form of RAS in order to transmit signals for cell proliferation and differentiation. In one embodiment, the RAS effectors are protein kinases, lipid kinases and guanine nucleotide exchange factors. Suitably, the RAS effectors are protein kinases. In one embodiment, the RAS effectors are selected from PLCε (epsilon), PKCζ(zeta), PI3K, RASSF, RAF, RalGEF, RIN, AF-6, GAP and TIAM1, suitably selected from PI3K, RAF and RalGEF.

Compounds

Aspects and embodiments of the compounds of the present invention are further defined in the numbered paragraphs which follow:

1. A compound of Formula I, or a salt or solvate thereof:

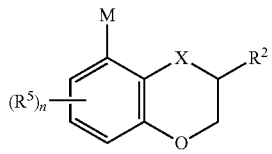

(I)

wherein,

X is selected from $NR^3$, $CR^4$ and O; where $R^3$ and $R^4$ are independently selected from hydrogen and $C_{1-6}$ alkyl;

$R^5$ is selected from hydrogen, hydroxyl, halogen, CN, $C_{1-6}$ haloalkyl, $C_{1-6}$ haloalkoxy, O—$C_{1-6}$ alkyl and $C_{1-6}$ alkyl optionally substituted by one or more $R^a$;

n is a number selected from 0, 1, 2, and 3;

each $R^a$ is independently selected from hydroxyl, halogen, $C_{1-6}$ alkyl, CN, $C_{1-6}$ haloalkyl, $C_{1-6}$ haloalkoxy, $C_{3-6}$ cycloalkyl, 3-10 membered heterocycloalkyl, wherein said $C_{1-6}$ alkyl, $C_{3-6}$ cycloalkyl and 3-10 membered heterocycloalkyl are optionally substituted with one or more groups selected from hydroxyl, halogen, CN, $NR^cR^d$, $C_{1-6}$ haloalkyl, $C_{3-6}$ cycloalkyl, $C_{1-6}$ alkyl and O—$C_{1-6}$ alkyl;

M is selected from a $C_{6-11}$ aryl optionally substituted by one or more $R^b$, $(C_{7-16})$alkylaryl optionally substituted by one or more $R^b$, $C_{3-11}$ cycloalkyl optionally substituted by one or more $R^b$, $(C_{1-6}alkyl)C_{4-17}$cycloalkyl optionally substituted by one or more $R^b$, 3-15 membered heterocycloalkyl optionally substituted by one or more $R^b$, 4-21 membered $(C_{1-6}alkyl)$heterocycloalkyl optionally substituted by one or more $R^b$, 5-15 membered heteroaryl optionally substituted by one or more $R^b$, and 6-21 membered $(C_{1-6}alkyl)$heteroaryl optionally substituted by one or more $R^b$;

each $R^b$ is independently selected from hydroxyl, =O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-10 membered heterocycloalkyl, —C(=O)$R^d$, —C(=O)O$R^d$, —C(=O)N$R^cR^d$, —C(O)C(=O)$R^d$, —N$R^cR^d$, —N$R^cC(=O)R^d$, —N$R^cC(=O)OR^d$, —N$R^cC(=O)NR^cR^d$, —N$R^cS(=O)_2R^d$, —N$R^cS(=O)_2NR^cR^d$, —O$R^d$, —S$R^d$, —OC(=O)$R^d$, —OC(=O)N$R^cR^d$, —OC(=O)O$R^d$, —S(=O)_2R^d$, —S(=O)$R^d$, —OS(=O)$R^d$, —OS(=O)_2R^d$, —OS(=O)_2OR^d$, —S(=O)N$R^cR^d$, —OS(=O)_2NR^cR^d$, —

S(=O)_2NR^cR^d$ and a group of Formula II; wherein said $C_{3-6}$ cycloalkyl, $C_{1-6}$ alkyl, and 3-10 membered heterocycloalkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $C_{1-6}$ alkyl, and O—$C_{1-6}$ alkyl; and wherein in Formula II:

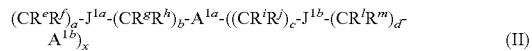

(II)

$R^e$, $R^f$, $R^g$, $R^h$, $R^i$, $R^j$, $R^l$, $R^m$ are independently selected from hydrogen and $C_{1-6}$ alkyl;

a, b, c and a are independently selected from 0, 1, 2, 3 and 4, and x is selected from 0 and 1;

$J^{1a}$ is selected from a direct bond, O, S, $CH_2$, C(O), C(O)N$R^{s1}$, $NR^{s1}C(O)$, $NR^{s1}C(O)NR^{s1}$, $NR^{s1}C(O)O$, OC(O)N$R^{s1}$ and $NR^{s1}$; where $R^{s1}$ is selected from hydrogen and $C_{1-6}$ alkyl;

$J^{1b}$ is selected from a direct bond, O, S, $CH_2$, C(O), C(O)N$R^{s1}$, $NR^{s1}C(O)$, $NR^{s1}C(O)NR^{s1}$, $NR^{s1}C(O)O$, OC(O)N$R^{s1}$ and $NR^{s1}$; where $R^{s1}$ is selected from hydrogen and $C_{1-6}$ alkyl;

$A^{1a}$ is selected from $C_{3-11}$cycloalkyl optionally substituted by one or more $R^k$, $C_{6-11}$ aryl optionally substituted by one or more $R^k$, 3-15 membered heterocycloalkyl optionally substituted by one or more $R^k$, 5-15 membered heteroaryl optionally substituted by one or more $R^k$; and $A^{1b}$ is selected from $C_{3-11}$cycloalkyl optionally substituted by one or more $R^r$, $C_{6-11}$ aryl optionally substituted by one or more $R^r$, 3-15 membered heterocycloalkyl optionally substituted by one or more $R^r$, 5-15 membered heteroaryl optionally substituted by one or more $R^r$; and $R^k$ and $R^r$ are independently selected from hydrogen, hydroxyl, =O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-10 membered heterocycloalkyl, phenyl, benzyl, alkylheteroaryl, alkylheterocycloalkyl, —C(=O)$R^d$, —C(=O)O$R^d$, —C(=O)N$R^cR^d$, —C(O)C(=O)$R^d$, —N$R^cR^d$, —N$R^cC(=O)R^d$, —N$R^cC(=O)OR^d$, —N$R^cC(=O)NR^cR^d$, —N$R^cS(=O)_2R^d$, —N$R^cS(=O)_2NR^cR^d$, —O$R^d$, —S$R^d$, —OC(=O)$R^d$, —OC(=O)N$R^cR^d$, —OC(=O)O$R^d$, —S(=O)_2R^d$, —S(=O)$R^d$, —OS(=O)$R^d$, —OS(=O)_2R^d$, —OS(=O)_2OR^d$, —S(=O)N$R^cR^d$, —OS(=O)_2NR^cR^d$, —S(=O)_2NR^cR^d$; where said $C_{3-6}$ cycloalkyl, $C_{1-6}$ alkyl, 3-10 membered heterocycloalkyl, phenyl, benzyl, alkylheteroaryl, and O—$C_{1-6}$alkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^cR^d$, $C_{1-6}$ alkyl, O—$C_{1-6}$ alkyl, and phenyl; and $R^2$ is selected from hydrogen, halogen, hydroxyl, —CN, —C(=O)$R^d$, —C(=O)O$R^d$, —C(=O)N$R^cR^d$, —C(O)C(=O)$R^d$, —N$R^cR^d$, —N$R^cC(=O)R^d$, —N$R^cC(=O)OR^d$, —N$R^cC(=O)NR^cR^d$, —N$R^cS(=O)_2R^d$, —N$R^cS(=O)_2NR^cR^d$, —O$R^d$, —S$R^d$, —OC(=O)$R^d$, —OC(=O)N$R^cR^d$, —OC(=O)O$R^d$, —S(=O)$R^d$, —S(=O)_2R^d$, —OS(=O)$R^d$, —OS(=O)_2R^d$, —OS(=O)_2OR^d$, —S(=O)N$R^cR^d$, —OS(=O)_2NR^cR^d$, —S(=O)_2NR^cR^d$, $C_{1-10}$ haloalkyl, $C_{1-10}$alkyl optionally substituted by one or more $R^n$, $C_{2-6}$alkenyl optionally substituted by one or more $R^n$, $C_{2-6}$alkynyl optionally substituted by one or more $R^n$, or a group of Formula III

(III)

wherein $R^n$ is independently selected from hydroxyl, =O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-10 membered heterocycloalkyl, —C(=O)$R^d$, —C(=O)O$R^d$, —C(=O)N$R^cR^d$, —N$R^cR^d$, —N$R^cC$(=O)$R^d$, —N$R^cC$(=O)O$R^d$, —N$R^cC$(=O)N$R^cR^d$, —N$R^cS$(=O)$_2R^d$, —N$R^cS$(=O)$_2$N$R^cR^d$, —O$R^d$, —S$R^d$, —OC(=O)$R^d$, —OC(=O)N$R^cR^d$, —OC(=O)O$R^d$, —S(=O)$_2R^d$, —S(=O)$R^d$, —OS(=O)$R^d$, —OS(=O)$_2R^d$, —OS(=O)$_2$O$R^d$, —S(=O)N$R^cR^d$, —OS(=O)$_2$N$R^cR^d$ and —S(=O)$_2$N$R^cR^d$; where said $C_{3-6}$ cycloalkyl, $C_{1-6}$ alkyl, 3-10 membered heterocycloalkyl, $C_{1-6}$ alkyl and O—$C_{1-6}$ alkyl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^cR^d$, $C_{1-6}$ alkyl, and O—$C_{1-6}$ alkyl; and $R^p$ and $R^q$ are independently selected from hydrogen, $C_{1-6}$ alkyl, $C_{3-7}$cycloalkyl optionally substituted by one or more $R^a$, 5-6 membered ($C_{1-6}$alkyl)aryl optionally substituted by one or more $R^a$, 5-6 membered aryl optionally substituted by one or more $R^a$, ($C_{1-6}$alkyl)$C_3$-cycloalkyl optionally substituted by one or more $R^a$, 3-7 membered heterocycloalkyl optionally substituted by one or more $R^a$, 3-7 membered ($C_{1-6}$alkyl)heterocycloalkyl optionally substituted by one or more $R^a$, 5-6 membered heteroaryl optionally substituted by one or more $R^a$, and 5-6 membered ($C_{1-6}$alkyl)heteroaryl optionally substituted by one or more $R^a$;

$R^u$, $R^v$, $R^w$, $R^x$, $R^y$, $R^z$ are independently selected from hydrogen and $C_{1-6}$ alkyl;

f, g, h, and j are independently selected from 0, 1, 2, 3 and 4, and y is selected from 0 and 1;

$J^{2a}$ is selected from a direct bond, O, S, C(O), CH$_2$, C(O)N$R^{s2}$, N$R^{s2}$C(O) and N$R^{s2}$; where $R^{s2}$ is selected from hydrogen, $C_{1-6}$ alkyl, $C_{3-7}$cycloalkyl optionally substituted by one or more $R^a$, 5-6 membered ($C_{1-6}$alkyl)aryl optionally substituted by one or more $R^a$, 5-6 membered aryl optionally substituted by one or more $R^a$, ($C_{1-6}$alkyl)$C_{3-7}$cycloalkyl optionally substituted by one or more $R^a$, 3-7 membered heterocycloalkyl optionally substituted by one or more $R^a$, 3-7 membered ($C_{1-6}$alkyl)heterocycloalkyl optionally substituted by one or more $R^a$, 5-6 membered heteroaryl optionally substituted by one or more $R^a$, and 5-6 membered ($C_{1-6}$alkyl)heteroaryl optionally substituted by one or more $R^a$;

$J^{2b}$ is selected from a direct bond, O, S, C(O), CH$_2$, C(O)N$R^{s2}$, N$R^{s2}$C(O) and N$R^{s2}$; where $R^{s2}$ is selected from hydrogen, $C_{1-6}$ alkyl, $C_{3-7}$cycloalkyl optionally substituted by one or more $R^a$, 5-6 membered ($C_{1-6}$alkyl)aryl optionally substituted by one or more $R^a$, 5-6 membered aryl optionally substituted by one or more $R^a$, ($C_{1-6}$alkyl)$C_{3-7}$cycloalkyl optionally substituted by one or more $R^a$, 3-7 membered heterocycloalkyl optionally substituted by one or more $R^a$, 3-7 membered ($C_{1-6}$alkyl)heterocycloalkyl optionally substituted by one or more $R^a$, 5-6 membered heteroaryl optionally substituted by one or more $R^a$, and 5-6 membered ($C_{1-6}$alkyl)heteroaryl optionally substituted by one or more $R^a$;

$A^{2a}$ is selected from $C_{3-11}$ cycloalkyl optionally substituted by one or more $R^t$, 3-15 membered heterocycloalkyl optionally substituted by one or more $R^t$, $C_{6-11}$ aryl optionally substituted by one or more $R^t$, 5-15 membered heteroaryl optionally substituted by one or more $R^t$;

$A^{2b}$ is selected from $C_{3-11}$ cycloalkyl optionally substituted by one or more $R^t$, 3-15 membered heterocycloalkyl optionally substituted by one or more $R^t$, $C_{6-11}$ aryl optionally substituted by one or more $R^t$, 5-15 membered heteroaryl optionally substituted by one or more $R^t$; and $R^t$ is selected from hydroxyl, =O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-10 membered heterocycloalkyl, —C(=O)$R^d$, —C(=O)O$R^d$, —C(=O)N$R^cR^d$, —C(O)C(=O)$R^d$, —N$R^cR^d$, —N$R^cC$(=O)$R^d$, —N$R^cC$(=O)O$R^d$, —N$R^cC$(=O)N$R^cR^d$, —N$R^cS$(=O)$_2R^d$, —N$R^cS$(=O)$_2$N$R^cR^d$, —O$R^d$, —S$R^d$, —OC(=O)$R^d$, —OC(=O)N$R^cR^d$, —OC(=O)O$R^d$, —S(=O)$_2R^d$, —S(=O)$R^d$, —OS(=O)$R^d$, —OS(=O)$_2R^d$, —OS(=O)$_2$O$R^d$, —S(=O)N$R^cR^d$, —OS(=O)$_2$N$R^cR^d$, —S(=O)$_2$N$R^cR^d$; where said $C_{3-6}$ cycloalkyl, $C_{1-6}$ alkyl, 3-10 membered heterocycloalkyl, $C_{1-6}$ alkyl and O—$C_{1-6}$alkyl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^cR^d$, $C_{1-6}$ alkyl, and O—$C_{1-6}$ alkyl; and wherein,
each $R^c$ is independently selected from hydrogen, hydroxyl, halogen, CN, $C_{1-6}$ haloalkyl, $C_{3-6}$ cycloalkyl, $C_{1-6}$ alkyl and O—$C_{1-6}$ alkyl;

each $R^d$ is independently selected from hydrogen, hydroxyl, halogen, CN, $C_{1-6}$ haloalkyl, 3-10 membered heterocycloalkyl, $C_{3-6}$ cycloalkyl, $C_{1-6}$ alkyl, O—$C_{1-6}$ alkyl and $C_{6-11}$ aryl, wherein said $C_{1-6}$ alkyl, O—$C_{1-6}$ alkyl, $C_{6-11}$ aryl, 3-10 membered heterocycloalkyl and $C_{3-6}$ cycloalkyl are optionally substituted with one or more groups selected from hydroxyl, =O, halogen, CN, NH$_2$, NHMe, NMe$_2$, $C_{1-6}$ haloalkyl, $C_{3-6}$ cycloalkyl, $C_{6-11}$ aryl, $C_{1-6}$ alkyl and O—$C_{1-6}$ alkyl; or $R^c$ and $R^d$, when attached to the same atom, together with the atom to which they are attached form a 3-10 membered ring, optionally containing one or more for heteroatoms selected from O, NH and S, and wherein said ring is optionally substituted with one or more $R^a$.

In one embodiment, the compound of formula I or paragraph 1 is not:

[4-[4-(2,3-dihydro-1,4-benzodioxin-5-yl)benzoyl]-1-piperazinyl](tetrahydro-2-furanyl)-methanone;

N-[2-[4-[4-(2,3-dihydro-1,4-benzodioxin-5-yl)phenyl]-1-piperazinyl]ethyl]-2-quinolinamine;

5-(2,3-dihydro-1,4-benzodioxin-5-yl)-4-methyl-1-[4-(trifluoromethoxy)phenyl]-2-pyridinone;

N-[6-amino-5-(7-chloro-2,3-dihydro-1,4-benzodioxin-5-yl)-2-pyrazinyl]-1-methyl-1H-pyrazole-5-carboxamide;

N-[6-amino-5-(7-chloro-2,3-dihydro-1,4-benzodioxin-5-yl)-2-pyrazinyl]-3-methyl-4-isoxazolecarboxamide;

N-[6-amino-5-(7-chloro-2,3-dihydro-1,4-benzodioxin-5-yl)-2-pyrazinyl]-5-methyl-4-isoxazolecarboxamide;

N-[6-amino-5-(7-chloro-2,3-dihydro-1,4-benzodioxin-5-yl)-2-pyrazinyl]-5-isoxazolecarboxamide;

N-[6-amino-5-(7-chloro-2,3-dihydro-1,4-benzodioxin-5-yl)-2-pyrazinyl]-4-methyl-1,2,5-oxadiazole-3-carboxamide;

N-[6-amino-5-(7-chloro-2,3-dihydro-1,4-benzodioxin-5-yl)-2-pyrazinyl]-4-isoxazolecarboxamide;

N-[6-amino-5-(7-chloro-2,3-dihydro-1,4-benzodioxin-5-yl)-2-pyrazinyl]-3-isoxazolecarboxamide;

3-(7-chloro-2,3-dihydro-1,4-benzodioxin-5-yl)-2,6-pyrazinediamine;

1-(4-(2,3-dihydro-1,4-benzodioxin-5-yl)-1-piperazinyl)methyl)-4-fluorobenzamide;

2-(4-(2,3-dihydro-1,4-benzodioxin-5-yl)-1-piperazinyl)-ethyl)-4-fluorobenzamide;
3-(4-(2,3-dihydro-1,4-benzodioxin-5-yl)-1-piperazinyl)-propyl)-benzamide;
4-(4-(2,3-dihydro-1,4-benzodioxin-5-yl)-1-piperazinyl)-butyl)-benzene;
4-(4-(2,3-dihydro-1,4-benzodioxin-5-yl)-1-piperazinyl)-butyl)-4-fluorobenzamide;
2-(2-(4-(2,3-dihydro-1,4-benzodioxin-5-yl)-1-piperazinyl)-ethyl)-2,3-dihydro-1H-isoindole-1-one;
2-(4-(4-(2,3-dihydro-1,4-benzodioxin-5-yl)-1-piperazinyl)-butyl)-2,3-dihydro-1H-isoindole-1-one;
2-(2-(4-(2,3-dihydro-1,4-benzodioxin-5-yl)-1-piperazinyl)-ethyl)-1,2-benzisothiazole-3(2H)-one-1,1-dioxide;
2-(4-(4-(2,3-dihydro-1,4-benzodioxin-5-yl)-1-piperazinyl)-butyl)-1,2-benzisothiazole-3(2H)-one-1,1-dioxide;
2-(4-(4-(7-chloro-2,3-dihydro-1,4-benzodioxin-5-yl)-1-piperazinyl)-butyl)-1,2-benzisothiazole-3(2H)-one-1,1-dioxide;
3-[[4-(2,3-dihydro-1,4-benzodioxin-5-yl)-1-piperazinyl]methyl]-5-(4-fluorophenyl)-pyridine;
1-(2,3-dihydro-1,4-benzodioxin-5-yl)-4-[[5-(4-fluorophenyl)-1-oxido-3-pyridinyl]methyl]-piperazine;
1-(2,3-dihydro-1,4-benzodioxin-5-yl)-4-[[5-(4-fluorophenyl)-3-pyridinyl]methyl]-4-oxido-piperazine;
1-(2,3-Dihydro-benzo[1,4]dioxin-5-yl)-piperazine;
N-[4-[2-[[(2,3-dihydro-8-phenyl-1,4-benzodioxin-2-yl)methyl]amino]ethyl]phenyl]-acetamide;
4-(2,3-dihydro-8-methoxy-1,4-benzodioxin-5-yl)-benzoic acid ethyl ester; or
4-(2,3-dihydro-8-methoxy-1,4-benzodioxin-5-yl)-benzoic acid.

2. A compound according to paragraph 1, or a salt or solvate thereof, wherein X is selected from $NR^3$ and O.

3. A compound according to any preceding paragraph, or a salt or solvate thereof, wherein X is O.

4. A compound according to any one of the preceding paragraphs, or a salt or solvate thereof, wherein M is selected from $C_{6-11}$aryl optionally substituted by one or more $R^b$, $(C_{7-16})$alkylaryl optionally substituted by one or more $R^b$, 5-15 membered heteroaryl optionally substituted by one or more $R^b$, and 6-21 membered $(C_{1-6}$alkyl)heteroaryl optionally substituted by one or more $R^b$.

5. A compound according to any one of the preceding paragraphs, or a salt or solvate thereof, wherein M is selected from $C_{6-11}$aryl optionally substituted by one or more $R^b$, 3-15 membered heterocycloalkyl optionally substituted by one or more $R^b$, and 5-15 membered heteroaryl optionally substituted by one or more $R^b$.

6. A compound according to any one of the preceding paragraphs, or a salt or solvate thereof, wherein M is selected from $C_{6-11}$aryl optionally substituted by one or more $R^b$ and 5-15 membered heteroaryl substituted by one or more $R^b$.

7. A compound according to any one of the preceding paragraphs, or a salt or solvate thereof, wherein M is selected from $C_{6-11}$aryl optionally substituted by one or more $R^b$ and 5-6 membered heteroaryl optionally substituted by one or more $R^b$.

8. A compound according to any one of paragraphs 1 to 3, or a salt or solvate thereof, wherein M is selected from phenyl optionally substituted by one or more $R^b$, a 5-6 membered heterocycloalkyl optionally substituted by one or more $R^b$, and a 5-6 membered heteroaryl optionally substituted by one or more $R^b$.

9. A compound according to any one of the preceding paragraphs, or a salt or solvate thereof, wherein M is selected from phenyl optionally substituted by one or more $R^b$ and a 5-6 membered heteroaryl optionally substituted by one or more $R^b$.

10. A compound according to any one of the preceding paragraphs, or a salt or solvate thereof, wherein M is selected from phenyl optionally substituted by one or more $R^b$ and a 6-membered heteroaryl optionally substituted by one or more $R^b$.

11. A compound according to any one of paragraphs 1 to 3, or a salt or solvate thereof, wherein M is selected from phenyl optionally substituted by one or more $R^b$, piperazinyl optionally substituted by one or more $R^b$, and pyridyl optionally substituted by one or more $R^b$.

12. A compound according to paragraph 11, or a salt or solvate thereof, wherein M is selected from phenyl optionally substituted by one or more $R^b$ and pyridyl optionally substituted by one or more $R^b$.

13. A compound according to any one paragraphs 1 to 3, or a salt or solvate thereof, wherein said compound is of sub-Formula (Ia) or (Ib):

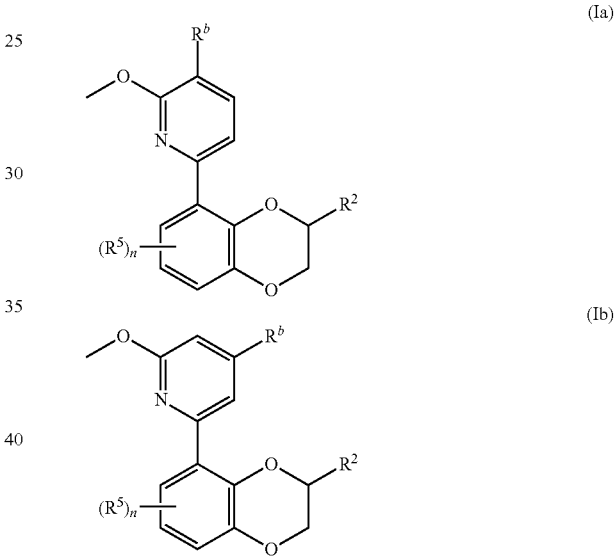

14. A compound according to any one of the preceding paragraphs, or a salt or solvate thereof, wherein $R^b$ is independently selected from hydroxyl, =O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-10 membered heterocycloalkyl, —$NR^cR^d$, and a group of Formula II.

15. A compound according to any one of the preceding paragraphs, or a salt or solvate thereof, wherein $R^b$ is independently selected from =O, $C_{1-6}$ haloalkyl, $C_{1-6}$ haloalkoxy, $C_{1-6}$ alkyl, O—$C_{1-6}$ alkyl, $C_{3-6}$ cycloalkyl, 3-10 membered heterocycloalkyl, —$NR^cR^d$, and a group of Formula II.

16. A compound according to any one of the preceding paragraphs, or a salt or solvate thereof, wherein $R^b$ is independently selected from =O, $C_{1-6}$ haloalkyl, $C_{1-6}$ haloalkoxy, $C_{1-6}$ alkyl, O—$C_{1-6}$ alkyl, —$NR^cR^d$, and a group of Formula II.

17. A compound according to any one of the preceding paragraphs, or a salt or solvate thereof, wherein $R^b$ is independently selected from =O, $C_{1-6}$ alkyl, O—$C_{1-6}$ alkyl, —$NR^cR^d$, and a group of Formula II.

18. A compound according to any one of the preceding paragraphs, or a salt or solvate thereof, wherein $R^b$ is independently selected from $=O$, $C_{1-6}$ alkyl, $O-C_{1-6}$ alkyl and $-NR^cR^d$.

19. A compound according to any one of paragraphs 1 to 14, or a salt or solvate thereof, wherein $R^b$ is a group of Formula II.

20. A compound according to any one of the preceding paragraphs, or a salt or solvate thereof, wherein a, b, c and d are independently selected from 0, 1, 2, suitably 0 and 1.

21. A compound according to any one of the preceding paragraphs, or a salt or solvate thereof, wherein a is 0 and b is selected from 0, 1 and 2, suitably 0 and 1, more suitably 0.

22. A compound according to any one of the preceding paragraphs, or a salt or solvate thereof, wherein a is selected from 0, 1 and 2, suitably 0 and 1, and b is 0.

23. A compound according to any one of the preceding paragraphs, or a salt or solvate thereof, wherein $J^{1a}$ is selected from a direct bond, $CH_2$, O, $NR^{s1}C(O)$, $NR^{s1}C(O)NR^{s1}$ and $NR^{s1}$.

24. A compound according to any one of the preceding paragraphs, or a salt or solvate thereof, wherein $J^{1a}$ is selected from a direct bond, O, $NR^{s1}C(O)$, $NR^{s1}C(O)NR^{s1}$ and $NR^{s1}$.

25. A compound according to any one of the preceding paragraphs, or a salt or solvate thereof, wherein $J^{1a}$ is selected from a $NR^{s1}C(O)$, $NR^{s1}C(O)NR^{s1}$ and $NR^{s1}$.

26. A compound according to any one of the preceding paragraphs, or a salt or solvate thereof, wherein $A^{1a}$ is selected from $C_{3-11}$ cycloalkyl optionally substituted by one or more $R^k$, $C_{6-11}$ aryl optionally substituted by one or more $R^k$, and 3-15 membered heterocycloalkyl optionally substituted by one or more $R^k$.

27. A compound according to any one of paragraphs 1 to 25, or a salt or solvate thereof, wherein $A^{1a}$ is selected from $C_{5-6}$ cycloalkyl optionally substituted by one or more $R^k$, phenyl optionally substituted by one or more $R^k$, 5-6 membered heterocycloalkyl optionally substituted by one or more $R^k$, and 5-6 membered heteroaryl optionally substituted by one or more $R^k$.

28. A compound according to any one of paragraphs 1 to 25, or a salt or solvate thereof, wherein $A^{1a}$ is selected from $C_{5-6}$ cycloalkyl optionally substituted by one or more $R^k$, phenyl optionally substituted by one or more $R^k$, and 5-6 membered heterocycloalkyl optionally substituted by one or more $R^k$.

29. A compound according to any one paragraphs 1 to 25, or a salt or solvate thereof, wherein $A^{1a}$ is selected from cyclopentyl optionally substituted by one or more $R^k$, phenyl optionally substituted by one or more $R^k$, and morpholine, piperidine or piperazine each optionally substituted by one or more $R^k$.

30. A compound according to any one of paragraphs 1 to 25, or a salt or solvate thereof, wherein $A^{1a}$ is selected from cyclopentyl optionally substituted by one or more $R^k$, phenyl optionally substituted by one or more $R^k$, pyridyl optionally substituted by one or more $R^k$, and morpholine, piperidine or piperazine each optionally substituted by one or more $R^k$.

31. A compound according to paragraph 1, or a salt or solvate thereof, wherein the compound is of sub-Formula Ic:

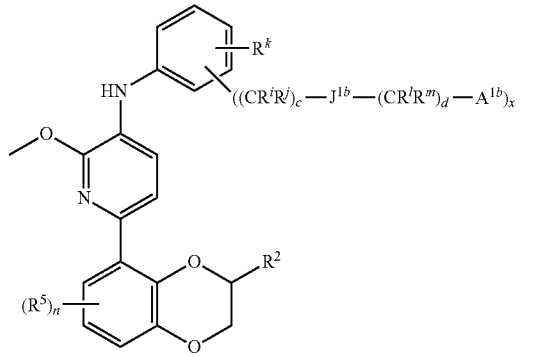

(Ic)

32. A compound according to paragraph 31, or a salt or solvate thereof, wherein the compound is of sub-Formula Ic1 or Ic2:

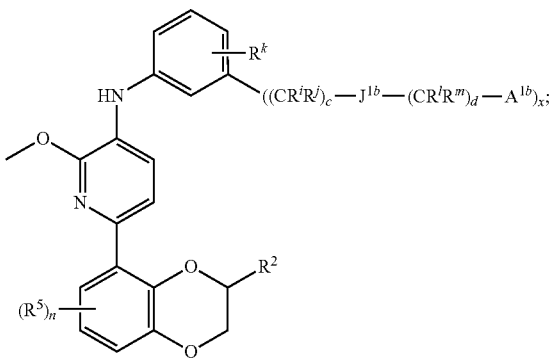

(Ic1)

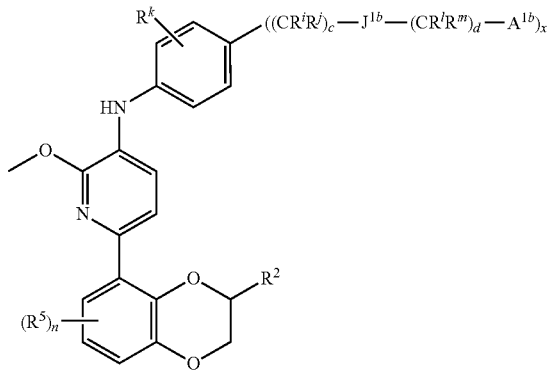

(Ic2)

33. A compound according to any preceding paragraphs, or a salt or solvate thereof, wherein $R^k$ is selected from hydrogen, $C_{1-6}$ alkyl, benzyl, $CH_2$heteroaryl, 3-10 membered heterocycloalkyl, $-C(=O)R^d$, $-C(=O)NR^cR^d$, and $-NR^cR^d$, where said $C_{1-6}$ alkyl, benzyl, $CH_2$heteroaryl and 3-10 membered heterocycloalkyl are optionally substituted with one or more groups selected from hydroxyl, halogen, $=O$, CN, $C_{1-6}$ haloalkyl, $C_{1-6}$ haloalkoxy, $C_{3-6}$ cycloalkyl, $NR^cR^d$, 5-6 membered heterocycloalkyl, $C_{1-6}$ alkyl, and $O-C_{1-6}$ alkyl.

34. A compound according to any preceding paragraphs, or a salt or solvate thereof, wherein $R^k$ is selected from hydrogen, $C_{1-6}$ alkyl, 3-10 membered heterocycloalkyl, —C(=O)$R^d$, —C(=O)$NR^cR^d$, and —$NR^cR^d$, where said $C_{1-6}$ alkyl and 3-10 membered heterocycloalkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^cR^d$, 5-6 membered heterocycloalkyl, $C_{1-6}$ alkyl, and O—$C_{1-6}$ alkyl.

35. A compound according to any preceding paragraphs, or a salt or solvate thereof, wherein $R^k$ is selected from hydrogen, $C_{1-6}$ alkyl, —C(=O)$R^d$, —C(=O)$NR^cR^d$, and —$NR^cR^d$, where said $C_{1-6}$ alkyl is optionally substituted with one or more groups selected from hydroxyl, halogen, =O, CN, $C_{1-6}$ haloalkyl, $C_{1-6}$ haloalkoxy, $C_{3-6}$ cycloalkyl, $NR^cR^d$, and O—$C_{1-6}$ alkyl.

36. A compound according to any preceding paragraphs, or a salt or solvate thereof, wherein $R^k$ is selected from hydrogen, $C_{1-6}$ alkyl, —C(=O)$R^d$, —C(=O)$NR^cR^d$, and —$NR^cR^d$, where said $C_{1-6}$ alkyl is optionally substituted with one or more groups selected from $C_{1-6}$ haloalkyl, $C_{1-6}$ haloalkoxy, $C_{3-6}$ cycloalkyl, $NR^cR^d$, and O—$C_{1-6}$ alkyl.

37. A compound according to any one of the preceding paragraphs, or a salt or solvate thereof, wherein x is 0.

38. A compound according to any one of the paragraphs 1 to 36, or a salt or solvate thereof, wherein x is 1.

39. A compound according to any one of paragraphs 31 to 36, or a salt or solvate thereof, wherein $R^k$ is hydrogen and x is 1.

40. A compound according to any one of paragraphs 31 to 36, or a salt or solvate thereof, wherein x is 0, and $R^k$ is selected from $C_{1-6}$ alkyl, 3-10 membered heterocycloalkyl, —C(=O)$R^d$, —C(=O)$NR^cR^d$, and —$NR^cR^d$, where said $C_{1-6}$ alkyl and 3-10 membered heterocycloalkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^cR^d$, $C_{1-6}$ alkyl, and O—$C_{1-6}$ alkyl.

41. A compound according to any one of paragraphs 31 to 36, or a salt or solvate thereof, wherein x is 0, and $R^k$ is selected from $C_{1-6}$ alkyl, —C(=O)$R^d$, —C(=O)$NR^cR^d$, and —$NR^cR^d$, where said $C_{1-6}$ alkyl is optionally substituted with one or more groups selected from hydroxyl, halogen, =O, CN, $C_{1-6}$ haloalkyl, $C_{1-6}$ haloalkoxy, $C_{3-6}$ cycloalkyl, $NR^cR^d$, 5-6 membered heterocycloalkyl, and O—$C_{1-6}$ alkyl.

42. A compound according to any one of the preceding paragraphs, or a salt or solvate thereof, wherein c is selected from 0 and 1 and a is selected from 0 and 1.

43. A compound according to any one of the preceding paragraphs, or a salt or solvate thereof, wherein c and d is 0, or c and d is 1.

44. A compound according to any one of paragraphs 1 to 36 or a salt or solvate thereof, wherein c is 0 and d is 1, or c is 1 and a is 0.

45. A compound according to any one of the preceding paragraphs, or a salt or solvate thereof, wherein $R^e$, $R^f$, $R^g$, $R^h$, $R^i$, $R^j$, $R^l$, $R^m$ are independently selected from methyl, ethyl and hydrogen.

46. A compound according to any one of the preceding paragraphs, or a salt or solvate thereof, wherein $R^e$, $R^f$, $R^g$, $R^h$, $R^i$, $R^j$, $R^l$, $R^m$ are hydrogen.

47. A compound according to any one of the preceding paragraphs, or a salt or solvate thereof, wherein J1$^b$ is selected from a direct bond, $NR^{s1}$C(O), $NR^{s1}$C(O)O and $NR^{s1}$.

48. A compound according to any one of the preceding paragraphs, or a salt or solvate thereof, wherein J1$^b$ is selected from $NR^{s1}$C(O), $NR^{s1}$C(O)O and $NR^{s1}$.

49. A compound according to any one of the preceding paragraphs, or a salt or solvate thereof, wherein $R^{s1}$ is independently selected from hydrogen, methyl and ethyl.

50. A compound according to any one of the preceding paragraphs, or a salt or solvate thereof, wherein $R^{s1}$ is hydrogen.

51. A compound according to any one of the preceding paragraphs, or a salt or solvate thereof, wherein $A^{1b}$ is selected from $C_{6-11}$ aryl optionally substituted by one or more $R^r$, 3-15 membered heterocycloalkyl optionally substituted by one or more $R^r$, and 5-15 membered heteroaryl optionally substituted by one or more $R^r$.

52. A compound according to any one of the preceding paragraphs, or a salt or solvate thereof, wherein $A^{1b}$ is selected from phenyl optionally substituted by one or more $R_r$, 5-6 membered heterocycloalkyl optionally substituted by one or more $R_r$ and a 5-6 membered heteroaryl optionally substituted by one or more $R_r$.

53. A compound according to any one of the preceding paragraphs, or a salt or solvate thereof, wherein $A^{1b}$ is selected from phenyl optionally substituted by one or more $R^r$, pyridyl optionally substituted by one or more $R^r$, and morpholine, piperidine or piperazine each optionally substituted by one or more $R^r$.

54. A compound according to any preceding paragraphs, or a salt or solvate thereof, wherein $R^r$ is selected from hydrogen, $C_{1-6}$ alkyl, benzyl, $CH_2$heteroaryl, 3-10 membered heterocycloalkyl, —C(=O)$R^d$, —C(=O)$NR^cR^d$, and —$NR^cR^d$, where said $C_{1-6}$ alkyl, benzyl, $CH_2$heteroaryl and 3-10 membered heterocycloalkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^cR^d$, 5-6 membered heterocycloalkyl, $C_{1-6}$ alkyl, and O—$C_{1-6}$ alkyl.

55. A compound according to any preceding paragraphs, or a salt or solvate thereof, wherein $R^r$ is selected from hydrogen, $C_{1-6}$ alkyl, 3-10 membered heterocycloalkyl, —C(=O)$R^d$, —C(=O)$NR^cR^d$, and —$NR^cR^d$, where said $C_{1-6}$ alkyl and 3-10 membered heterocycloalkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^cR^d$, 5-6 membered heterocycloalkyl, $C_{1-6}$ alkyl, and O—$C_{1-6}$ alkyl.

56. A compound according to any preceding paragraphs, or a salt or solvate thereof, wherein $R^r$ is selected from hydrogen, $C_{1-6}$ alkyl, —C(=O)$R^d$, —C(=O)$NR^cR^d$, and —$NR^cR^d$, where said $C_{1-6}$ alkyl is optionally substituted with one or more groups selected from hydroxyl, halogen, =O, CN, $C_{1-6}$ haloalkyl, $C_{1-6}$ haloalkoxy, $C_{3-6}$ cycloalkyl, $NR^cR^d$, and O—$C_{1-6}$ alkyl.

57. A compound according to any preceding paragraphs, or a salt or solvate thereof, wherein $R^r$ is selected from hydrogen, $C_{1-6}$ alkyl, —C(=O)$R^d$, —C(=O)$NR^cR^d$, and —$NR^cR^d$, where said $C_{1-6}$ alkyl is optionally substituted with one or more groups selected from $C_{1-6}$ haloalkyl, $C_{1-6}$ haloalkoxy, $C_{3-6}$ cycloalkyl, $NR^cR^d$, and O—$C_{1-6}$ alkyl.

58. A compound according to any one of the preceding paragraphs, or a salt or solvate thereof, wherein M is selected from

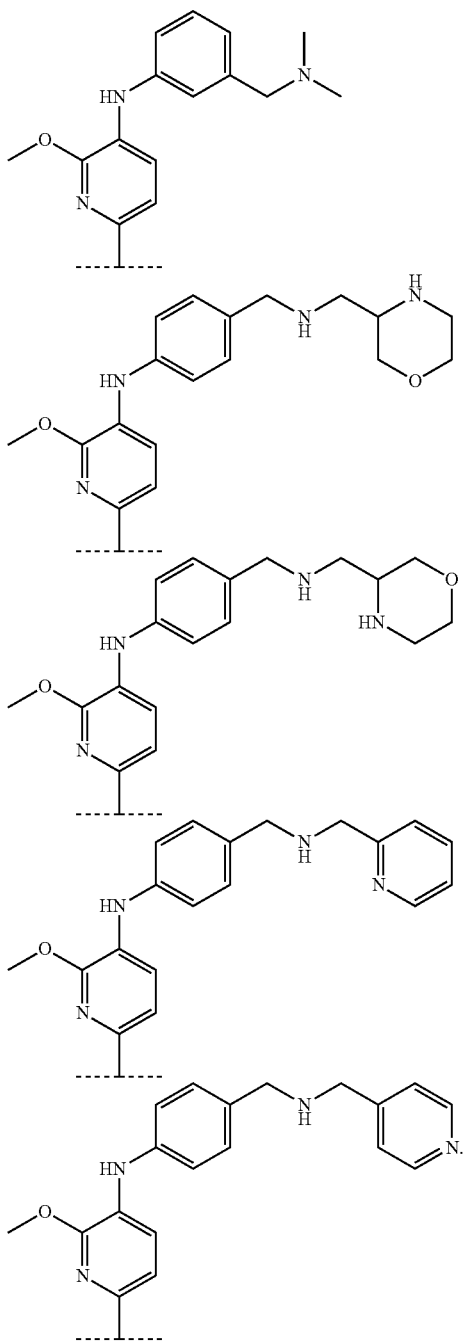

59. A compound according to any one of the preceding paragraphs, or a salt or solvate thereof, wherein $R^2$ is selected from hydrogen, hydroxyl, —CN, —C(=O)$R^d$, —C(=O)O$R^d$, —C(=O)N$R^cR^d$, —C(O)C(=O)$R^d$, —N$R^cR^d$, —N$R^c$C(=O)$R^d$, —N$R^c$C(=O)O$R^d$, —N$R^c$C(=O)N$R^cR^d$, —N$R^c$S(=O)$_2R^d$, —N$R^c$S(=O)$_2$N$R^cR^d$, —O$R^d$, —OC(=O)$R^d$, —OC(=O)N$R^cR^d$, —OC(=O)O$R^d$, —C$_{1-10}$haloalkyl, C$_{1-10}$alkyl optionally substituted by one or more $R^n$, C$_{2-6}$alkenyl optionally substituted by one or more $R^n$, C$_{2-6}$alkynyl optionally substituted by one or more $R^n$, or a group of Formula III.

60. A compound according to any one of the preceding paragraphs, or a salt or solvate thereof, wherein $R^2$ is selected from hydrogen, hydroxyl, —C(=O)$R^d$, —C(=O)O$R^d$, —C(=O)N$R^cR^d$, —N$R^cR^d$, —N$R^c$C(=O)$R^d$, —O$R^d$, C$_{1-10}$alkyl optionally substituted by one or more $R^n$, or a group of Formula III.

61. A compound according to any one of the preceding paragraphs, or a salt or solvate thereof, wherein $R^2$ is selected from hydrogen, C$_{1-10}$alkyl optionally substituted by one or more $R^n$ and or a group of Formula III.

62. A compound according to any one of the preceding paragraphs, or a salt or solvate thereof, wherein $R^n$ is selected from hydroxyl, =O, halogen, CN, C$_{1-6}$ haloalkyl, C$_{1-6}$ haloalkoxy, C$_{1-6}$ alkyl, O—C$_{1-6}$ alkyl, C$_{3-6}$ cycloalkyl, 3-10 membered heterocycloalkyl, —C(=O)$R^d$, —C(=O)O$R^d$, —C(=O)N$R^cR^d$, —C(O)C(=O)$R^d$, —N$R^cR^d$, —N$R^c$C(=O)$R^d$, —O$R^d$, —OC(=O)$R^d$, —OC(=O)N$R^cR^d$, and —OC(=O)O$R^d$; where said C$_{3-6}$ cycloalkyl, C$_{1-6}$ alkyl, 3-10 membered heterocycloalkyl, C$_{1-6}$ alkyl and O—C$_{1-6}$ alkyl are optionally substituted with one or more groups selected from hydroxyl, halogen, =O, CN, C$_{1-6}$ haloalkyl, C$_{1-6}$ haloalkoxy, C$_{3-6}$ cycloalkyl, N$R^cR^d$, C$_{1-6}$ alkyl, and O—C$_{1-6}$ alkyl.

63. A compound according to any one of the preceding paragraphs, or a salt or solvate thereof, wherein $R^n$ is selected from hydroxyl and 3-10 membered heterocycloalkyl wherein said 3-10 membered heterocycloalkyl, is optionally substituted with one or more groups selected from hydroxyl, halogen, =O, CN, C$_{1-6}$ haloalkyl, C$_{1-6}$ haloalkoxy, C$_{3-6}$ cycloalkyl, N$R^cR^d$, C$_{1-6}$ alkyl, and O—C$_{1-6}$ alkyl.

64. A compound according to any one of the preceding paragraphs, or a salt or solvate thereof, wherein $R^2$ is selected from hydrogen or a group of Formula III.

65. A compound according to any one of the preceding paragraphs, or a salt or solvate thereof, wherein f is selected from 0 and 1 and g is selected from 0 and 1.

66. A compound according to any one of the preceding paragraphs, or a salt or solvate thereof, wherein f is 1, and g is 0 or f is 0 and g is 1.

67. A compound according to any one of the preceding paragraphs, or a salt or solvate thereof, wherein f is 1, and g is 1 or f is 0 and g is 0.

68. A compound according to any one of the preceding paragraphs, or a salt or solvate thereof, wherein $J^{2a}$ is selected from O, C(O)N$R^{s2}$, N$R^{s2}$C(O) and N$R^{s2}$.

69. A compound according to any one of the preceding paragraphs, or a salt or solvate thereof, wherein $J^{2a}$ is selected from N$R^{s2}$C(O) and N$R^{s2}$.

70. A compound according to any one of the preceding paragraphs, or a salt or solvate thereof, wherein $R^p$, $R^q$, $R^u$, $R^v$, $R^w$, $R^x$, $R^y$, $R^z$ are independently selected from methyl, ethyl and hydrogen.

71. A compound according to any one of the preceding paragraphs, or a salt or solvate thereof, wherein $R^p$ and $R^q$ are independently selected from methyl and hydrogen, and $R^u$, $R^v$, $R^w$, $R^x$, $R^y$, $R^z$ are hydrogen.

72. A compound according to any one of the preceding paragraphs, or a salt or solvate thereof, wherein $R^p$, $R^q$, $R^u$, $R^v$, $R^w$, $R^x$, $R^y$, $R^z$ are hydrogen.

73. A compound according to any one of the preceding paragraphs, or a salt or solvate thereof, wherein the compound is of sub-Formula Id:

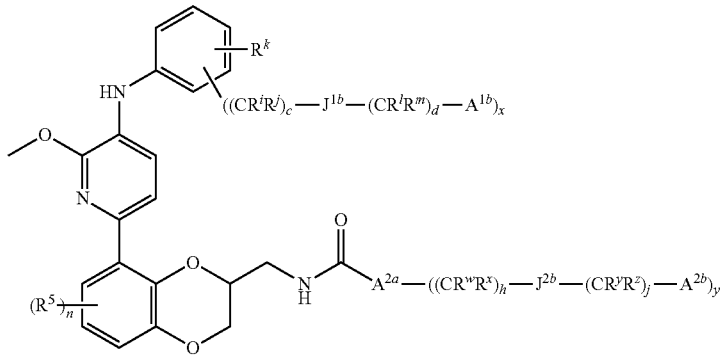

(Id)

74. A compound according to any one of the preceding paragraphs, or a salt or solvate thereof, wherein the compound is of sub-Formula Id1 or Id2:

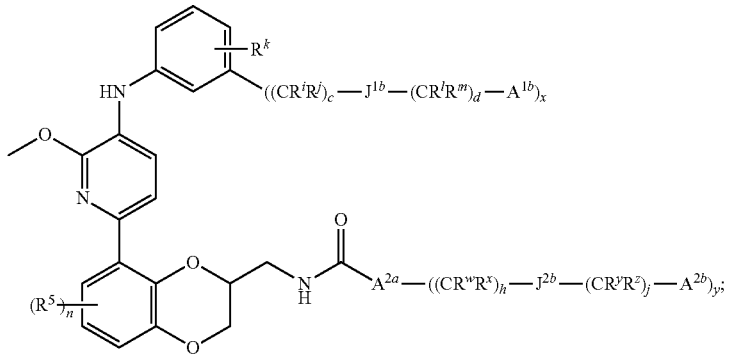

(Id1)

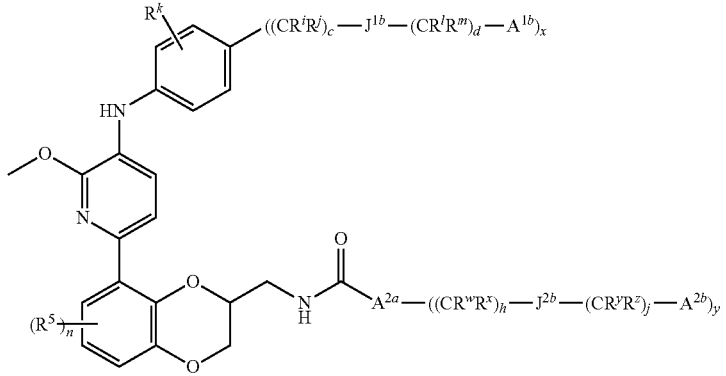

(Id2)

75. A compound according to any one of the preceding paragraphs, or a salt or solvate thereof, wherein $A^{2a}$ is selected from 3-15 membered heterocycloalkyl optionally substituted by one or more $R^t$, $C_{6-11}$ aryl optionally substituted by one or more $R^t$, 5-15 membered heteroaryl optionally substituted by one or more $R^t$.

76. A compound according to any one of the preceding paragraphs, or a salt or solvate thereof, wherein A2a is selected from phenyl optionally substituted by one or more $R^t$, 5-6 membered heterocycloalkyl optionally substituted by one or more $R^t$, and a 5-6 membered heteroaryl optionally substituted by one or more $R^t$.

77. A compound according to any one of the preceding paragraphs, or a salt or solvate thereof, wherein $A^{2a}$ is selected from phenyl optionally substituted by one or more $R^t$, tetrahydropyran optionally substituted by one or more $R^t$, piperidine optionally substituted by one or more $R^t$, pyridyl optionally substituted by one or more $R^t$, furan optionally substituted by one or more $R^t$, and oxazole optionally substituted by one or more $R^t$.

78. A compound according to any one of the preceding paragraphs, or a salt or solvate thereof, wherein y is 0.

79. A compound according to any one of the preceding paragraphs, or a salt or solvate thereof, wherein y is 1.

80. A compound according to any one of the preceding paragraphs, or a salt or solvate thereof, wherein h is selected from 0 and 1 and j is selected from 0 and 1.

81. A compound according to any one of the preceding paragraphs, or a salt or solvate thereof, wherein h is 1, and j is 0, or h is 0, and j is 0.

82. A compound according to any one of the preceding paragraphs, or a salt or solvate thereof, wherein $J^{2b}$ is a direct bond, $CH_2$ or $C(O)$.

83. A compound according to any one of the preceding paragraphs, or a salt or solvate thereof, wherein $A^{2b}$ is selected from phenyl optionally substituted by one or more $R^t$, 5-6 membered heterocycloalkyl optionally substituted by one or more $R^t$, and a 5-6 membered heteroaryl optionally substituted by one or more $R^t$.

84. A compound according to any one of the preceding paragraphs, or a salt or solvate thereof, wherein $A^{2b}$ is selected from phenyl optionally substituted by one or more $R^t$, piperazine optionally substituted by one or more $R^t$, piperidine optionally substituted by one or more $R^t$, morpholine optionally substituted by one or more $R^t$, tetrahydropyran optionally substituted by one or more $R^t$, pyridyl optionally substituted by one or more $R^t$ and pyrazine optionally substituted by one or more $R^t$.

85. A compound according to any one of the preceding paragraphs, or a salt or solvate thereof, wherein $R^t$ is selected from halogen, $C_{1-6}$ alkyl and $O$—$C_{1-6}$ alkyl, where said $C_{1-6}$ alkyl and $O$—$C_{1-6}$ alkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^cR^d$, $C_{1-6}$ alkyl, and $O$—$C_{1-6}$ alkyl.

86. A compound according to any one of the preceding paragraphs, or a salt or solvate thereof, wherein $R^t$ is selected from halogen, $C_{1-6}$ alkyl and $O$—$C_{1-6}$ alkyl, where said $C_{1-6}$ alkyl and $O$—$C_{1-6}$ alkyl are optionally substituted with one or more groups selected from hydroxyl, $C_{3-6}$ cycloalkyl, $NR^cR^d$, and $O$—$C_{1-6}$ alkyl.

87. A compound according to any one of the preceding paragraphs, or a salt or solvate thereof, wherein $R^c$ is independently selected from hydrogen and $C_{1-6}$ alkyl.

88. A compound according to any one of the preceding paragraphs, or a salt or solvate thereof, wherein $R^d$ is independently selected from hydrogen, 3-10 membered heterocycloalkyl, and $C_{1-6}$ alkyl, wherein said $C_{1-6}$ alkyl and 3-10 membered heterocycloalkyl are optionally substituted with one or more groups selected from hydroxyl, =O, halogen, CN, $NH_2$, NHMe, $NMe_2$, $C_{1-6}$ haloalkyl, $C_{3-6}$ cycloalkyl, $C_{6-11}$ aryl, $C_{1-6}$ alkyl and $O$—$C_{1-6}$ alkyl.

89. A compound according to any one of the preceding paragraphs, or a salt or solvate thereof, wherein $R^d$ is independently selected from hydrogen, 3-7 membered heterocycloalkyl, and $C_{1-6}$ alkyl, wherein said $C_{1-6}$ alkyl and 3-10 membered heterocycloalkyl are optionally substituted with one or more groups selected from hydroxyl, =O, halogen, CN, $NH_2$, NHMe, $NMe_2$, $C_{1-6}$ haloalkyl, $C_{3-6}$ cycloalkyl, $C_{6-11}$ aryl, $C_{1-6}$ alkyl and $O$—$C_{1-6}$ alkyl.

90. A compound according to any one of the preceding paragraphs, or a salt or solvate thereof, wherein $R^c$ and $R^d$, when attached to the same atom, together with the atom to which they are attached form a 5-6 membered ring, optionally containing one or more for heteroatoms selected from O, NH and S, and wherein said ring is optionally substituted with one or more $R^a$.

91. A compound according to any one of the preceding paragraphs, or a salt or solvate thereof, wherein $R^2$ is selected from hydrogen,

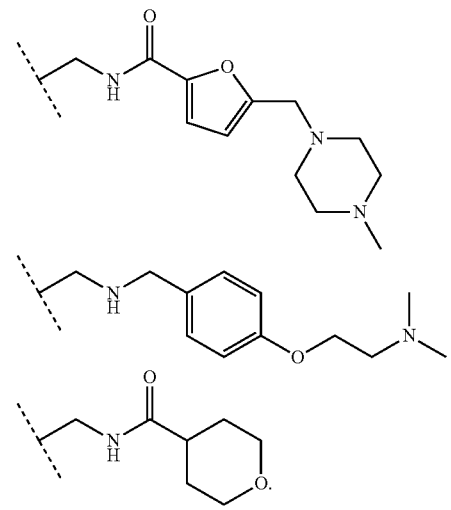

92. A compound according to any one of the preceding paragraphs, or a salt or solvate thereof, wherein $R^5$ is selected from hydrogen, $C_{1-3}$ alkyl and halogen, suitably hydrogen and $C_{1-3}$ alkyl, more suitably hydrogen.

93. A compound according to any one of the preceding paragraphs, or a salt or solvate thereof, wherein n is selected from 0, 1 and 2, suitably 0 and 1, more suitably 0.

94. A compound according to any one of the preceding paragraphs, or a salt or solvate thereof, wherein $R^{s2}$ is selected from hydrogen and $C_{1-3}$ alkyl.

95. A compound according to any one of the preceding paragraphs, or a salt or solvate, thereof, wherein $R^3$ and $R^4$ are independently selected from hydrogen, methyl and ethyl, suitably they are hydrogen.

96. A compound according to any one of the preceding paragraphs, or a salt or solvate thereof, wherein the compound is the R-enantiomer, suitably wherein the compound is the R-enantiomer at the chiral centre bonded to group $R^2$.

97. A compound, or a salt or solvate thereof, selected from:
2-(2,3-Dihydro-benzo[1,4]dioxin-5-yl)-6-methoxy-pyridine;
[8-(6-Methoxy-pyridin-2-yl)-2,3-dihydro-benzo[1,4]dioxin-2-yl]-methanol;
2-(2,3-Dihydro-benzo[1,4]dioxin-5-yl)-6-methoxy-pyridin-4-ylamine;
1-Methyl-piperidine-4-carboxylic acid [2-(2,3-dihydro-benzo[1,4]dioxin-5-yl)-6-methoxy-pyridin-4-yl]-amide;
3-Chloro-6-(2,3-dihydro-benzo[1,4]dioxin-5-yl)-2-methoxy-pyridine;
5-Chloro-2-(2,3-dihydro-benzo[1,4]dioxin-5-yl)-pyridine;
5-(4-Chloro-3-methoxy-phenyl)-2,3-dihydro-benzo[1,4]dioxine;
3-Chloro-6-(2,3-dihydro-benzo[1,4]dioxin-5-yl)-pyridazine;
2-Chloro-5-(2,3-dihydro-benzo[1,4]dioxin-5-yl)-pyrazine;
(R)-3-[2-(2,3-dihydro-benzo[1,4]dioxin-5-yl)-6-methoxy-pyridin-4-ylcarbamoyl]-pyrrolidine-1-carboxylic acid tert-butyl ester;
(R)-2-[2-(2,3-Dihydro-benzo[1,4]dioxin-5-yl)-6-methoxy-pyridin-4-ylcarbamoyl]-morpholine-4-carboxylic acid tert-butyl ester;
4-[2-(2,3-Dihydro-benzo[1,4]dioxin-5-yl)-6-methoxy-pyridin-4-ylcarbamoyl]-piperidine-1-carboxylic acid tert-butyl ester;

(S)-2-[2-(2,3-Dihydro-benzo[1,4]dioxin-5-yl)-6-methoxy-pyridin-4-ylcarbamoyl]-morpholine-4-carboxylic acid tert-butyl ester;

2-{2-methoxy-6-[(R)-3-({[5-(4-methyl-piperazin-1-ylmethyl)-furan-2-carbonyl]-amino}-methyl)-2,3-dihydro-benzo[1,4]dioxin-5-yl]-pyridin-4-ylcarbamoyl}-morpholine-4-carboxylic acid tert-butyl ester;

tert-butyl N-[(1S,3R)-3-[[2-(2,3-dihydro-1,4-benzodioxin-5-yl)-6-methoxy-4-pyridyl]carbamoyl]cyclopentyl]carbamate;

{4-[2-(2,3-Dihydro-benzo[1,4]dioxin-5-yl)-6-methoxy-pyridin-4-ylcarbamoyl]-cyclohexyl}-carbamic acid tert-butyl ester;

(R)-Pyrrolidine-3-carboxylic acid [2-(2,3-dihydro-benzo[1,4]dioxin-5-yl)-6-methoxy-pyridin-4-yl]-amide;

(R)-Morpholine-2-carboxylic acid [2-(2,3-dihydro-benzo[1,4]dioxin-5-yl)-6-methoxy-pyridin-4-yl]-amide;

Piperidine-4-carboxylic acid [2-(2,3-dihydro-benzo[1,4]dioxin-5-yl)-6-methoxy-pyridin-4-yl]-amide;

(S)-Morpholine-2-carboxylic acid [2-(2,3-dihydro-benzo[1,4]dioxin-5-yl)-6-methoxy-pyridin-4-yl]-amide;

4-Amino-cyclohexanecarboxylic acid [2-(2,3-dihydro-benzo[1,4]dioxin-5-yl)-6-methoxy-pyridin-4-yl]-amide;

3-[2-(2,3-Dihydro-benzo[1,4]dioxin-5-yl)-6-methoxy-pyridin-4-yl]-1-methyl-1-(1-methyl-piperidin-4-yl)-urea;

4-Methyl-piperazine-1-carboxylic acid [2-(2,3-dihydro-benzo[1,4]dioxin-5-yl)-6-methoxy-pyridin-4-yl]-amide;

4-Amino-piperidine-1-carboxylic acid [2-(2,3-dihydro-benzo[1,4]dioxin-5-yl)-6-methoxy-pyridin-4-yl]-amide;

5-(6-methoxy-2-pyridyl)-2,3-dihydro-1,4-benzodioxine-3-carbaldehyde;

{2-[4-({[8-(6-Methoxy-pyridin-2-yl)-2,3-dihydro-benzo[1,4]dioxin-2-ylmethyl]-amino}-methyl)-phenoxy]-ethyl}-dimethyl-amine;

[8-(6-Methoxy-pyridin-2-yl)-2,3-dihydro-benzo[1,4]dioxin-2-ylmethyl]-(1-methyl-piperidin-4-ylmethyl)-amine;

[8-(6-Methoxy-pyridin-2-yl)-2,3-dihydro-benzo[1,4]dioxin-2-ylmethyl]-pyridin-3-ylmethyl-amine;

[8-(6-Methoxy-pyridin-2-yl)-2,3-dihydro-benzo[1,4]dioxin-2-ylmethyl]-(tetrahydro-pyran-4-ylmethyl)-amine;

[4-({[8-(6-Methoxy-pyridin-2-yl)-2,3-dihydro-benzo[1,4]dioxin-2-ylmethyl]-amino}-methyl)-piperidin-1-yl]-pyrazin-2-yl-methanone;

[4-({[8-(6-Methoxy-pyridin-2-yl)-2,3-dihydro-benzo[1,4]dioxin-2-ylmethyl]-amino}-methyl)-piperidin-1-yl]-(tetrahydro-pyran-4-yl)-methanone;

{2-[4-({[8-(6-Methoxy-pyridin-2-yl)-2,3-dihydro-benzo[1,4]dioxin-2-ylmethyl]-pyridin-3-ylmethyl-amino}-methyl)-phenoxy]-ethyl}-dimethyl-amine;

2-(4-{[[8-(6-Methoxy-pyridin-2-yl)-2,3-dihydro-benzo[1,4]dioxin-2-ylmethyl]-(tetrahydro-pyran-4-ylmethyl)-amino]-methyl}-phenoxy)-ethyl]-dimethyl-amine;

toluene-4-sulfonic acid 8-(6-methoxy-pyridin-2-yl)-2,3-dihydro-benzo[1,4]dioxin-2-ylmethyl ester;

3-[8-(6-Methoxy-pyridin-2-yl)-2,3-dihydro-benzo[1,4]dioxin-2-ylmethyl]-8-methyl-1,3,8-triaza-spiro[4.5]decane-2,4-dione;

3-[8-(6-Methoxy-pyridin-2-yl)-2,3-dihydro-benzo[1,4]dioxin-2-ylmethyl]-5,5-dimethyl-imidazolidine-2,4-dione;

1-(6-Methoxy-pyridin-3-yl)-3-[8-(6-methoxy-pyridin-2-yl)-2,3-dihydro-benzo[1,4]dioxin-2-ylmethyl]-imidazolidine-2,4-dione;

3-[8-(6-Methoxy-pyridin-2-yl)-2,3-dihydro-benzo[1,4]dioxin-2-ylmethyl]-1-piperidin-4-yl-imidazolidine-2,4-dione;

4-(2-Dimethylamino-ethoxy)-2-fluoro-N-[8-(6-methoxy-pyridin-2-yl)-2,3-dihydro-benzo[1,4]dioxin-2-ylmethyl]-benzamide;

4-(2-Dimethylamino-ethoxy)-N-[8-(6-methoxy-pyridin-2-yl)-2,3-dihydro-benzo[1,4]dioxin-2-ylmethyl]-benzamide;

4-(2-Dimethylamino-ethoxy)-N—[(R)-8-(6-methoxy-pyridin-2-yl)-2,3-dihydro-benzo[1,4]dioxin-2-ylmethyl]-benzamide;

4-(2-Dimethylamino-ethoxy)-N—[(S)-8-(6-methoxy-pyridin-2-yl)-2,3-dihydrobenzo[1,4]dioxin-2-ylmethyl]-benzamide;

5-(4-Methyl-piperazin-1-ylmethyl)-furan-2-carboxylic acid [8-(2H-pyrazol-3-yl)-2,3-dihydro-benzo[1,4]dioxin-2-ylmethyl]-amide;

5-(4-Methyl-piperazin-1-ylmethyl)-furan-2-carboxylic acid [8-(6-methoxy-pyridin-2-yl)-2,3-dihydro-benzo[1,4]dioxin-2-ylmethyl]-amide;

5-(4-Methyl-piperazin-1-ylmethyl)-furan-2-carboxylic acid [(S)-8-(6-methoxy-pyridin-2-yl)-2,3-dihydro-benzo[1,4]dioxin-2-ylmethyl]-amide;

Tetrahydro-pyran-4-carboxylic acid [8-(6-methoxy-pyridin-2-yl)-2,3-dihydro-benzo[1,4]dioxin-2-ylmethyl]-amide;

5-(4-Methyl-piperazin-1-ylmethyl)-furan-2-carboxylic acid [8-(6-methoxy-pyridin-3-yl)-2,3-dihydro-benzo[1,4]dioxin-2-ylmethyl]-amide;

5-Morpholin-4-ylmethyl-furan-3-carboxylic acid [8-(6-methoxy-pyridin-2-yl)-2,3-dihydro-benzo[1,4]dioxin-2-ylmethyl]-amide;

3-Dimethylamino-N-[8-(6-methoxy-pyridin-2-yl)-2,3-dihydro-benzo[1,4]dioxin-2-ylmethyl]-propionamide;

1-Pyrazin-2-ylmethyl-piperidine-4-carboxylic acid [(R)-8-(6-methoxy-pyridin-2-yl)-2,3-dihydro-benzo[1,4]dioxin-2-ylmethyl]-amide;

5-(4-Methyl-piperazin-1-ylmethyl)-oxazole-2-carboxylic acid [8-(6-methoxy-pyridin-2-yl)-2,3-dihydro-benzo[1,4]dioxin-2-ylmethyl]-amide;

1-Methyl-piperidine-4-carboxylic acid [8-(6-methoxy-pyridin-2-yl)-2,3-dihydro-benzo[1,4]dioxin-2-ylmethyl]-amide;

5-(4-Methyl-piperazin-1-ylmethyl)-furan-2-carboxylic acid [(R)-8-(6-methoxy-pyridin-2-yl)-2,3-dihydro-benzo[1,4]dioxin-2-ylmethyl]-amide;

5-(4-Methyl-piperazin-1-ylmethyl)-furan-2-carboxylic acid [8-(6-oxo-1,6-dihydro-pyridin-2-yl)-2,3-dihydro-benzo[1,4]dioxin-2-ylmethyl]-amide;

4-(2-dimethylamino-ethoxy)-N-[8-(6-oxo-1,6-dihydro-pyridin-2-yl)-2,3-dihydro-benzo[1,4]dioxin-2-ylmethyl]-benzamide;

5-(4-methyl-piperazin-1-ylmethyl)-furan-2-carboxylic acid [8-(6-oxo-1,6-dihydro-pyridin-3-yl)-2,3-dihydro-benzo[1,4]dioxin-2-ylmethyl]-amide;

[6-(2,3-dihydro-benzo[1,4]dioxin-5-yl)-2-methoxy-pyridin-3-yl]-(3-dimethylaminomethyl-phenyl)-amine;

[6-(2,3-Dihydro-benzo[1,4]dioxin-5-yl)-2-methoxy-pyridin-3-yl]-(4-dimethylaminomethyl-phenyl)-amine;

[6-(2,3-Dihydro-benzo[1,4]dioxin-5-yl)-2-methoxy-pyridin-3-yl]-(5-dimethylaminomethyl-pyridin-2-yl)-amine;

[6-(2,3-Dihydro-benzo[1,4]dioxin-5-yl)-2-methoxy-pyridin-3-yl]-(4-imidazol-1-ylmethyl-phenyl)-amine;

[6-(2,3-Dihydro-benzo[1,4]dioxin-5-yl)-pyridin-3-yl]-(3-dimethylaminomethyl-phenyl)-amine; [6-(2,3-Dihydro-benzo[1,4]dioxin-5-yl)-2-methoxy-pyridin-3-yl]-(3-pyrrolidin-1-ylmethyl-phenyl)-amine;

[6-(2,3-Dihydro-benzo[1,4]dioxin-5-yl)-2-methoxy-pyridin-3-yl]-(3-morpholin-4-ylmethyl-phenyl)-amine;

5-{3-[6-(2,3-Dihydro-benzo[1,4]dioxin-5-yl)-2-methoxy-pyridin-3-ylamino]-phenyl}-pyrrolidin-2-one;

(R)-2-{3-[6-(2,3-Dihydro-benzo[1,4]dioxin-5-yl)-2-methoxy-pyridin-3-ylamino]-phenyl}-pyrrolidine-1-carboxylic acid tert-butyl ester;

(S)-2-{3-[6-(2,3-Dihydro-benzo[1,4]dioxin-5-yl)-2-methoxy-pyridin-3-ylamino]-phenyl}-pyrrolidine-1-carboxylic acid tert-butyl ester;

{4-[6-(2,3-Dihydro-benzo[1,4]dioxin-5-yl)-2-methoxy-pyridin-3-ylamino]-benzyl}-carbamic acid tert-butyl ester;

{3-[6-(2,3-Dihydro-benzo[1,4]dioxin-5-yl)-2-methoxy-pyridin-3-ylamino]-benzyl}-carbamic acid tert-butyl ester;

{3-[6-(2,3-Dihydro-benzo[1,4]dioxin-5-yl)-2-methoxy-pyridin-3-ylamino]-phenyl}-methanol;

[6-(2,3-Dihydro-benzo[1,4]dioxin-5-yl)-pyridazin-3-yl]-(3-dimethylaminomethyl-phenyl)-amine; [5-(2,3-Dihydro-benzo[1,4]dioxin-5-yl)-pyrazin-2-yl]-(3-dimethylaminomethyl-phenyl)-amine;

Tetrahydro-pyran-4-carboxylic acid {(S)-8-[5-(3-dimethylaminomethyl-phenylamino)-6-methoxy-pyridin-2-yl]-2,3-dihydro-benzo[1,4]dioxin-2-ylmethyl}-amide;

[4-(2,3-Dihydro-benzo[1,4]dioxin-5-yl)-phenyl]-(3-dimethylaminomethyl-phenyl)-amine;

1-Benzyl-4-(2,3-dihydro-benzo[1,4]dioxin-5-yl)-piperazine;

[4-(2,3-Dihydro-benzo[1,4]dioxin-5-yl)-2-methoxy-phenyl]-(3-dimethylaminomethyl-phenyl)-amine;

{4-[4-(2,3-Dihydro-benzo[1,4]dioxin-5-yl)-2-methoxy-phenylamino]-benzyl}-carbamic acid tert-butyl ester;

[6-(2,3-Dihydro-benzo[1,4]dioxin-5-yl)-2-methoxy-pyridin-3-yl]-((R)-3-pyrrolidin-2-yl-phenyl)-amine;

[6-(2,3-Dihydro-benzo[1,4]dioxin-5-yl)-2-methoxy-pyridin-3-yl]-((S)-3-pyrrolidin-2-yl-phenyl)-amine;

(4-Aminomethyl-phenyl)-[6-(2,3-dihydro-benzo[1,4]dioxin-5-yl)-2-methoxy-pyridin-3-yl]-amine;

(3-Aminomethyl-phenyl)-[6-(2,3-dihydro-benzo[1,4]dioxin-5-yl)-2-methoxy-pyridin-3-yl]-amine;

(4-Aminomethyl-phenyl)-[4-(2,3-dihydro-benzo[1,4]dioxin-5-yl)-2-methoxy-phenyl]-amine; N-{3-[6-(2,3-Dihydro-benzo[1,4]dioxin-5-yl)-2-methoxy-pyridin-3-ylamino]-benzyl}-nicotinamide;

N-{3-[6-(2,3-Dihydro-benzo[1,4]dioxin-5-yl)-2-methoxy-pyridin-3-ylamino]-benzyl}-isonicotinamide;

1H-Pyrazole-4-carboxylic acid 3-[6-(2,3-dihydro-benzo[1,4]dioxin-5-yl)-2-methoxy-pyridin-3-ylamino]-benzylamide;

Tetrahydro-pyran-4-carboxylic acid (8-{6-methoxy-5-[2-(1-methyl-piperidin-4-yl)-acetylamino]-pyridin-2-yl}-2,3-dihydro-benzo[1,4]dioxin-2-ylmethyl)-amide;

5-(4-Methyl-piperazin-1-ylmethyl)-furan-2-carboxylic acid (8-{5-[(tetrahydro-pyran-4-ylmethyl)-amino]-pyridin-2-yl}-2,3-dihydro-benzo[1,4]dioxin-2-ylmethyl)-amide;

Tetrahydro-pyran-4-carboxylic acid {8-[5-(3-dimethylaminomethyl-phenylamino)-6-methoxy-pyridin-2-yl]-2,3-dihydro-benzo[1,4]dioxin-2-ylmethyl}-amide;

3-(2,3-Dihydro-benzo[1,4]dioxin-5-yl)-6-(1-methyl-piperidin-4-ylmethoxy)-pyridazine; [6-(2,3-Dihydro-benzo[1,4]dioxin-5-yl)-2-methoxy-pyridin-3-yl]-(1-methyl-pyrrolidin-3-yl)-amine;

5-(4-Methyl-piperazin-1-ylmethyl)-furan-2-carboxylic acid [(R)-8-(5-amino-6-methoxy-pyridin-2-yl)-2,3-dihydro-benzo[1,4]dioxin-2-ylmethyl]-amide;

Tetrahydro-pyran-4-carboxylic acid {8-[6-methoxy-5-(pyridin-3-ylamino)-pyridin-2-yl]-2,3-dihydro-benzo[1,4]dioxin-2-ylmethyl}-amide;

Tetrahydro-pyran-4-carboxylic acid (8-{5-[4-(2-hydroxyethylcarbamoyl)-phenylamino]-6-methoxy-pyridin-2-yl}-2,3-dihydro-benzo[1,4]dioxin-2-ylmethyl)-amide;

Tetrahydro-pyran-4-carboxylic acid (8-{5-[3-(4-acetyl-piperazin-1-ylmethyl)-phenylamino]-6-methoxy-pyridin-2-yl}-2,3-dihydro-benzo[1,4]dioxin-2-ylmethyl)-amide;

Tetrahydro-pyran-4-carboxylic acid (8-{5-[4-(1-methyl-piperidin-4-ylcarbamoyl)-phenylamino]-pyridin-2-yl}-2,3-dihydro-benzo[1,4]dioxin-2-ylmethyl)-amide;

Tetrahydro-pyran-4-carboxylic acid ((R)-8-{5-[2-(1-methyl-piperidin-4-yl)-acetylamino]-pyridin-2-yl}-2,3-dihydro-benzo[1,4]dioxin-2-ylmethyl)-amide;

Tetrahydro-pyran-4-carboxylic acid {8-[5-(3-dimethylaminomethyl-phenylamino)-pyridin-2-yl]-2,3-dihydro-benzo[1,4]dioxin-2-ylmethyl}-amide;

Tetrahydro-pyran-4-carboxylic acid {8-[5-(4-dimethylcarbamoyl-phenylamino)-6-methoxy-pyridin-2-yl]-2,3-dihydro-benzo[1,4]dioxin-2-ylmethyl}-amide;

((1R,3S)-3-{3-[2-Methoxy-6-(3-{[(tetrahydro-pyran-4-carbonyl)-amino]-methyl}-2,3-dihydro-benzo[1,4]dioxin-5-yl)-pyridin-3-yl]-ureido}-cyclopentyl)-carbamic acid tert-butyl ester;

((1S,3R)-3-{3-[2-(3-{[(Tetrahydro-pyran-4-carbonyl)-amino]-methyl}-2,3-dihydro-benzo[1,4]dioxin-5-yl)-pyridin-4-yl]-ureido}-cyclopentyl)-carbamic acid tert-butyl ester;

tetrahydro-pyran-4-carboxylic acid [8-(4-chloro-pyridin-2-yl)-2,3-dihydro-benzo[1,4]dioxin-2-ylmethyl]-amide;

[6-(2,3-Dihydro-benzo[1,4]dioxin-5-yl)-2-methoxy-pyridin-3-yl]-(1-methyl-piperidin-4-yl)-amine;

1-{4-[6-(2,3-Dihydro-benzo[1,4]dioxin-5-yl)-2-methoxy-pyridin-3-ylamino]-piperidin-1-yl}-ethanone;

((1S,3R)-3-{3-[2-Methoxy-6-(3-{[(tetrahydro-pyran-4-carbonyl)-amino]-methyl}-2,3-dihydro-benzo[1,4]dioxin-5-yl)-pyridin-4-yl]-ureido}-cyclopentyl)-carbamic acid benzyl ester;

((1S,3R)-3-{3-[2-(2,3-Dihydro-benzo[1,4]dioxin-5-yl)-6-methoxy-pyridin-4-yl]-ureido}-cyclopentyl)-carbamic acid benzyl ester;

4-(2-Dimethylamino-ethoxy)-N-[8-(4-morpholin-4-yl-pyridin-2-yl)-2,3-dihydro-benzo[1,4]dioxin-2-ylmethyl]-benzamide;

4-(2-Dimethylamino-ethoxy)-N-[8-(6-dimethylamino-pyridin-2-yl)-2,3-dihydro-benzo[1,4]dioxin-2-ylmethyl]-benzamide;

4-(2-Dimethylamino-ethoxy)-N-(8-pyridin-2-yl-2,3-dihydro-benzo[1,4]dioxin-2-ylmethyl)-benzamide;

4-(2-Dimethylamino-ethoxy)-N-[8-(4-methoxy-pyridin-2-yl)-2,3-dihydro-benzo[1,4]dioxin-2-ylmethyl]-benzamide;

5-(4-Methyl-piperazin-1-ylmethyl)-furan-2-carboxylic acid [8-(4-benzyloxy-pyridin-2-yl)-2,3-dihydro-benzo[1,4]dioxin-2-ylmethyl]-amide;

5-(4-methyl-piperazin-1-ylmethyl)-furan-2-carboxylic acid {8-[5-(2-morpholin-4-yl-ethoxy)-pyridin-2-yl]-2,3-dihydro-benzo[1,4]dioxin-2-ylmethyl}-amide;

5-(4-Methyl-piperazin-1-ylmethyl)-furan-2-carboxylic acid [8-(4-morpholin-4-ylmethyl-phenyl)-2,3-dihydro-benzo[1,4]dioxin-2-ylmethyl]-amide;

5-(4-Methyl-piperazin-1-ylmethyl)-furan-2-carboxylic acid [8-(5-benzyloxy-pyridin-2-yl)-2,3-dihydro-benzo[1,4]dioxin-2-ylmethyl]-amide;

{8-[5-(2-Morpholin-4-yl-ethoxy)-pyridin-2-yl]-2,3-dihydro-benzo[1,4]dioxin-2-yl}-methanol;

Tetrahydro-pyran-4-carboxylic acid {8-[5-(2-morpholin-4-yl-ethoxy)-pyridin-2-yl]-2,3-dihydro-benzo[1,4]dioxin-2-ylmethyl}-amide;

Tetrahydro-pyran-4-carboxylic acid {(R)-8-[5-(3-dimethyl-aminomethyl-phenylamino)-6-methoxy-pyridin-2-yl]-2,3-dihydro-benzo[1,4]dioxin-2-ylmethyl}-amide;

N-[6-(2,3-Dihydro-benzo[1,4]dioxin-5-yl)-2-methoxy-pyridin-3-yl]-2-(1-methyl-piperidin-4-yl)-acetamide;

5-(4-Methyl-piperazin-1-ylmethyl)-furan-2-carboxylic acid [(R)-8-(4-amino-6-methoxy-pyridin-2-yl)-2,3-dihydro-benzo[1,4]dioxin-2-ylmethyl]-amide;

Tetrahydro-pyran-4-carboxylic acid [(S)-8-(5-chloro-6-methoxy-pyridin-2-yl)-2,3-dihydro-benzo[1,4]dioxin-2-ylmethyl]-amide;

{4-[2-Methoxy-6-(3-{[(tetrahydro-pyran-4-carbonyl)-amino]-methyl}-2,3-dihydro-benzo[1,4]dioxin-5-yl)-pyridin-3-ylamino]-benzyl}-carbamic acid tert-butyl ester;

tetrahydro-pyran-4-carboxylic acid {8-[5-(4-aminomethyl-phenylamino)-6-methoxy-pyridin-2-yl]-2,3-dihydro-benzo[1,4]dioxin-2-ylmethyl}-amide;

Tetrahydro-pyran-4-carboxylic acid {8-[6-methoxy-5-(4-{[(pyridin-2-ylmethyl)-amino]-methyl}-phenylamino)-pyridin-2-yl]-2,3-dihydro-benzo[1,4]dioxin-2-ylmethyl}-amide;

Tetrahydro-pyran-4-carboxylic acid {8-[6-methoxy-5-(4-{[(pyridin-4-ylmethyl)-amino]-methyl}-phenylamino)-pyridin-2-yl]-2,3-dihydro-benzo[1,4]dioxin-2-ylmethyl}-amide;

Tetrahydro-pyran-4-carboxylic acid {8-[6-methoxy-5-(4-{[(2H-pyrazol-3-ylmethyl)-amino]-methyl}-phenylamino)-pyridin-2-yl]-2,3-dihydro-benzo[1,4]dioxin-2-ylmethyl}-amide;

3-({4-[2-Methoxy-6-(3-{[(tetrahydro-pyran-4-carbonyl)-amino]-methyl}-2,3-dihydro-benzo[1,4]dioxin-5-yl)-pyridin-3-ylamino]-benzylamino}-methyl)-morpholine-4-carboxylic acid tert-butyl ester;

(R)-3-({4-[6-(2,3-Dihydro-benzo[1,4]dioxin-5-yl)-2-methoxy-pyridin-3-ylamino]-benzylamino}-methyl)-morpholine-4-carboxylic acid tert-butyl ester;

(S)-3-({4-[6-(2,3-Dihydro-benzo[1,4]dioxin-5-yl)-2-methoxy-pyridin-3-ylamino]-benzylamino}-methyl)-morpholine-4-carboxylic acid tert-butyl ester;

4-({3-[6-(2,3-Dihydro-benzo[1,4]dioxin-5-yl)-2-methoxy-pyridin-3-ylamino]-benzylamino}-methyl)-pyrazole-1-carboxylic acid tert-butyl ester;

3-({4-[4-(2,3-Dihydro-benzo[1,4]dioxin-5-yl)-2-methoxy-phenylamino]-benzylamino}-methyl)-morpholine-4-carboxylic acid tert-butyl ester;

[6-(2,3-Dihydro-benzo[1,4]dioxin-5-yl)-2-methoxy-pyridin-3-yl]-(3-{[(1H-pyrazol-4-ylmethyl)-amino]-methyl}-phenyl)-amine;

Tetrahydro-pyran-4-carboxylic acid {8-[6-methoxy-5-(4-{[(morpholin-3-ylmethyl)-amino]-methyl}-phenylamino)-pyridin-2-yl]-2,3-dihydro-benzo[1,4]dioxin-2-ylmethyl}-amide;

[6-(2,3-Dihydro-benzo[1,4]dioxin-5-yl)-2-methoxy-pyridin-3-yl]-(4-{[((R)-1-morpholin-3-ylmethyl)-amino]-methyl}-phenyl)-amine;

[6-(2,3-Dihydro-benzo[1,4]dioxin-5-yl)-2-methoxy-pyridin-3-yl]-(4-{[((S)-1-morpholin-3-ylmethyl)-amino]-methyl}-phenyl)-amine;

Morpholine-2-carboxylic acid {2-methoxy-6-[(R)-3-({[5-(4-methyl-piperazin-1-ylmethyl)-furan-2-carbonyl]-amino}-methyl)-2,3-dihydro-benzo[1,4]dioxin-5-yl]-pyridin-4-yl}-amide;

(R)-Pyrrolidine-2-carboxylic acid {2-methoxy-6-[3-({[5-(4-methyl-piperazin-1-ylmethyl)-furan-2-carbonyl]-amino}-methyl)-2,3-dihydro-benzo[1,4]dioxin-5-ylamino]-pyridin-3-yl}-amide;

[4-(2,3-Dihydro-benzo[1,4]dioxin-5-yl)-2-methoxy-phenyl]-(4-{[(morpholin-3-ylmethyl)-amino]-methyl}-phenyl)-amine;

(1R,3S)-3-Amino-cyclopentanecarboxylic acid [2-(2,3-dihydro-benzo[1,4]dioxin-5-yl)-6-methoxy-pyridin-4-yl]-amide;

(R)-2-{2-Methoxy-6-[3-({[5-(4-methyl-piperazin-1-ylmethyl)-furan-2-carbonyl]-amino}-methyl)-2,3-dihydro-benzo[1,4]dioxin-5-ylamino]-pyridin-3-ylcarbamoyl}-pyrrolidine-1-carboxylic acid tert-butyl ester;

Tetrahydro-pyran-4-carboxylic acid [3-(3-{4-[3-((1R,3S)-3-amino-cyclopentyl)-ureido]-6-methoxy-pyridin-2-yl}-2-hydroxy-phenoxy)-propyl]-amide;

1-((1R,3S)-3-Amino-cyclopentyl)-3-[2-(2,3-dihydro-benzo[1,4]dioxin-5-yl)-6-methoxy-pyridin-4-yl]-urea;

5-(4-Methyl-piperazin-1-ylmethyl)-furan-2-carboxylic acid [8-(1-methyl-1H-imidazol-4-yl)-2,3-dihydro-benzo[1,4]dioxin-2-ylmethyl]-amide;

5-(4-Methyl-piperazin-1-ylmethyl)-furan-2-carboxylic acid [8-(1-benzyl-1H-imidazol-4-yl)-2,3-dihydro-benzo[1,4]dioxin-2-ylmethyl]-amide;

5-(4-Chloro-phenyl)-2,3-dihydro-benzo[1,4]dioxine;

tetrahydro-pyran-4-carboxylic acid {8-[4-(3-dimethylaminomethyl-phenylamino)-pyridin-2-yl]-2,3-dihydro-benzo[1,4]dioxin-2-ylmethyl}-amide;

tetrahydro-pyran-4-carboxylic acid (8-{5-[3-((1S,3R)-3-amino-cyclopentyl)-ureido]-6-methoxy-pyridin-2-yl}-2,3-dihydro-benzo[1,4]dioxin-2-ylmethyl)-amide; and tetrahydro-pyran-4-carboxylic acid (8-{4-[3-((1R,3S)-3-amino-cyclopentyl)-ureido]-pyridin-2-yl}-2,3-dihydro-benzo[1,4]dioxin-2-ylmethyl)-amide.

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Salts and Solvates

The compounds (including final products and intermediates) described herein may be isolated and used per se or may be isolated in the form of a salt, suitably pharmaceutically acceptable salts. It should be understood that the terms "salt(s)" and "salt form(s)" used by themselves or in conjunction with another term or terms encompasses all inorganic and organic salts, including industrially acceptable salts, as defined herein, and pharmaceutically acceptable salts, as defined herein, unless otherwise specified. As used herein, industrially acceptable salts are salts that are generally suitable for manufacturing and/or processing (including purification) as well as for shipping and storage, but may not be salts that are typically administered for clinical or therapeutic use. Industrially acceptable salts may be prepared on a laboratory scale, i.e. multi-gram or smaller, or on a larger scale, i.e. up to and including a kilogram or more.

Pharmaceutically acceptable salts, as used herein, are salts that are generally chemically and/or physically compatible with the other ingredients comprising a formulation, and/or are generally physiologically compatible with the recipient thereof. Pharmaceutically acceptable salts may be prepared on a laboratory scale, i.e. multi-gram or smaller, or on a larger scale, i.e. up to and including a kilogram or more. It should be understood that pharmaceutically acceptable salts are not limited to salts that are typically administered or approved by the FDA or equivalent foreign regulatory body for clinical or therapeutic use in humans. A practitioner of ordinary skill will readily appreciate that some salts are both industrially acceptable as well as pharmaceutically acceptable salts. It should be understood that all such salts, including mixed salt forms, are within the scope of the application.

In one embodiment, the compounds of Formula I are isolated as pharmaceutically acceptable salts.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

In general, salts of the present application can be prepared in situ during the isolation and/or purification of a compound (including intermediates), or by separately reacting the compound (or intermediate) with a suitable organic or inorganic acid or base (as appropriate) and isolating the salt thus formed. The degree of ionisation in the salt may vary from completely ionised to almost non-ionised. In practice, the various salts may be precipitated (with or without the addition of one or more co-solvents and/or anti-solvents) and collected by filtration or the salts may be recovered by evaporation of solvent(s). Salts of the present application may also be formed via a "salt switch" or ion exchange/double displacement reaction, i.e. reaction in which one ion is replaced (wholly or in part) with another ion having the same charge. One skilled in the art will appreciate that the salts may be prepared and/or isolated using a single method or a combination of methods.

Representative salts include, but are not limited to, acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate and the like. Other examples of representative salts include alkali or alkaline earth metal cations such as sodium, lithium, potassium, calcium, magnesium, and the like, as well as non-toxic ammonium, quaternary ammonium and amine cations including, but not limited to, ammonium, tetramethylammonium, tetraethylammonium, lysine, arginine, benzathine, choline, tromethamine, diolamine, glycine, meglumine, olamine and the like.

Certain compounds of the Formula I may exist in solvated as well as unsolvated forms such as, for example, hydrated forms. It is to be understood that the invention encompasses all such solvated forms that possess antiproliferative activity.

Polymorphs

It is also to be understood that certain compounds of the Formula I may exhibit polymorphism, and that the invention encompasses all such forms that possess antiproliferative activity.

N-oxides

Compounds of the Formula I containing an amine function may also form N-oxides. A reference herein to a compound of the Formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4*th* Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

Tautomers

Compounds of the Formula I may exist in a number of different tautomeric forms and references to compounds of the Formula I include all such forms. For the avoidance of doubt, where a compound can exist in one of several tautomeric forms, and only one is specifically described or shown, all others are nevertheless embraced by Formula I. Examples of tautomeric forms include keto-, enol-, and enolate-forms, as in, for example, the following tautomeric pairs: keto/enol (illustrated below), pyrimidone/hydroxypyrimidine, imine/enamine, amide/imino alcohol, amidine/amidine, nitroso/oxime, thioketone/enethiol, and nitro/aci-nitro.

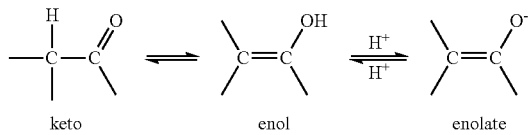

keto      enol      enolate

Isomers

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

Certain compounds of Formula I may have one or more asymmetric centers and therefore can exist in a number of stereoisomeric configurations. Consequently, such compounds can be synthesized and/or isolated as mixtures of enantiomers and/or as individual (pure) enantiomers, and, in the case of two or more asymmetric centers, single diastereomers and/or mixtures of diastereomers. It should be understood that the present application includes all such enantiomers and diastereomers and mixtures thereof in all ratios.

Isotopes

The compounds of the present invention are described herein using structural formulas that do not specifically recite the mass numbers or the isotope ratios of the constituent atoms. As such it is intended that the present application includes compounds in which the constituent atoms are present in any ratio of isotope forms. For example, carbon atoms may be present in any ratio of $^{12}C$, $^{13}C$, and $^{14}C$; hydrogen atoms may be present in any ratio of $^{1}H$, $^{2}H$, and $^{3}H$; etc. Preferably, the constituent atoms in the compounds of the present invention are present in their naturally occurring ratios of isotope forms.

Prodrugs and Metabolites

The compounds of Formula I may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula I and in-vivo cleavable amide derivatives that may be formed at a carboxy group or an amino group in a compound of the Formula I.

Accordingly, the present invention includes those compounds of the Formula I as defined hereinbefore when made available by organic synthesis and when made available within the human or animal body by way of cleavage of a pro-drug thereof. Accordingly, the present invention includes those compounds of the Formula I that are produced by organic synthetic means and also such compounds that are produced in the human or animal body by way of metabolism of a precursor compound, that is a compound of the Formula I may be a synthetically-produced compound or a metabolically-produced compound.

A suitable pharmaceutically acceptable pro-drug of a compound of the Formula I is one that is based on reasonable medical judgement as being suitable for administration to the human or animal body without undesirable pharmacological activities and without undue toxicity.

Various forms of pro-drug have been described, for example in the following documents:
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the Formula I that possesses a carboxy group is, for example, an in vivo cleavable ester thereof. An in vivo cleavable ester of a compound of the Formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the Formula I that possesses a hydroxy group is, for example, an in vivo cleavable ester or ether thereof. An in vivo cleavable ester or ether of a compound of the Formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_1$-10alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the Formula I that possesses a carboxy group is, for example, an in vivo cleavable amide thereof, for example an amide formed with an amine such as ammonia, a $C_{1-4}$alkylamine such as methylamine, a $(C_{1-4}$alkyl)$_2$amine such as dimethylamine, N-ethyl-N-methylamine or diethylamine, a $C_{1-4}$alkoxy-$C_{2-4}$alkylamine such as 2-methoxyethylamine, a phenyl-$C_1$-4alkylamine such as benzylamine and amino acids such as glycine or an ester thereof.

A suitable pharmaceutically acceptable pro-drug of a compound of the Formula I that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the Formula I may be exerted in part by one or more metabolites that are formed within the human or animal body after administration of a compound of the Formula I. As stated hereinbefore, the in vivo effects of a compound of the Formula I may also be exerted by way of metabolism of a precursor compound (a pro-drug).

Pharmaceutical Compositions

According to a further aspect of the invention there is provided a pharmaceutical composition which comprises a compound of the invention as defined hereinbefore, or a pharmaceutically acceptable salt or solvate thereof, and one or more pharmaceutically acceptable excipients.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

It is to be noted that dosages and dosing regimens may vary with the type and severity of the condition to be alleviated, and may include the administration of single or multiple doses, i.e. QD (once daily), BID (twice daily), etc., over a particular period of time (days or hours). It is to be further understood that for any particular subject or patient, specific dosage regimens may need to be adjusted over time according to the individual need and the professional judgment of the person administering or supervising the administration of the pharmaceutical compositions. For example, doses may be adjusted based on pharmacokinetic or pharmacodynamic parameters, which may include clinical effects such as toxic effects and/or laboratory values. Thus, the present application encompasses intra-patient dose-escalation as determined by the person skilled in the art. Procedures and processes for determining the appropriate dosage(s) and dosing regimen(s) are well-known in the relevant art and would readily be ascertained by the skilled artisan. As such, one of ordinary skill would readily appreciate and recognize that the dosage ranges set forth herein are exemplary only and are not intended to limit the scope or practice of the pharmaceutical compositions described herein.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The present invention provides compounds that function as inhibitors of RAS-effector protein-protein interaction.

The present invention therefore provides a method of inhibiting a RAS-effector protein-protein interaction in vitro or in vivo, said method comprising contacting a cell with an effective amount of a compound, or a pharmaceutically acceptable salt, hydrate or solvate thereof, as defined herein.

The present invention also provides a method of treating a disease or disorder in aberrant RAS-effector interaction is implicated in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of inhibiting cell proliferation, in vitro or in vivo, said method comprising contacting a cell with an effective amount of a compound, or a pharmaceutically acceptable salt, hydrate or solvate thereof, as defined herein.

The present invention provides a method of treating a proliferative disorder in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of treating cancer in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a compound, or a pharmaceutically acceptable salt, hydrate or solvate thereof, or a pharmaceutical composition as defined herein for use in therapy.

The present invention provides a compound, or a pharmaceutically acceptable salt, hydrate or solvate thereof, or a pharmaceutical composition as defined herein for use in the treatment of a proliferative condition.

The present invention provides a compound, or a pharmaceutically acceptable salt, hydrate or solvate thereof, or a pharmaceutical composition as defined herein for use in the treatment of cancer. In a particular embodiment, the cancer is human cancer.

The present invention provides a compound, or a pharmaceutically acceptable salt, hydrate or solvate thereof, as defined herein for use in the inhibition of a RAS-effector protein-protein interaction, suitably an aberrant RAS-effector protein-protein interaction.

The present invention provides a compound, or a pharmaceutically acceptable salt, hydrate or solvate thereof, as defined herein for use in the treatment of a disease or disorder in which aberrant RAS-effector protein-protein interaction is implicated.

The present invention provides a use of a compound, or a pharmaceutically acceptable salt, hydrate or solvate thereof, as defined herein in the manufacture of a medicament for the treatment of a proliferative condition.

The present invention provides a use of a compound, or a pharmaceutically acceptable salt, hydrate or solvate thereof, as defined herein in the manufacture of a medicament for the treatment of cancer. Suitably, the medicament is for use in the treatment of human cancers.

The present invention provides a use of a compound, or a pharmaceutically acceptable salt, hydrate or solvate thereof, as defined herein in the manufacture of a medicament for the inhibition of a RAS-effector protein-protein interaction, suitably an aberrant RAS-effector protein-protein interaction.

The present invention provides a use of a compound, or a pharmaceutically acceptable salt, hydrate or solvate thereof, as defined herein in the manufacture of a medicament for the treatment of a disease or disorder in which an aberrant RAS-effector protein-protein interaction is implicated.

The term "proliferative disorder" used herein pertains to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

The anti-proliferative effects of the compounds of the present invention have particular application in the treatment of human cancers (for instance, by virtue of their inhibition of RAS-effector protein-protein interactions).

In one embodiment, the compounds inhibit interaction of RAS (suitably NRAS, KRAS or HRAS, more suitably KRAS) with one or more effector proteins.

In another embodiment, the compounds inhibit interaction of RAS with one or more effector proteins selected from PLCε (epsilon), PKCζ (zeta), PI3K, RASSF, RAF, RalGEF, RIN, AF-6, GAP and TIAM1, suitably selected from PI3K, RAF and RalGEF.

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

In a particular embodiment of the invention, the proliferative condition to be treated is cancer. For example, lung cancer, colon cancer, rectum cancer, breast cancer, ovarian cancer, prostate cancer, liver cancer, pancreatic cancer, brain cancer and skin cancer.

In one embodiment, the cancer is selected from pancreatic cancer, colon cancer, rectum cancer and lung cancer.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery or radiotherapy or chemotherapy. Such chemotherapy may include one or more of the following categories of anti-tumour agents:

other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. (Critical reviews in oncology/haematology, 2005, Vol. 54, pp11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R$^{763}$, MP235, MP529, VX-528 AND AX39459) and cyclin dependent kinase inhibitors such as CDK2 and/or CDK4 inhibitors;

antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

vascular damaging agents such as Combretastatin A4 and compounds disclosed in International Patent Applications WO 99/02166, WO 00/40529, WO 00/41669, WO 01/92224, WO 02/04434 and WO 02/08213;

an endothelin receptor antagonist, for example zibotentan (ZD4054) or atrasentan;

antisense therapies, for example those which are directed to the targets listed above, such as ISIS 2503, an anti-ras antisense;

gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a particular embodiment, the antiproliferative treatment defined hereinbefore may involve, in addition to the compound of the invention, conventional surgery or radiotherapy or chemotherapy.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt, hydrate or solvate thereof, and another anti-tumour agent.

According to this aspect of the invention there is provided a combination for use in the treatment of a proliferative condition, such as cancer (for example a cancer involving a solid tumour), comprising a compound of the invention as defined hereinbefore, or a pharmaceutically acceptable salt, hydrate or solvate thereof, and any one of the anti-tumour agents listed herein above.

In a further aspect of the invention there is provided a compound of the invention or a pharmaceutically acceptable salt, hydrate or solvate thereof, for use in the treatment of cancer in combination with another anti-tumour agent, optionally selected from one listed herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination. In one embodiment, a combination refers to a combination product.

According to a further aspect of the invention there is provided a pharmaceutical composition which comprises a compound of the invention, or a pharmaceutically acceptable salt, hydrate or solvate thereof, in combination with an anti-tumour agent (optionally selected from one listed herein above), in association with a pharmaceutically acceptable diluent or carrier.

EXAMPLES

Chemistry

The following examples are provided solely to illustrate the present invention and are not intended to limit the scope of the invention, as described herein.

The compounds of the invention may be prepared using synthetic techniques that are known in the art (as illustrated by the examples herein).

Several methods for the chemical synthesis of the compounds of the present application are described herein. These and/or other well-known methods may be modified and/or adapted in various ways in order to facilitate the synthesis of additional compounds within the scope of the present application and claims. Such alternative methods and modifications should be understood as being within the spirit and scope of this application and claims. Accordingly, it should be understood that the methods set forth in the following descriptions, schemes and examples are intended for illustrative purposes and are not to be construed as limiting the scope of the disclosure.

Synthesis and Characterisation
Analytical Methods

Analysis of products and intermediates has been carried out using reverse phase analytical HPLC-MS using the parameters set out below.

HPLC Analytical Methods

AnalpH2_MeOH_4min: Phenomenex Luna C18 (2) 3 μm, 50×4.6 mm; A=water+0.1% formic acid; B=MeOH+0.1% formic acid; 45° C.; % B: 0.0 min 5%, 1.0 min 37.5%, 3.0 min 95%, 3.5 min 95%, 3.51 min 5%, 4.0 min 5%; 2.25 mL/min.

AnalpH9_MeOH_4 min: Phenomenex Luna C18 (2) 3 μm, 50×4.6 mm; A=water pH 9 (Ammonium Bicarbonate 10 mM); B=MeOH+0.1% formic acid; 45° C.; % B: 0.0 min 5%, 1.0 min 37.5%, 3.0 min 95%, 3.5 min 95%, 3.51 5%, 4.0 min 5%; 2.25 mL/min.

AnalpH2_MeOH_QC_V1: Phenomenex Gemini NX C18 5 μm, 150×4.6 mm; A=water+0.1% formic acid; B=MeOH+0.1% formic acid; 40° C.; % B: 0.0 min 5%, 0.5 min, 5%, 7.5 min 95%, 10.0 min 95%, 10.1 min 5%, 13.0 min 5%; 1.5 mL/min.

AnalpH9_MeOH_QC_V1: Phenomenex Gemini NX C18 5 μm, 150×4.6 mm; A=water+pH 9 (Ammonium Bicarbonate 10 mM); B=MeOH; 40° C.; % B: 0.0 min 5%, 0.50 min 5%, 7.5 min 95%, 10.0 min 95%, 10.1 min 5%, 13.0 min 5%; 1.5 mL/min.

UPLC Analytical Methods

AnalpH2_MeCN_UPLC_4 min: Acquity UPLC BEH C-18 1.7 μm, 2.1×50 mm, A=water+0.05% formic acid; B: acetonitrile+0.05% formic acid; 35° C.; % B: 0.0 min 10%, 0.5 min 10%, 1 min 35%, 1.5 min 45%, 2.3 min 90%, 3.2 min 90%, 3.6 min 10%, 4 min 10%; 0.55 mL/min AnalpH2_MeCN_UPLC_3.8 min: Acquity UPLC BEH C-18 1.7 μm, 2.1×50 mm, A=water+0.05% formic acid; B: acetonitrile+0.05% formic acid; 35° C.; % B: 0.0 min 2%, 0.5 min 2%, 1 min 15%, 1.5 min 45%, 2.3 min 90%, 3.2 min 90%, 3.6 min 2%, 3.8 min 2%; 0.55 mL/min AnalpH2_MeCN_UPLC_6 min: Acquity: UPLC BEH C-18 1.7 μm, 2.1×100 mm; A=water+0.05% formic acid; B: acetonitrile+0.05% formic acid; 35° C., % B: 0.0 min 50%, 3.0 min 90%, 5 min 90%, 6.0 min 50%; 0.4 mL/min $^1$H-NMR Spectra were obtained on a Bruker DRX 400 MHz or Jeol ECS 400 MHz spectrometer. Spectra are measured at 294K (unless otherwise stated) and chemical shifts (δ-values) are reported in parts per million (ppm), referenced to either TMS (0.0 ppm), DMSO-d6 (2.50 ppm), CDCl3 (7.26 ppm). Coupling constants (J) are reported in Hertz (Hz), spectra splitting pattern are designated as singlet (s), doublet (d), triplet (t), quadruplet (q), multiplet or more overlapping signals (m), broad signal (br); solvent is given in parentheses.

Abbreviations

The following abbreviations are used in the Examples and other parts of the description.

ABCN: azobis cyclohexanecarbonitrile
Boc: tert-butyloxycarbonyl
DavePhos: 2-dicyclohexylphosphino-2'-(N,N-dimethylamino)biphenyl
dba: tris(dibenzylideneacetone)
DBU: 1,8-diazabicyclo[5.4.0]undec-7-ene
DCE: 1,2-dichloroethane
DCM: dichloromethane
DIAD: diisopropyl azodicarboxylate
dioxane: 1,4-dioxane
DMA: dimethyl acetamide
DMAP: 4-(dimethylamino)pyridine
DMF: N,N-dimethylformamide
DMSO: dimethylsulfoxide
Dppf: 1,1'-bis(diphenylphosphino)ferrocene
dtbpf: ([1,1'-bis(di-tert-butylphosphino)ferrocene]
EDCl: 1-ethyl-3-(3-dimethylaminopropyl)carbodiimide hydrochloride
EtOAc: ethyl acetate
h: hour(s)
HATU: 2-(7-aza-1H-benzotriazole-1-yl)-1,1,3,3-tetramethyluronium. hexafluorophosphate
HBTU: (2-(1H-benzotriazol-1-yl)-1,1,3,3-tetramethyluronium hexafluorophosphate
HPLC: High-performance liquid chromatography
min: minute(s)
LCMS: Liquid chromatography-mass spectrometry
MS: mass spectroscopy
Pet-ether: petroleum ether (b.p. 60-80° C.)
quant.: quantitative (conversion)
Rt: retention time
RT: room temperature
SCX: strong cation exchange
TBAF: tetra-n-butylammonium fluoride
TEA: triethylamine
TFA: trifluoroacetic acid
THF: tetrahydrofuran
TsCl: p-toluenesulfonyl chloride
XPhos: 2-dicyclohexylphosphino-2',4',6'-triisopropylbiphenyl
XantPhos: 4,5-bis(diphenylphosphino)-9,9-dimethylxanthene General Procedures General Procedure A—Suzuki Coupling Using PdCl$_2$ (Dtbpf)

A solution of aryl halide (1.0 eq), PdCl$_2$(dtbpf) ([1,1'-Bis(di-tert-butylphosphino)ferrocene]dichloropalladium(II)) (0.1 eq), Na$_2$CO$_3$ (2.0-3.0 eq), and the appropriate organoboronic acid (1.5-1.8 eq) in 9:1 1,4-dioxane:H$_2$O was purged with N$_2$ for 15 min and the mixture was heated to 110° C. for 1 h. Once complete the reaction was either filtered to remove any inorganic salts or loaded onto a SCX cartridge, washed with methanol then eluted with ammonia in methanol and the filtrate was concentrated in vacuo to yield the crude material which was purified by column chromatography or prep HPLC.

General Procedure B—One-Pot Miyaura Borylation Followed by Suzuki Coupling Using Pd(PPh$_3$)$_4$ A solution of bis(pinacolato)diboron (2.0-2.2 eq), potassium acetate (3.0 eq) and Pd(dppf)Cl$_2$·DCM ([1,1'-Bis(diphenylphosphino)ferrocene]dichloropalladium(II), complex with dichloromethane) (0.1 eq) in dry 1,4-dioxane was purged with N$_2$ for 15 min and the mixture was heated to 110-120° C. for 2.5-4.0 h. The formation of the boronic ester was monitored by LCMS. The reaction was then cooled, and to it the appropriate aryl halide (1.0 eq), Pd(PPh$_3$)$_4$ (0.1 eq), K$_2$CO$_3$ (2.0 eq) and H$_2$O (¹⁄₁₀th of volume of 1,4-dioxane)

were added. The reaction was purged with $N_2$ for 10 min and the mixture was heated to 110° C. for 1.5 h-2 h. Once the boronic ester intermediate was consumed the reaction mixture was either, filtered to remove any inorganic salts and the product purified by column chromatography or prep HPLC; or alternatively, the residue was taken through an aqueous work-up prior to further purification: the residue was taken up in EtOAc and the solution was washed with H2O then brine, and dried over $MgSO_4$, filtered and concentration in vacuo to yield the crude material which was purified by column chromatography or prep HPLC.

General Method C—Buchwald

A solution of aryl halide (1.0 eq), Pd catalyst [$Pd(OAc)_2$ or $Pd_2(dba)_3$ (tris(dibenzylideneacetone) dipalladium(0))] (0.1 eq), phosphine ligand (XPhos (2-dicyclohexylphosphino-2',4',6'-triisopropylbiphenyl), or XantPhos (4,5-Bis (diphenylphosphino)-9,9-dimethylxanthene), or DavePhos (2-Dicyclohexylphosphino-2'-(N,N-dimethylamino)biphenyl)) (0.3 eq), sodium tert-butoxide (1.5 eq), and the appropriate amine or aniline (1.0-1.5 eq) in dry 1,4-dioxane or toluene was purged with nitrogen for 15 min and the mixture was heated to 80-110° C. for 2-16 h thermally or in microwave reactor. Reaction was monitored by LCMS. On consumption of starting material the reaction was filtered to remove any inorganic salts and the filtrate was concentrated under reduced pressure to yield the crude material which was purified by column chromatography or prep HPLC.

General Method D—Amide Coupling Using HBTU

To a solution of carboxylic acid (1.0-1.5 eq), amine (1.0 eq) and N,N-diisopropylethylamine (3.0 eq) in anhydrous DMF or DCM was added HBTU (2-(1H-benzotriazol-1-yl)-1,1,3,3-tetramethyluronium hexafluorophosphate) (1.5 eq) and the reaction was stirred at RT for 16 h. Solvent was removed in vacuo and the residue was taken up in EtOAc which was washed with $NaHCO_3$(aq) solution, $H_2O$ then brine. The organic phase was dried over $Na_2SO_4$ or $MgSO_4$, filtered and concentrated in vacuo to yield the crude material which was purified by column chromatography or prep HPLC.

General Procedure E—Reductive Amination Using $NaBH(OAc)_3$

To a solution of aldehyde (1.0 eq) in DCM was added the appropriate amine (1.0 eq) and AcOH (1.0 eq). $NaBH(OAc)_3$ (1.5 eq) was then added either immediately, or after 1-2 h in order to allow time for the imine intermediate to preform. The resulting reaction mixture was stirred at RT for 4-16 h. The reaction mixture was quenched with saturated $NaHCO_3$(aq) solution, and the aqueous phase was extracted with DCM (3×). The combined organic phases dried over $Na_2SO_4$ or $MgSO_4$, filtered and concentrated in vacuo to yield the crude material which was purified by column chromatography or prep HPLC.

General Procedure E1—Reductive Amination Using $NaBH(OAc)_3$

To a solution of aldehyde (0.5-1.0 eq) in DCM, DCE or DMF was added the appropriate amine (1.0 eq) and AcOH (1.0-2 eq). $NaBH(OAc)_3$ (1.5-5 eq) was then added either immediately, or after 1-2 h in order to allow time for the imine intermediate to preform. The resulting reaction mixture was stirred at RT for 4-16 h. The reaction mixture was quenched with saturated $NaHCO_3$(aq) solution, and the aqueous phase was extracted with DCM (3×). The combined organic phases dried over $Na_2SO_4$ or $MgSO_4$, filtered and concentrated under reduced pressure to yield the crude material which was purified by column chromatography or prep HPLC.

General Procedure F—BOC Deprotection

To a solution of BOC protected compound (1 eq) in DCM under nitrogen atmosphere at about 0° C. was added trifluoroacetic acid (xs) dropwise. The mixture was stirred at about 0° C. for 20 mins then at RT for about 1 h. The reaction was concentrated in vacuo, then the crude was neutralised with a solution of ammonia in methanol, 7M and concentrated in vacuo again.

General Procedure F1—Boc Deprotection

A solution of Boc protected amine in 10:1 DCM:TFA was stirred at RT. Reaction were monitored by LCMS. On consumption of starting material the reaction mixture was concentrated in vacuo.

The crude product was either:

a) dissolved in MeOH and concentrated in vacuo before drying under reduced pressure, giving the product as the TFA salt.

b) Alternatively, the reaction was basified with saturated $NaHCO_3$(aq) solution, and the aqueous phase was extracted with DCM (3×). The combined organic phases were dried over $Na_2SO_4$ or $MgSO_4$, filtered and concentrated in vacuo to yield the crude material which was purified by column chromatography or prep HPLC.

c) The reaction was concentrated in vacuo, then the crude was neutralised with a solution of ammonia in methanol 7M (1.5 mL) and concentrated in vacuo. The compound was purified by reverse phase preparative HPLC.

d) The reaction was concentrated in vacuo and the resulting residue was loaded onto a SCX cartridge, washed with methanol then eluted with ammonia in methanol and concentrated in vacuo. The compound was purified by column chromatography or by reverse phase preparative HPLC.

General Method G—Amide Coupling Using EDCl

To a solution of carboxylic acid (1.0-1.5 eq), amine (1.0-1.3 eq) and triethylamine (1.5 eq) in anhydrous DCM was added N-(3-dimethylaminopropyl)-N'-ethylcarbodiimide hydrochloride (1-2 eq) followed by 1-hydroxy-7-azabenzotriazole (0.5 eq), and the reaction mixture stirred at RT for 1-96 h. The reaction was diluted with DCM and water, and the organic layer separated. The aqueous layer was extracted with DCM. The combined organic layers were dried over $Na_2SO_4$ or $MgSO_4$ or by phase separator, filtered and concentrated in vacuo to yield the crude material which was purified by column chromatography or prep HPLC.

General Method H—Amide Coupling Using HATU

To a solution of amine (1.1 eq), O-(7-azabenzotriazol-1-yl)-N,N,N',N'-tetramethyluronium hexafluorophosphate (1.1 eq) and carboxylic acid (1.0 eq) in anhydrous DMF was added triethylamine (1.1 eq) and the reaction mixture was stirred at RT for 1-72 h. The reaction mixture was purified without aqueous workup by column chromatography or prep HPLC.

General Procedure K—Urea Formation Using Triphosgene

To a solution of triphosgene (1 eq) in DCM under nitrogen atmosphere cooled to −20° C. was slowly added the aniline (1.2 eq) in DCM, then triethylamine (6 eq) and the reaction mixture was stirred at −20° C. for 15 mins then at RT for 1 h. Then the reaction mixture was cooled to −20° C. and the amine (1.2 eq) in DCM was added slowly. The reaction mixture was stirred at −20° C. for 15 mins then at RT for 12 h. the reaction mixture was concentrated in vacuo and the compound was purified by gel column chromatography.

General Method L—Tosyl Displacement

A suspension of the amine (1.5 eq) and potassium carbonate (7.0 eq) in DMF under nitrogen atmosphere was sonicated for 10 minutes. Then a solution of the tosylate (1 eq) in DMF was added to the mixture and the reaction was heated at 60° C. for 12 h. The reaction was concentrated in vacuo and the residue was triturated with ethyl acetate and methanol. The precipitate was removed by filtration and the combined filtrate and washings containing the compound were concentrated under reduced pressure. The compound was purified by reverse phase preparative HPLC-MS.

General Procedure M—Suzuki Coupling Using Pd(PPh$_3$)$_4$

A mixture of boronic ester (1 eq.), aryl halide (1.0-2.2 eq), Pd(PPh$_3$)$_4$ (0.1 eq) and K$_2$CO$_3$ (2.0 eq) in 9:1 dioxane:H$_2$O was purged with N$_2$ for 10 min and heated to 110° C. for 1.5 h-2 h. Once the boronic ester intermediate was consumed the reaction mixture was either, filtered to remove any inorganic salts and the product purified by column chromatography or prep HPLC, or alternatively, the residue was taken through an aqueous work-up prior to further purification: the residue was taken up in EtOAc and the solution was washed with H$_2$O then brine, and dried over MgSO$_4$, filtered and concentration in vacuo to yield the crude material which was purified by column chromatography or prep HPLC.

Preparations

Synthesis of Toluene-4-sulfonic acid 8-nitro-2,3-dihydro-benzo[1,4]dioxin-2-ylmethyl ester

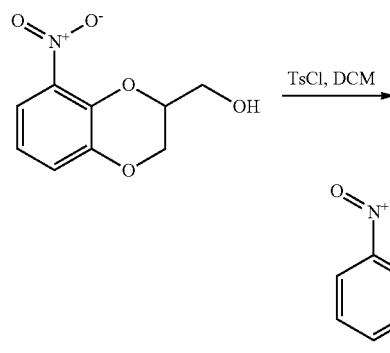

To a solution of (8-nitro-2,3-dihydro-benzo[1,4]dioxin-2-yl)-methanol (33 g, 156.3 mmol) in DCM (300 ml) was added TEA (63.0 mL, 625.7 mmol) dropwise for 10 min and then, TsCl (35.7 g, 187.6 mmol) for 30 min. Reaction mixture was stirred at room temperature under N$_2$ for 16 h. The reaction mixture was quenched with water and extracted with DCM (2×300 mL). The combined organic layers were washed with water (2×200 mL) and brine (2×200 mL), dried over Na$_2$SO$_4$ and concentrated under reduced pressure to afford the crude product. Purification by column chromatography on silica gel using 20% EA/Pet ether as a eluent afforded toluene-4-sulfonic acid 8-nitro-2,3-dihydro-benzo[1,4]dioxin-2-ylmethyl ester (47 g, 82%) as an off white solid.

AnalpH2_MeCN_UPLC_4 min: Rt: 2.29 min, 366.28 [M+H]$^+$

Synthesis of 2-Azidomethyl-8-nitro-2,3-dihydro-benzo[1,4]dioxine

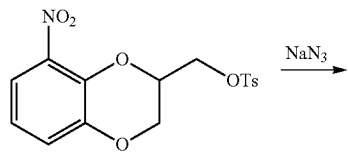

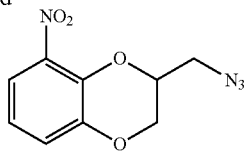

To a solution of toluene-4-sulfonic acid 8-nitro-2,3-dihydro-benzo[1,4]dioxin-2-ylmethyl ester (47 g, 128.7 mmol) in DMF (500 mL) was added NaN$_3$ (83.69 g, 1287. mmol) and the mixture was stirred at 80° C. under N$_2$ for 5 h. The reaction mixture was quenched with water and extracted with EtOAc (2×300 mL). The combined organic layers were washed with water (2×200 mL) and brine (2×200 mL), dried over Na$_2$SO$_4$ and concentrated under reduced pressure to afford 2-azidomethyl-8-nitro-2,3-dihydro-benzo[1,4]dioxine (29 g, 96%), which was used without further purification.

$^1$H NMR (400 MHz, CDCl$_3$): 7.52 (d, J=8 Hz, 1H), 7.14 (d, J=8 Hz, 1H), 6.93 (t, J=8.2 Hz, 1H), 4.43-4.48 (m, 1H), 4.37 (dd, J=12 & 2.4 Hz, 1H), 4.11-4.20 (m, 1H) 3.63 (d, J=5.6 Hz, 2H)

AnalpH2_MeCN_UPLC_4 min: Rt: 2.08 min (parent ion not observed)

Synthesis of C-(8-Nitro-2,3-dihydro-benzo[1,4]dioxin-2-yl)-methylamine

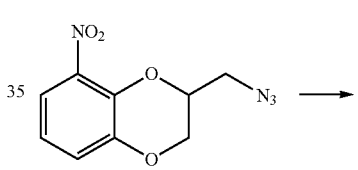

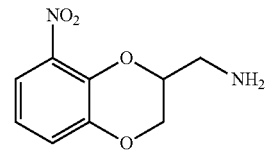

To a solution of 2-azidomethyl-8-nitro-2,3-dihydro-benzo[1,4]dioxine (15 g, 63.5 mmol) in THF (150 mL) was added water (1.5 mL) followed by triphenylphosphine (21.6 g, 82.0 mmol) slowly at room temperature. The mixture was stirred at 45° C. under N$_2$ for 5 h. The reaction mixture was diluted with water (300 mL) and extracted with EtOAc (2×100 mL). The combined organic layers were washed with water (1×200 mL) and brine (1×150 mL), dried over Na$_2$SO$_4$ and concentrated under reduced pressure to afford the crude product. Purification by column chromatography on silica gel using 20-30% EtOAc/Pet ether as a eluent afforded C-(8-nitro-2,3-dihydro-benzo[1,4]dioxin-2-yl)-methylamine (6.0 g, 45%) as a brown viscous oil.

AnalpH2_MeCN_UPLC_3.8 min: Rt: 1.35 min, 211.08 [M+H]$^+$

Synthesis of N-(2-bromo-6-methoxy-4-pyridyl)-1-methyl-piperidine-4-carboxamide

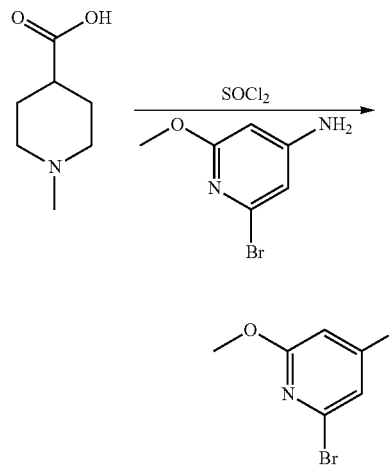

A solution of 1-methylpiperidine-4-carboxylic acid (1 eq, 0.49 mmol) in thionyl chloride (2 mL) was stirred under nitrogen atmosphere at RT for 1 h. The reaction was concentrated in vacuo under nitrogen to give a pale yellow solid which was dissolved in DCM (1.5 mL) and cooled to 0 C. Then pyridine (2.5 eq, 0.1 mL) and 2-bromo-6-methoxy-pyridin-4-amine (0.8 eq, 0.39 mmol) were added. The mixture was stirred at OC for 5 mins then a RT for 1 h. The compound was extracted with dichloromethane, washed with water, brine, dried over magnesium sulphate, filtered and concentrated in vacuo. The compound was then purified by reverse phase preparative HPLC-MS to afford N-(2-bromo-6-methoxy-4-pyridyl)-1-methyl-piperidine-4-carboxamide (90 mg, 56%) as a white solid.

Synthesis of [1-(pyrazine-2-carbonyl)-piperidin-4-ylmethyl]-carbamic acid tert-butyl ester

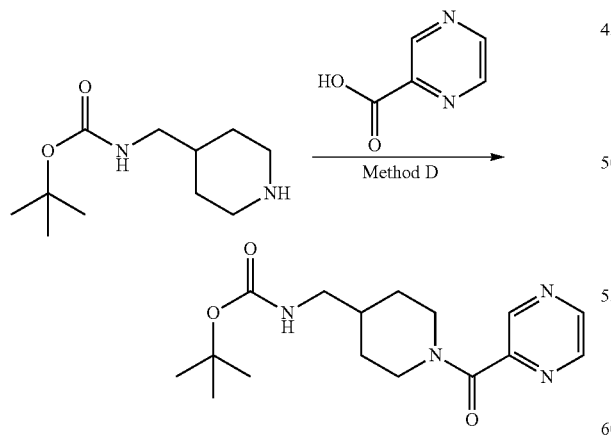

To a solution of pyrazine 2-carboxylic acid (182 mg, 1.5 mmol, 1.05 eq) in DMF (10 mL) was added HBTU (531 mg, 1.5 mmol, 1.05 eq), tert-butyl N-(4-piperidylmethyl)carbamate (300 mg, 1.4 mmol, 1 eq) and N,N-diisopropylethylamine (731 uL, 4.2 mmol, 3.0 eq) and the reaction was stirred at RT overnight. The solvent was removed in vacuo and the residue was taken up in EtOAc and washed with NaHCO$_3$(aq) solution, H$_2$O then brine. The organic phase was dried over Na$_2$SO$_4$, filtered and concentrated in vacuo to yield tert-butyl N-[[1-(pyrazine-2-carbonyl)-4-piperidyl]methyl]carbamate (quant.) as a brown oil. The compound was used for the next step without any further purification.
AnalpH2_MeOH_4 min, Rt: 2.59 min; m/z 321.4 [M+H]$^+$ Synthesis of (4-Aminomethyl-piperidin-1-yl)-pyrazin-2-yl-methanone

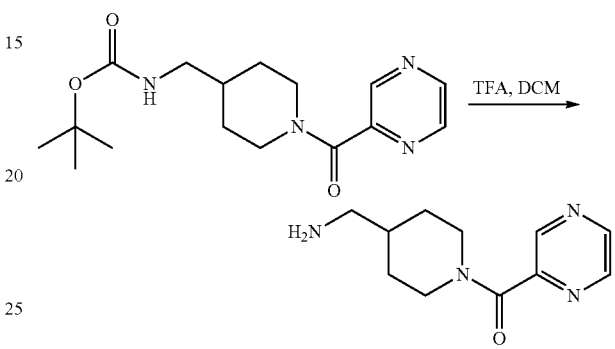

To a solution of tert-butyl N-[[1-(pyrazine-2-carbonyl)-4-piperidyl]methyl]carbamate (1.56 mmol) in DCM (10 mL) under nitrogen atmosphere at RT was added TFA (1 mL) and the mixture was stirred for 2 h. Then, toluene was added and the reaction was concentrated in vacuo. The resulting brown oil was dissolved in MeOH, passed through an SCX-2 cartridge and eluting with 1M NH$_3$/MeOH to afford [4-(aminomethyl)-1-piperidyl]-pyrazin-2-yl-methanone (288 mg, 94% over two steps) as a brown oil.
AnalpH9_MeOH_4 min, Rt: 0.52 min; m/z 221.2 [M+H]$^+$ Synthesis of [1-(Tetrahydro-pyran-4-carbonyl)-piperidin-4-ylmethyl]-carbamic acid tert-butyl ester

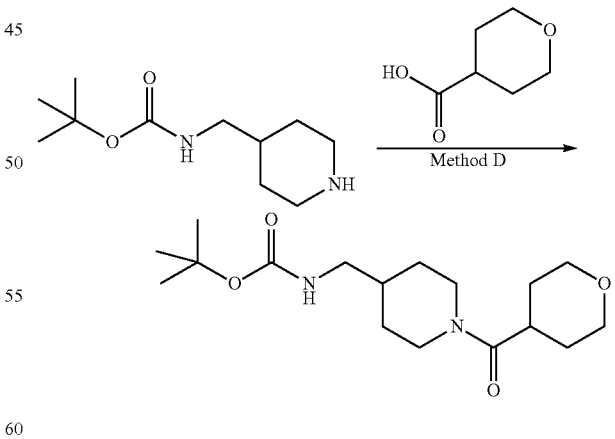

The compound was synthesised using tert-butyl N-(4-piperidylmethyl)carbamate and tetrahydropyran-4-carboxylic acid applying general method D to afford tert-butyl N-[[1-(tetrahydropyran-4-carbonyl)-4-piperidyl]methyl]carbamate (quant.) as a light brown solid. The compound was used for the next step without further purification.
AnalpH2_MeOH_4 min, Rt: 2.65 min; m/z 327.3 [M+H]$^+$

Synthesis of (4-Aminomethyl-piperidin-1-yl)-(tetra-hydro-pyran-4-yl)-methanone

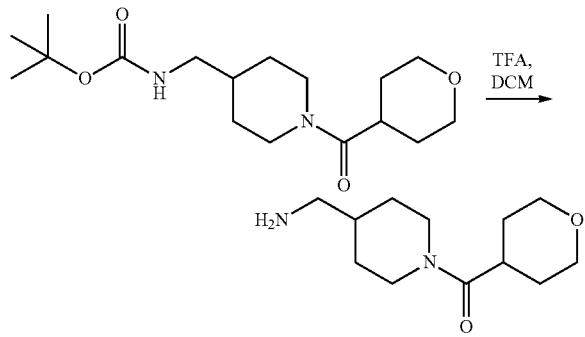

To a solution of tert-butyl N-[[1-(tetrahydropyran-4-carbonyl)-4-piperidyl]methyl]carbamate (1 eq, 1.68 mmol) in DCM (10 mL) under nitrogen atmosphere at RT was added TFA (1 mL) and the mixture was stirred for 12 h. Then, toluene was added and the reaction was concentrated in vacuo. The crude was then dissolved in MeOH, passed through an SCX-2 cartridge and eluting with 1M $NH_3$/MeOH to afford [4-(aminomethyl)-1-piperidyl]-tetrahydropyran-4-yl-methanone (337 mg, 80% over two steps) as a colourless gum.

AnalpH9_MeOH_4 min, Rt: 1.27 min; m/z 227.3 $[M+H]^+$

Synthesis of 1-(6-methoxy-3-pyridyl)imidazolidine-2,4-dione

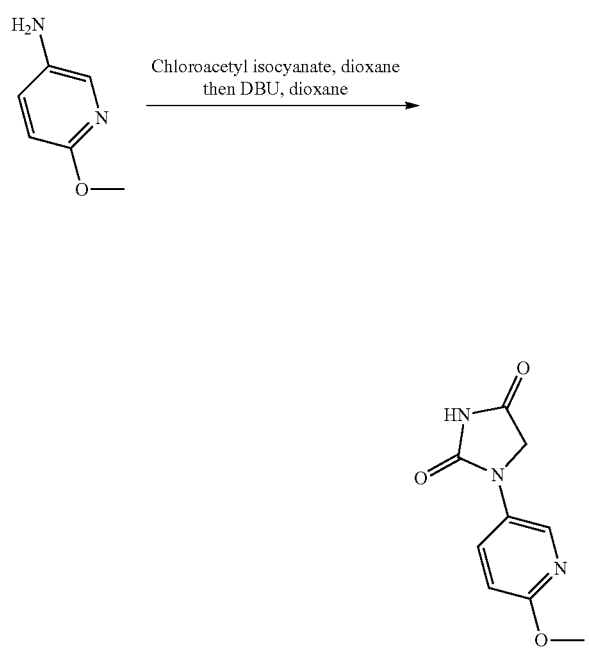

To a solution of 6-methoxypyridin-3-amine (4.03 mmol, 1 eq) in dioxane (10 mL) under nitrogen atmosphere at RT was added chloroacetyl isocyanate (4.03 mmol, 1 eq,) and the reaction was stirred for 2 h. Then DBU (10.1 mmol, 2.5 eq,) was added and the mixture was stirred at RT for 4 h. Then water was added and compound was extracted (partially) with ethyl acetate, then dichloromethane/methanol. Compound remaining in the aqueous layer was recovered by evaporation of the aqueous layer under reduced pressure, and purification of the residue by column chromatography eluting with dichloromethane with 0-10% methanol. The product-containing fractions were further purified by column chromatography eluting with dichloromethane with 0-5% methanol to give the desired compound as a red solid. This solid was then triturated with dichloromethane/isohexane, filtered and washed with dichloromethane:isohexane (1:1) to afford 1-(6-methoxy-3-pyridyl)imidazolidine-2,4-dione (250 mg, 30%) as a pale red solid.

AnalpH2_MeOH_4MIN: Rt: 1.82 min, m/z 208.2 $[M+H]^+$

Synthesis of tert-butyl 4-[(2-ethoxy-2-oxo-ethyl)amino]piperidine-1-carboxylate

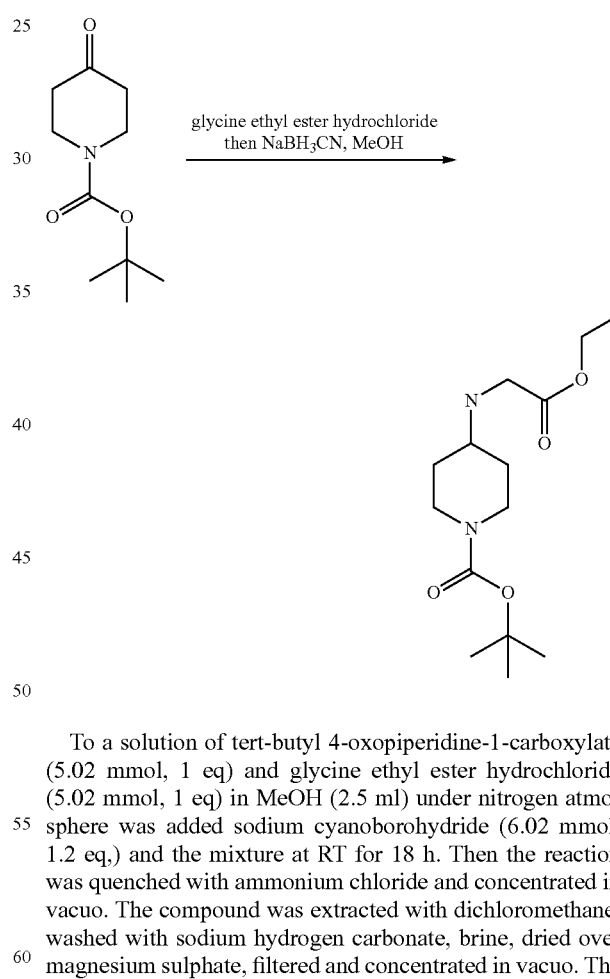

To a solution of tert-butyl 4-oxopiperidine-1-carboxylate (5.02 mmol, 1 eq) and glycine ethyl ester hydrochloride (5.02 mmol, 1 eq) in MeOH (2.5 ml) under nitrogen atmosphere was added sodium cyanoborohydride (6.02 mmol, 1.2 eq,) and the mixture at RT for 18 h. Then the reaction was quenched with ammonium chloride and concentrated in vacuo. The compound was extracted with dichloromethane, washed with sodium hydrogen carbonate, brine, dried over magnesium sulphate, filtered and concentrated in vacuo. The compound was purified by column chromatography eluting with dichloromethane with 0-5% methanol to give tert-butyl 4-[(2-ethoxy-2-oxo-ethyl)amino]piperidine-1-carboxylate (1.11 g, 77%) as a colourless oil.

AnalpH2_MeOH_4MIN: Rt: 1.64 min, m/z 287.3 $[M+H]^+$

Synthesis of Individual Amines for Buchwald Reaction

Synthesis of (R)-2-(3-amino-phenyl)-pyrrolidine-1-carboxylic acid tert-butyl ester

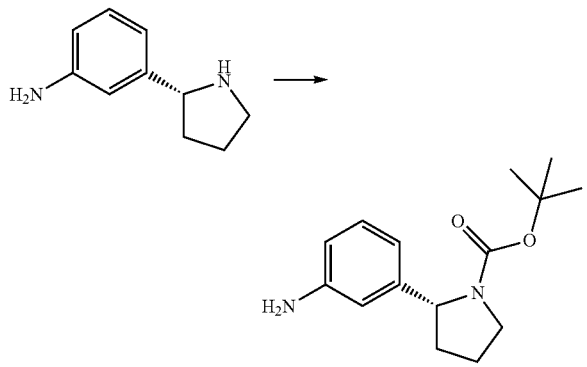

To a stirred solution of (R)-3-pyrrolidin-2-yl-phenylamine·HCl (150 mg, 0.75 mMol) in anhydrous DCM (2 mL) at 0° C. was added triethylamine (160 µL, 1.59 mMol) and di-tert-butyl dicarbonate (157 mg, 0.72 mMol) and the reaction was stirred at 0° C. for 1 h. The reaction mixture was diluted with DCM (10 mL), washed with water (30 mL), dried (hydrophobic frit) and concentrated in vacuo to give a yellow oil. The crude material was purified by silica column chromatography eluting with 0-100% ethyl acetate/iso-hexane to give the title product as an off white solid (103 mg, 0.39 mMol, 52%).

$^1$H NMR (400 MHz, DMSO-d6): δ 6.85 (t, J=7.6 Hz, 1H), 6.21-6.33 (m, 3H), 4.91 (s, 2H), 4.69-4.35 (m, 1H), 3.49-3.29 (m, 2H), 2.24-1.99 (m, 1H), 1.85-1.51 (m, 3H), 1.46-0.95 (m, 9H)

Synthesis of (S)-2-(3-amino-phenyl)-pyrrolidine-1-carboxylic acid tert-butyl ester

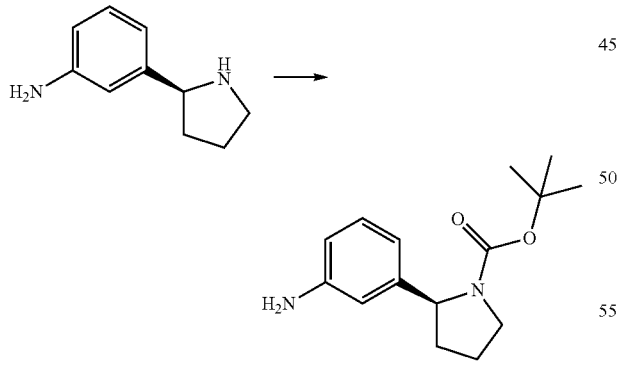

To a stirred solution of (S)-3-pyrrolidin-2-yl-phenylamine·hydrochloride (150 mg, 0.75 mMol) in anhydrous DCM (2 mL) at 0° C. was added triethylamine (160 µL, 1.59 mMol) and di-tert-butyl dicarbonate (157 mg, 0.72 mMol) and the reaction mixture was stirred at 0° C. for 1 h. The reaction mixture was diluted with DCM (10 mL), washed with water (30 mL), dried (hydrophobic frit) and concentrated in vacuo to give a yellow oil. The crude material was purified by silica column chromatography eluting with 0-100% ethyl acetate/iso-hexane to give the title product as an off white solid (98 mg, 0.37 mMol, 49%).

Synthesis of ethyl 5-[(4-methylpiperazin-1-yl)methyl]oxazole-2-carboxylate

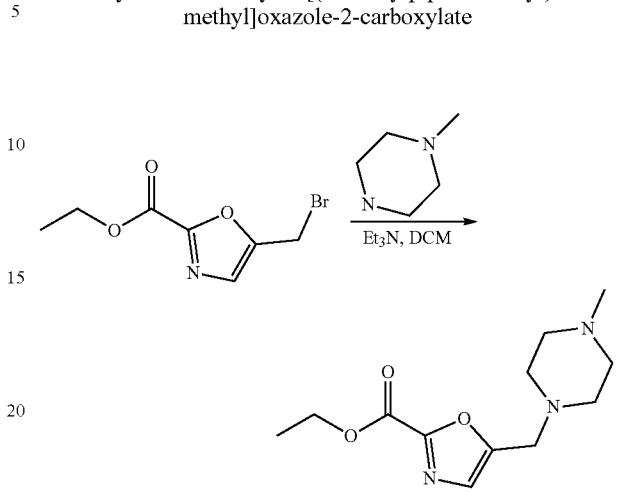

A solution of ethyl 5-(bromomethyl)oxazole-2-carboxylate (1 eq, 2.56 mmol), 1-methylpiperazine (1.1 eq, 2.82 mmol), triethylamine (1.2 eq, 3.07 mmol) in DCM (10 mL) was stirred at RT for 12 h. Then water was added to the mixture and the compound was extracted with dichloromethane, dried filtered and concentrated in vacuo to afford ethyl 5-[(4-methylpiperazin-1-yl)methyl]oxazole-2-carboxylate (500 mg, 77%) as a yellow oil.

AnalpH2_MeOH_4 min, Rt: 2.13 min; m/z 254 [M+H]$^+$

Synthesis of 5-[(4-methylpiperazin-1-yl)methyl]oxazole-2-carboxylic acid, lithium salt

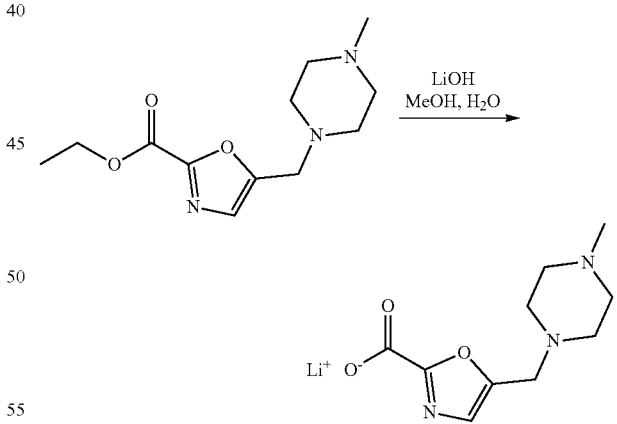

A solution of ethyl 5-[(4-methylpiperazin-1-yl)methyl]oxazole-2-carboxylate (1 eq, 1.98 mmol) in MeOH/H$_2$O 1:1 (10 mL) was added LiOH (1 eq, 1.98 mmol) and the mixture was stirred at RT for 2 h. then the compound was concentrated in vacuo. Then methanol was added and concentrated in vacuo. The compound was then dissolved in MeCN/H$_2$O and lyophilised to afford 5-[(4-methylpiperazin-1-yl)methyl]oxazole-2-carboxylic acid. lithium salt (403 mg, 88%) as a white solid.

AnalpH2_MeOH_4 min, Rt: 0.31 min; m/z 226 [M+H]$^+$

Synthesis of ethyl 5-(bromomethyl)oxazole-2-carboxylate

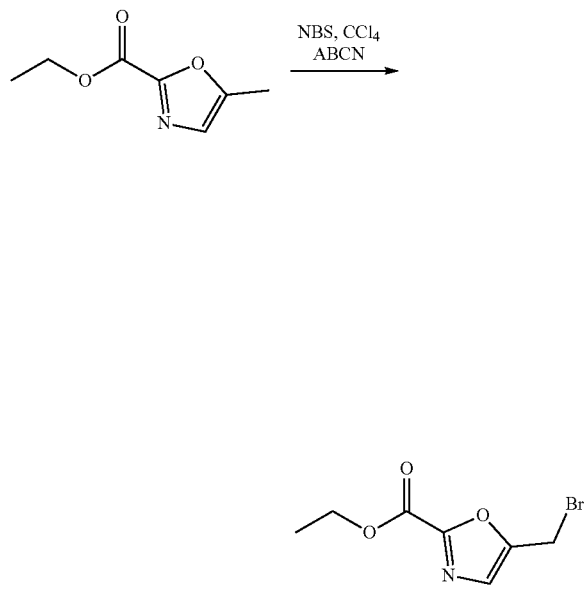

A solution of ethyl 5-methyloxazole-2-carboxylate (1 eq, 1.29 mmol), N-bromosuccinimide (1.2 eq, 1.54 mmol), and azobis cyclohexanecarbonitrile (ABCN, 0.1 eq, 0.12 mmol) in CCl$_4$ (5 ml) was heated at 80C for 4 h. Then the reaction was cooled to RT, filtered through celite and washed with dichloromethane and concentrated in vacuo. The crude product was purified by column chromatography on silica gel eluting with 0-20% ethyl acetate in isohexane to afford ethyl 5-(bromomethyl)oxazole-2-carboxylate (250 mg, 83%) as a pale yellow oil.

AnalpH2_MeOH_4 min, Rt: 2.44 min; m/z 234/236 [M+H]$^+$

Synthesis of Precursors for Boronylation-Suzuki Reaction

Synthesis of N-(6-Bromo-2-methoxy-pyridin-3-yl)-2-(1-methyl-piperidin-4-yl)-acetamide

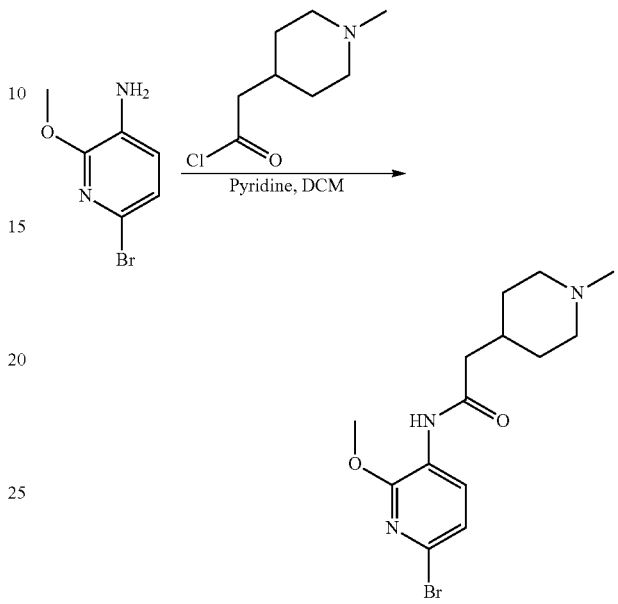

To a solution of (1-methyl-4-piperidinyl)acetyl chloride (223 mg, 1.27 mMol) in anhydrous DCM (5 mL) was added 6-bromo-2-methoxy-pyridin-3-ylamine (245 mg, 1.21 mMol) and pyridine (108 μL, 1.33 mMol) and the resulting solution was stirred at room temperature for 40 min. The reaction was quenched with NaHCO$_3$(aq.) and the phases separated. The aqueous phase was extracted with DCM and the combined organic phases washed with brine, dried (Na$_2$SO$_4$) and concentrated to give a brown solid. The crude material was purified by silica column chromatography eluting with 0-10% methanol/DCM to give the desired product as a pink solid (209 mg).

LCMS: ANALPH9_MEOH_4MIN: Rt: 2.54 min, m/z 342.3/344.3 [M+H]$^+$

The following compound was made by analogous method:

| Compound | | Analytical data | Mass, % yield, state |
|---|---|---|---|
| N-(6-Chloro-pyridin-3-yl)-2-(1-methyl-piperidin-4-yl)-acetamide | | AnalpH9_MeOH_4MIN: Rt: 2.17 min, m/z 268.3 [M + H]+ | 457 mg, 75%, off white solid |

Synthesis of (6-Bromo-2-methoxy-pyridin-3-yl)-(1-methyl-piperidin-4-yl)-amine

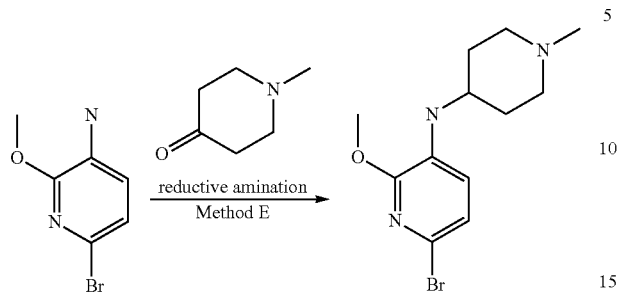

To a solution of 1-methyl-4-piperidone (111 mg, 0.99 mmol, 1.0 eq) and 3-amino-6-bromo-2-methoxypyridine (200 mg, 0.99 mmol, 1.0 eq) in DCM (5 mL) was added TFA (83 uL, 1.1 mmol, 1.1 eq). After 1 h, NaBH(OAc)$_3$ (313 mg, 1.5 mmol, 1.5 eq) was added and the reaction mixture was stirred at RT for 16 h. The reaction mixture was concentrated in vacuo and the crude material was purified by silica column chromatography to yield (6-bromo-2-methoxy-pyridin-3-yl)-(1-methyl-piperidin-4-yl)-amine (206 mg, 70%) as a brown gum.

AnalpH2_MeOH_4MIN: Rt: 1.50 min, m/z 300.2/302.2 [M+H]$^+$

The following compound was made using analogous procedure using general method E:

| Compound | | Analytical data | Mass, % yield, state |
|---|---|---|---|
| 1-[4-(6-Bromo-2-methoxy-pyridin-3-ylamino)-piperidin-1-yl]-ethanone | | ANALPH2_MEOH_4MIN, Rt: 2.83 min, m/z 328.1/330.2 [M + H]$^+$ | 213 mg, 66%, brown gum |

Synthesis of 3-Bromo-6-(1-methyl-piperidin-4-yl-methoxy)-pyridazine

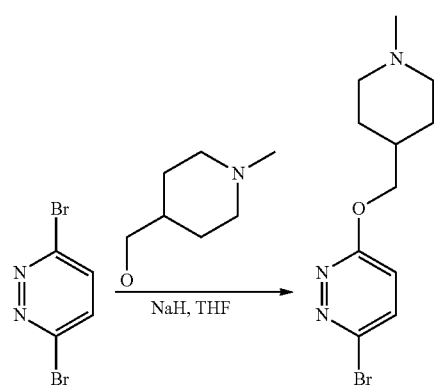

To a solution of 3,6-dibromopyridazine (400 mg, 1.68 mMol, 1.0 eq.) in dry THF (19 mL) at 10° C. was added NaH (8.1 mg, 2.02 mMol, 1.2 eq., 60% in mineral oil) and the reaction was stirred at 10° C. for 10 min. A solution of (1-methyl-piperidin-4-yl)-methanol (239 mg, 1.85 mMol, 1.1 eq.) in dry THF (1 mL) was added and the reaction was allowed to warm to RT and stirred at RT for 4.5 h then at 40° C. for 16 h. The reaction was quenched with NaHCO$_3$(aq.) and the THF removed under reduced pressure. The aqueous phase was extracted with ethyl acetate (3×) and the combined organic phases washed with brine, dried (MgSO$_4$) and concentrated to give a white solid. The crude material was purified by silica column chromatography eluting with 0-10% methanol/DCM to give the desired product as a white solid (183 mg, 0.64 mMol, 38%).

AnalpH9_MeOH_4MIN: Rt: 2.45 min, m/z 286.2/288.1 [M+H]$^+$

The following intermediates were prepared using General Method C:

| Compound | Analytiocal data | Mass, % yield, state |
|---|---|---|
| (6-Chloro-pyridin-3-yl)-(tetrahydro-pyran-4-ylmethyl)-amine | AnalpH9_MeOH_4MIN Rt: 2.68 min, m/z 227.2 $[M + H]^+$ | 179 mg, 42%, yellow solid |
| (6-Chloro-2-methoxy-pyridin-3-yl)-(3-dimethylaminomethyl-phenyl)-amine | AnalpH9_MeOH_4MIN Rt: 3.38 min, m/z 292.3 $[M + H]^+$ | 86 mg, 40%, orange oil |
| (6-chloro-2-methoxy-pyridin-3-yl)-(1-methyl-pyrrolidin-3-yl)-amine | ANALPH2_MEOH_4MIN Rt: 2.96 min, m/z 242.3/244.3 $[M + H]^+$ | 33.4 mg, 19%, brown oil |
| (6-Chloro-2-methoxy-pyridin-3-yl)-pyridin-3-yl-amine | ANALPH2_MEOH_4MIN Rt: 1.78 min, m/z 236.2/238.2 $[M + H]^+$ | 228 mg, pale brown solid |
| 4-(6-Chloro-2-methoxy-pyridin-3-ylamino)-N-(2-hydroxy-ethyl)-benzamide | ANALPH2_MEOH_4MIN Rt: 2.77 min, m/z 322.3 $[M + H]^+$ | 139 mg, 65%, brown solid |

-continued

| Compound | | Analytical data | Mass, % yield, state |
|---|---|---|---|
| 1-{4-[3-(6-Chloro-2-methoxy-pyridin-3-ylamino)-benzyl]-piperazin-1-yl}-ethanone | | ANALPH2_MEOH_4MIN Rt: 2.01 min, m/z 375.3/377.3 [M + H]$^+$ | 226 mg, 94%, brown solid |
| 4-(6-Chloro-pyridin-3-ylamino)-N-(1-methyl-piperidin-4-yl)-benzamide | | AnalpH9_MeOH_4MIN, Rt: 2.67 min, m/z 345.3/347.3 [M + H]$^+$ | 421 mg, 68%, yellow solid |
| (6-Chloro-pyridin-3-yl)-(3-dimethylaminomethyl-phenyl)-amine | | AnalpH9_MeOH_4MIN, Rt: 2.75 min, m/z 262.2/264.2 [M + H]$^+$ | 256 mg, 98%, brown solid |
| 4-(6-Chloro-2-methoxy-pyridin-3-ylamino)-N,N-dimethyl-benzamide | | ANALPH2_MEOH_4MIN, Rt: 3.01 min, m/z 306.3/308.3 [M + H]$^+$ | 224 mg, 79%, brown solid |

| Compound | | Analytical data | Mass, % yield, state |
|---|---|---|---|
| [4-(6-Chloro-2-methoxy-pyridin-3-ylamino)-benzyl]-carbamic acid tert-butyl ester | 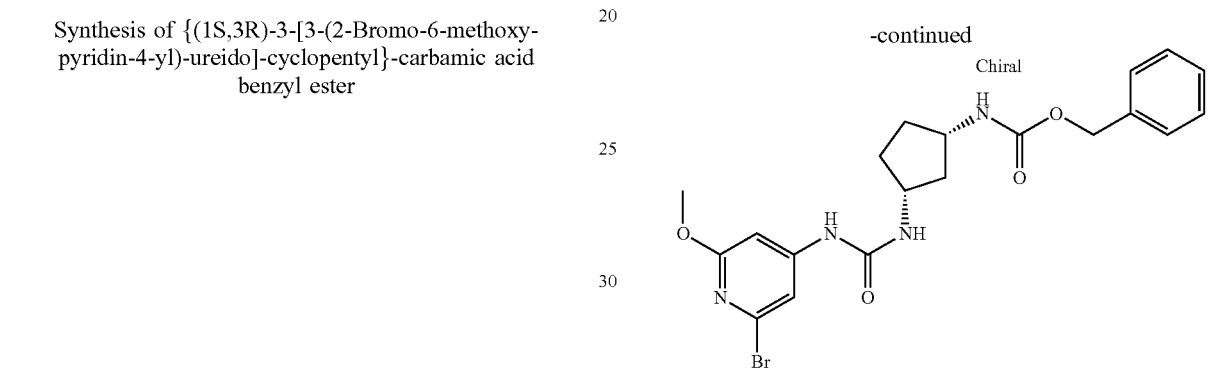 | AnalpH2_MeOH_4MIN, Rt: 3.37 min, m/z 308.3/310.3 [M + H]⁺ | 426 mg, orange oil |

Synthesis of {(1S,3R)-3-[3-(2-Bromo-6-methoxy-pyridin-4-yl)-ureido]-cyclopentyl}-carbamic acid benzyl ester

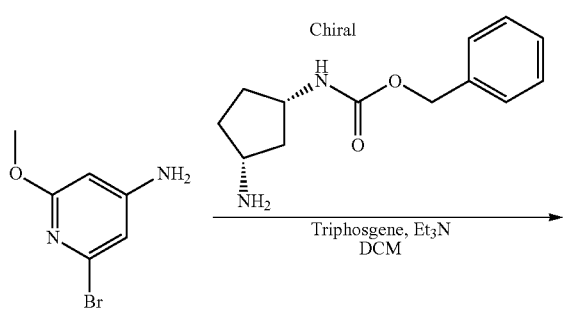

To a stirred solution of triphosgene (1 eq, 0.83 mmol) in DCM (16 mL) at −20° C. and under an atmosphere of N₂ was added a solution of 2-bromo-6-methoxy-pyridin-4-ylamine (1 eq, 0.83 mmol) in DCM (6 mL) followed by triethylamine (2.5 eq, 2.08 mmol). The reaction was stirred at −20° C. for 15 mins then allowed to warm to RT and stirred at RT for 30 mins. The reaction was cooled to −20° C. and a solution of ((1S,3R)-(3-amino-cyclopentyl)-carbamic acid benzyl ester in dry DCM (3 mL) was added and the reaction stirred at −20° C. for 15 mins then at RT for 90 mins. More triethylamine (2 eq, 1.66 mmol) was added and the reaction was at RT for 1 h. The reaction was quenched with methanol and concentrated in vacuo. The crude was purified by column chromatography to benzyl N-[(1S,3R)-3-[(2-bromo-6-methoxy-4-pyridyl)carbamoylamino]cyclopentyl]carbamate (311 mg, 81%) as a light yellow gum.

AnalpH2_MeOH_4 min, Rt: 3.21 min; m/z 463/465[M+H]⁺

The following intermediates were prepared using General Urea Formation Method K:

| | | | |
|---|---|---|---|
| {(1R,3S)-3-[3-(6-Bromo-2-methoxy-pyridin-3-yl)-ureido]-cyclopentyl}-carbamic acid tert-butyl ester | 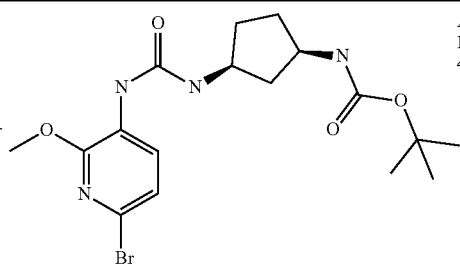 | AnalpH2_MeOH_4min, Rt: 3.31 min; m/z 429.2/431.2 [M + H]⁺ | 161 mg; 50% white solid |

| | | |
|---|---|---|
| {(1S,3R)-3-[3-(2-Chloro-pyridin-4-yl)-ureido]-cyclopentyl}-carbamic acid tert-butyl ester | 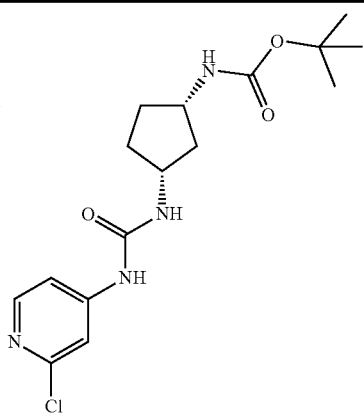 | AnalpH2_MeOH_4min, 152 Rt: 2.97 min; m/z 355.3mg; [M + H]$^+$ 27% white solid |

Synthesis of (R)-2-(6-Bromo-2-methoxy-pyridin-3-ylcarbamoyl)-pyrrolidine-1-carboxylic acid tert-butyl ester

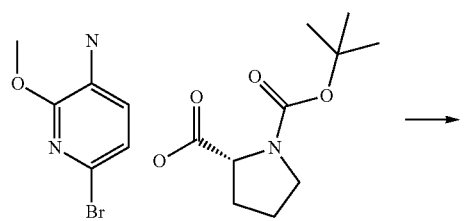

↓

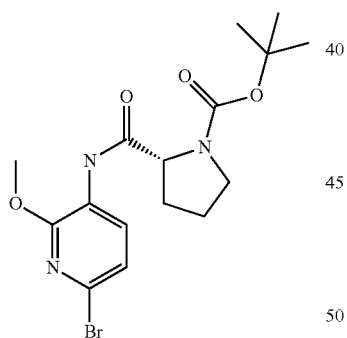

To a solution of (R)-pyrrolidine-1,2-dicarboxylic acid 1-tert-butyl ester (80 mg, 0.39 mMol, 1 eq.), 6-bromo-2-methoxy-pyridin-3-ylamine (85 mg, 0.39 mMol, 1 eq.) and N,N-diisopropylethylamine (153 mg, 1.18 mMol, 3 eq.) in anhydrous DMF (20 mL) was added HATU (150 mg, 0.39 mMol, 1 eq) and the reaction mixture was stirred at 50C for 24 h. An additional aliquot of HATU (90 mg, 0.23 mMol, 0.6 eq) and the reaction was stirred at 50C for 72 h. The solvent was removed in vacuo and the residue was taken up in EtOAc which was washed with 1N HCl (aq), NaHCO$_3$(aq) solution, H$_2$O then brine. The organic phase was dried over MgSO$_4$, filtered and concentrated in vacuo to yield the title compound (128 mg, 82%) which was used directly in subsequent reactions.

Synthesis of 5-(4-Methyl-piperazin-1-ylmethyl)-furan-2-carboxylic acid (8-amino-2,3-dihydro-benzo[1,4]dioxin-2-ylmethyl)-amide

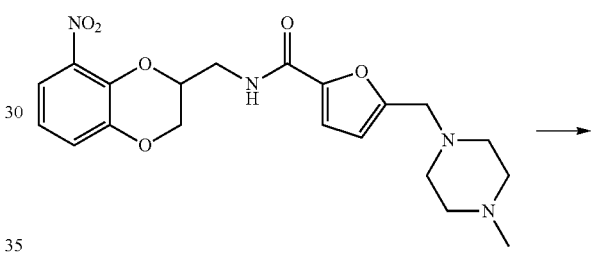

↓

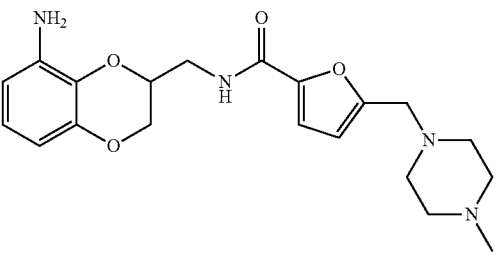

A stirred solution of 5-(4-methyl-piperazin-1-ylmethyl)-furan-2-carboxylic acid (8-nitro-2,3-dihydro-benzo[1,4]dioxin-2-ylmethyl)-amide (811 mg, 1.95 mMol, 1 eq.) in EtOH (25 mL) was purged with N$_2$ for 15 min followed by addition of ammonium formate (1.23 g, 19.5 mMol, 10 eq.) and 10% Pd/C (60 mg). The reaction was heated at 80° C. for 50 min, cooled to RT and filtered through celite washing with MeOH. The filtrate was loaded onto a SCX cartridge, washed with methanol then eluted with 0.1 M ammonia in methanol. The fractions containing product were combined, concentrated in vacuo and purified by reverse phase preparative HPLC-MS to give 5-(4-methyl-piperazin-1-ylmethyl)-furan-2-carboxylic acid (8-amino-2,3-dihydro-benzo[1,4]dioxin-2-ylmethyl)-amide (58 mg, 0.15 mMol, 8%)

AnalpH2_MeOH_QC_V1: Rt: 3.28 min, m/z 387.2 [M+H]$^+$

AnalpH9_MeOH_QC_V1: Rt: 6.56 min, m/z 387.2 [M+H]$^+$

Synthesis of 5-(4-methyl-piperazin-1-ylmethyl)-furan-2-carboxylic acid [8-(4,4,5,5-tetramethyl-[1,3,2]dioxaborolan-2-yl)-2,3-dihydro-benzo[1,4]dioxin-2-ylmethyl]-amide

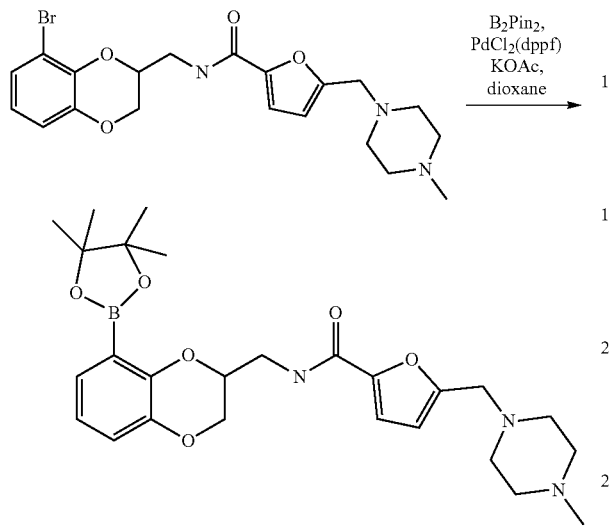

A solution of N-[(5-bromo-2,3-dihydro-1,4-benzodioxin-3-yl)methyl]-5-[(4-methylpiperazin-1-yl)methyl]furan-2-carboxamide (1 eq, 1.22 mmol) in dioxane (10 ml) was purged with N₂ for 15 mins. Then bis(pinacolato)diboron (2.5 eq, 3.05 mmol), potassium acetate (3 eq, 3.79 mmol) and Pd(dppf)Cl₂·DCM (0.1 eq, 0.12 mmol) were added and the mixture was heated to 110° C. for 3.5 h. The reaction was concentrated in vacuo and the residue was sonicated with ether. The dark residue was filtered through celite and the resulting filtrate was concentrated in vacuo to afford 5-(4-methyl-piperazin-1-ylmethyl)-furan-2-carboxylic acid [8-(4,4,5,5-tetramethyl-[1,3,2]dioxaborolan-2-yl)-2,3-dihydro-benzo[1,4]dioxin-2-ylmethyl]-amide (1.21 g, quant.) as an orange solid.

AnalpH2_MeOH_4 min, Rt: 2.69 min; m/z 416.5 boronic acid [M+H]⁺

General scheme 1

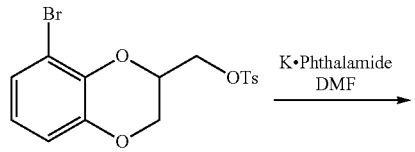

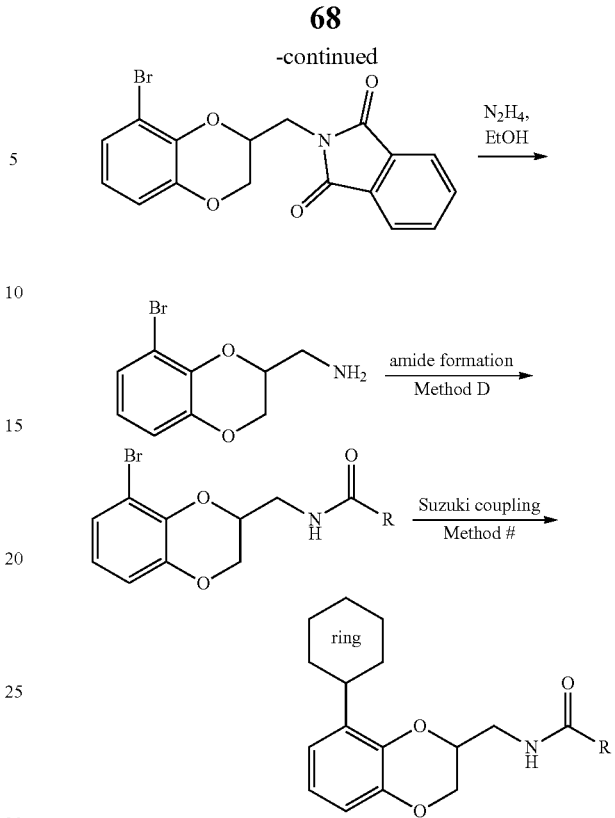

Synthesis of 2-(8-Bromo-2,3-dihydro-benzo[1,4]dioxin-2-ylmethyl)-isoindole-1,3-dione To a solution of toluene-4-sulfonic acid 8-bromo-2,3-dihydro-benzo[1,4]dioxin-2-ylmethyl ester (1.0 eq) in dry DMF was added potassium phthalimide (2.0 eq) and the reaction was stirred at 90° C. under N₂ for 3 h. Once complete the reaction was quenched with H2O and extracted with EtOAc (3×). The combined organics were washed with H2O (2×) and brine (2×), dried over Na₂SO₄ and concentrated in vacuo. The crude product was purified by column chromatography on silica gel (100-200 mesh) eluting with 20-30% EtOAc/Pet ether to afford 2-(8-bromo-2,3-dihydro-benzo[1,4]dioxin-2-ylmethyl)-isoindole-1,3-dione as an off white solid (18.0 g, 96.0%,)

Rf=0.4 in 30% EtOAc in Pet ether). AnalpH2_MeCN_UPLC_6 min Rt: 1.92 min, 374.2, 376.2 [M+H]⁺

The following compounds were made using analogous procedures

| Compound | | Analytical data | Mass, % yield, state |
|---|---|---|---|
| 2-((S)-8-Bromo-2,3-dihydro-benzo[1,4]dioxin-2-ylmethyl)-isoindole-1,3-dione | | 1H NMR (400 MHz, CDCl₃): δ 7.87-7.90 (m, 2H), 7.74-7.76 (m, 2H), 7.09 (dd, J = 7.6 & 1.6 Hz, 1H), 6.83-6.85 (m, 1H), 6.73 (t, J = 8.2 Hz, 1H), 4.60-4.65 (m, 1H), 4.31-4.34 (m, 1H), 4.07-4.19 (m, 2H), 3.90-3.95 (m, 1H) | 8.7 g, 87%, Off white solid |

| Compound | Analytical data | Mass, % yield, state |
|---|---|---|
| 2-((R)-8-Bromo-2,3-dihydro-benzo[1,4]dioxin-2-ylmethyl)-isoindole-1,3-dione | | 25 g, 90%, Off white solid |

Synthesis of C-(8-Bromo-2,3-dihydro-benzo[1,4]dioxin-2-yl)-methylamine

To a solution of 2-(8-Bromo-2,3-dihydro-benzo[1,4]dioxin-2-ylmethyl)-isoindole-1,3-dione (1.0 eq) in ethanol was added hydrazine hydrate (10.0 eq) and the mixture was stirred at 90° C. under $N_2$ for 2 h. Once complete, the reaction was filtered, the residue was washed with DCM (2×), and the combined filtrates were concentrated in vacuo. The crude product was purified by reverse-phase chromatography to afford C-(8-bromo-2,3-dihydro-benzo[1,4]dioxin-2-yl)-methylamine as a yellow liquid (6.0 g, 51%).

AnalpH2_MeCN_UPLC_6 min: Rt: 1.13 min, found 244.2, 246.2 [M+H]$^+$.

The following compounds were made using analogous procedures

| Compound | Analytical data | Mass, % yield, state |
|---|---|---|
| C-((S)-8-Bromo-2,3-dihydro-benzo[1,4]dioxin-2-yl)-methylamine | Rt: 1.08 min, 244.2, 246.2 [M + H]$^+$. | 3.5 g, 61%, pale yellow oil |
| C-((R)-8-Bromo-2,3-dihydro-benzo[1,4]dioxin-2-yl)-methylamine | Rt: 1.08 min, 244.2, 246.2 [M + H]$^+$. | 3.0 g, 32%, pale yellow oil |

The following compounds were made using General Method D

| Compound | Analytical data | Mass, % yield, state |
|---|---|---|
| N-(8-Bromo-2,3-dihydro-benzo[1,4]dioxin-2-ylmethyl)-4-(2-dimethylamino-ethoxy)-benzamide | AnalpH2_MeOH_QC_V1: Rt: 5.11 min, m/z 450.1 [M + H]+ AnalpH9_MeOH_QC_V1: Rt: 7.76 min, m/z 450.1 [M + H]+ | 33 mg, 29%, white solid |

-continued

| Compound | | Analytical data | Mass, % yield, state |
|---|---|---|---|
| N-((R)-8-Bromo-2,3-dihydro-benzo[1,4]dioxin-2-ylmethyl)-4-(2-dimethylamino-ethoxy)-benzamide | 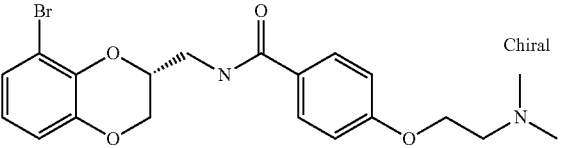 [SMILES: CN(C)CCOc1ccc(C(=O)NC[C@@H]2COc3cccc(Br)c3O2)cc1] Chiral | AnalpH2_MeOH_4MIN: Rt: 2.02 min, m/z 435.2/437.2 [M + H]+ AnalpH9_MeOH_4MIN: Rt: 3.22 min, m/z 435.2/437.2 [M + H]+ | 437 mg, 81%, white solid |
| N-((S)-8-Bromo-2,3-dihydro-benzo[1,4]dioxin-2-ylmethyl)-4-(2-dimethylamino-ethoxy)-benzamide | 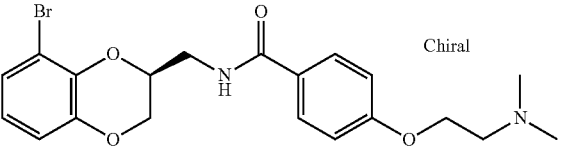 [SMILES: CN(C)CCOc1ccc(C(=O)NC[C@H]2COc3cccc(Br)c3O2)cc1] Chiral | AnalpH9_MeOH_4MIN: Rt: 3.20 min, m/z 435.2/437.2 [M + H]+ | 812 mg, >100%, white solid |
| 5-(4-Methyl-piperazin-1-ylmethyl)-furan-2-carboxylic acid (8-bromo-2,3-dihydro-benzo[1,4]dioxin-2-ylmethyl)-amide | 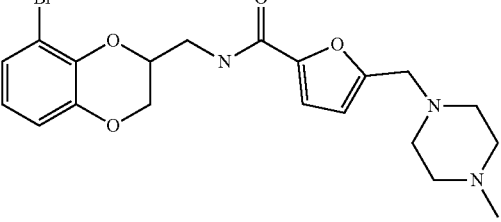 | AnalpH2_MeOH_QC_V1: Rt: 5.22 min, m/z 435.1/437.1 [M + H]+ AnalpH9_MeOH_QC_V1: Rt: 8.00 min, m/z 435.1/437.1 [M + H]+ | 33 mg, 29%, white solid |
| 5-(4-Methyl-piperazin-1-ylmethyl)-furan-2-carboxylic acid ((S)-8-bromo-2,3-dihydro-benzo[1,4]dioxin-2-ylmethyl)-amide | 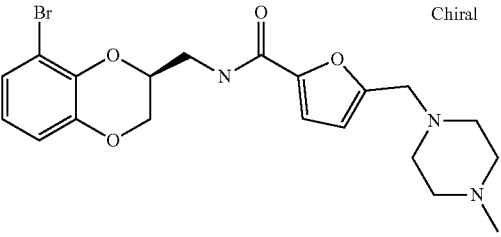 [SMILES: CN1CCN(Cc2ccc(C(=O)NC[C@H]3COc4cccc(Br)c4O3)o2)CC1] Chiral | AnalpH9_MeOH_4MIN: Rt: 3.07 min, m/z 450.2/452.2 [M + H]+ | 762 mg, quant., off white solid |
| 5-(4-Methyl-piperazin-1-ylmethyl)-furan-2-carboxylic acid ((R)-8-bromo-2,3-dihydro-benzo[1,4]dioxin-2-ylmethyl)-amide | 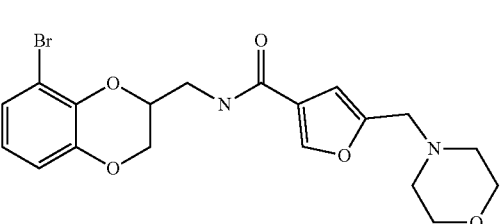 Chiral | AnalpH2_MeOH_4MIN: Rt: 1.95 min, m/z 450.2/452.2 [M + H]+ | 0.78 g, 85%, off white solid |
| 5-Morpholin-4-ylmethyl-furan-3-carboxylic acid (8-bromo-2,3-dihydro-benzo[1,4]dioxin-2-ylmethyl)-amide | 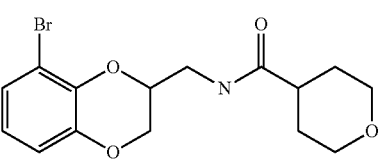 [SMILES: O=C(NCC1COc2cccc(Br)c2O1)C1CCOCC1] | AnalpH2_MeOH_QC_V1: Rt: 5.11 min, m/z 437.2/439.2 [M + H]+ AnalpH9_MeOH_QC_V1: Rt: 7.58 min, m/z 437.2/439.2 [M + H]+ | 44.8 mg, 25%, white solid |
| Tetrahydro-pyran-4-carboxylic acid (8-bromo-2,3-dihydro-benzo[1,4]dioxin-2-ylmethyl)-amide | | AnalpH2_MeOH_QC_V1: Rt: 7.23 min, m/z 356.2/358.2 [M + H]+ AnalpH9_MeOH_QC_V1: Rt: 7.25 min, m/z 356.1/358.1 [M + H]+ | 20.6 mg, 13%, white solid |

-continued

| Compound | | Analytical data | Mass, % yield, state |
|---|---|---|---|
| Tetrahydro-pyran-4-carboxylic acid ((R)-8-bromo-2,3-dihydro-benzo[1,4]dioxin-2-ylmethyl)-amide | | AnalpH2_MeOH_4MIN: Rt 2.87 min, m/z 356.1/358.1 [M + H]+ | 265 mg, 90%, off white solid |
| N-(8-Bromo-2,3-dihydro-benzo[1,4]dioxin-2-ylmethyl)-3-dimethylamino-propionamide | | AnalpH2_MeOH_QC_V1: Rt: 4.07 min, m/z 343.2/345.2 [M + H]+ AnalpH9_MeOH_QC_V1: Rt: 7.26 min, m/z 343.1/345.1 [M + H]+ | 25.3 mg, 8%, colourless clear oil |
| 1-Pyrazin-2-ylmethyl-piperidine-4-carboxylic acid ((R)-8-bromo-2,3-dihydro-benzo[1,4]dioxin-2-ylmethyl)-amide | Chiral | AnalpH9_MeOH_4MIN: Rt: 2.94 min, m/z 477.2/449.2 [M + H]+ | 183 mg, 50%, Brown powder |
| 1-Methyl-piperidine-4-carboxylic acid (8-bromo-2,3-dihydro-benzo[1,4]dioxin-2-ylmethyl)-amide | | AnalpH2_MeOH_QC_V1: Rt: 4.23 min, m/z 369.1 [M + H]+ AnalpH9_MeOH_QC_V1: Rt: 7.24 min, m/z 369.1 [M + H]+ | 65.3 mg, 39%, white solid |
| Tetrahydro-pyran-4-carboxylic acid ((S)-8-bromo-2,3-dihydro-benzo[1,4]dioxin-2-ylmethyl)-amide | | AnalpH2_MeOH_4MIN: Rt: 2.90 min, m/z 356.2/358.2 [M + H]+ | 565 mg, 77%, White solid |
| 5-(4-Methyl-piperazin-1-ylmethyl)-furan-2-carboxylic acid (8-nitro-2,3-dihydro-benzo[1,4]dioxin-2-ylmethyl)-amide | | AnalpH2_MeOH_QC_V1: Rt: 4.54 min, m/z 417.21 [M + H]+ AnalpH9_MeOH_QC_V1: Rt: 7.16 min, m/z 417.28 [M + H]+ | 859 mg, 42%, orange solid |

Synthesis of 1-pyrazin-2-ylmethyl-piperidine-4-carboxylic acid

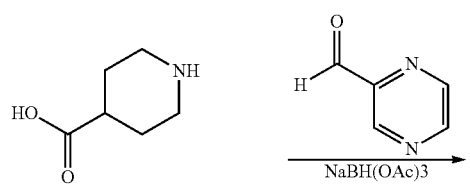

-continued

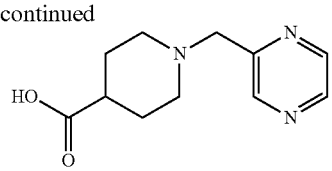

To a suspension of isonipecotic acid (300 mg, 2.3 mmol, 1 eq) in DMA (15 mL) was added pyrazine 2-carboxaldehyde (377 mg, 3.5 mmol, 1.5 eq) and acetic acid (133 uL, 2.3 mmol, 1 eq). After 5 min, sodium triacetoxyborohydride (738 mg, 3.5 mmol, 1.5 eq) was added and the reaction mixture stirred overnight. The reaction mixture was concentrated under reduced pressure and the residue dissolved in MeOH (3 mL) and loaded onto SCX-2 cartridge. The cartridge was washed with MeOH, and the compound eluted using 1M ammonia in methanol. The product-containing fractions were concentrated under reduced pressure to give the 1-pyrazin-2-ylmethyl-piperidine-4-carboxylic acid (435 mg) as a brown gum.

AnalpH2_MeOH_4MIN Rt: 0.33 min, m/z 222.3 [M+H]$^+$

The crude product was used directly in subsequent reactions without further purification.

Synthesis of
4-(2-dimethylamino-ethoxy)-2-fluorobenzoic acid
methyl ester

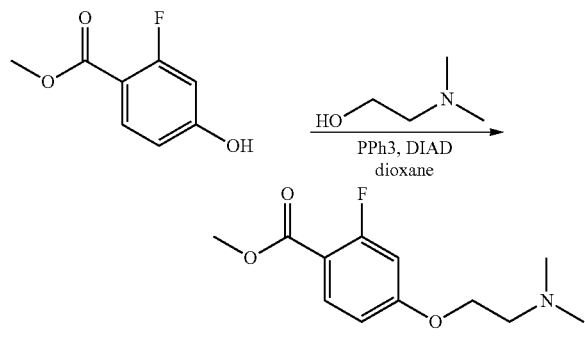

To a stirred solution of methyl-2-fluoro-4-hydroxybenzoate (375 mg, 2.2 mmol) in dioxane (5 mL) at 0 C was added triphenyl phosphine (1.16 g, 4.4 mmol), followed by DIAD (0.866 mL, 4.4 mmol), and after 2 mins, 2-(dimethylamino) ethanol (0.44 mL, 4.4 mmol). The reaction mixture was stirred at room temperature for 20 mins, then heated to 100C for 15 mins. The reaction mixture was concentrated and the residue purified using SCX-2, by washing with MeOH and eluting with 0.5M ammonia in methanol to afford the title compound which was used directly in subsequent reaction.

Synthesis of N-(8-Bromo-2,3-dihydro-benzo[1,4]
dioxin-2-ylmethyl)-4-(2-dimethylamino-ethoxy)-2-
fluoro-benzamide

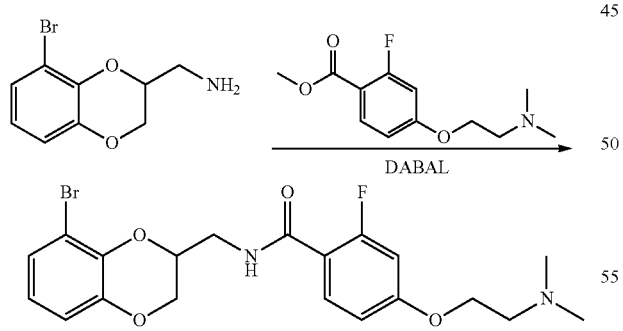

A solution of C-(8-bromo-2,3-dihydro-benzo[1,4]dioxin-2-yl)-methylamine (200 mg, 0.82 mMol, 1 eq.) and 4-(2-dimethylamino-ethoxy)-2-fluorobenzoic acid methyl ester (296 mg, 1.23 mMol, 1.5 eq.) in dry THF (10 mL) was purged with $N_2$ for 10 min followed by addition of bis (trimethylaluminum)-1,4-diazabicyclo[2.2.2]octane adduct (378 mg, 1.47 mMol, 1.8 eq.). The reaction was heated at 130° C. for 0.5 h using a microwave reactor then allowed to stand at RT for 16 h. The reaction was poured into a 10% aq. sol of Rochelle salt, stirred for 20 min, and extracted with ethyl acetate (2×). The combined organic phases were washed with brine, dried over MgSO$_4$, filtered and concentrated in vacuo to yield the crude material which was purified by reverse phase preparative HPLC-MS to afford N-(8-bromo-2,3-dihydro-benzo[1,4]dioxin-2-ylmethyl)-4-(2-dimethylamino-ethoxy)-2-fluoro-benzamide (107 mg, 0.24 mMol, 30%) as a yellow oil.

AnalpH2_MeOH_QC_V1: Rt: 5.38 min, m/z 453.3/455.3 [M+H]$^+$

AnalpH9_MeOH_QC_V1: Rt: 8.19 min, m/z 453.3/455.3 [M+H]$^+$

Synthesis of 5-(4-methyl-piperazin-1-ylmethyl)-
oxazole-2-carboxylic acid (8-bromo-2,3-dihydro-
benzo[1,4]dioxin-2-ylmethyl)-amide

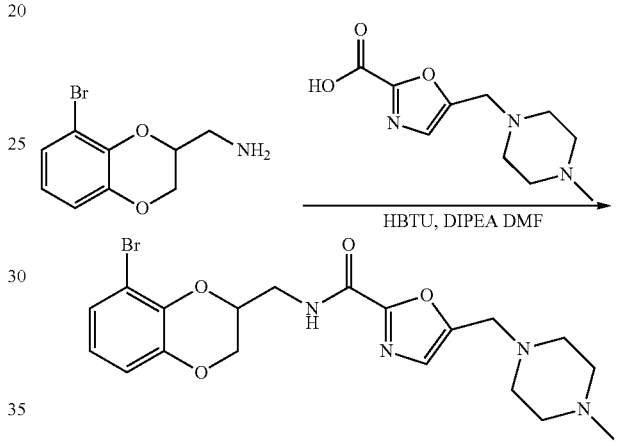

The title compound was synthesised using 5-[(4-methylpiperazin-1-yl)methyl]oxazole-2-carboxylic acid. lithium salt and C-(8-bromo-2,3-dihydro-benzo[1,4]dioxin-2-yl)-methylamine using General Method D (amide coupling using HBTU) to afford 5-(4-methyl-piperazin-1-ylmethyl)-oxazole-2-carboxylic acid (8-bromo-2,3-dihydro-benzo[1,4] dioxin-2-ylmethyl)-amide (33 mg, 21%) as a pale brown solid.

AnalpH9_MeOH_4 min, Rt: 2.44 min; m/z 451/453 [M+H]$^+$

EXAMPLES

Example 1: Synthesis of 2-(2,3-Dihydro-benzo[1,4]
dioxin-5-yl)-6-methoxy-pyridine using General
method A (Suzuki)

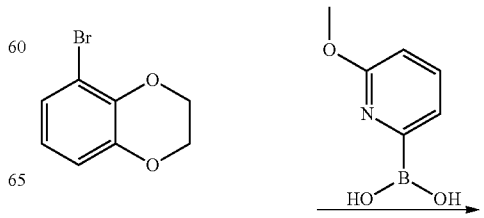

-continued

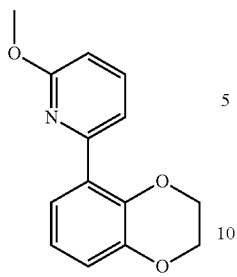

A solution of 5-bromo-2,3-dihydro-benzo[1,4]dioxine (90 mg, 0.42 mmol, 1.0 eq), PdCl$_2$(dtbpf) ([1,1'-bis(di-tert-butylphosphino)ferrocene] dichloropalladium(II)) (27 mg, 0.042 mmol, 0.1 eq), Na$_2$CO$_3$ (133 mg, 2.2 eq) and 6-methoxypyridine-2-boronic acid (128 mg, 0.84 mmol, 2.0 eq) in 9:1 1,4-dioxane:H$_2$O (5 mL) was purged with N$_2$ for 15 min and the mixture was heated to 110° C. for 1 h. Once complete the reaction was filtered to remove any inorganic salts and the filtrate was concentrated in vacuo to yield the crude material which was purified by prep HPLC to give 2-(2,3-dihydro-benzo[1,4]dioxin-5-yl)-6-methoxy-pyridine as an off-white solid (56.5 mg, 55%)

AnalpH2_MeOH_QC_V1: Rt: 7.77 min, m/z 244.3 [M+H]$^+$

AnalpH9_MeOH_QC_V1: Rt: 7.86 min, m/z 244.3 [M+H]$^+$

The following compound was made using analogous procedures:

| | Compound | | Analytical data | Mass, % yield, state |
|---|---|---|---|---|
| 2 | [8-(6-Methoxy-pyridin-2-yl)-2,3-dihydro-benzo[1,4]dioxin-2-yl]-methanol | | AnalpH2_MeOH_QC_V1, Rt: 7.24 min, m/z 274.2 [M + H]+ AnalpH9_MeOH_QC_V1, Rt: 7.38 min, m/z 274.2 [M + H]+ | 8.9 mg, 16%, colourless gum |

Example 3: Synthesis of 2-(2,3-Dihydro-benzo[1,4]dioxin-5-yl)-6-methoxy-pyridin-4-ylamine using General method B

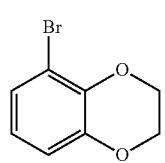 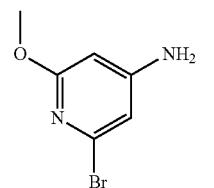

-continued

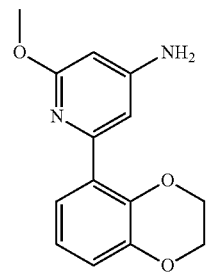

A solution of 5-bromo-2,3-dihydro-benzo[1,4]dioxine (1.0 eq, 4.65 mmol), PdCl$_2$(dtbpf) ([1,1'-bis(di-tert-butylphosphino)ferrocene] dichloropalladium(II)) (0.1 eq, 0.46 mmol), KOAc (2.5 eq, 11.6 mmol), and bis(pinacolato)diboron (1.5 eq, 10.2 mmol) in dioxane (10 mL) was purged with N$_2$ for 10 min and the mixture was heated to 120° C. for 3 h. Then, 2-bromo-6-methoxy-pyridin-4-amine (1.0 eq, 4.65 mmol), Pd(PPh$_3$)$_4$ (0.1 eq, 0.46 mmol), K$_2$CO$_3$ (2.0 eq, 9.30 mmol) and H$_2$O (1 mL) were added. The reaction was purged with N$_2$ for 10 min and the mixture was heated to 110° C. for 2.5 h. the mixture was cooled to RT then the solvent was removed. The dark residue was dissolved in ethyl acetate and filtered over celite. The compound in this organic layer was directly washed with water, brine, dried over magnesium sulphate, filtered and the reaction was concentrated in vacuo. The compound was purified by column chromatography eluting with dichloromethane then increasing the polarity with 0-5% MeOH. Then the compound was purified by preparative HPLC-MS to afford 2-(2,3-dihydro-1,4-benzodioxin-5-yl)-6-methoxy-pyridin-4-amine (780 mg, 65%) as a white solid.

AnalpH2_MeOH_QC_V1, Rt: 3.93 min, m/z 259.3 [M+H]$^+$

AnalpH9_MeOH_QC_V1, Rt: 6.46 min, m/z 259.3 [M+H]$^+$

The following compounds were made using analogous procedures:

| | Compound | | Analytical data | Mass, % yield, state |
|---|---|---|---|---|
| 4 | 1-Methyl-piperidine-4-carboxylic acid [2-(2,3-dihydro-benzo[1,4]dioxin-5-yl)-6-methoxy-pyridin-4-yl]-amide | 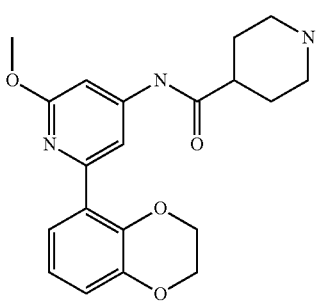 | AnalpH2_MeOH_QC_V1, Rt: 4.77 min, m/z 384.2 [M + H]$^+$<br>AnalpH9_MeOH_QC_V1, Rt: 7.59 min, m/z 384.2 [M + H]$^+$<br>$^1$H NMR (400 MHz, DMSO-d$_6$): δ 10.27 (s, 1H), 7.57 (t, J = 1.6 Hz, 1H), 7.40 (t, J = 4.8 Hz, 1H), 7.23 (d, J = 1.6 Hz, 1H), 6.90-6.91 (m, 2H), 4.32 (br s, 4H), 3.85 (s, 3H), 2.80-2.83 (m, 2H), 2.34-2.26 (m, 1H), 2.16 (s, 3H), 1.74-1.87 (m, 4H), 1.57-1.67 (m, 2H) | 25 mg, 44%, white solid |
| 5 | 3-Chloro-6-(2,3-dihydro-benzo[1,4]dioxin-5-yl)-2-methoxy-pyridine | 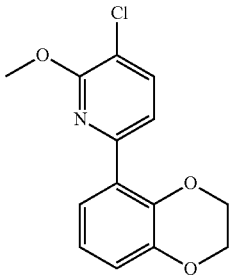 [SMILES: COc1nc(-c2cccc3c2OCCO3)ccc1Cl] | AnalpH2_MeOH_4min_V1: Rt: 3.46 min, m/z 278.2/280.2 [M + H]+ | 125 mg, 32%, white solid |
| 6 | 5-Chloro-2-(2,3-dihydro-benzo[1,4]dioxin-5-yl)-pyridine | 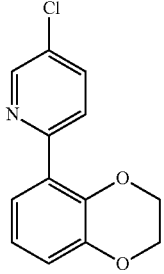 [SMILES: Clc1ccc(-c2cccc3c2OCCO3)nc1] | AnalpH2_MeOH_4MIN: Rt: 3.07 min, m/z 248 [M + H]+ | 68 mg, 28%, pale yellow solid |
| 7 | 5-(4-Chloro-3-methoxy-phenyl)-2,3-dihydro-benzo[1,4]dioxine | 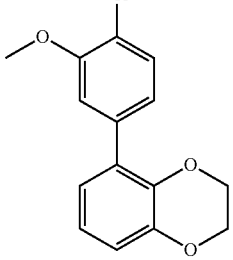 | AnalpH2_MeOH_4min_V1: Rt: 3.37 min, m/z 277 (weak) [M + H]+ | 535 mg, 83%, colourless oil |

-continued
| | Compound | | Analytical data | Mass, % yield, state |
|---|---|---|---|---|
| 8 | 3-Chloro-6-(2,3-dihydro-benzo[1,4]dioxin-5-yl)-pyridazine | | AnalpH2_MeOH_4min_V1: Rt: 2.54 min, m/z 249 [M + H]+ | 120 mg, 41%, orange oil |
| 9 | 2-Chloro-5-(2,3-dihydro-benzo[1,4]dioxin-5-yl)-pyrazine | | AnalpH2_MeOH_4MIN: Rt: 3.04 min, m/z 249 [M + H]+ | 40 mg, 7%, white solid |
General Scheme 2
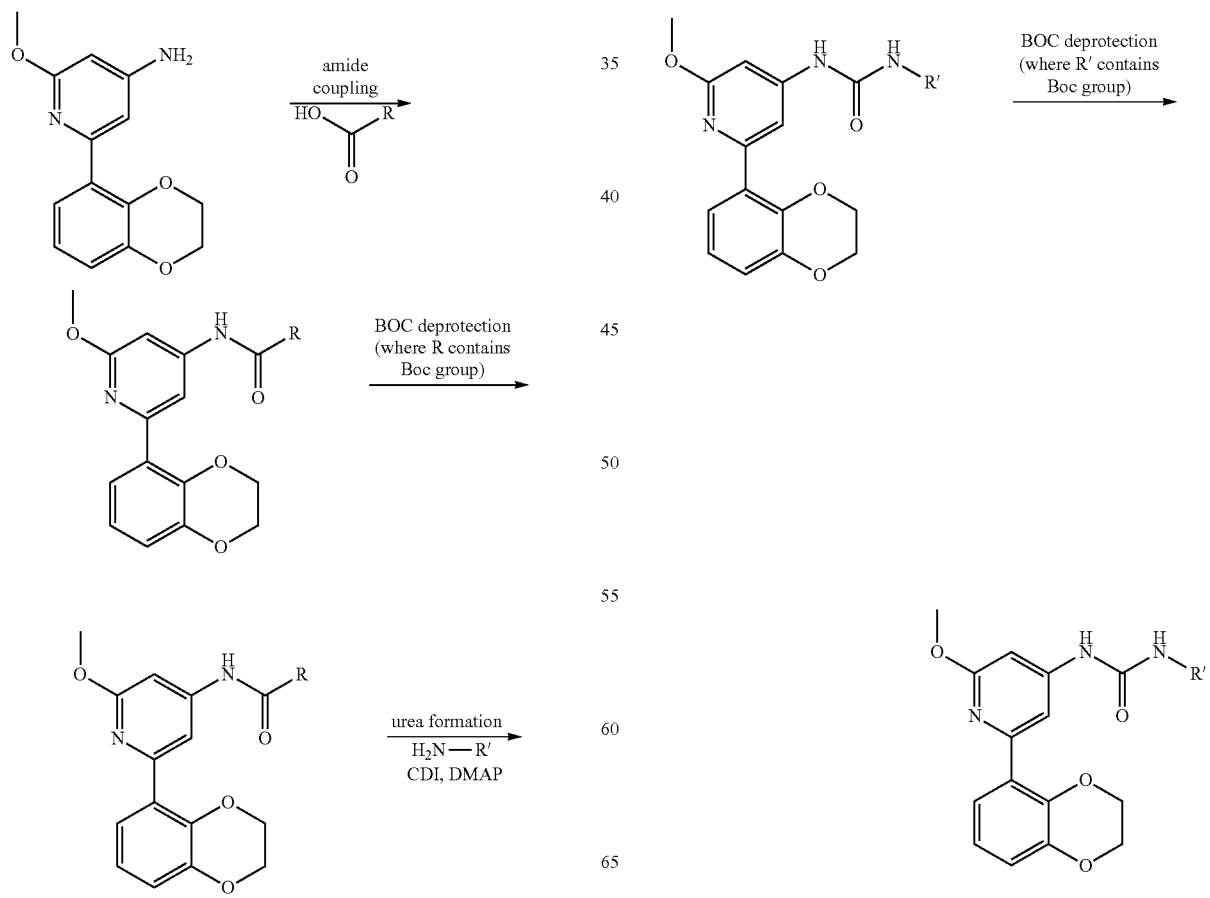

Synthesis of (R)-3-[2-(2,3-dihydro-benzo[1,4]dioxin-5-yl)-6-methoxy-pyridin-4-ylcarbamoyl]-pyrrolidine-1-carboxylic acid tert-butyl ester

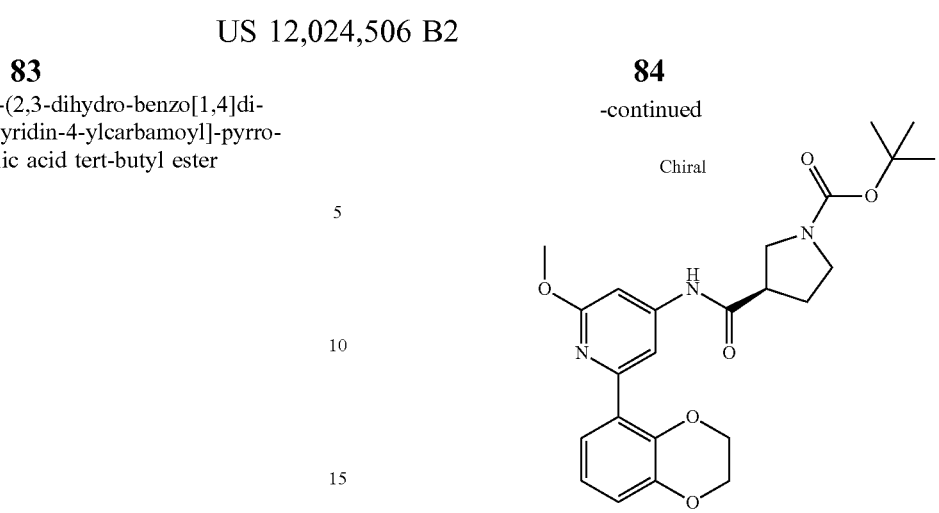

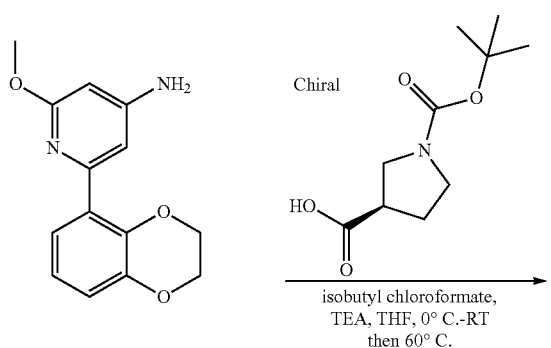

To a solution of (3R)-1-tert-butoxycarbonylpyrrolidine-3-carboxylic acid (1 eq, 0.11 mmol) in THF (2 mL) under nitrogen atmosphere was added TEA (1.5 eq, 0.17 mmol) and the mixture was cooled to 0° C. Isobutyl chloroformate (1.1 eq, 0.12 mmol) was added dropwise and the mixture was stirred at 0° C. for 15 mins then 2 h at RT. Then a solution of 2-(2,3-dihydro-1,4-benzodioxin-5-yl)-6-methoxy-pyridin-4-amine (1.0 eq, 0.11 mmol) in THF (2 mL) was added. The reaction was stirred at RT for 16 h then at 40° C. for 1.5. The volatiles were evaporated and the compound was extracted with ethyl acetate, washed with water, brine, dried over magnesium sulphate, filtered and concentrated in vacuo. The compound was then purified by reverse phase preparative HPLC-MS to afford tert-butyl (3R)-3-[[2-(2,3-dihydro-1,4-benzodioxin-5-yl)-6-methoxy-4-pyridyl]carbamoyl]pyrrolidine-1-carboxylate (44 mg, 50%) as a white solid.

AnalpH2_MeOH_4 min, Rt: 3.37 min; m/z 456.2 [M+H]$^+$

The following derivatives are prepared using analogous procedures:

| 10 | Compound | Analytical data | Mass, % yield, state |
|---|---|---|---|
| 11 | (R)-2-[2-(2,3-Dihydro-benzo[1,4]dioxin-5-yl)-6-methoxy-pyridin-4-ylcarbamoyl]-morpholine-4-carboxylic acid tert-butyl ester | AnalpH2_MeOH_4min, Rt: 3.39 min; m/z 472.4 [M + H]$^+$ | 102 mg, 91%, brown oil |

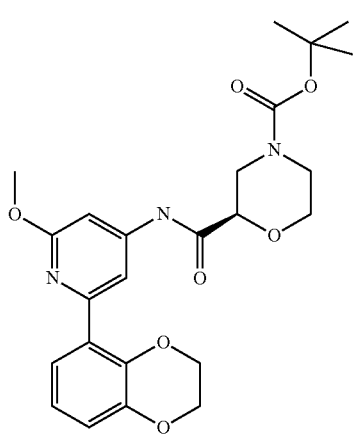 [SMILES: COc1cc(NC(=O)[C@H]2CN(C(=O)OC(C)(C)C)CCO2)cc(-c2cccc3c2OCCO3)n1]

| 10 | Compound | | Analytical data | Mass, % yield, state |
|---|---|---|---|---|
| 12 | 4-[2-(2,3-Dihydro-benzo[1,4]dioxin-5-yl)-6-methoxy-pyridin-4-ylcarbamoyl]-piperidine-1-carboxylic acid tert-butyl ester | | AnalpH2_MeOH_4min, Rt: 3.42 min; m/z 470.3 [M + H]⁺ | 74 mg, 58%, brown oil |
| 13 | (S)-2-[2-(2,3-Dihydro-benzo[1,4]dioxin-5-yl)-6-methoxy-pyridin-4-ylcarbamoyl]-morpholine-4-carboxylic acid tert-butyl ester | | AnalpH2_MeOH_4min, Rt: 3.40 min; m/z 472.4 [M + H]⁺ | 63 mg, 70%, brown oil |
| 14 | 2-{2-methoxy-6-[(R)-3-({[5-(4-methyl-piperazin-1-ylmethyl)-furan-2-carbonyl]-amino}-methyl)-2,3-dihydro-benzo[1,4]dioxin-5-yl]-pyridin-4-ylcarbamoyl}-morpholine-4-carboxylic acid tert-butyl ester | | AnalpH2_MeOH_4min, Rt: 2.68 min; m/z 707.3 [M + H]⁺ AnalpH9_MeOH_4min, Rt: 3.46 min; m/z 707.3 [M + H]⁺ | 39 mg, quant. |

-continued

| | Compound | | Analytical data | Mass, % yield, state |
|---|---|---|---|---|
| 15 | tert-butyl N-[(1S,3R)-3-[[2-(2,3-dihydro-1,4-benzodioxin-5-yl)-6-methoxy-4-pyridyl]carbamoyl]cyclopentyl]carbamate | 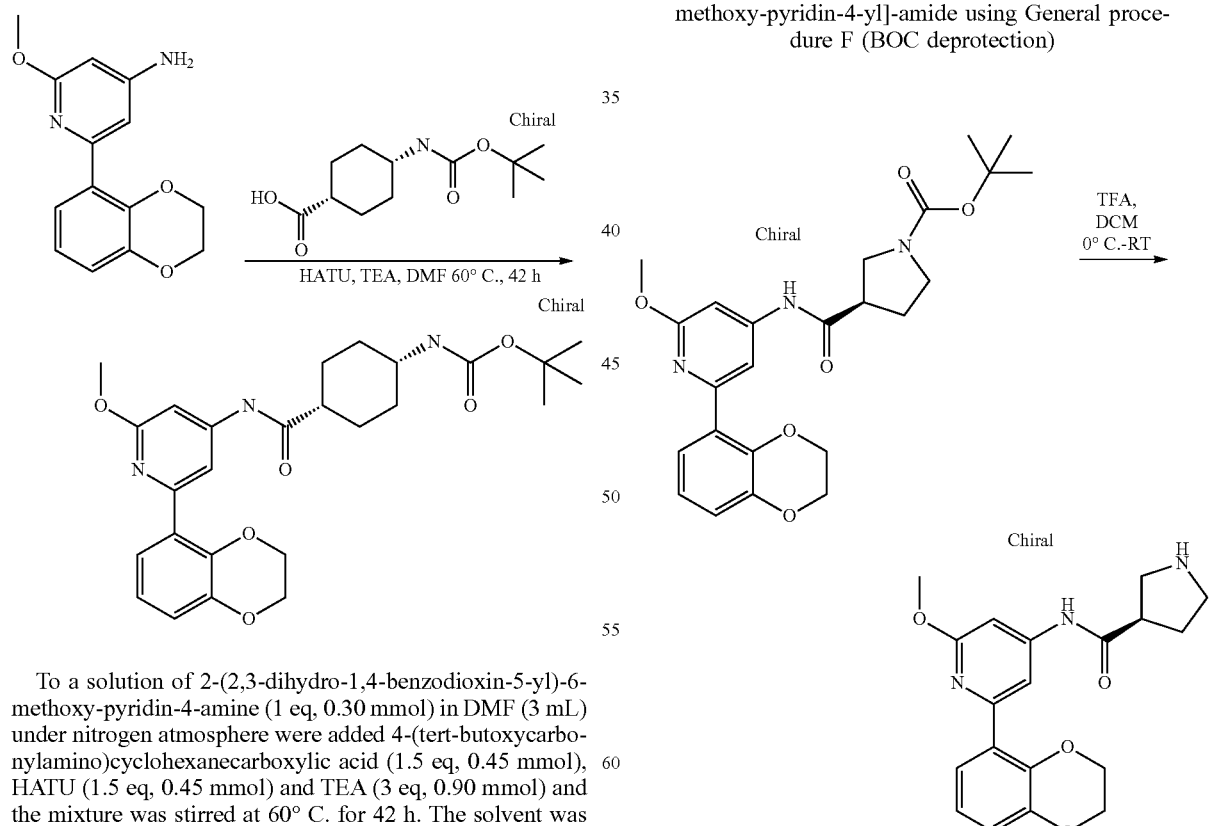 | AnalpH2_MeOH_4min, Rt: 3.38 min; m/z 470.3 [M + H]$^+$ | 33 mg, 26%, brown solid |

Example 16: Synthesis of {4-[2-(2,3-Dihydro-benzo[1,4]dioxin-5-yl)-6-methoxy-pyridin-4-ylcarbamoyl]-cyclohexy}-carbamic acid tert-butyl ester using 1-3-oxide [bis(dimethylamino)methylone]-1H-1,2,3-triazolo[4,5-b]pyridinium hexafluorophosphate (HATU)

To a solution of 2-(2,3-dihydro-1,4-benzodioxin-5-yl)-6-methoxy-pyridin-4-amine (1 eq, 0.30 mmol) in DMF (3 mL) under nitrogen atmosphere were added 4-(tert-butoxycarbonylamino)cyclohexanecarboxylic acid (1.5 eq, 0.45 mmol), HATU (1.5 eq, 0.45 mmol) and TEA (3 eq, 0.90 mmol) and the mixture was stirred at 60° C. for 42 h. The solvent was then evaporated and the compound was extracted with ethyl acetate, washed with water, brine, dried over magnesium sulphate, filtered and concentrated in vacuo. The compound was then purified using silica gel column chromatography eluting with CH$_2$Cl$_2$ and increasing the polarity to 15% MeOH. The compound was then purified by reverse phase preparative HPLC-MS to afford tert-butyl N-[4-[[2-(2,3-dihydro-1,4-benzodioxin-5-yl)-6-methoxy-4-pyridyl]carbamoyl]cyclohexyl]carbamate (30 mg, 20%) as a white solid.

AnalpH2_MeOH_4 min, Rt: 3.41 min; m/z 484.4 [M+H]$^+$

Example 17: Synthesis of (R)-Pyrrolidine-3-carboxylic acid [2-(2,3-dihydro-benzo[1,4]dioxin-5-yl)-6-methoxy-pyridin-4-yl]-amide using General procedure F (BOC deprotection)

To a solution of tert-butyl (3R)-3-[[2-(2,3-dihydro-1,4-benzodioxin-5-yl)-6-methoxy-4-pyridyl]carbamoyl]pyrrolidine-1-carboxylate (1 eq, 0.096 mmol) in DCM (5 mL)

under nitrogen atmosphere at 0° C. was added trifluoroacetic acid (0.5 mL) dropwise. The mixture was stirred at 0° C. for 20 mins then at RT for 1 h. The reaction was concentrated in vacuo, then the crude was neutralised with a solution of ammonia in methanol, 7M (1.5 mL) and concentrated in vacuo again. The compound was purified by reverse phase preparative HPLC-MS to afford (3R)—N-[2-(2,3-dihydro-1,4-benzodioxin-5-yl)-6-methoxy-4-pyridyl]pyrrolidine-3-carboxamide (10 mg, 30%) as a white solid.

AnalpH2_MeOH_QC_V1, Rt: 4.74 min, m/z 356.2 [M+H]$^+$

AnalpH9_MeOH_QC_V1, Rt: 7.26 min, m/z 356.2 [M+H]$^+$

The following derivatives were prepared using analogous procedures.

| | Compound | | Analytical data | Mass, % yield, state |
|---|---|---|---|---|
| 18 | (R)-Morpholine-2-carboxylic acid [2-(2,3-dihydro-benzo[1,4]dioxin-5-yl)-6-methoxy-pyridin-4-yl]-amide | | AnalpH2_MeOH_QC_V1, Rt: 4.80 min, m/z 372.2 [M + H]$^+$ AnalpH9_MeOH_QC_V1, Rt: 7.16 min, m/z 372.2 [M + H]$^+$ | 38 mg, 77%, white solid |
| 19 | Piperidine-4-carboxylic acid [2-(2,3-dihydro-benzo[1,4]dioxin-5-yl)-6-methoxy-pyridin-4-yl]-amide | | AnalpH2_MeOH_QC_V1, Rt: 4.71 min, m/z 370.3 [M + H]$^+$ AnalpH9_MeOH_QC_V1, Rt: 7.20 min, m/z 370.3 [M + H]$^+$ | 14 mg, 51%, white solid |
| 20 | (S)-Morpholine-2-carboxylic acid [2-(2,3-dihydro-benzo[1,4]dioxin-5-yl)-6-methoxy-pyridin-4-yl]-amide | | AnalpH2_MeOH_QC_V1, Rt: 4.79 min, m/z 372.2 [M + H]$^+$ AnalpH9_MeOH_QC_V1, Rt: 7.14 min, m/z 372.2 [M + H]$^+$ | 10 mg, 15%, white solid |

-continued

| | Compound | | Analytical data | Mass, % yield, state |
|---|---|---|---|---|
| 21 | 4-Amino-cyclohexanecarboxylic acid [2-(2,3-dihydro-benzo[1,4]dioxin-5-yl)-6-methoxy-pyridin-4-yl]-amide | 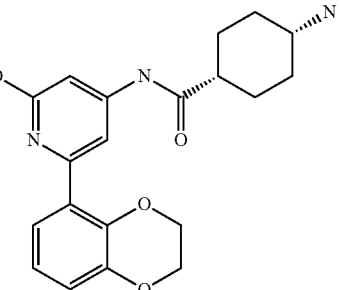 | AnalpH2_MeOH_QC_V1, Rt: 4.73 min, m/z 384.3 [M + H]$^+$ AnalpH9_MeOH_QC_V1, Rt: 7.12 min, m/z 384.3 [M + H]$^+$ | 16 mg, 69%, white solid |

Example 22: Synthesis of 3-[2-(2,3-Dihydro-benzo[1,4]dioxin-5-yl)-6-methoxy-pyridin-4-yl]-1-methyl-1-(1-methyl-piperidin-4-yl)-urea

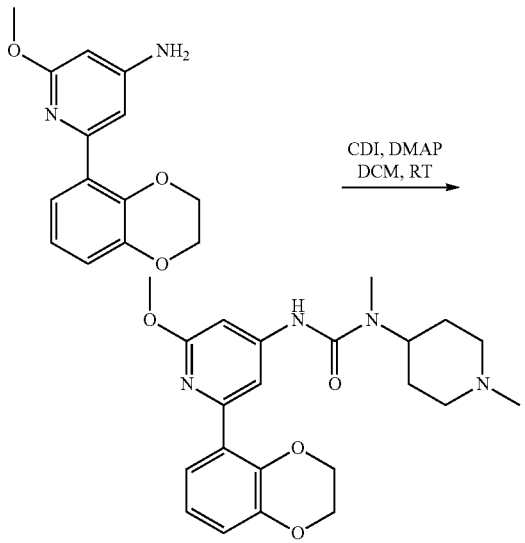

To a solution of 2-(2,3-dihydro-1,4-benzodioxin-5-yl)-6-methoxy-pyridin-4-amine (0.15 mmol, 1 eq) in DCM (2 mL) under nitrogen atmosphere at RT was added 1,1'-carbonyldiimidazole (0.23 mmol, 1.5 eq) then DMAP (0.16 mmol, 1.1 eq) and the mixture was stirred for 30 mins. Then another portion of 1,1'-carbonyldiimidazole (1.5 eq, 0.23 mmol) was added and the mixture was stirred for 30 mins. Then N, 1-dimethylpiperidin-4-amine (5 eq, 0.75 mmol) was added and the mixture was stirred for 12 h at RT. The reaction was concentrated in vacuo and the compound was purified by reverse phase preparative HPLC-MS to afford 3-[2-(2,3-dihydro-1,4-benzodioxin-5-yl)-6-methoxy-4-pyridyl]-1-methyl-1-(1-methyl-4-piperidyl)urea (32 mg, 66%) as a white solid.

$^1$H NMR (400 MHz, DMSO-d$_6$): δ 8.73 (s, 1H), 7.64 (d, J=1.8 Hz, 1H), 7.41 (dd, J=5.6 Hz, 4.0 Hz, 1H), 7.11 (d, J=1.6 Hz, 1H), 6.98 (d, J=1.6 Hz, 1H), 6.97 (s, 1H), 4.38 (s, 4H), 4.12-4.04 (m, 1H), 3.92 (s, 3H), 2.89-2.92 (m, 5H), 2.25 (s, 3H), 2.06-2.00 (m, 2H), 1.85-1.75 (m, 2H), 1.59-1.56 (m, 2H).

AnalpH2_MeOH_QC_V1, Rt: 3.95 min, m/z 411.2 [M+H]$^-$

AnalpH9_MeOH_QC_V1, Rt: 7.60 min, m/z 411.2 [M+H]$^-$

The following compounds were made using analogous procedures

| | Compound | | Analytical data | Mass, % yield, state |
|---|---|---|---|---|
| 23 | 4-Methyl-piperazine-1-carboxylic acid [2-(2,3-dihydro-benzo[1,4]dioxin-5-yl)-6-methoxy-pyridin-4-yl]-amide | | $^1$H NMR (400 MHz, DMSO-d$_6$): δ 9.02 (s, 1H), 7.63 (d, J = 2 Hz, 1H), 7.44 (dd, J = 2 Hz, 4 Hz, 1H), 7.11 (d, J = 2 Hz, 1H), 6.99 (d, J = 2 Hz, 1H), 6.97 (s, 1H), 4.38 (s, 4H), 3.92 (s, 3H), 3.55-3.53 (m, 4H), 2.41-2.39 (m, 4H), 2.28 (s, 3H). AnalpH2_MeOH_QC_V1, Rt: 3.80 min, m/z 385.4 [M + H]$^+$ AnalpH9_MeOH_QC_V1, Rt: 7.31 min, m/z 385.4 [M + H]$^+$ | 39 mg, 78%, white solid |

| | Compound | | Analytical data | Mass, % yield, state |
|---|---|---|---|---|
| 24 | 4-Amino-piperidine-1-carboxylic acid [2-(2,3-dihydro-benzo[1,4]dioxin-5-yl)-6-methoxy-pyridin-4-yl]-amide | 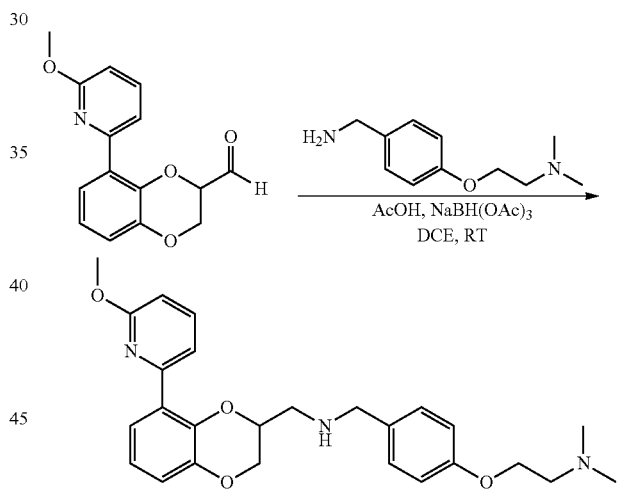 | AnalpH2_MeOH_QC_V1, Rt: 3.76 min, m/z 383.2 [M + H]⁻ AnalpH9_MeOH_QC_V1, Rt: 6.90 min, m/z 383.2 [M + H]⁻ | 59 mg, 80%, white solid |

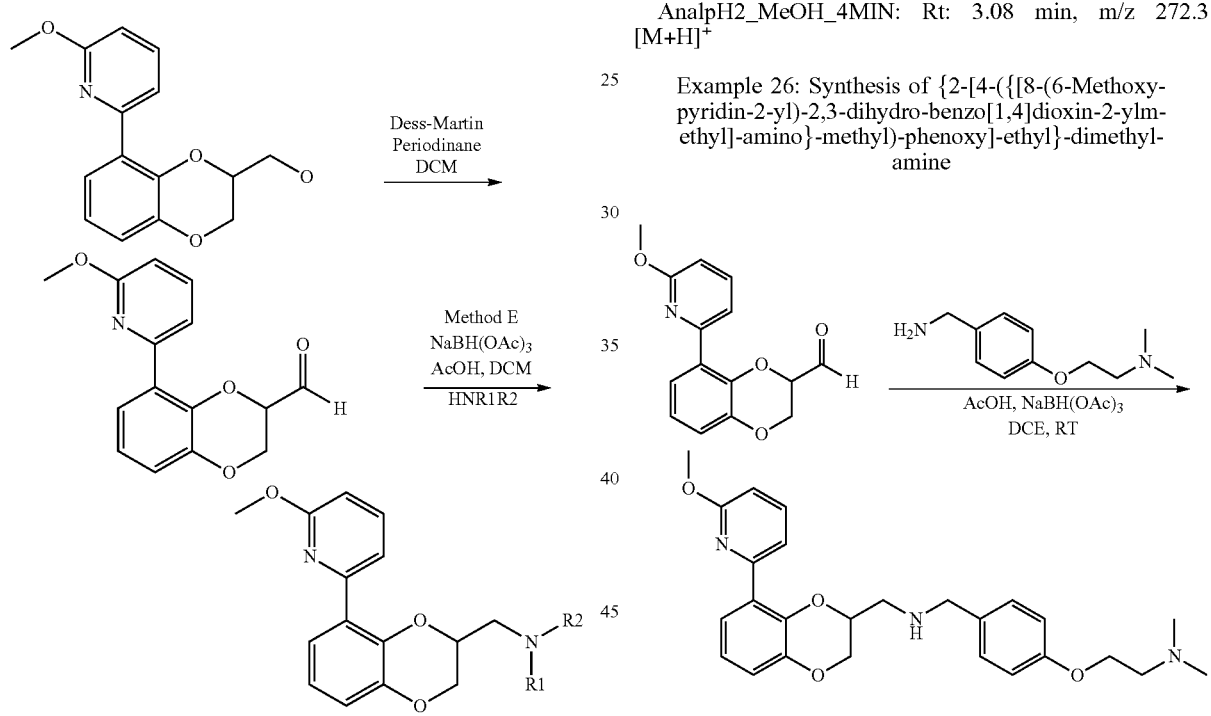

General Scheme 3

Example 25: Synthesis of 5-(6-methoxy-2-pyridyl)-2,3-dihydro-1,4-benzodioxine-3-carbaldehyde To a solution of [8-(6-methoxy-pyridin-2-yl)-2,3-dihydro-benzo[1,4]dioxin-2-yl]-methanol (80 mg, 0.29 mmol, 1 eq) in DCM (3 mL) at RT was added Dess-Martin Periodinane (149 mg, 0.35 mmol, 1.2 eq) and the reaction was stirred at RT for 2 h. The reaction was cooled to 0° C. and cold Et₂O was added. The precipitate formed was filtered with celite and washed with ice-cold Et₂O (2×). The filtrate was concentrated in vacuo to yield the crude product which was partially-purified by passing through short silica column. The product-containing fractions were concentrated under reduced pressure to afford 5-(6-methoxy-2-pyridyl)-2,3-dihydro-1,4-benzodioxine-3-carbaldehyde (89 mg) as a pale yellow gum which was used directly in subsequent reactions without further purification.

AnalpH2_MeOH_4MIN: Rt: 3.08 min, m/z 272.3 [M+H]⁺

Example 26: Synthesis of {2-[4-({[8-(6-Methoxy-pyridin-2-yl)-2,3-dihydro-benzo[1,4]dioxin-2-ylmethyl]-amino}-methyl)-phenoxy]-ethyl}-dimethyl-amine To a solution of 5-(6-methoxy-2-pyridyl)-2,3-dihydro-1,4-benzodioxine-3-carbaldehyde (50 mg, 1 eq, 0.18 mmol) in DCE (2 ml) under nitrogen atmosphere at RT were added [2-(4-aminomethyl-phenoxy)-ethyl]-dimethyl-amine (50 mg, 1.4 eq, 0.26 mmol) and AcOH (11 uL, 1.0 eq, 0.18 mmol). After 5 minutes, NaBH(OAc)₃ (58 mg, 1.5 eq, 0.27 mmol) was added and the reaction was stirred at RT for 1 h. The reaction was neutralised with sodium hydrogen carbonate, and the compound was extracted with dichloromethane, washed with brine, dried over magnesium sulphate and concentrated in vacuo. The compound was purified by reverse phase preparative HPLC to afford {2-[4-({[8-(6-Methoxy-pyridin-2-yl)-2,3-dihydro-benzo[1,4]dioxin-2-yl-methyl]-amino}-methyl)-phenoxy]-ethyl}-dimethyl-amine (5.2 mg, 6%) as a white gum.

AnalpH2_MeOH_QC_V1: Rt: 3.95 min, m/z 450.3 [M+H]⁺

AnalpH9_MeOH_QC_V1: Rt: 8.71 min, m/z 450.3 [M+H]⁺

The following compounds were made using analogous procedures

| | Compound | | Analytical data | Mass, % yield, state |
|---|---|---|---|---|
| 27 | [8-(6-Methoxy-pyridin-2-yl)-2,3-dihydro-benzo[1,4]dioxin-2-ylmethyl]-(1-methyl-piperidin-4-ylmethyl)-amine | | AnalpH2_MeOH_QC_V1: Rt: 3.40 min, m/z 384.3 [M + H]⁺ AnalpH9_MeOH_QC_V1: Rt: 8.14 min, m/z 384.3 [M + H]⁺ $^1$H NMR (400 MHz, DMSO-d6): δ 7.71 (t, J = 7 Hz, 1H), 7.59 (d, J = 7 Hz, 1H), 7.46 (t, J = 4.8 Hz, 1H), 6.90-6.96 (m, 2H), 6.76 (d, J = 7 Hz, 1H), 4.38 (dd, J = 2.4 Hz, 8.8 Hz, 1H), 4.30-4.25(m, 1H), 4.06 (dd, J = 4.4 Hz, 7.2 Hz, 1H), 3.89 (s, 3H), 2.80 (dd, J = 2.8 Hz, 4 4 Hz, 2H), 2.67-2.75 (m, 1H), 2.42 (dd, J = 2.8Hz, 4.4 Hz, 2H), 2.11 (s, 3H), 1.73-1.80 (m, 2H), 1.58-1.62 (m, 2H), 1.32-1.24 (m, 1H), 1.12-1.02 (m, 2H). | 12 mg, 10%, white solid |
| 28 | [8-(6-Methoxy-pyridin-2-yl)-2,3-dihydro-benzo[1,4]dioxin-2-ylmethyl]-pyridin-3-ylmethyl-amine | | AnalpH2_MeOH_QC_V1: Rt: 4.87 min, m/z 364.3 [M + H]⁺ AnalpH9_MeOH_QC_V1: Rt: 7.83 min, m/z 364.3 [M + H]⁺ | 11 mg, 10%, light yellow gum |
| 29 | [8-(6-Methoxy-pyridin-2-yl)-2,3-dihydro-benzo[1,4]dioxin-2-ylmethyl]-(tetrahydro-pyran-4-ylmethyl)-amine | | AnalpH2_MeOH_QC_V1: Rt: 5.12 min, m/z 371.3 [M + H]⁺ AnalpH9_MeOH_QC_V1: Rt: 8.02 min, m/z 371.3 [M + H]⁺ | 13 mg, 12%, light yellow gum |
| 29a | [4-({[8-(6-Methoxy-pyridin-2-yl)-2,3-dihydro-benzo[1,4]dioxin-2-ylmethyl]-amino}-methyl)-piperidin-1-yl]-pyrazin-2-yl-methanone | | AnalpH2_MeOH_QC_V1: Rt: 5.14 min, m/z 476.3 [M + H]⁺ AnalpH9_MeOH_QC_V1: Rt: 7.78 min, m/z 476.3 [M + H]⁺ | 29 mg, 29%, light brown solid |

| | Compound | | Analytical data | Mass, % yield, state |
|---|---|---|---|---|
| 30 | [4-({[8-(6-Methoxy-pyridin-2-yl)-2,3-dihydro-benzo[1,4]dioxin-2-ylmethyl]-amino}-methyl)-piperidin-1-yl]-(tetrahydro-pyran-4-yl)-methanone | | AnalpH2_MeOH_QC_V1: Rt: 5.24 min, m/z 482.3 [M + H]$^+$ AnalpH9_MeOH_QC_V1: Rt: 7.88 min, m/z 482.3 [M + H]$^+$ | 22 mg, 27%, white solid |

Example 31: Synthesis of {2-[4-({[8-(6-Methoxy-pyridin-2-yl)-2,3-dihydrobenzo[1,4]dioxin-2-ylmethyl]-pyridin3-ylmethyl-amino}-methyl)-phenoxy]-ethyl}-dimethyl-amine

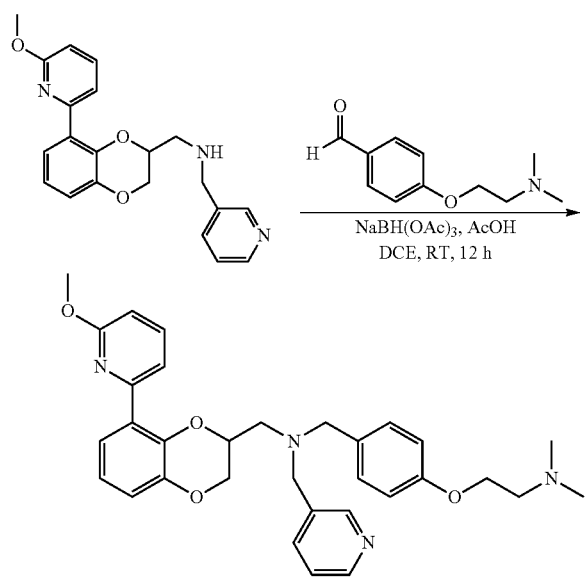

To a solution of [8-(6-methoxy-pyridin-2-yl)-2,3-dihydro-benzo[1,4]dioxin-2-ylmethyl]-pyridin-3-ylmethyl-amine (53 mg, 0.14 mmol, 1 eq) in DCE (3 mL) under nitrogen atmosphere at RT were added 4-[2-(dimethyl-amino)ethoxy]benzaldehyde (34 mg, 0.17 mmol, 1.2 eq) and AcOH (8 uL, 0.14 mmol, 1 eq). After 5 minutes, NaBH(OAc)$_3$ (37 mg, 0.17 mmol, 1.2 eq) and the reaction was stirred at RT for 12 h. NaBH(OAc)$_3$ (15 mg, 0.5 eq) was added and the mixture was heated at 100° C. for 30 minutes. Then AcOH (0.28 mmol, 2 eq) and NaBH(OAc)$_3$ (72 mg, 0.34 mmol, 2 eq,) were added and the mixture was stirred at 30° C. for 5 h. Then AcOH (2 eq, 0.28 mmol) and NaBH(OAc)$_3$ (72 mg, 0.34 mmol, 2 eq) were added and the mixture was stirred at 30° C. for 12 h. The reaction was neutralised with sodium hydrogen carbonate and the compound was extracted with dichloromethane, washed with water, brine, dried over magnesium sulphate and evaporated in vacuo. The crude product was dissolved in DCE (3 mL) under nitrogen atmosphere at RT 4-[2- and (dimethylamino) ethoxy]benzaldehyde (34 mg, 0.17 mmol, 1.2 eq) and AcOH (8 uL, 0.14 mmol, 1 eq) were added. After 5 minutes, NaBH(OAc)$_3$ (37 mg, 0.17 mmol, 1.2 eq) and the reaction was stirred at 30C for 2.5 h. Then the reaction mixture was extracted as described above. The compound was purified by reverse phase preparative HPLC, passed through an SCX-2 cartridge and eluting with 1M NH$_3$/MeOH to afford {2-[4-({[8-(6-Methoxy-pyridin-2-yl)-2,3-dihydro-benzo[1,4]dioxin-2-ylmethyl]-pyridin-3-ylmethyl-amino}-methyl)-phenoxy]-ethyl}-dimethyl-amine (12.5 mg, 16%) as a white gum.

AnalpH2_MeOH_QC_V1: Rt: 5.09 min, m/z 541.3 [M+H]$^+$

AnalpH9_MeOH_QC_V1: Rt: 9.03 min, m/z 541.3 [M+H]$^+$

The following compounds were prepared in an analogous method (see general method E):

| | Compound | | Analytical data | Mass, % yield, state |
|---|---|---|---|---|
| 32 | [2-(4-{[[8-(6-Methoxy-pyridin-2-yl)-2,3-dihydro-benzo[1,4]dioxin-2-ylmethyl]-(tetrahydro-pyran-4-ylmethyl)-amino]-methyl}-phenoxy)-ethyl]-dimethyl-amine | | AnalpH2_MeOH_QC_V1: Rt: 4.55 min, m/z 548.3 [M + H]$^+$ AnalpH9_MeOH_QC_V1: Rt: 9.21 min, m/z 548.3 [M + H]$^+$ | 13 mg, 17%, light brown gum |

General scheme 4

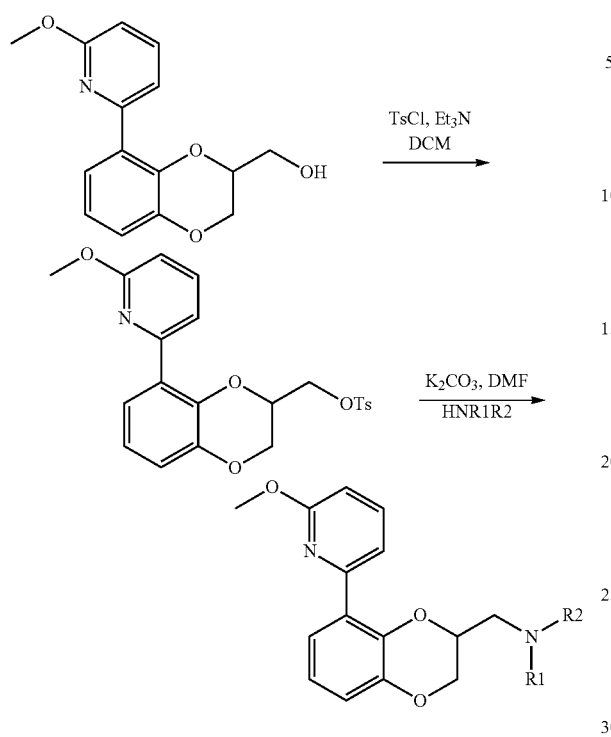

Example 33: Synthesis of toluene-4-sulfonic acid 8-(6-methoxy-pyridin-2-yl)-2,3-dihydro-benzo[1,4]dioxin-2-ylmethyl ester

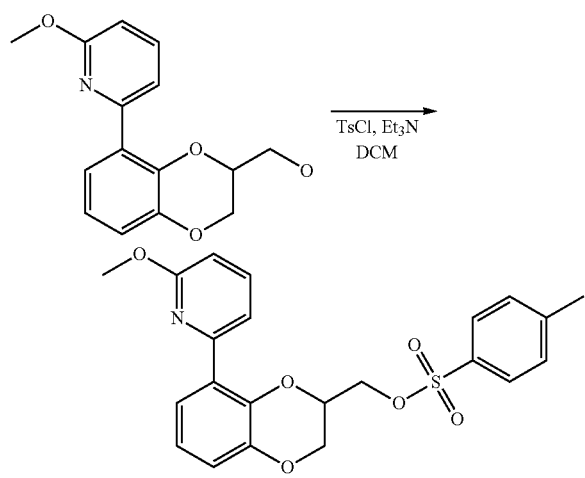

To a solution of [5-(6-methoxy-2-pyridyl)-2,3-dihydro-1,4-benzodioxin-3-yl]methanol (266 mg, 0.97 mmol, 1.0 eq) in dry DCM (10 mL) was added Et$_3$N (543 uL, 3.89 mmol, 4.0 eq) followed by p-toluenesulfonyl chloride (223 mg, 1.17 mmol, 1.2 eq) and the reaction was stirred at RT overnight. An additional portion of p-toluenesulfonyl chloride (185 mg, 0.97 mmol, 1.0 eq) was added and the mixture stirred at RT for 1 h. The reaction was quenched with sodium hydrogen carbonate and the compound was extracted with dichloromethane, washed with brine, dried over sodium sulphate, filtered and concentrated in vacuo. The crude material was purified by column chromatography to give toluene-4-sulfonic acid 8-(6-methoxy-pyridin-2-yl)-2,3-dihydro-benzo[1,4]dioxin-2-ylmethyl ester (384 mg, 92%) as a light yellow oil.

AnalpH2_MeOH_4MIN: Rt: 3.45 min, m/z 428.2 [M+H]$^+$

Example 34: Synthesis of 3-[8-(6-Methoxy-pyridin-2-yl)-2,3-dihydro-benzo[1,4]dioxin-2-ylmethyl]-8-methyl-1,3,8-triaza-spiro[4.5]decane-2,4-dione

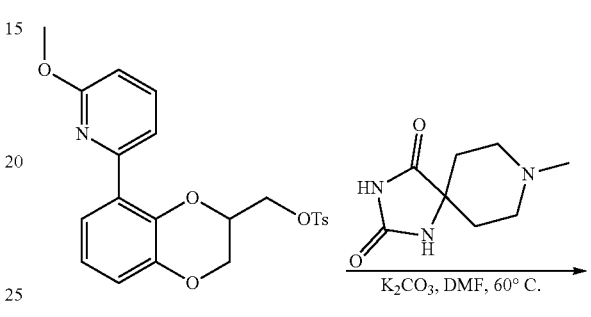

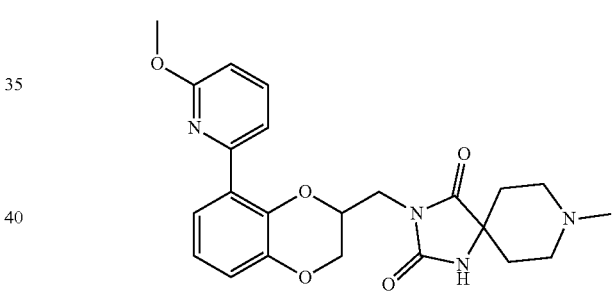

A suspension of 8-methyl-1,3,8-triazaspiro[4.5]decane-2,4-dione (48 mg, 0.26 mmol, 1.5 eq) and potassium carbonate (170 mg, 1.23 mmol, 7.0 eq) in DMF (5 mL) under nitrogen atmosphere was sonicated for 10 minutes. Then a solution of toluene-4-sulfonic acid 8-(6-methoxy-pyridin-2-yl)-2,3-dihydro-benzo[1,4]dioxin-2-ylmethyl ester (75 mg, 0.17 mmol, 1 eq) in DMF was added to the mixture and the reaction was heated at 60° C. for 12 h. The reaction mixture was concentrated in vacuo and the residue was triturated with ethyl acetate and methanol. The white precipitate was removed by filtrate and the combined filtrate and washings containing the compound were concentrated in vacuo to give a viscous yellow oil. The compound was purified by reverse phase preparative HPLC-MS to afford 3-[8-(6-methoxy-pyridin-2-yl)-2,3-dihydro-benzo[1,4]dioxin-2-ylmethyl]-8-methyl-1,3,8-triaza-spiro[4.5]decane-2,4-dione (25 mg, 32%) as a white solid.

AnalpH2_MeOH_QC_V1, Rt: 5.14 min, m/z 439.3 [M+H]$^+$

AnalpH9_MeOH_QC_V1, Rt: 7.59 min, m/z 439.3 [M+H]$^+$

The following compounds were made using analogous procedures (see general method L)

| | Compound | | Analytical data | Mass, % yield, state |
|---|---|---|---|---|
| 35 | 3-[8-(6-Methoxy-pyridin-2-yl)-2,3-dihydro-benzo[1,4]dioxin-2-ylmethyl]-5,5-dimethyl-imidazolidine-2,4-dione | | AnalpH2_MeOH_QC_V1, Rt: 7.49 min, m/z 384.2 [M + H]$^+$ AnalpH9_MeOH_QC_V1, Rt: 7.57 min, m/z 384.2 [M + H]$^+$ | 37 mg, 56% white solid |
| 36 | 1-(6-Methoxy-pyridin-3-yl)-3-[8-(6-methoxy-pyridin-2-yl)-2,3-dihydro-benzo[1,4]dioxin-2-ylmethyl]-imidazolidine-2,4-dione | | AnalpH2_MeOH_QC_V1, Rt: 7.93 min, m/z 463.2 [M + H]$^+$ AnalpH9_MeOH_QC_V1, Rt: 7.98 min, m/z 463.2 [M + H]$^+$ | 17 mg, 24%, White solid |

Example 37: Synthesis of 3-[8-(6-Methoxy-pyridin-2-yl)-2,3-dihydro-benzo[1,4]dioxin-2-ylmethyl]-1-piperidin-4-yl-imidazolidine-2,4-dione

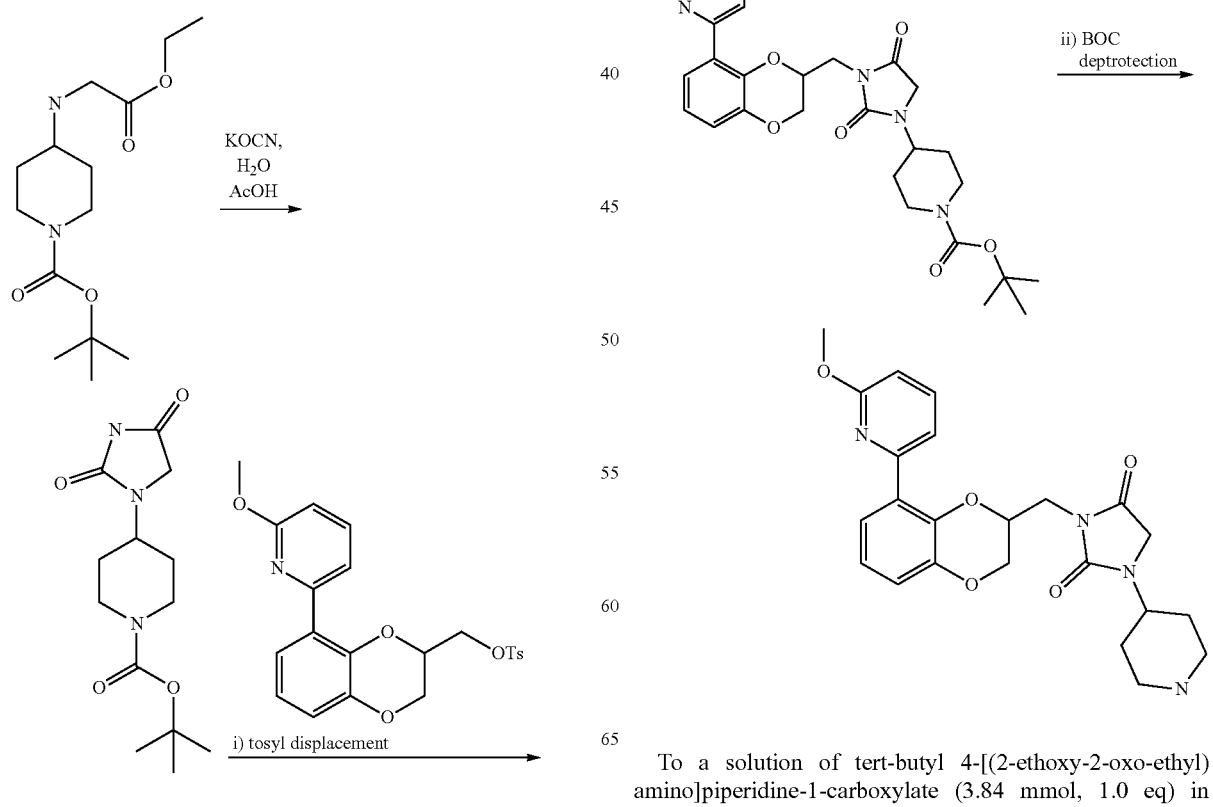

To a solution of tert-butyl 4-[(2-ethoxy-2-oxo-ethyl)amino]piperidine-1-carboxylate (3.84 mmol, 1.0 eq) in water (21 ml) under nitrogen atmosphere was added potassium cyanate (1 eq, 3.84 mmol) and AcOH (7 mL) to adjust the pH of the reaction to 5. The mixture was then heated to 40° C. for 15 h. The reaction was then quenched with sodium hydrogen carbonate and the compound was extracted with ethyl acetate, washed with water, brine, dried over sodium sulphate, filtered and concentrated in vacuo to give tert-butyl 4-(2,4-dioxoimidazolidin-1-yl)piperidine-1-carboxylate. AnalpH2_MeOH_4MIN: Rt: 2.53 min, m/z 284.2 [M+H]$^+$ The crude product was used directly in the next step without further purification.

4-{3-[8-(6-Methoxy-pyridin-2-yl)-2,3-dihydro-benzo[1,4]dioxin-2-ylmethyl]-2,4-dioxo-imidazolidin-1-yl}-piperidine-1-carboxylic acid tert-butyl ester was prepared from tert-butyl 4-(2,5-dioxoimidazolidin-4-yl)piperidine-1-carboxylate and toluene-4-sulfonic acid 8-(6-methoxy-pyridin-2-yl)-2,3-dihydro-benzo[1,4]dioxin-2-ylmethyl ester using Method L. The reaction mixture stirred 60° C. for 20 h then at RT for 12 h to afford the title compound (105 mg) as a colourless oil. AnalpH2_MeOH_4MIN: Rt: 3.55 min, m/z 539.4 [M+H]$^+$ The crude product was used directly in the next step without further purification.

The crude 4-{3-[8-(6-methoxy-pyridin-2-yl)-2,3-dihydro-benzo[1,4]dioxin-2-ylmethyl]-2,4-dioxo-imidazolidin-1-yl}-piperidine-1-carboxylic acid tert-butyl ester was subjected to BOC deprotection using general method F to afford 3-[8-(6-methoxy-pyridin-2-yl)-2,3-dihydro-benzo[1,4]dioxin-2-ylmethyl]-1-piperidin-4-yl-imidazolidine-2,4-dione (13.7 mg, 25%) as a white solid.

AnalpH2_MeOH_QC_V1, Rt: 5.11 min, m/z 439.3 [M+H]$^+$

AnalpH9_MeOH_QC_V1, Rt: 7.48 min, m/z 439.3 [M+H]$^+$

The following compounds were prepared using General Method A (Suzuki coupling):

| | Compound | | Analytical data | Mass, %e yield, state |
|---|---|---|---|---|
| 38 | 4-(2-Dimethylamino-ethoxy)-2-fluoro-N-[8-(6-methoxy-pyridin-2-yl)-2,3-dihydro-benzo[1,4]dioxin-2-ylmethyl]-benzamide | | AnalpH2_MeOH_QC_V1: Rt: 5.70 min, m/z 482.4 [M + H]+ AnalpH9_MeOH_QC_V1: Rt: 8.33 min, m/z 482.4 [M + H]+ | 61.3 mg, 64%, brown gum |
| 39 | 4-(2-Dimethylamino-ethoxy)-N-[8-(6-methoxy-pyridin-2-yl)-2,3-dihydro-benzo[1,4]dioxin-2-ylmethyl]-benzamide | Chiral | AnalpH2_MeOH_QC_V1: Rt: 5.58 min, m/z 464.3 [M + H]+ AnalpH9_MeOH_QC_V1: Rt: 8.19 min, m/z 464.3 [M + H]+ | 33.2 mg, 51%, white solid |
| 40 | 4-(2-Dimethylamino-ethoxy)-N-[(R)-8-(6-methoxy-pyridin-2-yl)-2,3-dihydro-benzo[1,4]dioxin-2-ylmethyl]-benzamide | Chiral | AnalpH2_MeOH_QC_V1: Rt: 5.62 min, m/z 464.37 [M + H]+ AnalpH9_MeOH_QC_V1: Rt: 8.23 min, m/z 464.37 [M + H]+ | 52.5 mg, 38%, brown solid |
| 41 | 4-(2-Dimethylamino-ethoxy)-N-[(S)-8-(6-methoxy-pyridin-2-yl)-2,3-dihydrobenzo[1,4]dioxin-2-ylmethyl]-benzamide | Chiral | AnalpH2_MeOH_QC_V1: Rt: 5.58 min, m/z 464.3 [M + H]+ AnalpH9_MeOH_QC_V1: Rt: 8.22 min, m/z 464.3 [M + H]+ | 26.1 mg, 18%, pink solid |

| | Compound | | Analytical data | Mass, %e yield, state |
|---|---|---|---|---|
| 42 | 5-(4-Methyl-piperazin-1-ylmethyl)-furan-2-carboxylic acid [8-(2H-pyrazol-3-yl)-2,3-dihydro-benzo[1,4]dioxin-2-ylmethyl]-amide | | AnalpH2_MeOH_QC_V1: Rt: 4.94 min, m/z 438.2 [M + H]+ AnalpH9_MeOH_QC_V1: Rt: 7.33 min, m/z 438.2 [M + H]+ 1H NMR (400 MHz, DMSO-d6): δ 12.86 (s, 1H), 8.55-8.70 (m, 1H), 7.29-7.65 (m, 2H), 7.08 (d, J = 3.5 Hz, 1H) 6.92-6.72 (m, 3H) 6.45 (d, J = 3.3 Hz, 1H) 4.44-4.34 (m, 2H) 4.02 (dd, J = 11.4, 7.3 Hz, 1H) 3.72-3.58 (m, 2H) 352 (s, 2H) 2.48-2.20 (m, 8H) 2.14 (s, 3H) | 50.3 mg, 66%, pale brown solid |
| 43 | 5-(4-Methyl-piperazin-1-ylmethyl)-furan-2-carboxylic acid [8-(6-methoxy-pyridin-2-yl)-2,3-dihydro-benzo[1,4]dioxin-2-ylmethyl]-amide | | AnalpH2_MeOH_QC_V1: Rt: 5.54 min, m/z 479.4 [M + H]+ AnalpH9_MeOH_QC_V1: Rt: 8.02 min, m/z 479.4 [M + H]+ | 30.9 mg, 22%, off white solid |
| 44 | 5-(4-Methyl-piperazin-1-ylmethyl)-furan-2-carboxylic acid [(S)-8-(6-methoxy-pyridin-2-yl)-2,3-dihydro-benzo[1,4]dioxin-2-ylmethyl]-amide | | AnalpH2_MeOH_QC_V1: Rt: 5.52 min, m/z 479.4 [M + H]+ AnalpH9_MeOH_QC_V1: Rt: 8.02 min, m/z 479.4 [M + H]+ | 37.4 mg, 34%, beige solid |
| 45 | Tetrahydro-pyran-4-carboxylic acid [8-(6-methoxy-pyridin-2-yl)-2,3-dihydro-benzo[1,4]dioxin-2-ylmethyl]-amide | | AnalpH2_MeOH_QC_V1: Rt: 7.56 min, m/z 385.29 [M + H]+ AnalpH9_MeOH_QC_V1: Rt: 7.64 min, m/z 385.3 [M + H]+ | 64.1 mg, 76%, off white solid |

-continued

| | Compound | | Analytical data | Mass, %e yield, state |
|---|---|---|---|---|
| 45a | 5-(4-Methyl-piperazin-1-ylmethyl)-furan-2-carboxylic acid [8-(6-methoxy-pyridin-3-yl)-2,3-dihydro-benzo[1,4]dioxin-2-ylmethyl]-amide | | AnalpH2_MeOH_QC_V1: Rt: 5.55 min, m/z 479.3 [M + H]+ AnalpH9_MeOH_QC_V1: Rt: 7.90 min, m/z 479.3 [M + H]+ | 20.2 mg, 15%, pale brown solid |
| 46 | 5-Morpholin-4-ylmethyl-furan-3-carboxylic acid [8-(6-methoxy-pyridin-2-yl)-2,3-dihydro-benzo[1,4]dioxin-2-ylmethyl]-amide | | AnalpH2_MeOH_QC_V1: Rt: 5.67 min, m/z 466.4 [M + H]+ AnalpH9_MeOH_QC_V1: Rt: 7.86 min, m/z 466.4 [M + H]+ | 35.9 mg, 37%, white solid |
| 47 | 3-Dimethylamino-N-[8-(6-methoxy-pyridin-2-yl)-2,3-dihydro-benzo[1,4]dioxin-2-ylmethyl]-propionamide | | AnalpH2_MeOH_QC_V1: Rt: 4.97 min, m/z 372.3 [M + H]+ AnalpH9_MeOH_QC_V1: Rt: 7.66 min, m/z 372.3 [M + H]+ | 46.1 mg, 50%, light brown gum |
| 48 | 1-Pyrazin-2-ylmethyl-piperidine-4-carboxylic acid [(R)-8-(6-methoxy-pyridin-2-yl)-2,3-dihydro-benzo[1,4]dioxin-2-ylmethyl]-amide | | AnalpH2_MeOH_QC_V1: Rt: 5.25 min, m/z 476.3 [M + H]+ AnalpH9_MeOH_QC_V1: Rt: 7.65 min, m/z 476.3 [M + H]+ | 50.0 mg, 59%, light brown oil |

| | Compound | | Analytical data | Mass, %e yield, state |
|---|---|---|---|---|
| 49 | 5-(4-Methyl-piperazin-1-ylmethyl)-oxazole-2-carboxylic acid [8-(6-methoxy-pyridin-2-yl)-2,3-dihydro-benzo[1,4]dioxin-2-ylmethyl]-amide | | AnalpH2_MeOH_QC_V1: Rt: 5.47 min, m/z 480.3 [M + H]+ AnalpH9_MeOH_QC_V1: Rt: 7.84 min, m/z 480.3 [M + H]+ | 24.1 mg, 85%, light brown solid |
| 50 | 1-Methyl-piperidine-4-carboxylic acid [8-(6-methoxy-pyridin-2-yl)-2,3-dihydro-benzo[1,4]dioxin-2-ylmethyl]-amide | | AnalpH2_MeOH_QC_V1: Rt: 5.07 min, m/z 398.3 [M + H]+ AnalpH9_MeOH_QC_V1: Rt: 7.65 min, m/z 398.3 [M + H]+ | 32.2 mg, 54%, off white solid |
| 51 | 5-(4-Methyl-piperazin-1-ylmethyl)-furan-2-carboxylic acid [(R)-8-(6-methoxy-pyridin-2-yl)-2,3-dihydro-benzo[1,4]dioxin-2-ylmethyl]-amide | | AnalpH2_MeOH_QC_V1: Rt: 5.43 min, m/z 479.3 [M + H]+ AnalpH9_MeOH_QC_V1: Rt: 7.91 min, m/z 479.3 [M + H]+ | 54.5 mg, 11%, brown solid |

Example 52: Synthesis of 5-(4-Methyl-piperazin-1-ylmethyl)-furan-2-carboxylic acid [8-(6-oxo-1,6-dihydro-pyridin-2-yl)-2,3-dihydro-benzo[1,4]dioxin-2-ylmethyl]-amide

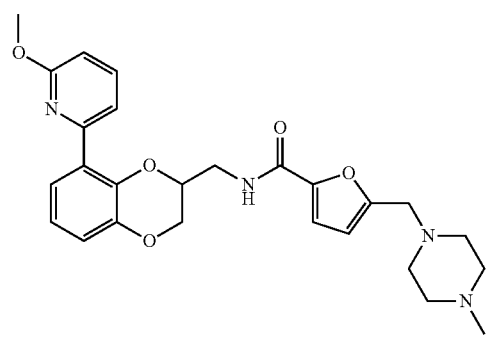

→

-continued

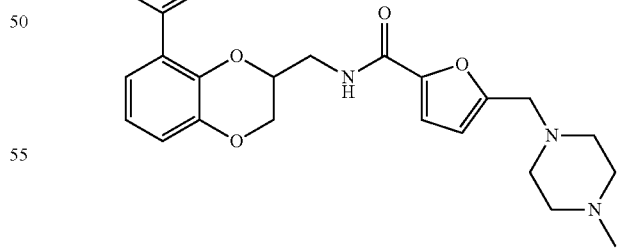

To a solution of 5-(4-methyl-piperazin-1-ylmethyl)-furan-2-carboxylic acid [8-(6-methoxy-pyridin-2-yl)-2,3-dihydro-benzo[1,4]dioxin-2-ylmethyl]-amide (43) (80 mg, 0.17 mMol) in 1,4-dioxane (2 mL) was added 3M HCl (2 mL) and the reaction was heated to 90° C. for 16 h and monitored by LCMS. The reaction was concentrated under reduced pressure then azeotroped with toluene (×3) to give crude product as a brown gum. Purified by reverse phase preparative HPLC-MS to afford 5-(4-methyl-piperazin-1-ylmethyl)-furan-2-carboxylic acid [8-(6-oxo-1,6-dihydro-pyridin-2-yl)-2,3-dihydro-benzo[1,4]dioxin-2-ylmethyl]-amide (35.9 mg, 0.077 mMol, 30%) as a pale brown solid.

AnalpH2_MeOH_QC_V1: Rt: 4.68 min, m/z 465.3 [M+H]+

AnalpH9_MeOH_QC_V1: Rt: 7.04 min, m/z 465.3 [M+H]+

$^1$H NMR (400 MHz, DMSO-d6): δ 11.48 (s, 1H) 8.49 (t, J=6.1 Hz, 1H) 7.37 (dd, J=9.1, 6.8 Hz, 1H) 7.10 (d, J=3.3 Hz, 1H) 7.02-6.88 (m, 3H) 6.44 (d, J=3.3 Hz, 1H) 6.40-6.34 (m, 1H) 6.28 (dd, J=9.1, 1.0 Hz, 1H) 4.44 (qd, J=6.3, 2.3 Hz, 1H) 4.31 (dd, J=11.6, 2.3 Hz 1H) 4.07 (dd, J=11.6, 6.3 Hz, 1H) 3.63-3.43 (m, 2H) 3.52 (s, 2H) 2.48-2.20 (m, 8H) 2.14 (s, 3H)

The following compounds were made using analogous procedures

| | Compound | | Analytical data | Mass, % yield, state |
|---|---|---|---|---|
| 53 | 4-(2-dimethylamino-ethoxy)-N-[8-(6-oxo-1,6-dihydro-pyridin-2-yl)-2,3-dihydro-benzo[1,4]dioxin-2-ylmethyl]-benzamide | | AnalpH2_MeOH_QC_V1: Rt: 4.76 min, m/z 450.2 [M + H]+ AnalpH9_MeOH_QC_V1: Rt: 7.38 min, m/z 450.2 [M + H]+ | 20.6 mg, 53%, white solid |
| 54 | 5-(4-methyl-piperazin-1-ylmethyl)-furan-2-carboxylic acid [8-(6-oxo-1,6-dihydro-pyridin-3-yl)-2,3-dihydro-benzo[1,4]dioxin-2-ylmethyl]-benzamide | | AnalpH2_MeOH_QC_V1: Rt: 5.55 min, m/z 479.3 [M + H]+ AnalpH9_MeOH_QC_V1: Rt: 8.32 min, m/z 479.3 [M + H]+ | 20.2 mg, 27%, Off white solid |

General scheme 5

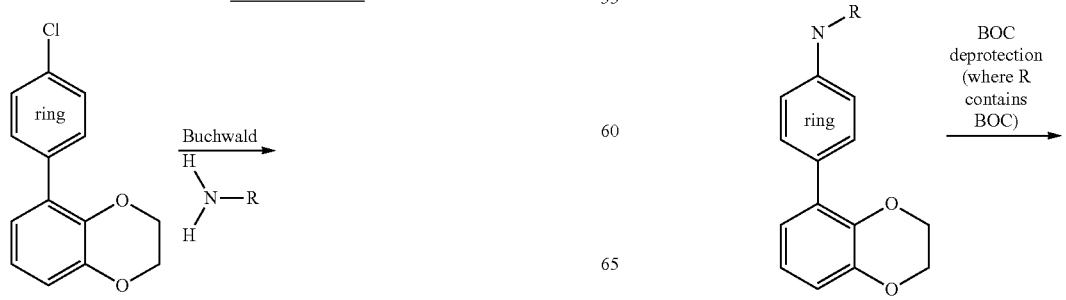

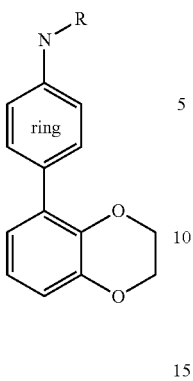

Example 55: Synthesis of [6-(2,3-dihydro-benzo[1,4]dioxin-5-yl)-2-methoxy-pyridin-3-yl]-(3-dimethyl-aminomethyl-phenyl)-amine

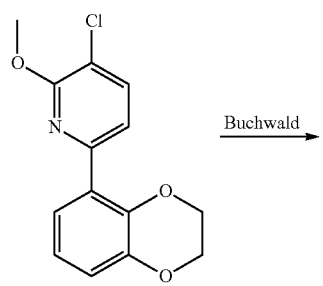 Buchwald⟶

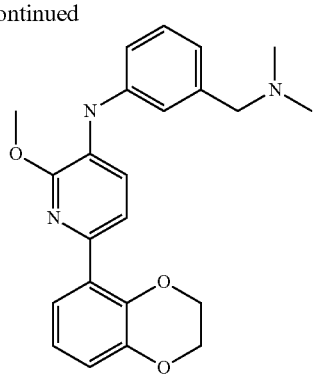

To a solution of 3-chloro-6-(2,3-dihydro-benzo[1,4]dioxin-5-yl)-2-methoxy-pyridine (80 mg, 0.30 mMol, 1.0 eq.) and 1,4-dioxane (4 mL) was added 3-amino-N,N-dimethyl-benzylamine (45 mg, 0.3 mMol, 1 eq.), Pd$_2$(dba)$_3$ (27 mg, 0.03 mMol, 0.1 eq.), XantPhos (51 mg, 0.09 mMol, 0.3 eq.) and NaO$^t$Bu (43 mg, 0.45 mMol, 1.5 eq.). The reaction mixture was degassed with N$_2$ for 10 min and heated at 110° C. for 1 h. The reaction was cooled and Pd(OAc)$_2$ (0.1 eq.) and XPhos (0.3 eq.) were added and the reaction mixture was degassed with N$_2$ for 10 min and heated at 110° C. for 16 h. The reaction was filtered, washing with EtOAc, and the filtrate concentrated under reduced pressure to yield the crude material. Purification by column chromatography eluting 0-100% Ethyl acetate/iso-hexane then 0-9% MeOH in DCM (containing 1% Et$_3$N) followed by reverse phase preparative HPLC-MS to afford [6-(2,3-dihydro-benzo[1,4]dioxin-5-yl)-2-methoxy-pyridin-3-yl]-(3-dimethylaminomethyl-phenyl)-amine (29.6 mg, 0.08 mMol, 26%) as a yellow gum.

AnalpH2_MeOH_QC_V1: Rt: 5.84 min, m/z 392.3 [M+H]$^+$

AnalpH9_MeOH_QC_V1: Rt: 8.62 min, m/z 392.3 [M+H]$^+$

The following compounds were prepared in an analogous method:

| | Compound | Analytical data | Mass, % yield, state |
|---|---|---|---|
| 56 | [6-(2,3-Dihydro-benzo[1,4]dioxin-5-yl)-2-methoxy-pyridin-3-yl]-(4-dimethylaminomethyl-phenyl)-amine | AnalpH2_MeOH_QC_V1: Rt: 5.79 min, m/z 392.3 [M + H]+ AnalpH9_MeOH_QC_V1: Rt: 8.57 min, m/z 392.3 [M + H]+ | 23 mg, 32%, Off white solid |

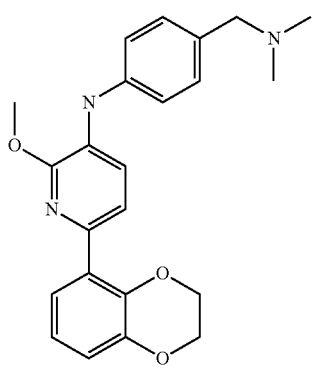 [SMILES: COc1nc(-c2cccc3c2OCCO3)ccc1Nc1ccc(CN(C)C)cc1]

| | | Compound | Analytical data | Mass, % yield, state |
|---|---|---|---|---|
| 57 | [6-(2,3-Dihydro-benzo[1,4]dioxin-5-yl)-2-methoxy-pyridin-3-yl]-(5-dimethylaminomethyl-pyridin-2-yl)-amine | | AnalpH2_MeOH_QC_V1:<br>Rt: 5.41 min, m/z 393.3<br>[M + H]+<br>AnalpH9_MeOH_QC_V1:<br>Rt: 8.32 min, m/z 393.3<br>[M + H]+ | 19 mg, 27%,<br>Off white solid |
| 58 | [6-(2,3-Dihydro-benzo[1,4]dioxin-5-yl)-2-methoxy-pyridin-3-yl]-(4-imidazol-1-ylmethyl-phenyl)-amine | | AnalpH2_MeOH_QC_V1:<br>Rt: 5.90 min, m/z 415.2<br>[M + H]+<br>AnalpH9_MeOH_QC_V1:<br>Rt: 8.16 min, m/z 415.3<br>[M + H]+ | 22 mg, 30%,<br>white solid |
| 59 | [6-(2,3-Dihydro-benzo[1,4]dioxin-5-yl)-pyridin-3-yl]-(3-dimethylaminomethyl-phenyl)-amine | | AnalpH2_MeOH_QC_V1:<br>Rt: 3.79 min, m/z 362.3<br>[M + H]+<br>AnalpH9_MeOH_QC_V1:<br>Rt: 7.85 min, m/z 362.3<br>[M + H]+ | 34 mg, 34%,<br>white solid |
| 60 | [6-(2,3-Dihydro-benzo[1,4]dioxin-5-yl)-2-methoxy-pyridin-3-yl]-(3-pyrrolidin-1-ylmethyl-phenyl)-amine | | AnalpH2_MeOH_QC_V1:<br>Rt: 5.83 min, m/z 418.4<br>[M + H]+<br>AnalpH9_MeOH_QC_V1:<br>Rt: 8.59 min, m/z 418.4<br>[M + H]+ | 7 mg, 7%,<br>white solid |

-continued

| | Compound | | Analytical data | Mass, % yield, state |
|---|---|---|---|---|
| 61 | [6-(2,3-Dihydro-benzo[1,4]dioxin-5-yl)-2-methoxy-pyridin-3-yl]-(3-morpholin-4-ylmethyl-phenyl)-amine | | AnalpH2_MeOH_QC_V1:<br>Rt: 5.76 min, m/z 434.4<br>[M + H]+<br>AnalpH9_MeOH_QC_V1:<br>Rt: 8.41 min, m/z 434.4<br>[M + H]+ | 16 mg, 15%,<br>white solid |
| 62 | 5-{3-[6-(2,3-Dihydro-benzo[1,4]dioxin-5-yl)-2-methoxy-pyridin-3-ylamino]-phenyl}-pyrrolidin-2-one | | AnalpH2_MeOH_QC_V1:<br>Rt: 7.95 min, m/z 418.2<br>[M + H]+<br>AnalpH9_MeOH_QC_V1:<br>Rt: 7.97 min, m/z 418.3<br>[M + H]+ | 12 mg, 11%,<br>white solid |
| 63 | (R)-2-{3-[6-(2,3-Dihydro-benzo[1,4]dioxin-5-yl)-2-methoxy-pyridin-3-ylamino]-phenyl}-pyrrolidine-1-carboxylic acid tert-butyl ester | | AnalpH2_MeOH_4MIN:<br>Rt: 3.66 min, m/z 504.3<br>[M + H]+ | 113 mg, 62%,<br>Pale brown oil |
| 64 | (S)-2-{3-[6-(2,3-Dihydro-benzo[1,4]dioxin-5-yl)-2-methoxy-pyridin-3-ylamino]-phenyl}-pyrrolidine-1-carboxylic acid tert-butyl ester | | AnalpH2_MeOH_4MIN:<br>Rt: 3.65 min, m/z 504.3<br>[M + H]+ | 160 mg, 88%,<br>pale orange oil |

| | Compound | | Analytical data | Mass, % yield, state |
|---|---|---|---|---|
| 65 | {4-[6-(2,3-Dihydro-benzo[1,4]dioxin-5-yl)-2-methoxy-pyridin-3-ylamino]-benzyl}-carbamic acid tert-butyl ester | 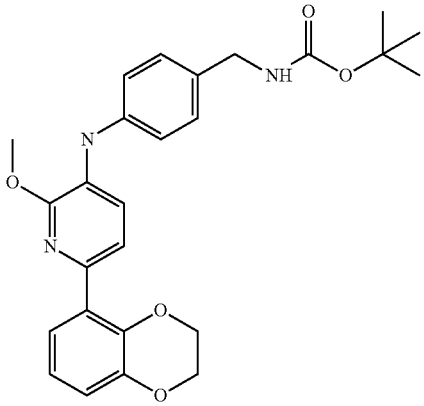 [SMILES: COc1nc(-c2cccc3c2OCCO3)ccc1Nc1ccc(CNC(=O)OC(C)(C)C)cc1] | AnalpH2_MeOH_4MIN: Rt: 3.49 min, m/z 464.4 [M + H]+ | 268 mg, 76%, Brown oil |
| 66 | {3-[6-(2,3-Dihydro-benzo[1,4]dioxin-5-yl)-2-methoxy-pyridin-3-ylamino]-benzyl}-carbamic acid tert-butyl ester | 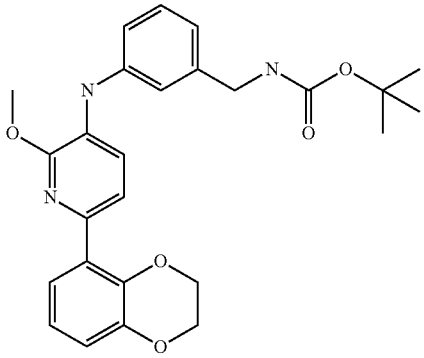 [SMILES: COc1nc(-c2cccc3c2OCCO3)ccc1Nc1cccc(CNC(=O)OC(C)(C)C)c1] | AnalpH2_MeOH_4MIN: Rt: 3.49 min, m/z 464.4 [M + H]+ | 383 mg, 76%, Brown oil |
| 67 | {3-[6-(2,3-Dihydro-benzo[1,4]dioxin-5-yl)-2-methoxy-pyridin-3-ylamino]-phenyl}-methanol | 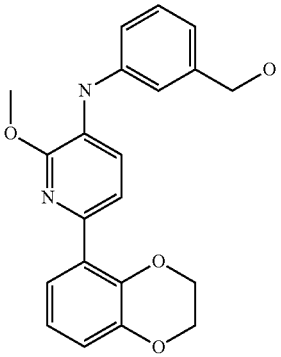 | AnalpH2_MeOH_4MIN: Rt: 3.22 min, m/z 365.3 [M + H]+ | 60 mg, 30%, pale brown gum |
| 67a | [6-(2,3-Dihydro-benzo[1,4]dioxin-5-yl)-pyridazin-3-yl]-(3-dimethylaminomethyl-phenyl)-amine | 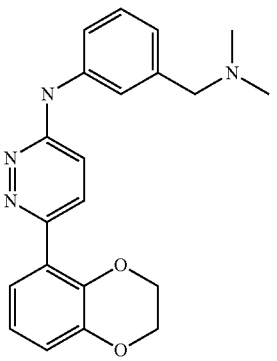 [SMILES: CN(C)Cc1cccc(Nc2ccc(-c3cccc4c3OCCO4)nn2)c1] | AnalpH2_MeOH_QC_V1: Rt: 4.40 min, m/z 363.2 [M+H]+ AnalpH9_MeOH_QC_V1: Rt: 7.38 min, m/z 363.2 [M+H]+ 1H NMR (400 MHz, DMSO-d6): δ 9.34 (s, 1H) 7.80 (d, J = 9.3 Hz, 1H) 7.75 (t, J = 1.6 Hz, 1H) 7.68 (dd, J = 8.0 1.6 Hz, 1H) 7.30-7.23 (m, 2H) 7.14 (d, J = 9.4 Hz, 1H) 6.95 (s, 1H) 6.93 (d, J = 1.6 Hz, 1H) 6.88 (d, J = 7.7 Hz, 1H) 4.30 (s, 4H) 3.37 (s, 2H) 2.16 (2, 6H) | 8 mg, 6%, white solid |

| | Compound | | Analytical data | Mass, % yield, state |
|---|---|---|---|---|
| 68 | [5-(2,3-Dihydro-benzo[1,4]dioxin-5-yl)-pyridazin-3-yl]-(3-dimethylaminomethyl-phenyl)-amine | | AnalpH2_MeOH_QC_V1: Rt: 5.25 min, m/z 363.2 [M+H]+ AnalpH9_MeOH_QC_V1: Rt: 8.00 min, m/z 363.2 [M+H]+ 1H NMR (400 MHz, DMSO-d6): δ 9.57 (s, 1H) 8.66 (d, J = 1.3 Hz, 1H) 8.31 (d, J = 1.3 Hz, 1H) 7.68 (d, J = 8.1 Hz, 1H) 7.63 (t, J = 1.9 Hz, 1H) 7.32 (dd, J = 7.4, 2.0 Hz, 1H) 7.25 (t, J = 7.9 Hz, 1H) 6.94-6.86 (m, 3H) 4.37-4.28 (m, 4H) 3.37 (s, 2H) 2.16 (s, 6H) | 50 mg, 34%, yellow gum |
| 69 | Tetrahydro-pyran-4-carboxylic acid {(S)-8-[5-3-dimethylaminomethyl-phenylamino)-6-methoxy-pyridin-2-yl]-2,3-dihydro-benzo[1,4]dioxin-2-ylmethyl}-amide | | AnalpH2_MeOH_QC_V1: Rt: 5.75 min, m/z 533.3 [M+H]+ AnalpH9_MeOH_QC_V1: Rt: 8.28 min, m/z 533.4 [M+H]+ | 45 mg, 38%, pale yellow solid |
| 70 | [4-(2,3-Dihydro-benzo[1,4]dioxin-5-yl)-phenyl]-(3-dimethylaminomethyl-phenyl)-amine. formate salt | | AnalpH2_MeOH_QC_V1: Rt: 5.74 min, m/z 361.2 [M+H]+ AnalpH9_MeOH_QC_V1: Rt: 8.20 min, m/z 361.1 [M+H]+ 1H NMR (400 MHz, DMSO-d6): δ 8.25 (s, 1H) 7.38 (d, J = 8.3 Hz, 2H), 7.18 (t, J = 7.8 Hz, 1H), 7.11-7.06 (m, 3H), 7.00 (dd, J = 8.0, 1.6 Hz, 1H), 6.87-6.73 (m, 4H), 4.25 (dd, J = 5.0, 3.4 Hz, 4H), 3.39 (s, 2H), 2.19 (s, 6H) | 100 mg, 68%, brown oil |
| 71 | 1-Benzyl-4-(2,3-dihydro-benzo[1,4]dioxin-5-yl)-piperazine | | AnalpH2_MeOH_QC_V1: Rt: 4.41 min, m/z 311.3 [M+H]+ AnalpH9_MeOH_QC_V1: Rt: 8.09 min, m/z 311.3 [M+H]+ 1H NMR (400 MHz, DMSO-d6): δ 7.36-7.22 (m, 5H) 6.69 (t, J = 7.8 Hz, 1H) 6.48 (dd, J = 8.1, 1.5 Hz, 1H) 6.44 (dd, J = 8.0, 1.5 Hz, 1H) 4.24-4.17 (m, 4H) 3,51 (s, 2H) 3.32 (s, 4H) 2.95 (s, 4H) | 50 mg, 35%, pale yellow oil |

-continued

| | Compound | | Analytical data | Mass, % yield, state |
|---|---|---|---|---|
| 72 | [4-(2,3-Dihydro-benzo[1,4]dioxin-5-yl)-2-methoxy-phenyl]-(3-dimethylaminomethyl-phenyl)-amine formate salt | | AnalpH2_MeOH_QC_V1: Rt: 5.85 min, m/z 391.2 [M+H]+ AnalpH9_MeOH_QC_V1: Rt: 8.38 min, m/z 391.2 [M+H]+ 1H NMR (400 MHz, DMSO-d6): δ 7.35 (s, 1H), 7.06-7.18 (m, 3H), 7.02-6.92 (m, 3H), 6.89-6.75 (m, 3H), 6.70 (d, J = 7.5 Hz, 1H) 4.26-4.20 (m, 4H), 3.80 (s, 3H), 3.32 (s, 2H), 2.14 (s, 6H) | 50 mg, 35% Pink oil |
| 73 | {4-[4-(2,3-Dihydro-benzo[1,4]dioxin-5-yl)-2-methoxy-phenylamino]-benzyl}-carbamic acid tert-butyl ester | 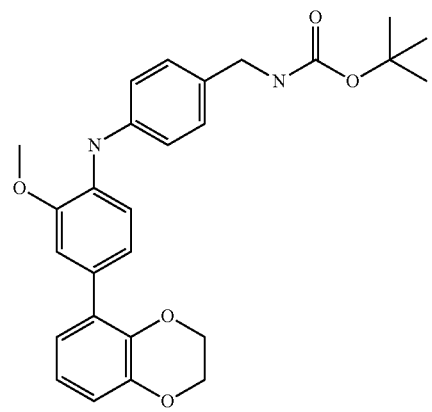 [SMILES: COc1cc(-c2cccc3c2OCCO3)ccc1Nc1ccc(CNC(=O)OC(C)(C)C)cc1] | used crude in subsequent reaction | 100 mg, 15% |

BOC Deprotection

The following compounds were prepared using General Method F (BOC deprotection)

| | Compound | | Analytical data | Mass, % yield, state |
|---|---|---|---|---|
| 74 | [6-(2,3-Dihydro-benzo[1,4]dioxin-5-yl)-2-methoxy-pyridin-3-yl]-((R)-3-pyrrolidin-2-yl-phenyl)-amine | | AnalpH2_MeOH_QC_V1: Rt: 6.02 min, m/z 404.2 [M+H]+ AnalpH9_MeOH_QC_V1: Rt: 7.84 min, m/z 404.2 [M+H]+ ¹H NMR (400 MHz, DMSO-d6): δ 7.60 (s, 1H), 7.47-7.51 (m, 3H), 7.14-7.19 (m, 2H), 6.97-6.99 (m, 1H), 6.81-6.91 (m, 3H), 4.28-4.32 (m, 4H), 3.94-3.99 (m, 4H), 2.82-3.02 (m, 2H), 2.04-2.12 (m, 1H), 1.67-1.79 (m, 2H), 1.42-1.51 (m, 1H). | 36.2 mg, 40%, white solid |

| | | | | |
|---|---|---|---|---|
| 75 | [6-(2,3-Dihydro-benzo[1,4]dioxin-5-yl)-2-methoxy-pyridin-3-yl]-((S)-3-pyrrolidin-2-yl-phenyl)-amine | 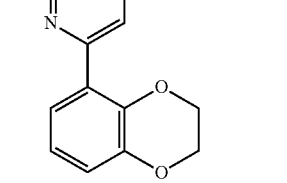 | AnalpH2_MeOH_QC_V1: Rt: 6.02 min, m/z 404.2 [M+H]+ AnalpH9_MeOH_QC_V1: Rt: 7.86 min, m/z 404.2 [M+H]+ | 35.0 mg, 27%, white solid |
| 76 | (4-Aminomethyl-phenyl)-[6-(2,3-dihydro-benzo[1,4]dioxin-5-yl)-2-methoxy-pyridin-3-yl]-amine | 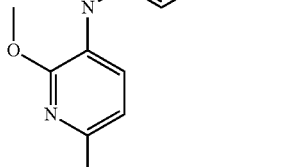 | AnalpH2_MeOH_4MIN: Rt: 2.24 min, m/z 364.3 [M + H]+ | 198 mg, 94%, light bown gum |
| 77 | (3-Aminomethyl-phenyl)-[6-(2,3-dihydro-benzo[1,4]dioxin-5-yl)-2-methoxy-pyridin-3-yl]-amine | 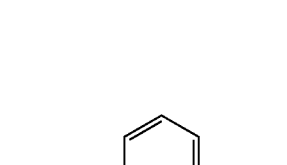 | AnalpH2_MeOH_4MIN: Rt: 2.26 min, m/z 364.3 [M + H]+ | 294 mg, 98%, yellow solid |
| 78 | (4-Aminomethyl-phenyl)-[4-(2,3-dihydro-benzo[1,4]dioxin-5-yl)-2-methoxy-phenyl]-amine | 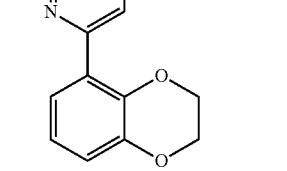 | AnalpH2_MeOH_4MIN: Rt: 2.20 min, m/z 316 [M + H]+ | 130 mg, quant., orange oil |

General scheme 6

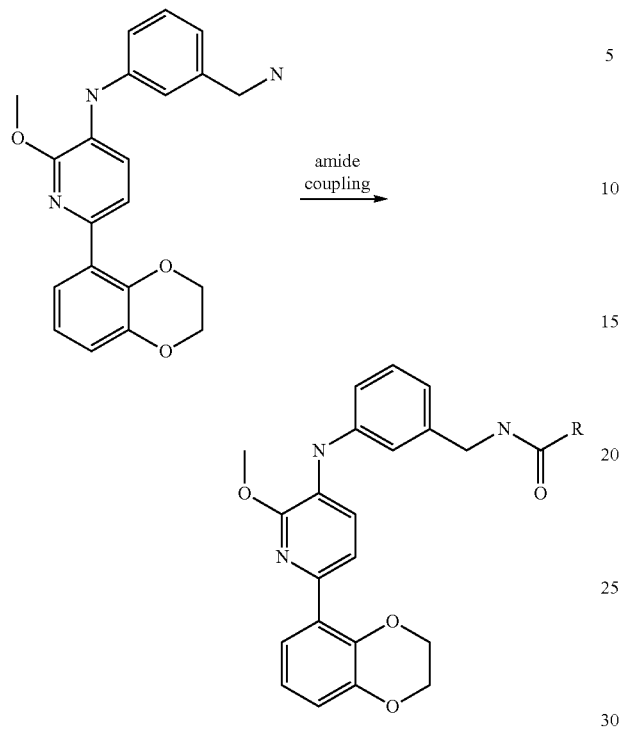

The following compounds were made using general method D:

| | | Compound | Analytical data | Mass, % yield, state |
|---|---|---|---|---|
| 79 | N-{3-[6-(2,3-Dihydro-benzo[1,4]dioxin-5-yl)-2-methoxy-pyridin-3-ylamino]-benzyl}-nicotinamide | | AnalpH2_MeOH_QC_V1: Rt: 7.95 min, m/z 469.2 [M+H]+ AnalpH9_MeOH_QC_V1: Rt: 7.99 min, m/z 469.2 [M+H]+ | 30.2 mg, 38%, white solid |
| 80 | N-{3-[6-(2,3-Dihydro-benzo[1,4]dioxin-5-yl)-2-methoxy-pyridin-3-ylamino]-benzyl}-isonicotinamide | | AnalpH2_MeOH_QC_V1: Rt: 7.93 min, m/z 469.2 [M+H]+ AnalpH9_MeOH_QC_V1: Rt: 7.99 min, m/z 469.2 [M+H]+ | 26.7 mg, 27%, off white solid |

| | Compound | Analytical data | Mass, % yield, state |
|---|---|---|---|
| 81 | 1H-Pyrazole-4-carboxylic acid 3-[6-(2,3-dihydro-benzo[1,4]dioxin-5-yl)-2-methoxy-pyridin-3-ylamino]-benzylamide | AnalpH2_MeOH_QC_V1: Rt: 7.76 min, m/z 458.2 [M+H]+ AnalpH9_MeOH_QC_V1: Rt: 7.76 min, m/z 458.2 [M+H]+ | 16.4 mg, 17%, white solid |

General scheme 7

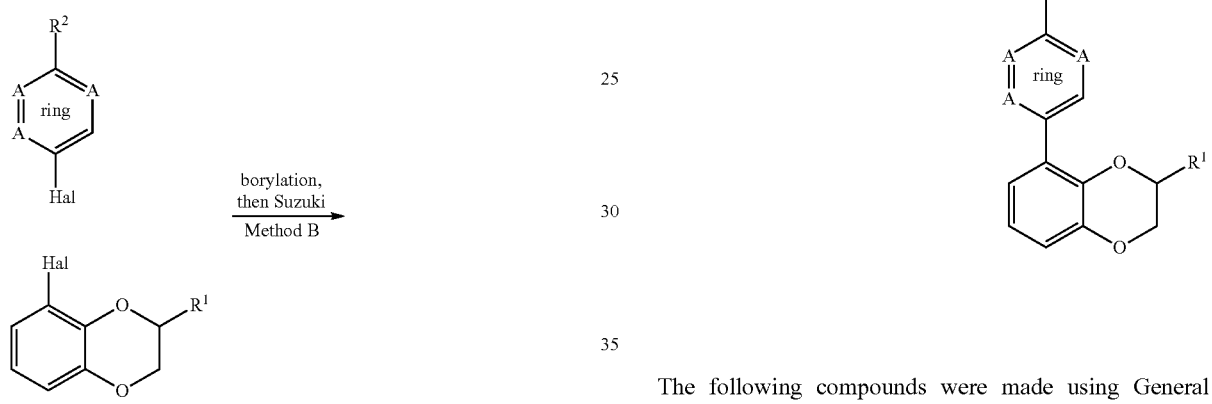

The following compounds were made using General Method B:

| | Compound | Analytical data | Mass, % yield, state |
|---|---|---|---|
| 82 | Tetrahydro-pyran-4-carboxylic acid (8-{6-methoxy-5-[2-(1-methyl-piperidin-4-yl)-acetylamino]-pyridin-2-yl}-2,3-dihydro-benzo[1,4]dioxin-2-ylmethyl)-amide | AnalpH2_MeOH_QC_V1: Rt: 5.29 min, m/z 539.4 [M+H]+ AnalpH9_MeOH_QC_V1: Rt: 7.57 min, m/z 539.3 [M+H]+ | 49 mg, 41%, White solid |

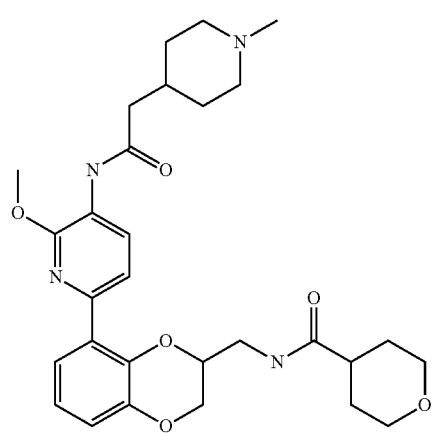 [SMILES: COc1nc(-c2cccc3c2OC(CNC(=O)C2CCOCC2)CO3)ccc1NC(=O)CC1CCN(C)CC1]

| | Compound | | Analytical data | Mass, % yield, state |
|---|---|---|---|---|
| 83 | 5-(4-Methyl-piperazin-1-ylmethyl)-furan-2-carboxylic acid (8-{5-[(tetrahydro-pyran-4-ylmethyl)-amino]-pyridin-2-yl}-2,3-dihydro-benzo[1,4]dioxin-2-ylmethyl)-amide | | AnalpH2_MeOH_QC_V1: Rt: 4.02 min, m/z 562.4 [M+H]+ AnalpH9_MeOH_QC_V1: Rt: 7.60 min, m/z 562.4 [M+H]+ | 20.08 mg, 24%, White solid |
| 84 | Tetrahydro-pyran-4-carboxylic acid {8-[5(3-dimethylamino-methyl-phenylamino)-6-methoxy-pyridin-2-yl]-2,3-dihydro-benzo[1,4]dioxin-2-ylmethyl}-amide | | AnalpH2_MeOH_QC_V1: Rt: 5.76 min, m/z 533.5 [M+H]+ AnalpH9_MeOH_QC_V1: Rt: 8.36 min, m/z 533.4 [M+H]+ | 11.2 mg, 11%, White solid |
| 85 | 3-(2,3-Dihydro-benzo[1,4]dioxin-5-yl)-6-(1-methyl-piperidin-4-ylmethoxy)-pyridazine | | ANALPH2_MeOH_QC_V1: Rt: 4.49 min, m/z 342.3 [M+H]+ ANALPH9_MeOH_QC_V1: Rt: 7.43 min, m/z 342.3 [M+H]+ | 19.2 mg, 15%, brown solid |
| 86 | [6-(2,3-Dihydro-benzo[1,4]dioxin-5-yl)-2-methoxy-pyridin-3-yl]-(1-methyl-pyrrolidin-3-yl)-amine | | ANALPH2_MeOH_QC_V1: Rt: 5.03 min, m/z 342.3 [M+H]+ ANALPH9_MeOH_QC_V1: Rt: 8.11 min, m/z 342.3 [M+H]+ | 8.2 mg, 7%, white solid |

-continued

| | Compound | | Analytical data | Mass, % yield, state |
|---|---|---|---|---|
| 87 | 5-(4-Methyl-piperazin-1-ylmethyl)-furan-2-carboxylic acid [(R)-8-(5-amino-6-methoxy-pyridin-2-yl)-2,3-dihydro-benzo[1,4]dioxin-2-ylmethyl]-amide | Chiral | AnalpH2_MeOH_QC_V1: Rt: 5.09 min, m/z 494.3 [M+H]+ AnalpH9_MeOH_QC_V1: Rt: 7.52 min, m/z 394.3 [M+H]+ | 6.0 mg, 5%, orange solid |
| 88 | Tetrahydro-pyran-4-carboxylic acid {8-[6-methoxy-5-(pyridin-3-ylamino)-pyridin-2-yl]-2,3-dihydro-benzo[1,4]dioxin-2-ylmethyl}-amide | | AnalpH2_MeOH_QC_V1: Rt: 5.89 min, m/z 477.3 [M+H]+ AnalpH9_MeOH_QC_V1: Rt: 7.73 min, m/z 477.3 [M+H]+ | 5.1 mg, 9%, yellow solid |
| 89 | Tetrahydro-pyran-4-carboxylic acid (8-{5-[4-(2-hydroxy-ethylcarbamoyl)-phenylamino]-6-methoxy-pyridin-2-yl}-2,3-dihydro-benzo[1,4]dioxin-2-ylmethyl)-amide | | AnalpH2_MeOH_QC_V1: Rt: 7.45 min, m/z 563.3 [M+H]+ AnalpH9_MeOH_QC_V1: Rt: 7.46 min, m/z 563.3 [M+H]+ | 13.5 mg, 12%, white solid |
| 90 | Tetrahydro-pyran-4-carboxylic acid (8-{5-[3-(4-acetyl-piperazin-1-ylmethyl)-phenylamino]-6-methoxy-pyridin-2-yl}-2,3-dihydro-benzo[1,4]dioxin-2-ylmethyl)-amide | | AnalpH2_MeOH_QC_V1: Rt: 5.88 min, m/z 616.3 [M+H]+ AnalpH9_MeOH_QC_V1: Rt: 8.05 min, m/z 616.3 [M+H]+ | 10.9 mg, 11%, white solid |

-continued

| | Compound | | Analytical data | Mass, % yield, state |
|---|---|---|---|---|
| 91 | Tetrahydro-pyran-4-carboxylic acid (8-{5-[4-(1-methyl-piperidin-4-ylcarbamoyl)-phenylamino]-pyridin-2-yl-2,3-dihydro-benzo[1,4]dioxin-2-ylmethyl)-amide | 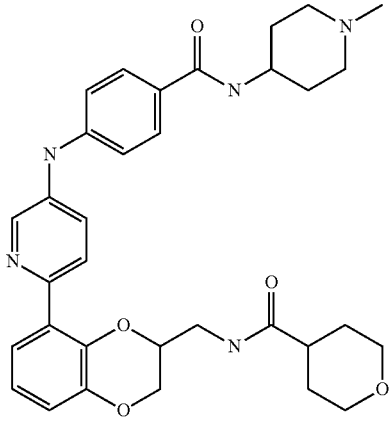 [SMILES: CN1CCC(NC(=O)c2ccc(Nc3ccc(-c4cccc5c4OC(CNC(=O)C4CCOCC4)CO5)nc3)cc2)CC1] | AnalpH2_MeOH_QC_V1: Rt: 4.36 min, m/z 586.3 [M+H]+ AnalpH9_MeOH_QC_V1: Rt: 7.49 min, m/z 586.3 [M+H]+ | 34.6 mg, 35%, off-white solid |
| 92 | Tetrahydro-pyran-4-carboxylic acid ((R)-8-{5-[2-(1-methyl-piperidin-4-yl)-acetylamino]-pyridin-2-yl}-2,3-dihydro-benzo[1,4]dioxin-2-ylmethyl)-amide | 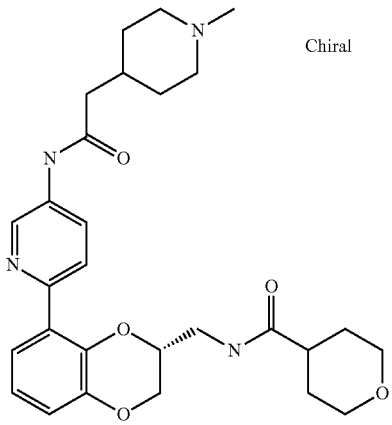 [SMILES: CN1CCC(CC(=O)Nc2ccc(-c3cccc4c3O[C@H](CNC(=O)C3CCOCC3)CO4)nc2)CC1] Chiral | ANALPH2_MeOH_QC_V1: Rt: 4.27 min, m/z 509.4 [M+H]+ ANALPH9_MeOH_QC_V1: Rt: 7.24 min, m/z 509.4 [M+H]+ | 33 mg, 36%, white solid |
| 93 | Tetrahydro-pyran-4-carboxylic acid {8-[5-0-dimethylamino-methyl-phenylamino)-pyridin-2-yl]-2,3-dihydro-benzo[1,4]dioxin-2-ylmethyl}-amide | 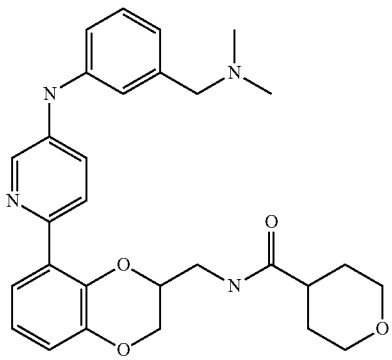 [SMILES: CN(C)Cc1cccc(Nc2ccc(-c3cccc4c3OC(CNC(=O)C3CCOCC3)CO4)nc2)c1] | ANALPH2_MeOH_QC_V1: Rt: 4.07 min, m/z 503.4 [M+H]+ ANALPH9_MeOH_QC_V1: Rt: 7.80 min, m/z 503.4 [M+H]+ | 15 mg, 14%, white solid |

-continued

| | Compound | Analytical data | Mass, % yield, state |
|---|---|---|---|
| 94 Tetrahydro-pyran-4-carboxylic acid {8-[5-(4-dimethyl-carbamoyl-phenylamino)-6-methoxy-pyridin-2-yl]-2,3-dihydro-benzo[1,4]dioxin-2-ylmethyl}-amide | 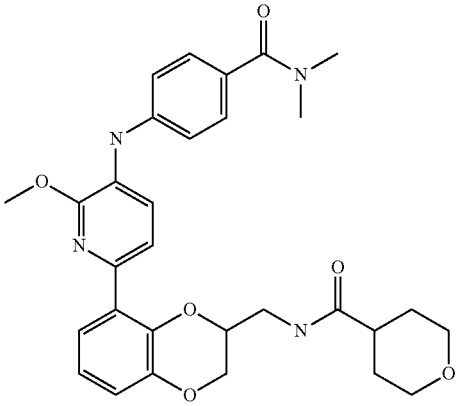 [SMILES: COc1nc(-c2cccc3c2OC(CNC(=O)C2CCOCC2)CO3)ccc1Nc1ccc(C(=O)N(C)C)cc1] | ANALPH2_MeOH_QC_V1: Rt: 7.72 min, m/z 547.3 [M+H]+ ANALPH9_MeOH_QC_V1: Rt: 7.74 min, m/z 574.4 [M+H]+ | 31 mg, 25% white solid |
| 95 ((1R,3S)-3-{3-[2-Methoxy-6-(3-{[(tetrahydro-pyran-4-carbonyl)-amino]-methyl}-2,3-dihydro-benzo[1,4]dioxin-5-yl)-pyridin-3-yl]-ureido}-cyclopentyl)-carbamic acid tert-butyl ester | 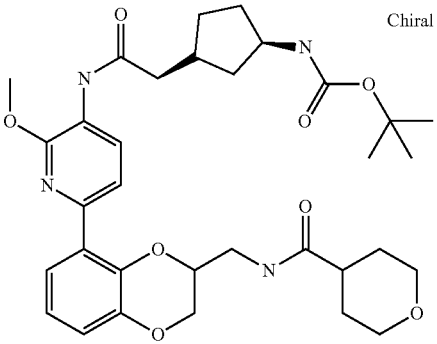 Chiral | AnalpH2_MeOH_4min, Rt: 3.27 min; m/z 626.5 [M+H]+ | 136 mg; 77%; brown gum |
| 96 ((1S,3R)-3-{3-[2-(3-{[(Tetrahydro-pyran-4-carbonyl)-amino]-methyl}-2,3-dihydro-benzo[1,4]dioxin-5-yl)-pyridin-4-yl]-ureido}-cyclopentyl)-carbamic acid tert-butyl ester | 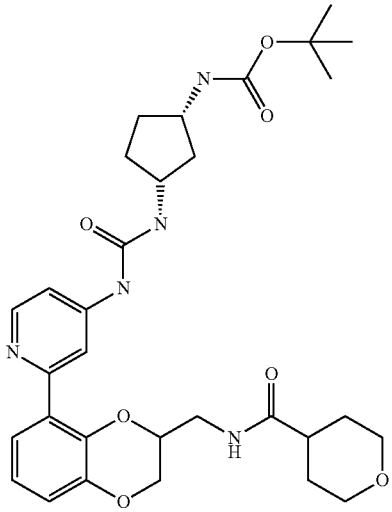 | AnalpH2_MeOH_4min, Rt: 3.15 min; m/z 404.5 [M+H]+ | |
| 97 tetrahydro-pyran-4-carboxylic acid [8-(4-chloro-pyridin-2-yl)-2,3-dihydro-benzo[1,4]dioxin-2-ylmethyl]-amide | 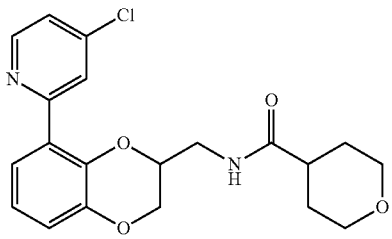 [SMILES: O=C(NCC1COc2cccc(-c3cc(Cl)ccn3)c2O1)C1CCOCC1] | AnalpH2_MeOH_4min, Rt: 2.92 min; m/z 389.3 [M+H]+ | 91 mg, 69%, brown gum |

-continued

| | Compound | Analytical data | Mass, % yield, state |
|---|---|---|---|
| 98 [6-(2,3-Dihydro-benzo[1,4]dioxin-5-yl)-2-methoxy-pyridin-3-yl]-(1-methyl-piperidin-4-yl)-amine | | AnalpH2_MeOH_QC_V1 Rt: 4.98 min, m/z 356.4 [M+H]+ AnalpH9_MeOH_QC_V1 Rt: 8.10 min, m/z 356.4 [M+H]+ | 12.4 mg, 8%, yellow solid |
| 99 1-{4-[6-(2,3-Dihydro-benzo[1,4]dioxin-5-yl)-2-methoxy-pyridin-3-ylamino]-piperidin-1-yl}-ethanone | | AnalpH2_MeOH_QC_V1 Rt: 7.50 min, m/z 384.4 [M+H]+ AnalpH9_MeOH_QC_V1 Rt: 7.53 min, m/z 384.4 [M+H]+ | 32 mg, 18%, off white solid |
| 100 ((1S,3R)-3-{3-[2-Methoxy-6-(3-{[(tetrahydro-pyran-4-carbonyl)-amino]-methyl}-2,3-dihydro-benzo[1,4]dioxin-5-yl)-pyridin-4-yl]-ureido}-cyclopentyl)-carbamic acid benzyl ester | | AnalpH2_MeOH_QC_V1 Rt: 7.52 min, m/z 660.3 [M+H]+ AnalpH9_MeOH_QC_V1 Rt: 8.14 min, m/z 660.3 [M+H]+ | 6.8 mg, 3%, Light brown solid |

-continued

| | Compound | Analytical data | Mass, % yield, state |
|---|---|---|---|
| 101 ((1S,3R)-3-{3-[2-(2,3-Dihydro-benzo[1,4]dioxin-5-yl)-6-methoxy-pyridin-4-yl]-ureido}-cyclopentyl)-carbamic acid benzyl ester | | AnalpH2_MeOH_4MIN, Rt: 3.00 min; m/z 579.2 [M+H]+ | 73 mg, 55%, yellow oil |
| 102 4-(2-Dimethylamino-ethoxy)-N-[8-(4-morpholin-4-yl-pyridin-2-yl)-2,3-dihydro-benzo[1,4]dioxin-2-ylmethyl]-benzamide | | AnalpH2_MeOH_QC_V1 Rt: 3.56 min, m/z 519.3 [M+H]+ AnalpH9_MeOH_QC_V1 Rt: 7.72 min, m/z 519.3 [M+H]+ | 39.7 mg, 29%, white solid |
| 103 4-(2-Dimethylamino-ethoxy)-N-[8-(6-dimethylamino-pyridin-2-yl)-2,3-dihydro-benzo[1,4]dioxin-2-ylmethyl]-benzamide | | AnalpH2_MeOH_QC_V1 Rt: 5.28 min, m/z 477.3 [M+H]+ AnalpH9_MeOH_QC_V1 Rt: 8.35 min, m/z 477.4 [M+H]+ | 15.9 mg, 15% White solid |
| 104 4-(2-Dimethylamino-ethoxy)-N-(8-pyridin-2-yl-2,3-dihydro-benzo[1,4]dioxin-2-ylmethyl)-benzamide | | AnalpH2_MeOH_QC_V1 Rt: 3.63 min, m/z 434.3 [M+H]+ AnalpH9_MeOH_QC_V1 Rt: 7.70 min, m/z 434.3 [M+H]+ | 31 mg, 29%, white solid |
| 105 4-(2-Dimethylamino-ethoxy)-N-[8-(4-methoxy-pyridin-2-yl)-2,3-dihydro-benzo[1,4]dioxin-2-ylmethyl]-benzamide | | AnalpH2_MeOH_QC_V1 Rt: 3.63 min, m/z 434.3 [M+H]+ AnalpH9_MeOH_QC_V1 Rt: 7.70 min, m/z 434.3 [M+H]+ | 12.3 mg, 11%, Beige gummy solid |

-continued

| | Compound | Analytical data | Mass, % yield, state |
|---|---|---|---|
| 106 5-(4-Methyl-piperazin-1-ylmethyl)-furan-2-carboxylic acid [8-(4-benzyloxy-pyridin-2-yl)-2,3-dihydro-benzo[1,4]dioxin-2-ylmethyl]-amide | | AnalpH2_MeOH_QC_V1 Rt: 4.60 min, m/z 555.32 [M+H]+ AnalpH9_MeOH_QC_V1 Rt: 8.31 min, m/z 555.4 [M+H]+ 1H NMR (400 MHz, DMSO-d6): δ 8.51(t, J = 5.7 Hz, 1H) 8.44 (d, 5.6 Hz, 1H) 7.54 (d, J = 2.0 Hz, 1H) 7.45-7.32 (m, 5H) 7.03 (d, J = 3.3 Hz, 1H) 6.97-6.89 (m, 3H) 6.34 (d, J = 3.5 Hz, 1H) 5.21-5.11 (m, 2H) 4.42 (m, 1H) 4.33 (dd, J = 11.6, 2.5 Hz, 1H) 4.11 (dd, J = 11.6, 6.1 Hz, 1H) 3.65-3.45 (m, 2H) 3.42 (s, 2H) 2.48-2.17 (m, 8H) 2.13 (s, 3H) | 20.3 mg, 19%, white solid |
| 107 5-(4-methyl-piperazin-1-ylmethyl)-furan-2-carboxylic acid {8-[5-(2-morpholin-4-yl-ethoxy)-pyridin-2-yl]-2,3-dihydro-benzo[1,4]dioxin-2-ylmethyl}-amide | | AnalpH2_MeOH_QC_V1 Rt: 3.24 min, m/z 578.4 [M+H]+ AnalpH9_MeOH_QC_V1 Rt: 7.49 min, m/z 578.4 [M+H]+ | 80 mg, 35%, white solid |
| 108 5-(4-Methyl-piperazin-1-ylmethyl)-furan-2-carboxylic acid [8-(4-morpholin-4-ylmethyl-phenyl)-2,3-dihydro-benzo[1,4]dioxin-2-ylmethyl]-amide | | AnalpH2_MeOH_QC_V1 Rt: 3.24 min, m/z 578.4 [M+H]+ AnalpH9_MeOH_QC_V1 Rt: 7.49 min, m/z 578.4 [M+H]+ | 11.7 mg, 13%, off white solid |

-continued

| | Compound | Analytical data | Mass, % yield, state |
|---|---|---|---|
| 109 5-(4-Methyl-piperazin-1-ylmethyl)-furan-2-carboxylic acid [8-(5-benzyloxy-pyridin-2-yl)-2,3-dihydro-benzo[1,4]dioxin-2-ylmethyl]-amide | | AnalpH2_MeOH_QC_V1 Rt: 5.59 min, m/z 555.3 [M+H]+ AnalpH9_MeOH_QC_V1 Rt: 8.18 min, m/z 555.3 [M+H]+ | 31.5 mg, 32%, White solid |
| 110 {8-[5-(2-Morpholin-4-yl-ethoxy)-pyridin-2-yl]-2,3-dihydro-benzo[1,4]dioxin-2-yl}-methanol | | AnalpH2_MeOH_QC_V1 Rt: 3.40 min, m/z 373.3 [M+H]+ AnalpH9_MeOH_QC_V1 Rt: 6.92 min, m/z 373.3 [M+H]+ | 59.9 mg, 49%, light brown solid |
| 111 Tetrahydro-pyran-4-carboxylic acid {8-[5-(2-morpholin-4-yl-ethoxy)-pyridin-2-yl]-2,3-dihydro-benzo[1,4]dioxin-2-ylnethyl}-amide | | AnalpH2_MeOH_QC_V1 Rt: 3.99 min, m/z 484.2 [M+H]+ AnalpH9_MeOH_QC_V1 Rt: 7.08 min, m/z 484.4 [M+H]+ | 41 mg, 39%, white solid |
| 112 Tetrahydro-pyran-4-carboxylic acid {(R)-8-[5-(3-dimethylamino-methyl-phenylamino)-6-methoxy-pyridin-2-yl]-2,3-dihydro-benzo[1,4]dioxin-2-ylmethyl}-amide | | AnalpH2_MeOH_QC_V1 Rt: 5.79 min, m/z 533.3 [M+H]+ AnalpH9_MeOH_QC_V1 Rt: 8.29 min, m/z 533.3 [M+H]+ | 5 mg, 5%, white solid |

-continued

| | Compound | Analytical data | Mass, % yield, state |
|---|---|---|---|
| 113 N-[6-(2,3-Dihydro-benzo[1,4]dioxin-5-yl)-2-methoxy-pyridin-3-yl]-2-(1-methyl-piperidin-4-yl)-acetamide | | AnalpH2_MeOH_QC_V1 Rt: 5.29 min, m/z 398.3 [M+H]+ AnalpH9_MeOH_QC_V1 Rt: 7.93 min, m/z 398.3 [M+H]+ | 47.6 mg, 68%, white solid |
| 114 5-(4-Methyl-piperazin-1-ylmethyl)-furan-2-carboxylic acid [(R)-8-(4-amino-6-methoxy-pyridin-2-yl)-2,3-dihydro-benzo[1,4]dioxin-2-ylmethyl]-amide | | AnalpH2_MeOH_QC_V1 Rt: 3.16 min, m/z 494.3 [M+H]+ AnalpH9_MeOH_QC_V1 Rt: 7.22 min, m/z 494.3 [M+H]+ | 35 mg, 19%, white solid |
| 115 Tetrahydro-pyran-4-carboxylic acid [(S)-8-(5-chloro-6-methoxy-pyridin-2-yl)-2,3-dihydro-benzo[1,4]dioxin-2-ylmethyl]-amide | | used directly in subsequent reaction | 96 mg, 31%, pale orange solid |
| 116 {4-[2-Methoxy-6-(3-{[(tetrahydro-pyran-4-carbonyl)-amino]-methyl}-2,3-dihydro-benzo[1,4]dioxin-5-yl)-pyridin-3-ylamino]-benzyl}-carbamic acid tert-butyl ester | | used directly in subsequent reaction | 270 mg, 40%, white solid |

Example 117: Synthesis of tetrahydro-pyran-4-carboxylic acid {8-[5-(4-aminomethyl-phenylamino)-6-methoxy-pyridin-2-yl]-2,3-dihydro-benzo[1,4]dioxin-2-ylmethyl}-amide AnalpH2_MeOH_4MIN, Rt: 2.14 min, m/z 505.5 [M+H]+

General scheme 8

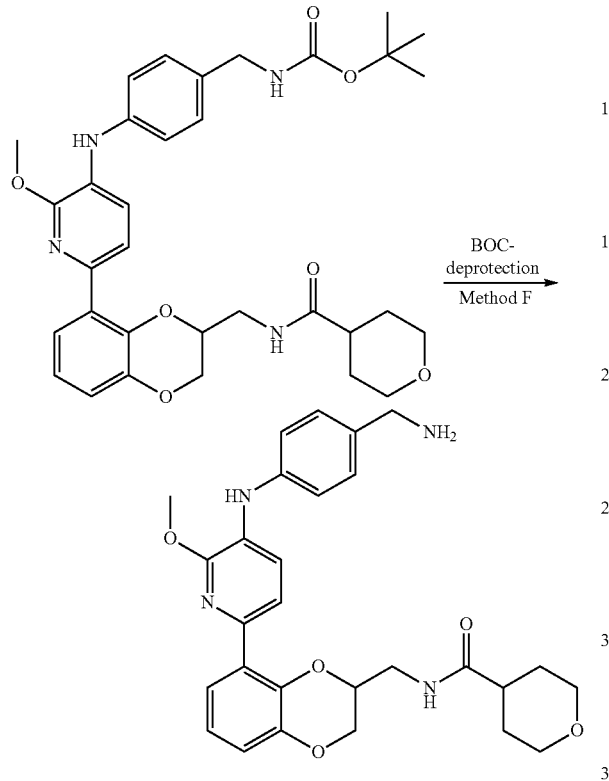

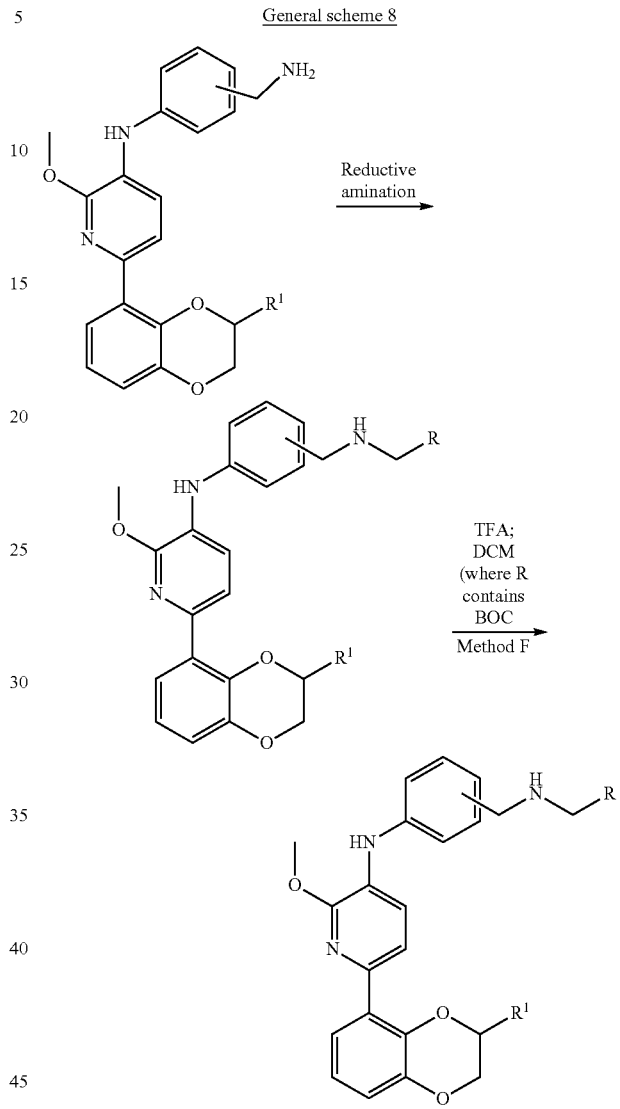

To a solution of {4-[2-methoxy-6-(3-{[(tetrahydro-pyran-4-carbonyl)-amino]-methyl}-2,3-dihydro-benzo[1,4]dioxin-5-yl)-pyridin-3-ylamino]-benzyl}-carbamic acid tert-butyl ester (270 mg, 0.45 mMol, 1.0 eq.) at was added trifluoroacetic acid and the reaction was stirred at RT for 2 h. The reaction was concentrated in vacuo and the resulting residue was loaded onto a SCX cartridge, washed with methanol then eluted with 0.5 M ammonia in methanol. The ammonia in methanol fractions were concentrated in vacuo to give a colourless gum which was dissolved in H2O/MeCN (1:1) and evaporated in the freeze drier to give (4-aminomethyl-phenyl)-[6-(2,3-dihydro-benzo[1,4]dioxin-5-yl)-2-methoxy-pyridin-3-yl]-amine (187 mg, 0.37 mMol, 83%) as a white solid.

The following compounds were made using general method E:

| | Compound | | Analytical data | Mass, % yield, state |
|---|---|---|---|---|
| 118 | Tetrahydro-pyran-4-carboxylic acid {8-[6-methoxy-5-(4-{[(pyridin-2-ylmethyl)-amino]-methyl}-phenylamino)-pyridin-2-yl]-2,3-dihydro-benzo[1,4]dioxin-2-ylmethyl}-amide | | AnalpH2_MeOH_QC_V1: Rt: 5.91 min, m/z 596.5 [M + H]+ AnalpH9_MeOH_QC_V1: Rt: 7.97 min, m/z 596.5 [M + H]+ | 17.3 mg, 33%, white solid |

| | | Compound | Analytical data | Mass, % yield, state |
|---|---|---|---|---|
| 119 | Tetrahydro-pyran-4-carboxylic acid {8-[6-methoxy-5-(4-{[(pyridin-4-ylmethyl)-amino]-methyl}-phenylamino)-pyridin-2-yl]-2,3-dihydro-benzo[1,4]dioxin-2-ylmethyl}-amide | | AnalpH2_MeOH_QC_V1: Rt: 5.58 min, m/z 596.5 [M + H]+ <br> AnalpH9_MeOH_QC_V1: Rt: 7.93 min, m/z 596.5 [M + H]+ | 29.3 mg, 55%, white solid |
| 120 | Tetrahydro-pyran-4-carboxylic acid {8-[6-methoxy-5-(4-{[(2H-pyrazol-3-ylmethyl)-amino]-methyl}-phenylamino)-pyridin-2-yl]-2,3-dihydro-benzo[1,4]dioxin-2-ylmethyl}-amide | | AnalpH2_MeOH_QC_V1: Rt: 5.71 min, m/z 585.6 [M + H]+ <br> AnalpH9_MeOH_QC_V1: Rt: 7.70 min, m/z 585.5 [M + H]+ | 13.2 mg, 25%, white solid |
| 121 | 3-({4-[2-Methoxy-6-(3-{[(tetrahydro-pyran-4-carbonyl)-amino]-methyl}-2,3-dihydro-benzo[1,4]dioxin-5-yl)-pyridin-3-ylamino]-benzylamino}-methyl)-morpholine-4-carboxylic acid tert-butyl ester | | AnalpH9_MeOH_4MIN: Rt: 2.51 min, m/z 704.6 [M + H]+ | 38 mg, 52%, white solid |

| | Compound | | Analytical data | Mass, % yield, state |
|---|---|---|---|---|
| 122 | (R)-3-({4-[6-(2,3-Dihydro-benzo[1,4]dioxin-5-yl)-2-methoxy-pyridin-3-ylamino]-benzylamino]-methyl)-morpholine-4-carboxylic acid tert-butyl ester | | AnalpH2_MeOH_4MIN: Rt: 2.57 min, m/z 563.3 [M + H]+ | 71 mg, 47% colourless oil |
| 123 | (S)-3-({4-[6-(2,3-Dihydro-benzo[1,4]dioxin-5-yl)-2-methoxy-pyridin-3-ylamino]-benzylamino}-methyl)-morpholine-4-carboxylic acid tert-butyl ester | | AnalpH2_MeOH_4MIN: Rt: 2.57 min, m/z 563.3 [M + H]+ | 66 mg, 43%, colourless oil |
| 124 | 4-({3-[6-(2,3-Dihydro-benzo[1,4]dioxin-5-yl)-2-methoxy-pyridin-3-ylamino]-benzylamino}-methyl)-pyrazole-1-carboxylic acid tert-butyl ester | | AnalpH2_MeOH_4MIN: Rt: 2.53 min, m/z 544.3 [M + H]+ | 50 mg, 43%, white solid |

-continued

| | Compound | | Analytical data | Mass, % yield, state |
|---|---|---|---|---|
| 125 | 3-({4-[4-2,3-Dihydro-benzo[1,4]dioxin-5-yl)-2-methoxy-phenylamino]-benzylamino}-methyl)-morpholine-4-carboxylic acid tert-butyl ester | 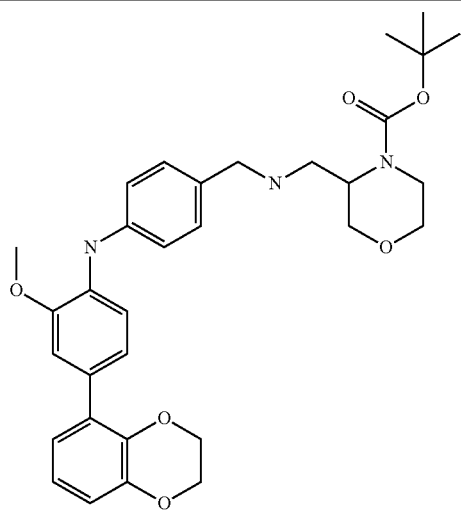 | AnalpH2_MeOH_4MIN: Rt: 2.57 min, m/z 562 [M + H]+ | 120 mg, 59%, orange oils |

Boc Deprotection:
The following compounds were prepared using general method F

| | Compound | | Analytical data | Mass, % yield, state |
|---|---|---|---|---|
| 126 | [6-(2,3-Dihydro-benzo[1,4]dioxin-5-yl)-2-methoxy-pyridin-3-yl]-(3-{[(1H-pyrazol-4-ylmethyl)-amino]-methyl}-phenyl)-amine | | AnalpH2_MeOH_QC_V1: Rt: 5.94 min, m/z 444.2 [M + H]+ AnalpH9_MeOH_QC_V1: Rt: 7.92 min, m/z 444.2 [M + H]+ | 19.7 mg, 48%, white solid |
| 127 | Tetrahydro-pyran-4-carboxylic acid{8-[6-methoxy-5-(4-{[(morpholin-3-ylmethyl)-amino]-methyl}-phenylamino)-pyridin-2-yl]-2,3-dihydro-benzo[1,4]dioxin-2-ylmethyl}-amide | 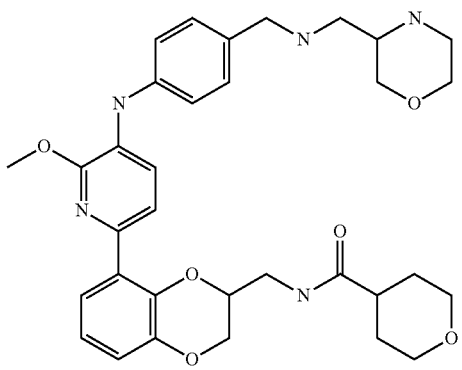 [SMILES: COc1nc(-c2cccc3c2OC(CNC(=O)C2CCOCC2)CO3)ccc1Nc1ccc(CNCC2COCCN2)cc1] | AnalpH2_MeOH_QC_V1: Rt: 4.80 min, m/z 604.4 [M + H]+ AnalpH9_MeOH_QC_V1: Rt: 7.76 min, m/z 604.4 [M + H]+ | 19.2 mg, 59%, white solid |

-continued

| | Compound | | Analytical data | Mass, % yield, state |
|---|---|---|---|---|
| 128 | [6-(2,3-Dihydro-benzo[1,4]dioxin-5-yl)-2-methoxy-pyridin-3-yl]-(4-{[((R)-1-morpholin-3-ylmethyl)-amino]-methyl}-phenyl)-amine | | AnalpH2_MeOH_QC_V1: Rt: 4.84 min, m/z 463.2 [M + H]+ AnalpH9_MeOH_QC_V1: Rt: 8.13 min, m/z 463.3 [M + H]+ | 20.1 mg, 34%, pale yellow solid |
| 129 | [6-(2,3-Dihydro-benzo[1,4]dioxin-5-yl)-2-methoxy-pyridin-3-yl]-(4-{[((S)-1-morpholin-3-ylmethyl)-amino]-methyl}-phenyl)-amine | | AnalpH2_MeOH_QC_V1: Rt: 4.83 min, m/z 463.2 [M + H]+ AnalpH9_MeOH_QC_V1: Rt: 8.13 min, m/z 463.3 [M + H]+ | 26.4 mg, 49%, white solid |
| 130 | Morpholine-2-carboxylic acid{2-methoxy-6-[(R)-3-({[5-(4-methyl-piperazin-1-ylmethyl)-furan-2-carbonyl]-amino}-methyl)-2,3-dihydro-benzo[1,4]dioxin-5-yl]-pyridin-4-yl}-amide | | AnalpH2_MeOH_QC_V1: Rt: 4.12 min, m/z 607.3 [M + H]+ AnalpH9_MeOH_QC_V1: Rt: 7.87 min, m/z 607.3 [M + H]+ | 23 mg, 67%, white solid |
| 131 | (R)-Pyrrolidine-2-carboxylic acid{2-methoxy-6-[3-({[5-(4-methyl-piperazin-1-ylmethyl)-furan-2-carbonyl]-amino}-methyl)-2,3-dihydro-benzo[1,4]dioxin-5-ylamino]-pyridin-3-yl}-amide | | AnalpH2_MeOH_QC_V1: Rt: 4.18 min, m/z 606.3 [M + H]+ AnalpH9_MeOH_QC_V1: Rt: 8.07 min, m/z 606.3 [M + H]+ | 9.2 mg, 46%, off white solid |

| | Compound | | Analytical data | Mass, % yield, state |
|---|---|---|---|---|
| 132 | [4-(2,3-Dihydro-benzo[1,4]dioxin-5-yl)-2-methoxy-phenyl]-(4-{[(morpholin-3-ylmethyl)-amino]-methyl}-phenyl)-amine | 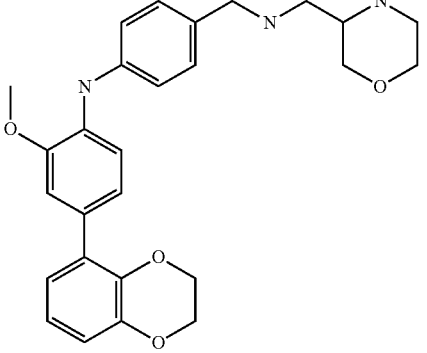 | AnalpH2_MeOH_QC_V1: Rt: 4.96 min, m/z 462.3 [M + H]+ AnalpH9_MeOH_QC-V1: Rt: 7.89 min, m/z 462.3 [M + H]+ 1H NMR(400 MHz, DMSO-d6): δ 7.34(s, 1H) 7.17(dd, J = 8.3, 3.2 Hz, 3H)7.05(d, J = 8.2 Hz, 2H)6.99(dd, J = 8.1, 1.9 Hz, 1H)6.91-6.78(m, 3H) 4.28-4.22(m, 4H)3.84(s, 3H)3.69(dd, J = 10.9, 3.0 Hz, 1H)3.65-3.57(m, 3H) 3.33-3.31(m, 1H)3.04(t, J = 10.2 Hz, 1H) 2.78-2.65 (m, 3H) 2.54-2.52 (m, 1H) 2.39 (m, 1H) | 10 mg, 20%, pink solid |
| 133 | (1R,3S)-3-Amino-cyclopentanecarboxylic acid[2-(2,3-dihydro-benzo[1,4]dioxin-5-yl)-6-methoxy-pyridin-4-yl]-amide | 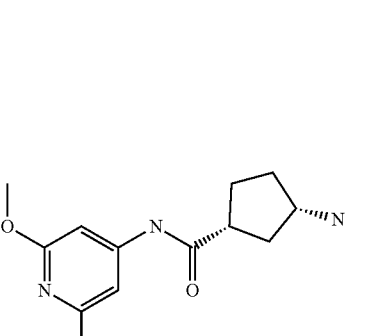 | AnalpH2_MeOH_QC_V1: Rt: 4.77 min, m/z 370.3 [M + H]+ AnalpH9_MeOH_QC_V1: Rt: 7.28 min, m/z 370.3 [M + H]+ | 7 mg, 27%, light brown solid |

Example 134: Synthesis of (R)-2-{2-Methoxy-6-[3-({[5-(4-methyl-piperazin-1-ylmethyl)-furan-2-carbonyl]-amino}-methyl)-2,3-dihydro-benzo[1,4]dioxin-5-ylamino]-pyridin-3-ylcarbamoyl}-pyrrolidine-1-carboxylic acid tert-butyl ester

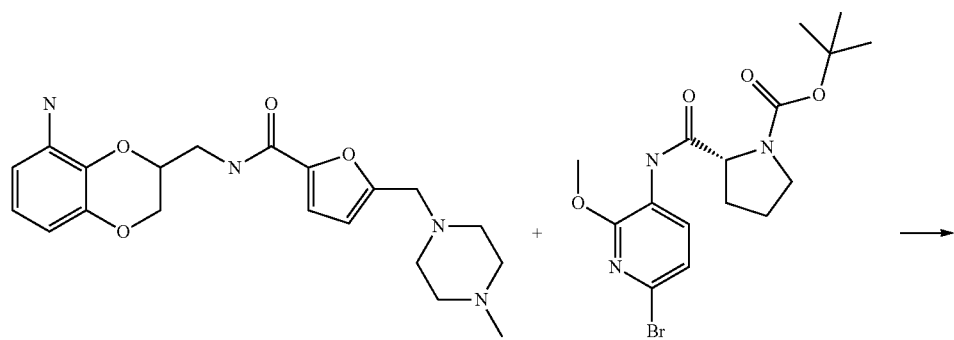

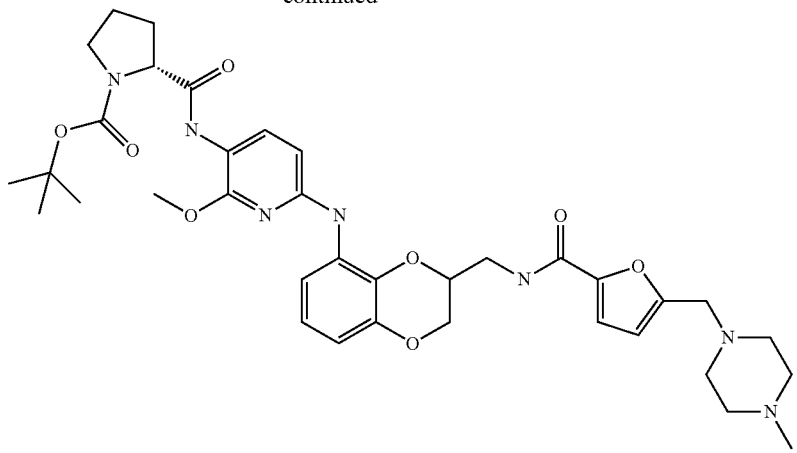

A mixture of 5-(4-methyl-piperazin-1-ylmethyl)-furan-2-carboxylic acid (8-amino-2,3-dihydro-benzo[1,4]dioxin-2-ylmethyl)-amide (157 mg, 0.4 mMol, 1.3 eq.), (R)-2-(6-bromo-2-methoxy-pyridin-3-ylcarbamoyl)-pyrrolidine-1-carboxylic acid tert-butyl ester (125 mg, 0.31 mMol, 1 eq.), $Pd_2(dba)_3$ (29 mg, 0.03 mMol, 0.1 eq.), DavePhos (25 mg, 0.06 mMol, 0.2 eq.) and $NaO^tBu$ (45 mg, 0.47 mMol, 1.5 eq.) in dry 1,4 dioxane was purged with $N_2$ for 10 min. The reaction mixture was heated at 100° C. for 0.5 h, concentrated in vacuo and the resulting residue was loaded onto a SCX cartridge, washed with methanol then eluted with 0.5 M ammonia in methanol. The fractions containing product were combined, concentrated in vacuo and purified by reverse phase preparative HPLC to give (R)-2-{2-Methoxy-6-[3-({[5-(4-methyl-piperazin-1-ylmethyl)-furan-2-carbonyl]-amino}-methyl)-2,3-dihydro-benzo[1,4]dioxin-5-ylamino]-pyridin-3-ylcarbamoyl}-pyrrolidine-1-carboxylic acid tert-butyl ester (17 mg, 0.024 mMol, 8%).

AnalpH2_MeOH_4 min, Rt: 2.54 min; m/z 706.3 $[M+H]^+$

Example 135: Synthesis of Tetrahydro-pyran-4-carboxylic acid [3-(3-{4-[3-((1R,3S)-3-amino-cyclopentyl)-ureido]-6-methoxy-pyridin-2-yl}-2-hydroxy-phenoxy)-propyl]-amide

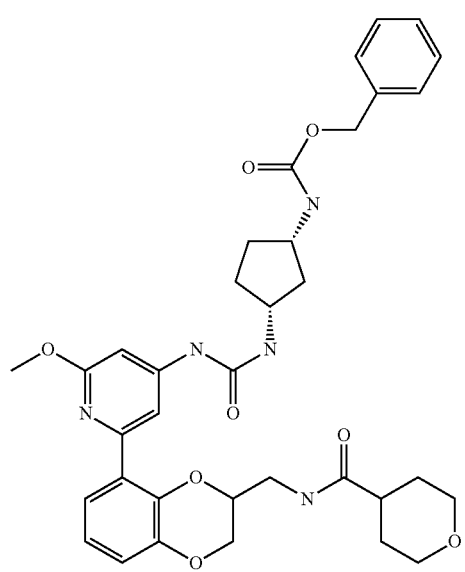

→

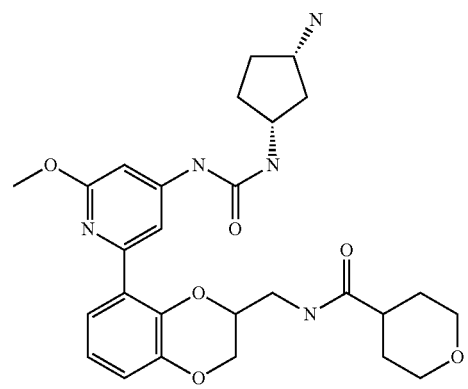

A mixture of ((1S,3R)-3-{3-[2-methoxy-6-(3-{[(tetra-hydro-pyran-4-carbonyl)-amino]-methyl}-2,3-dihydro-benzo[1,4]dioxin-5-yl)-pyridin-4-yl]-ureido}-cyclopentyl)-carbamic acid benzyl ester (20.7 mg, 0.03 mMol) and 10% palladium on carbon (60 mg) in EtOH (20 mL) and 4 M HCl in dioxane (0.1 mL) were stirred under an atmosphere of $H_2$ at RT for 4 h. The reaction mixture was filtered through celite washing with MeOH and the filtrate concentrated in vacuo to yield the crude material which was purified by reverse phase preparative HPLC-MS to afford tetrahydro-pyran-4-carboxylic acid [3-(3-{4-[3-((1R,3S)-3-amino-cyclopentyl)-ureido]-6-methoxy-pyridin-2-yl}-2-hydroxy-phenoxy)-propyl]-amide (10.1 mg, 0.029 mMol, 64%)

AnalpH2_MeOH_QC_V1: Rt: 4.52 min, m/z 526.4 $[M+H]^+$

AnalpH9_MeOH_QC_V1: Rt: 7.37 min, m/z 526.4 $[M+H]^+$

Example 136: Synthesis of 1-((1R,3S)-3-Amino-cyclopentyl)-3-[2-(2,3-dihydro-benzo[1,4]dioxin-5-yl)-6-methoxy-pyridin-4-yl]-urea

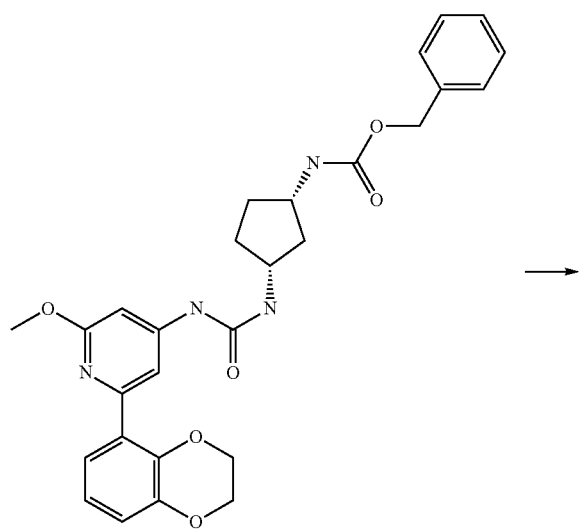

A mixture of ((1S,3R)-3-{3-[2-(2,3-dihydro-benzo[1,4]dioxin-5-yl)-6-methoxy-pyridin-4-yl]-ureido}-cyclopentyl)-carbamic acid benzyl ester (73 mg, 0.14 mMol) and 10% palladium on carbon (32 mg) in EtOH (20 mL) and 4 M HCl in dioxane (0.2 mL) were stirred under an atmosphere of $H_2$ at RT for 18 h. The reaction mixture was filtered through celite washing with MeOH and the filtrate concentrated in vacuo to yield the crude material which was purified by reverse phase preparative HPLC-MS to afford 1-((1R,3S)-3-amino-cyclopentyl)-3-[2-(2,3-dihydro-benzo[1,4]dioxin-5-yl)-6-methoxy-pyridin-4-yl]-urea (22 mg, 0.057 mMol, 40.8%).

AnalpH9_MeOH_QC_V1: Rt: 7.03 min, m/z 385.3 [M+H]$^+$

AnalpH2_MeOH_QC_V1: Rt: 4.08 min, m/z 385.3 [M+H]$^+$

Example 137: Synthesis of 5-(4-Methyl-piperazin-1-ylmethyl)-furan-2-carboxylic acid [8-(1-methyl-1H-imidazol-4-yl)-2,3-dihydro-benzo[1,4]dioxin-2-ylmethyl]-amide using General method M

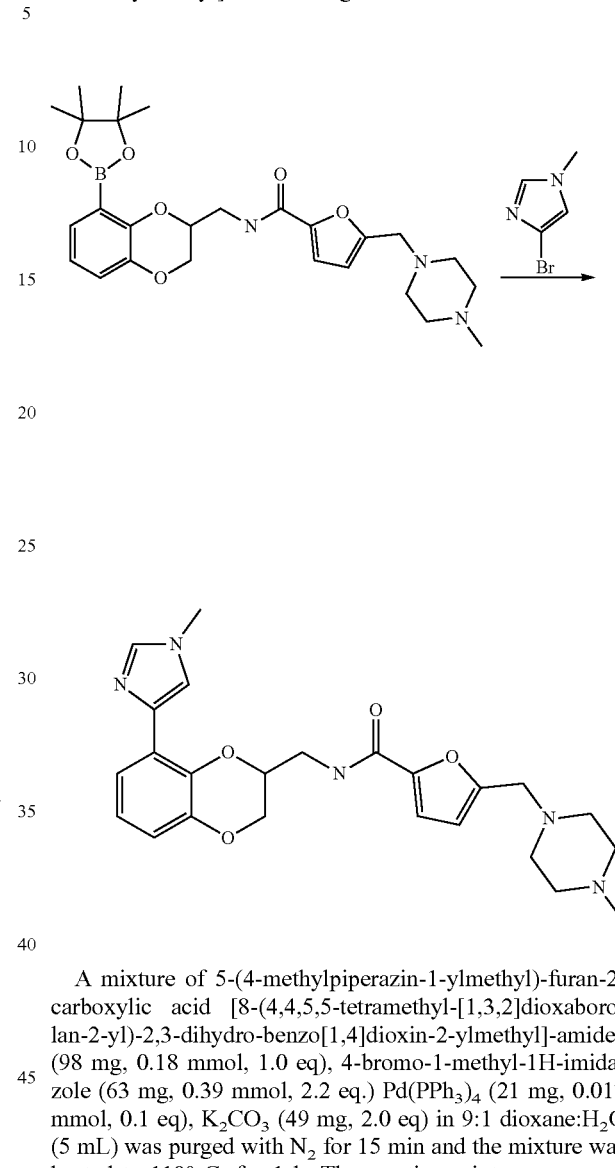

A mixture of 5-(4-methylpiperazin-1-ylmethyl)-furan-2-carboxylic acid [8-(4,4,5,5-tetramethyl-[1,3,2]dioxaborolan-2-yl)-2,3-dihydro-benzo[1,4]dioxin-2-ylmethyl]-amide (98 mg, 0.18 mmol, 1.0 eq), 4-bromo-1-methyl-1H-imidazole (63 mg, 0.39 mmol, 2.2 eq.) Pd(PPh$_3$)$_4$ (21 mg, 0.017 mmol, 0.1 eq), $K_2CO_3$ (49 mg, 2.0 eq) in 9:1 dioxane:$H_2O$ (5 mL) was purged with $N_2$ for 15 min and the mixture was heated to 110° C. for 1 h. The reaction mixture was concentrated under reduced pressure and the residue dissolved in MeOH and loaded onto a SCX-2 cartridge. The cartridge was washed with MeOH, and the compound eluted using 0.5M ammonia in methanol. The product-containing fractions were concentrated under reduced pressure to yield the crude material which was purified by prep HPLC to give 5-(4-methyl-piperazin-1-ylmethyl)-furan-2-carboxylic acid [8-(1-methyl-1H-imidazol-4-yl)-2,3-dihydro-benzo[1,4]dioxin-2-ylmethyl]-amide (13.3 mg, 16.4%) as an off-white solid AnalpH9_MeOH_QC_V1: Rt: 6.93 min, m/z 452.4 [M+H]+

$^1$H NMR (400 MHz, DMSO-d6): δ 8.65 (t, J=6.0 Hz, 1H) 7.62-7.57 (m, 3H) 7.13 (d, J=3.5 Hz, 1H) 6.82 (t, J=7.3 Hz, 1H) 6.70 (dd, J=7.8, 1.5 Hz, 1H) 6.46 (d, J=3.3 Hz, 1H) 4.42-4.35 (m, 2H) 3.97 (dd, J=11.9, 8.6 Hz, 2H) 3.77-3.68 (m, 1H) 3.56 (s, 3H) 3.51 (s, 2H) 2.48-2.20 (m, 8H) 2.16 (s, 3H)

The following compounds were prepared using General Method M:

| | Compound | | Analytical data | Mass, % yield, state |
|---|---|---|---|---|
| 138 | 5-(4-Methyl-piperazin-1-ylmethyl)-furan-2-carboxylic acid[8-(1-benzyl-1H-imidazol-4-yl)-2,3-dihydro-benzo[1,4]dioxin-2-ylmethy]-amide | | AnalpH2_MeOH_QC_V1: Rt: 4.38 min, m/z 528.4[M + H]+ AnalpH9_MeOH_QC_V1: Rt: 7.69 min, m/z 528.4[M + H]+ 1H NMR(400 MHz, DMSO-d6): δ 8.64(t, J = 6.0 Hz, 1H)7.75 (dd, J = 9.3, 1.0 Hz, 2H)7.61(dd, J = 7.8, 1.8 Hz, 1H)7.36-7.25 (m, 5H)7.08(d, J = 3.3 Hz,1H)6.83 (t, J = 7.8 Hz, 1H) 6.72(dd, J = 8.1, 1.8 Hz, 1H)6.42(d, J = 3.5 Hz, 1H)5.16-5.06(m, 2H)4.42-4.38(m, 2H)4.02-3.95(m, 1H)3.76-3.66(m, 1H)3.61-3.52(m, 1H) 3.46(s, 2H)2.48-2.17(m, 8H)2.12(s, 3H) | 9.9 mg, 19%, white solid |
| 139 | 5-(4-Chloro-phenyl)-2,3-dihydro-benzo[1,4]dioxine | | AnalpH2_MeOH_4MIN: Rt: 3.45 min | 425 mg, 78%, colourless oil |

Example 140: Synthesis of tetrahydro-pyran-4-carboxylic acid {8-[4-(3-dimethylaminomethyl-phenylamino)-pyridin-2-yl]-2,3-dihydro-benzo[1,4]dioxin-2-ylmethyl}-amide

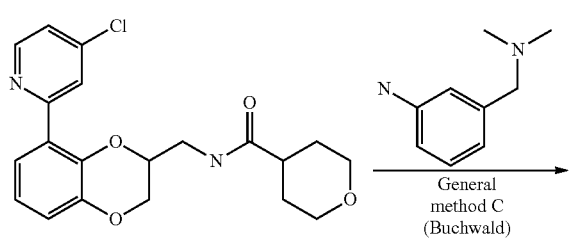

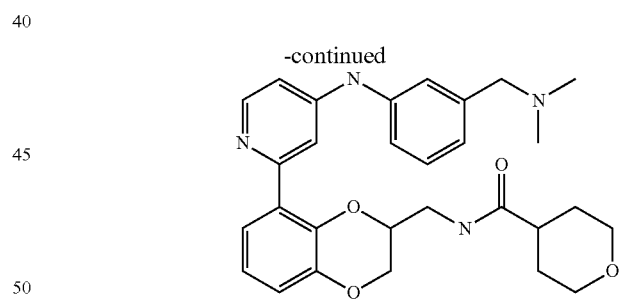

The title compound was synthesised using tetrahydro-pyran-4-carboxylic acid [8-(4-chloro-pyridin-2-yl)-2,3-dihydro-benzo[1,4]dioxin-2-ylmethyl]-amide and 3-[(dimethylamino)methyl]aniline using General method C (Buchwald-Hartwig cross coupling using Pd catalyst and phosphine ligand) to afford tetrahydro-pyran-4-carboxylic acid {8-[4-(3-dimethylaminomethyl-phenylamino)-pyridin-2-yl]-2,3-dihydro-benzo[1,4]dioxin-2-ylmethyl}-amide (12.7 mg, 11%) as a white solid.

AnalpH2_MeOH_QC_V1: Rt: 3.58 min, m/z 503.4 [M+H]+

AnalpH9_MeOH_QC_V1: Rt: 7.83 min, m/z 503.4 [M+H]+

Example 141: Synthesis of tetrahydro-pyran-4-carboxylic acid (8-{5-[3-((1S,3R)-3-amino-cyclopentyl)-ureido]-6-methoxy-pyridin-2-yl}-2,3-dihydro-benzo[1,4]dioxin-2-ylmethyl)-amide

Example 142: Synthesis of tetrahydro-pyran-4-carboxylic acid (8-{4-[3-((1R,3S)-3-amino-cyclopentyl)-ureido]-pyridin-2-yl}-2,3-dihydro-benzo[1,4]dioxin-2-ylmethyl)-amide

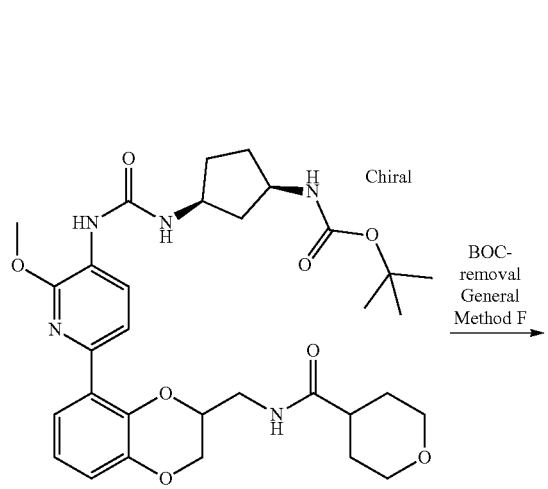

BOC-removal General Method F

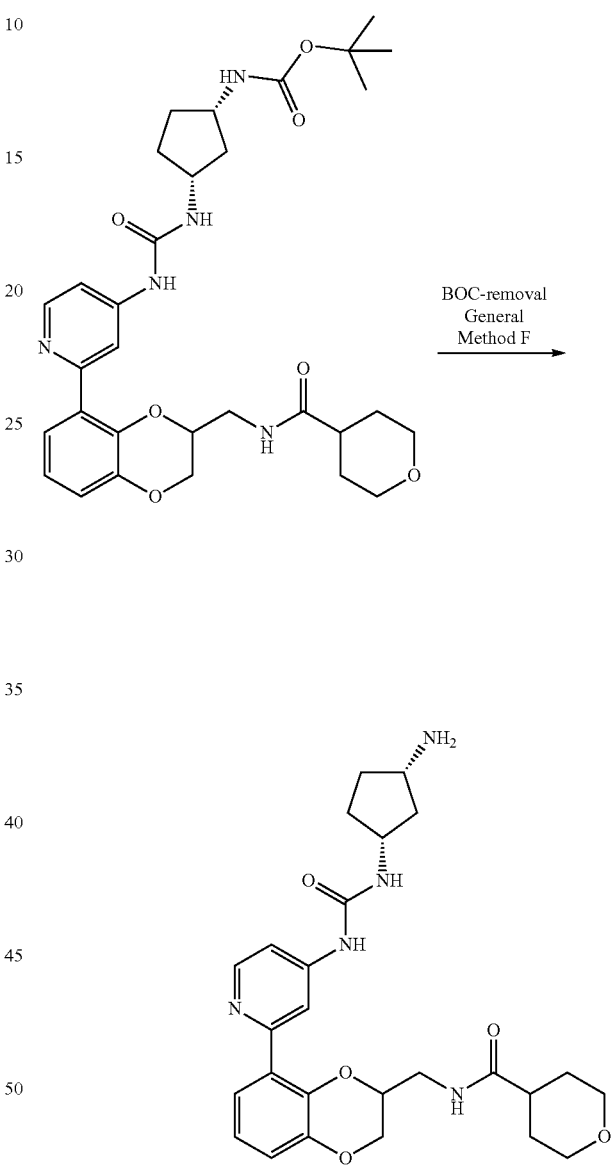

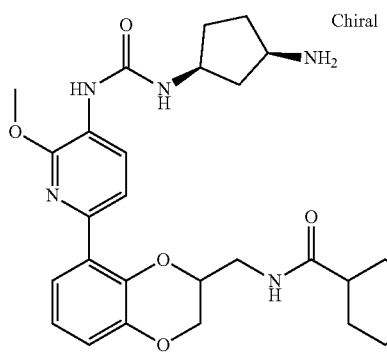

The title compound was synthesised from ((1R,3S)-3-{3-[2-methoxy-6-(3-{[(tetrahydro-pyran-4-carbonyl)-amino]-methyl}-2,3-dihydro-benzo[1,4]dioxin-5-yl)-pyridin-3-yl]-ureido}-cyclopentyl)-carbamic acid tert-butyl ester using general method F. The compound was purified by reverse phase preparative HPLC-MS to afford tetrahydro-pyran-4-carboxylic acid (8-{5-[3-((1S,3R)-3-amino-cyclopentyl)-ureido]-6-methoxy-pyridin-2-yl}-2,3-dihydro-benzo[1,4]dioxin-2-ylmethyl)-amide as a white solid (31.1 mg, 27%).

AnalpH2_MeOH_QC_V1: Rt: 5.46 min, m/z 526.4 [M+H]+

AnalpH9_MeOH_QC_V1: Rt: 7.25 min, m/z 526.3 [M+H]+

The title compound was synthesised from ((1S,3R)-3-{3-[2-(3-{[(tetrahydro-pyran-4-carbonyl)-amino]-methyl}-2,3-dihydro-benzo[1,4]dioxin-5-yl)-pyridin-4-yl]-ureido}-cyclopentyl)-carbamic acid tert-butyl ester using general method F with workup D. The compound was purified by reverse phase preparative HPLC-MS to afford tetrahydro-pyran-4-carboxylic acid (8-{4-[3-((1R,3S)-3-amino-cyclopentyl)-ureido]-pyridin-2-yl}-2,3-dihydro-benzo[1,4]dioxin-2-ylmethyl)-amide (16.1 mg, 20%) as a white solid.

AnalpH2_MeOH_QC_V1: Rt: 3.53 min, m/z 496.4 [M+H]+

AnalpH9_MeOH_QC_V1: Rt: 6.83 min, m/z 496.4 [M+H]+

169

Route to [4-(2,3-Dihydro-benzo[1,4]dioxin-5-yl)-piperazin-1-yl]-(3-dimethylaminomethyl-phenyl)-methanone

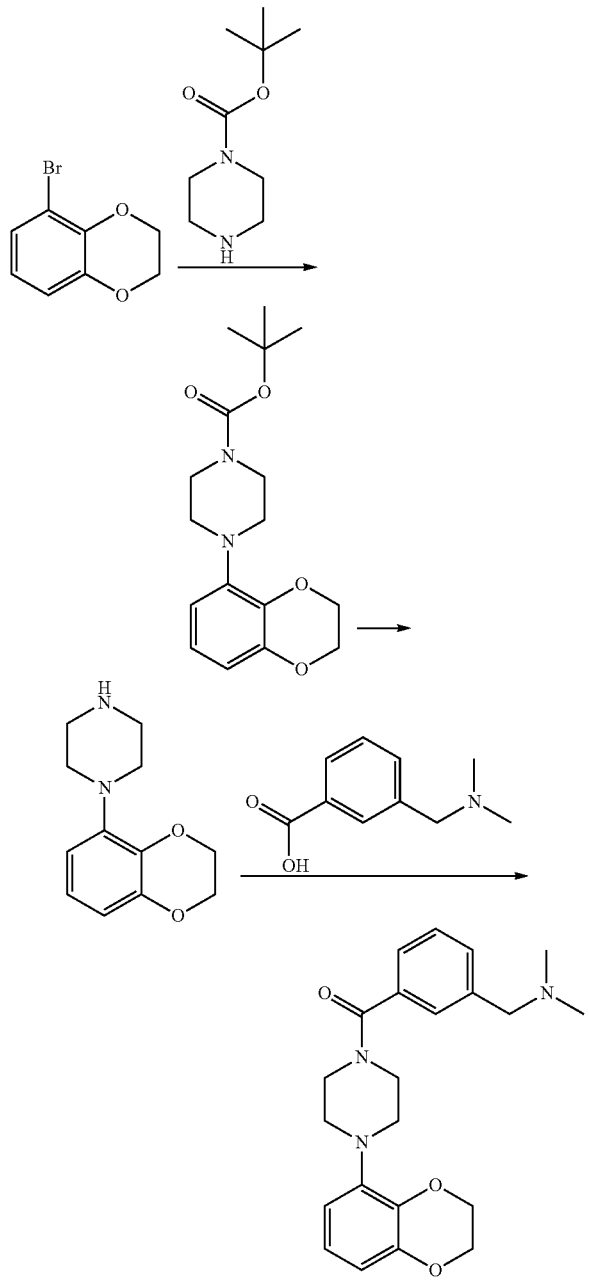

Synthesis of 4-(2,3-Dihydro-benzo[1,4]dioxin-5-yl)-piperazine-1-carboxylic acid tert-butyl ester The title compound was prepared from 5-bromo-2,3-dihydro-benzo[1,4]dioxine (500 mg, 2.33 mmol) and 1-BOC-piperazine (434 mg, 2.33 mmol) using general method C (Buchwald coupling) to afford 4-(2,3-dihydro-benzo[1,4]dioxin-5-yl)-piperazine-1-carboxylic acid tert-butyl ester (505 mg, 1.58 mmol, 68%) as a brown oil.

AnalpH2_MeOH_4 min; Rt: 3.22 min; m/z 321 [M+H]$^+$

170

Synthesis of 1-(2,3-Dihydro-benzo[1,4]dioxin-5-yl)-piperazine

The title compound was prepared from 4-(2,3-dihydro-benzo[1,4]dioxin-5-yl)-piperazine-1-carboxylic acid tert-butyl ester (505 mg, 1.58 mmol) using general BOC-deprotection method F to afford 1-(2,3-dihydro-benzo[1,4]dioxin-5-yl)-piperazine (348 mg, 1.58 mmol, 100%) as a black solid AnalpH2_MeOH_4 min; Rt: 1.10/1.22 min, m/z 221 [M+H]$^+$ Example 156: Synthesis of [4-(2,3-Dihydro-benzo[1,4]dioxin-5-yl)-piperazin-1-yl]-(3-dimethylaminomethyl-phenyl)-methanone The title compound was prepared from 1-(2,3-dihydro-benzo[1,4]dioxin-5-yl)-piperazine (100 mg, 0.454 mmol) and 3-dimethylaminomethyl benzoic acid (82 mg, 0.45 mmol) using general method D (amide coupling) to afford [4-(2,3-dihydro-benzo[1,4]dioxin-5-yl)-piperazin-1-yl]-(3-dimethylaminomethyl-phenyl)-methanone (35 mg, 0.091 mmol, 20%) as a yellow oil.

AnalpH9_MeOH_QC_V1; Rt: 7.41 min, m/z 382.3 [M+H]$^+$

AnalpH2_MeOH_QC_V1; Rt: 4.55 min, m/z 382.3 [M+H]$^+$

Example 157: Synthesis of {3-[4-(2,3-Dihydro-benzo[1,4]dioxin-5-yl)-piperazin-1-ylmethyl]-benzyl}-dimethyl-amine

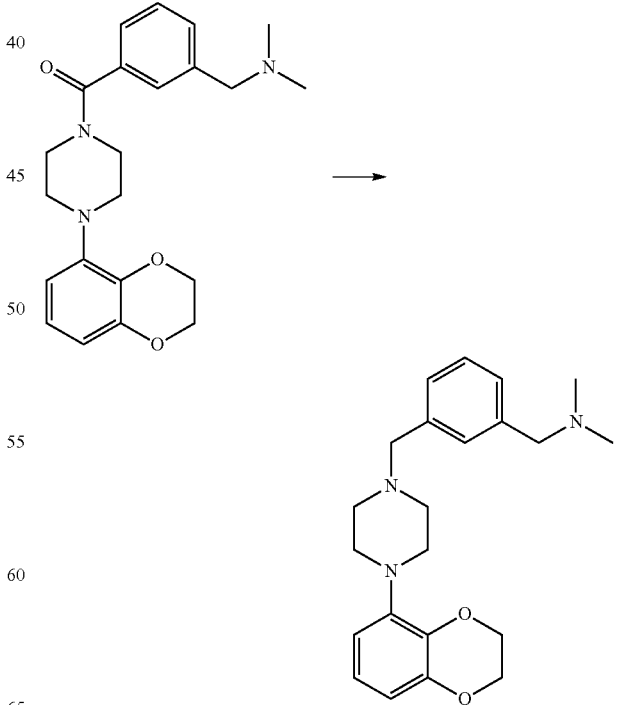

A solution of [4-(2,3-dihydro-benzo[1,4]dioxin-5-yl)-piperazin-1-yl]-(3-dimethylaminomethyl-phenyl)-methanone (20 mg, 0.053 mmol) in THF (10 ml) was cooled to 0° C. and purged with $N_2$ for 15 min. $LiAlH_4$ (1M in THF, 250 µl, 0.25 mmol) was added dropwise and the reaction mixture was stirred at RT overnight. The reaction was quenched with $Na_2CO_3$ (1.0M aq solution, 10 ml). The resulting mixture was extracted with DCM (3×10 mL), dried over $MgSO_4$, filtered and the solvent removed under reduced pressure. The crude product was purified by prep HPLC to afford {3-[4-(2,3-dihydro-benzo[1,4]dioxin-5-yl)-piperazin-1-yl-methyl]-benzyl}-dimethyl-amine (16 mg, 0.044 mmol, 83%) as a yellow oil.

AnalpH9_MeOH_QC_V1; Rt: 8.15 min, m/z 368.3 [M+H]+

AnalpH2_MeOH_QC_V1; Rt: 2.81/2.89 min, m/z ES+368.3 [M+H]+

$^1$H NMR (CDCl$_3$, 400 MHz) δ 7.35-7.25 (m, 4H) 6.77 (t, 1H, J=8.2 Hz) 6.58 (dd, 1H, J=8.2, 1.4 Hz) 6.53 (dd, 1H, J=7.8, 1.4 Hz) 4.36-4.21 (m, 4H) 3.64-3.55 (m, 4H) 3.09 (brs, 4H) 2.66 (brs, 4H) 2.35 (s, 6H)

Example 169: Synthesis of {4-[4-(2,3-Dihydro-benzo[1,4]dioxin-5-yl)-piperazine-1-carbonyl]-benzyl}-carbamic acid tert-butyl Ester

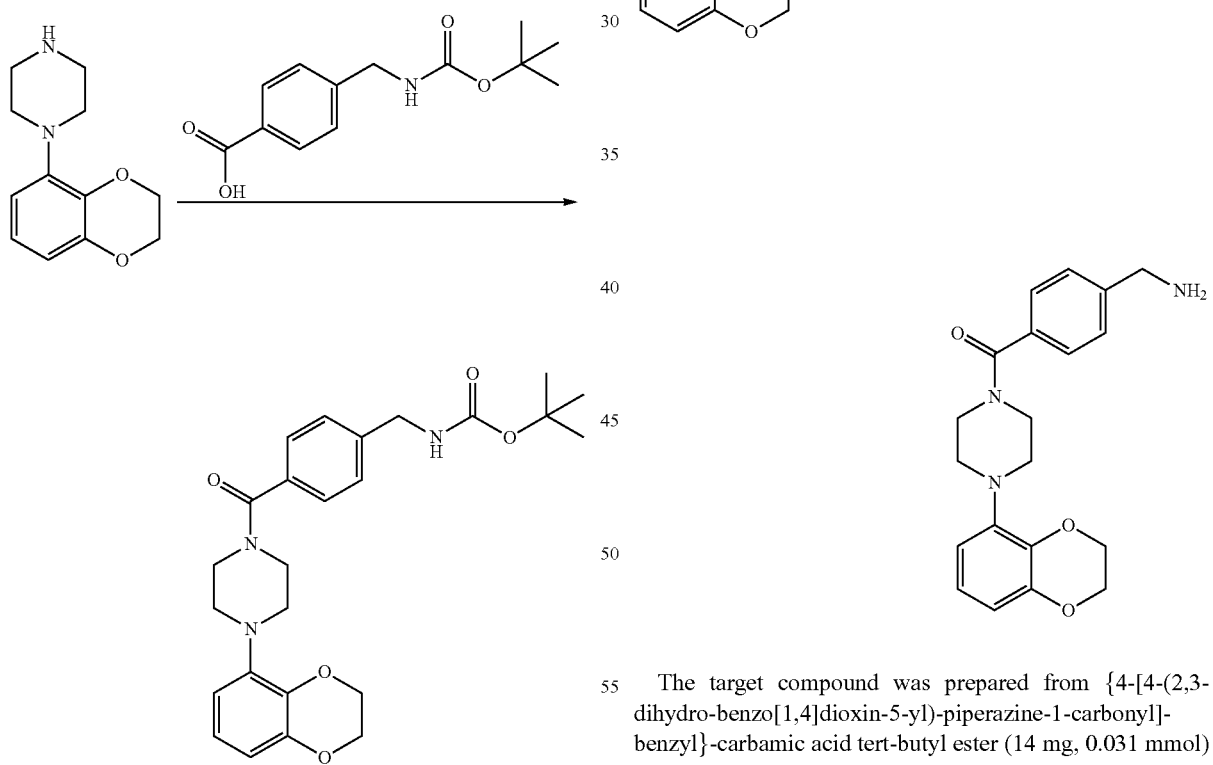

The title compound was prepared from 1-(2,3-dihydro-benzo[1,4]dioxin-5-yl)-piperazine (100 mg, 0.454 mmol) and 4-(tert-butoxycarbonylamino-methyl)-benzoic acid (114 mg, 0.454 mmol) using the general amide coupling procedure D to afford {4-[4-(2,3-dihydro-benzo[1,4]dioxin-5-yl)-piperazine-1-carbonyl]-benzyl}-carbamic acid tert-butyl ester (35 mg, 0.077 mmol, 17%) as a white solid.

AnalpH9_MeOH_QC_V1; Rt: 7.99 min, m/z 454.3 [M+H]+

AnalpH2_MeOH_QC_V1; Rt: 7.97 min, m/z 454.3 [M+H]+

Example 184: Synthesis of (4-Aminomethyl-phenyl)-[4-(2,3-dihydro-benzo[1,4]dioxin-5-yl)-piperazin-1-yl]-methanone

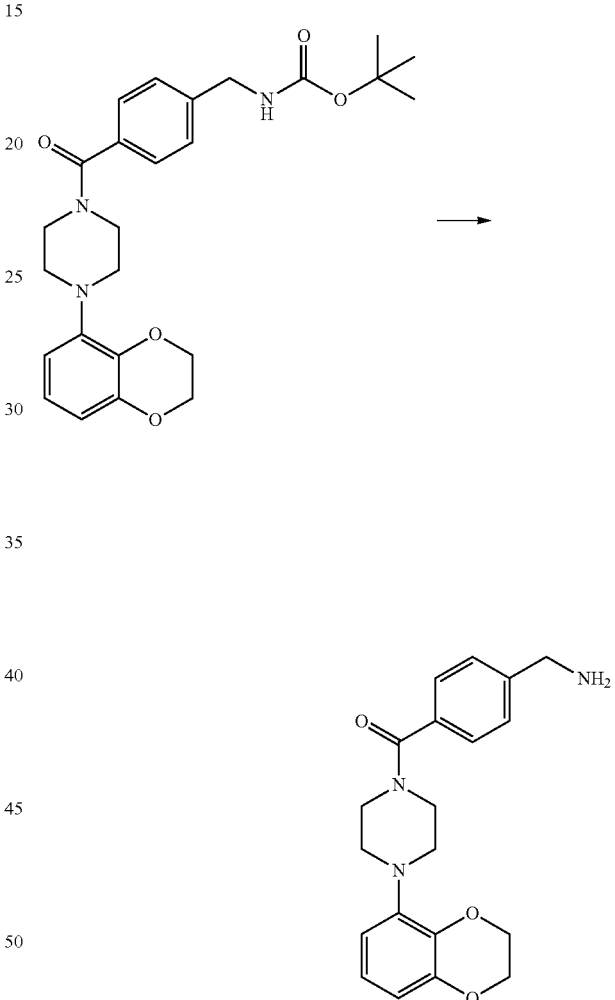

The target compound was prepared from {4-[4-(2,3-dihydro-benzo[1,4]dioxin-5-yl)-piperazine-1-carbonyl]-benzyl}-carbamic acid tert-butyl ester (14 mg, 0.031 mmol) using the general BOC-deprotection procedure F to afford (4-aminomethyl-phenyl)-[4-(2,3-dihydro-benzo[1,4]dioxin-5-yl)-piperazin-1-yl]-methanone (11 mg, 0.031 mmol, 94%) as an off white solid AnalpH9_MeOH_QC_V1; Rt: 7.99 min, m/z 354.3 [M+H]+

AnalpH2_MeOH_QC_V1; Rt: 7.97 min, m/z 354.3 [M+H]+

The following compounds were prepared using general method C:

| Compound | | Method | Analytical data | Mass, % yield, state |
|---|---|---|---|---|
| 2-[6-(2,3-Dihydro-benzo[1,4]dioxin-5-yl)-2-methoxy-pyridin-3-ylamino]-benzoic acid ethyl ester | 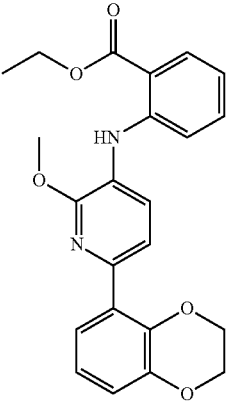 [SMILES: CCOC(=O)c1ccccc1Nc1ccc(-c2cccc3c2OCCO3)nc1OC] | using 3-chloro-6-(2,3-dihydro-benzo[1,4]dioxin-5-yl)-2-methoxy-pyridine and 2-amino-benzoic acid ethyl ester; Pd(OAc)$_2$, XPhos, 85° C., 6h; purified by column chromatography | AnalpH2_MeOH_4 min: Rt: 3.73 min, m/z 407[M + H]+ | 190 mg, 87%, yellow gum |
| 3-[6-(2,3-Dihydro-benzo[1,4]dioxin-5-yl)-2-methoxy-pyridin-3-ylamino]-benzoic acid ethyl ester | 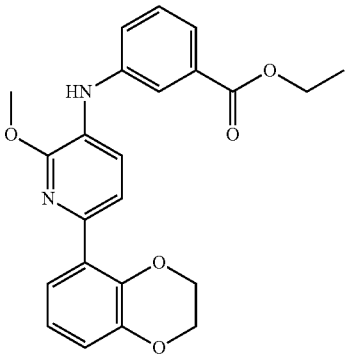 [SMILES: CCOC(=O)c1cccc(Nc2ccc(-c3cccc4c3OCCO4)nc2OC)c1] | using 3-chloro-6-(2,3-dihydro-benzo[1,4]dioxin-5-yl)-2-methoxy-pyridine and 3-amino-benzoic acid ethyl ester; Pd(OAc)$_2$, XPhos, 90° C., 3h; purified by column chromatography | AnalpH2_MeOH_4 min: Rt: 3.55 min, m/z 407[M + H]+ | 240 mg, 55%, yellow gum |
| 4-[6-(2,3-Dihydro-benzo[1,4]dioxin-5-yl)-2-methoxy-pyridin-3-ylamino]-benzoic acid methyl ester | 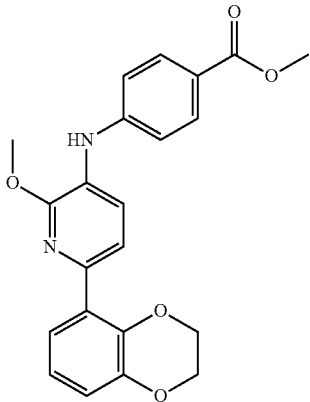 [SMILES: COC(=O)c1ccc(Nc2ccc(-c3cccc4c3OCCO4)nc2OC)cc1] | using 3-chloro-6-(2,3-dihydro-benzo[1,4]dioxin-5-yl)-2-methoxy-pyridine and 4-amino-benzoic acid methyl ester; Pd(OAc)$_2$, XPhos, 110° C., 2h; purified by column chromatography | AnalpH2_MeOH_4 min: Rt: 3.66 min, m/z 393.4[M + H]+ | 348 mg, 49%, white solid |
| {4-[6-(2,3-Dihydro-benzo[1,4]dioxin-5-yl)-2-methoxy-pyridin-3-ylamino]-phenyl}-acetic acid methyl ester | 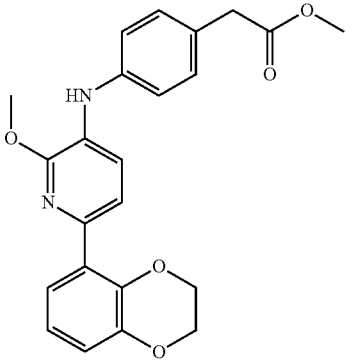 [SMILES: COC(=O)Cc1ccc(Nc2ccc(-c3cccc4c3OCCO4)nc2OC)cc1] | using 3-chloro-6-(2,3-dihydro-benzo[1,4]dioxin-5-yl)-2-methoxy-pyridine and (4-amino-phenyl)-acetic acid methyl ester; Pd(OAc)$_2$, XPhos, 100° C., 1h; purified by column chromatography | AnalpH2_MeOH_4 min: Rt: 2.96 min, m/z 407.2[M + H]+ | 140 mg, 24%, orange oil |

| Compound | | Method | Analytical data | Mass, % yield, state |
|---|---|---|---|---|
| {3-[6-(2,3-Dihydro-benzo[1,4]dioxin-5-yl)-2-methoxy-pyridin-3-ylamino]-phenyl}-acetic acid | 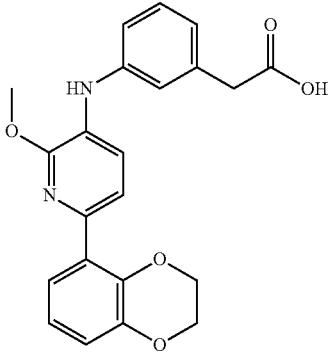 [SMILES: COc1nc(-c2cccc3c2OCCO3)ccc1Nc1cccc(CC(=O)O)c1] | using 3-chloro-6-(2,3-dihydro-benzo[1,4]dioxin-5-yl)-2-methoxy-pyridine and (3-amino-phenyl)-acetic acid ethyl ester; Pd(OAc)$_2$, XPhos, 90°C, 1.5h; purified by column chromatography | AnalpH2_MeOH_4 min: Rt: 3.29 min, m/z 393.4[M + H]+ | 190 mg, 62%, yellow oil |
| [4-(tert-Butyl-diphenyl-silanyloxymethyl)-phenyl]-[6-(2,3-dihydro-benzo[1,4]dioxin-5-yl)-2-methoxy-pyridin-3-yl]-amine | 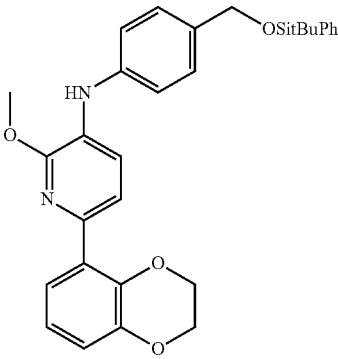 | using 3-chloro-6-(2,3-dihydro-benzo[1,4]dioxin-5-yl)-2-methoxy-pyridine and 4-(tert-butyl-diphenyl-silanyloxymethyl)-phenylamine; Pd(OAc)$_2$, XPhos, 120° C., 2h; purified by column chromatography | AnalpH2_50-95 MeOH_4min: Rt: 3.08 min, m/z 603.4 [M + H]+ | 1.15 g, 86%, brown oil |
| [3-(tert-Butyl-diphenyl-silanyloxymethyl)-phenyl]-[6-(2,3-dihydro-benzo[1,4]dioxin-5-yl)-2-methoxy-pyridin-3-yl]amine | 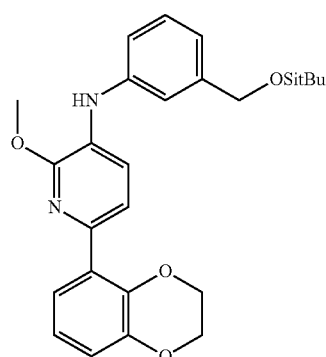 | using 3-chloro-6-(2,3-dihydro-benzo[1,4]dioxin-5-yl)-2-methoxy-pyridine and 3-(tert-butyl-diphenyl-silanyloxymethyl)-phenylamine; Pd(OAc)$_2$, XPhos, 90° C., 2.5h; purified by column chromatography | AnalpH2_50-95MeOH_4min: Rt: 2.56 min, m/z 604.0 [M + H]+ | 0.35 g, 106%, orange oil |
| [6-(2,3-Dihydro-benzo[1,4]dioxin-5-yl)-2-methoxy-pyridin-3-yl]-(3-[1,3]dioxolan-2-yl-phenyl)-amine | 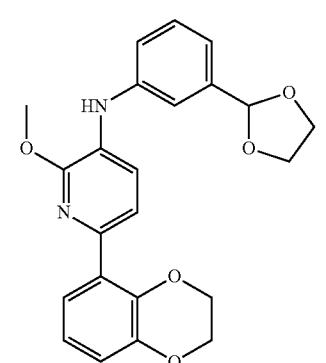 | using 3-chloro-6-(2,3-dihydro-benzo[1,4]dioxin-5-yl)-2-methoxy-pyridin and 3-(1,3-dioxolan-2-l)aniline; Pd(OAc)$_2$, XPhos, 90° C., 3h; purified by column chromatography | AnalpH2_MeOH_4 min: Rt: 3.40 min, m/z 407.2[M + H]+ | 0.46 g, 113%, orange oil |

Synthesis of 2-[6-(2,3-Dihydro-benzo[1,4]dioxin-5-yl)-2-methoxy-pyridin-3-ylamino]-benzoic acid

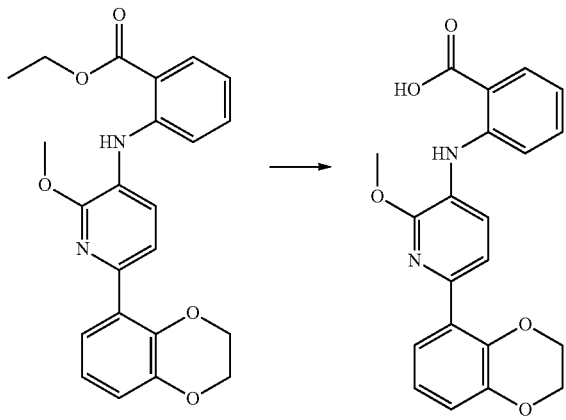 [SMILES: CCOC(=O)c1ccccc1Nc1ccc(-c2cccc3c2OCCO3)nc1OC ; COc1nc(-c2cccc3c2OCCO3)ccc1Nc1ccccc1C(=O)O]

To a stirred solution of 2-[6-(2,3-dihydro-benzo[1,4]dioxin-5-yl)-2-methoxy-pyridin-3-ylamino]-benzoic acid ethyl ester (0.19 g, 0.47 mmol) in a mixture of THF (2 mL), MeOH (0.5 mL) and water (0.5 mL) was added lithium hydroxide monohydrate (78.8 mg, 1.88 mmol) and the reaction mixture was stirred at room temperature for 16 h. The mixture was concentrated under reduced pressure and the resulting residue dissolved in water, adjusted to pH2 with aq. 2M HCl and collected by filtration to give the desired product as a yellow solid (0.14 g, 0.37 mmol 79%).
AnalpH2_MeOH_4 min, Rt: 3.47 min; m/z 379.2 [M+H]$^+$ Synthesis of 3-[6-(2,3-Dihydro-benzo[1,4]dioxin-5-yl)-2-methoxy-pyridin-3-ylamino]-benzoic acid

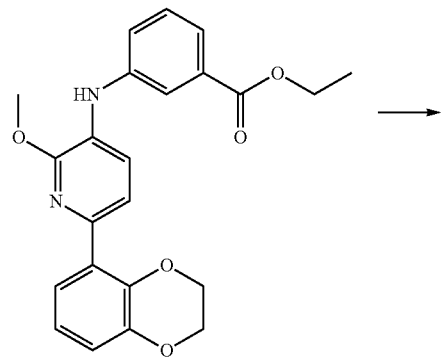

To a stirred solution of 3-[6-(2,3-dihydro-benzo[1,4]dioxin-5-yl)-2-methoxy-pyridin-3-ylamino]-benzoic acid ethyl ester (0.24 g, 0.59 mmol) in a mixture of THF (2 mL), MeOH (0.5 mL) and water (0.5 mL) was added lithium hydroxide (57 mg, 2.36 mmol) and the reaction mixture was stirred at room temperature for 16 h. The mixture was concentrated under reduced pressure and the resulting residue dissolved in water, adjusted to pH4 with aq. 2M HCl and collected by filtration to give the desired product as an off-white solid (0.19 g, 0.51 mmol 86%) AnalpH2_MeOH_4 min, Rt: 3.29 min; m/z 379.2 [M+H]$^+$ Synthesis of 4-[6-(2,3-Dihydro-benzo[1,4]dioxin-5-yl)-2-methoxy-pyridin-3-ylamino]-benzoic acid

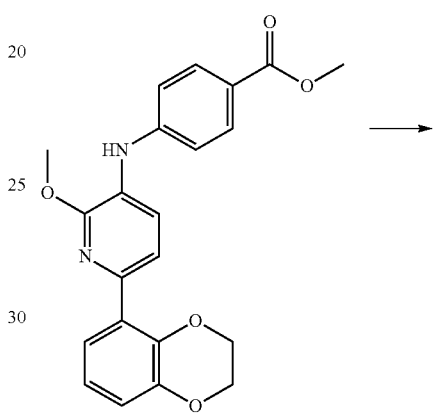

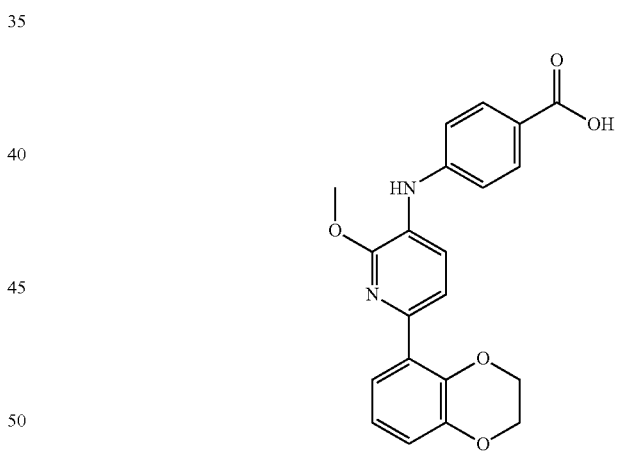

To a stirred solution of 4-[6-(2,3-dihydro-benzo[1,4]dioxin-5-yl)-2-methoxy-pyridin-3-ylamino]-benzoic acid methyl ester (0.85 g, 2.17 mmol) in a mixture of THF (5 mL), MeOH (1.0 mL) and water (1.0 mL) was added lithium hydroxide (210 mg, 8.68 mmol) and the reaction mixture was stirred at 40° C. for 16 h. The reaction mixture was concentrated under reduced pressure and the residue partitioned between DCM and aq. sat. NH$_4$Cl solution. The organic layer was separated and the aqueous layer extracted with DCM. The combined organic layers were dried (phase separator) and concentrated under reduced pressure to give the desired product as a yellow solid (280 mg, 0.74 mmol, 34%) AnalpH2_MeOH_4 min, Rt: 3.23 min; m/z 379 [M+H]$^+$

179

Synthesis of {4-[6-(2,3-Dihydro-benzo[1,4]dioxin-5-yl)-2-methoxy-pyridin-3-ylamino]-phenyl}-acetic acid

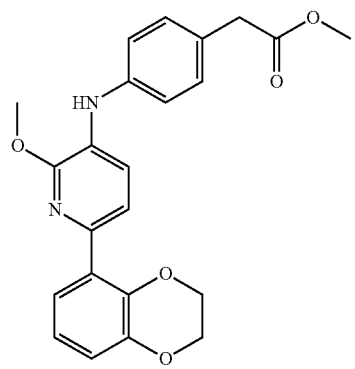

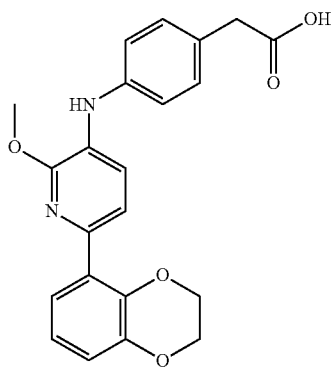

To a stirred solution of {4-[6-(2,3-dihydro-benzo[1,4]dioxin-5-yl)-2-methoxy-pyridin-3-ylamino]-phenyl}-acetic acid methyl ester (014 g, 0.34 mmol) in THF (5 mL) was added lithium hydroxide (200 mg, 8.35 mmol) and the reaction was stirred at 70° C. for 1 h. The reaction mixture was concentrated under reduced pressure and the residue partitioned between DCM and aq. sat. NH$_4$Cl sol. The organic layer was separated and the aqueous layer extracted with DCM. The combined organic layers were dried (phase separator) and concentrated under reduced pressure to give the desired product as a yellow oil (130 mg, 0.33 mmol, 97%)

AnalpH2_MeOH_4 min, Rt: 3.28 min; m/z 393 [M+H]$^+$

180

Example 152: Synthesis of 4-({2-[6-(2,3-dihydro-benzo[1,4]dioxin-5-yl)-2-methoxy-pyridin-3-ylamino]-benzoylamino}-methyl)-piperidine-1-carboxylic acid tert-butyl ester using General method G

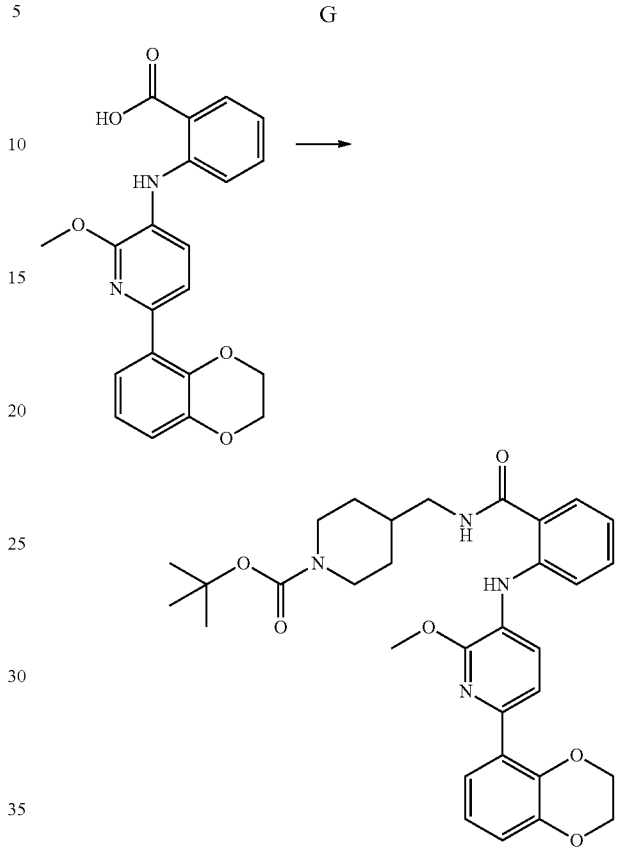

To a solution of 2-[6-(2,3-dihydro-benzo[1,4]dioxin-5-yl)-2-methoxy-pyridin-3-ylamino]-benzoic acid (70 mg, 0.18 mmol), 4-aminomethyl-piperidine-1-carboxylic acid tert-butyl ester (49 mg, 0.23 mmol) and triethylamine (27 mg, 0.27 mmol) in anhydrous DCM (6 mL) was added N-(3-dimethylaminopropyl)-N'-ethylcarbodiimide hydrochloride (52 mg, 0.27 mmol) followed by 1-hydroxy-7-azabenzotriazole (12 mg, 0.09 mmol) and the reaction mixture stirred at RT for 72 h. The reaction mixture was diluted with DCM and water, and the organic layer separated. The aqueous layer was extracted with DCM. The combined organic layers were washed with brine, dried (MgSO$_4$), filtered and concentrated in vacuo to yield the crude material which was purified by column chromatography followed by prep HPLC to give 4-({2-[6-(2,3-dihydro-benzo[1,4]dioxin-5-yl)-2-methoxy-pyridin-3-ylamino]-benzoylamino}-methyl)-piperidine-1-carboxylic acid tert-butyl ester (19.1 mg, 0.03 mmol, 29%) as an off-white solid.

AnalpH2_MeOH_QC_V1: Rt: 8.81 min, m/z 575.3 [M+H]$^+$

AnalpH9_MeOH_QC_V1: Rt: 8.81 min, m/z 575.3 [M+H]+

$^1$H-NMR (400 MHz, DMSO-D6) δ 9.68 (s, 1H), 8.53 (t, J=5.7 Hz, 1H), 7.67-7.56 (m, 2H), 7.54-7.41 (m, 2H), 7.41-7.29 (m, 2H), 6.95-6.72 (m, 3H), 4.42-4.17 (m, 4H), 3.96 (s, 3H), 3.18-2.98 (m, 2H), 2.94-2.79 (m, 2H), 2.41-2.30 (m, 2H), 1.73-1.43 (m, 3H), 1.12-0.85 (m, 2H)

The following compounds were made using General method G

| | Compound | Method | Analytical data | Mass, % yield, state |
|---|---|---|---|---|
| Example 162<br>3-[6-(2,3-Dihydro-benzo[1,4]dioxin-5-yl)-2-methoxy-pyridin-3-ylamino]-N-(6-methyl-pyridin-2-ylmethyl)-benzamide | 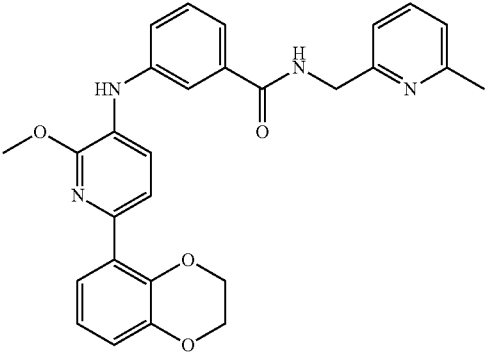 | Method G using 3-[6-(2,3-dihydro-benzo[1,4]dioxin-5-yl)-2-methoxy-pyridin-3-ylamino]-benzoic acid and C-(6-methyl-pyridin-2-yl)-methylamine; 96h; purified by prep HPLC | AnalpH2_MeOH_QC_V1: Rt: 7.57 min, m/z 483.2 $[M + H]^+$<br>AnalpH9_MeOH_QC_V1: Rt: 8.53 min, m/z 483.2 $[M + H]^+$<br>1H-NMR (400 MHz, DMSO-D6) δ 8.97(t, J = 6.0 Hz, 1H), 7.85(s, 1H), 7.69-7.41 (m, 5H), 7.40-7.16(m, 3H), 7.06(t, J = 8.5 Hz, 2H), 6.93-6.73(m, 2H), 4.53-4.37(m, 2H), 4.35-4.18(m, 4H), 3.95(s, 3H), 2.41(s, 3H) | 20.2 mg, 28%, off-white solid |
| Example 163<br>3-[6-(2,3-Dihydro-benzo[1,4]dioxin-5-yl)-2-methoxy-pyridin-3-ylamino]-N-(1-methyl-piperidin-4-ylmethyl)-benzamide | 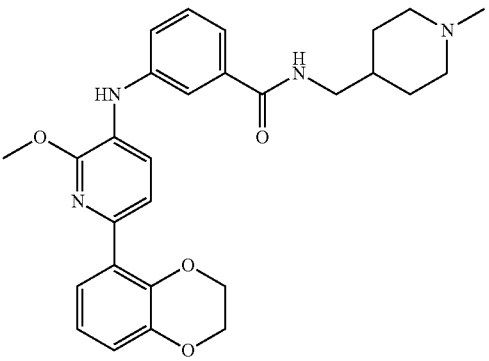 | Method G using 3-[6-(2,3-dihydro-benzo[1,4]dioxin-5-yl)-2-methoxy-pyridin-3-ylamino]-benzoic acid and C-(1-methyl-piperidin-4-yl)-methylamine; 96h; purified by prep HPLC | AnalpH2_MeOH_QC_V1: Rt: 6.34 min, m/z 489.3 $[M + H]^+$<br>AnalpH9_MeOH_QC_V1: Rt: 8.16 min, m/z 489.3 $[M + H]^+$<br>1H-NMR (400 MHz, DMSO-D6) δ 8.33(t, J = 5.7 Hz, 1H), 7.8 (s, 1H), 7.62-7.39 (m, 4H), 7.35-7.10 (m, 3H), 6.93-6.74 (m, 2H), 4.52-4.16 (m, 4H), 3.94(s, 3H), 3.15-3.00(m, 2H), 2.77-2.64(m, 2H),<br><br>2.08(s, 3H), 1.82-1.66 (m, 2H), 1.63-1.53 (m, 2H), 1.51-1.33 (m, 1H), 1.17-1.04 (m, 2H) | 16.8 mg, 23%, off-white solid |
| Example 164<br>3-[6-(2,3-Dihydro-benzo[1,4]dioxin-5-yl)-2-methoxy-pyridin-3-ylamino]-N-(6-oxo-piperidin-3-ylmethyl)-benzamide | 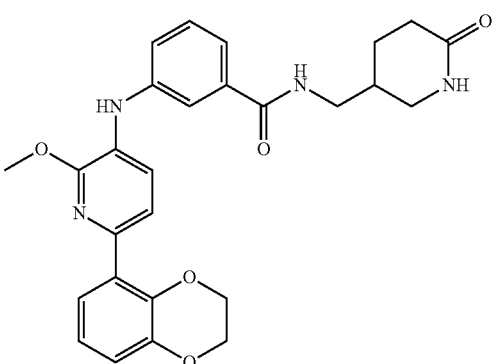 | Method G using 3-[6-(2,3-dihydro-benzo[1,4]dioxin-5-yl)-2-methoxy-pyridin-3-ylamino]-benzoic acid and 5-aminomethyl-piperidin-2-one; 16h; purified by prep HPLC | AnalpH2_MeOH_QC_V1: Rt: 7.99 min, m/z 489.2 $[M + H]^+$<br>AnalpH9_MeOH_QC_V1: Rt: 8.00 min, m/z 489.2 $[M + H]^+$ | 20.6 mg, 28%, white solid |
| Example 165<br>3-[6-(2,3-Dihydro-benzo[1,4]dioxin-5-yl)-2-methoxy-pyridin-3-ylamino]-N-(2-oxo-1,2-dihydro-pyridin-4-ylmethyl)-benzamide | 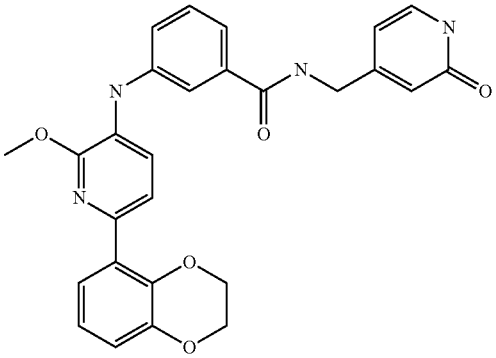 [SMILES: COc1nc(-c2cccc3c2OCCO3)ccc1Nc1cccc(C(=O)NCc2cc[nH]c(=O)c2)c1] | Method G using 3-[6-(2,3-dihydro-benzo[1,4]dioxin-5-yl)-2-methoxy-pyridin-3-ylamino]-benzoic acid and 4-aminomethyl-1H-pyridin-2-one; 16h; purified by prep HPLC | AnalpH2_MeOH_QC_V1: Rt: 7.92 min, m/z 485.2$[M+H]^+$<br>AnalpH9_MeOH_QC_V1: Rt: 7.92 min, m/z 485.2 $[M + H]^+$ | 20.2 mg, 28%, White solid |

-continued

| Compound | | Method | Analytical data | Mass, % yield, state |
|---|---|---|---|---|
| Example 166 3-[6-(2,3-Dihydro-benzo[1,4]dioxin-5-yl)-2-methoxy-pyridin-3-ylamino]-N-(5-oxo-pyrrolidin-3-ylmethyl)-benzamide | 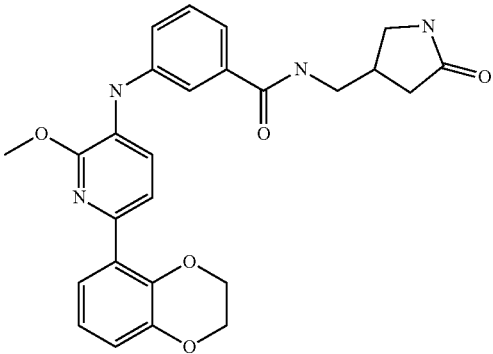 [SMILES: COc1nc(-c2cccc3c2OCCO3)ccc1Nc1cccc(C(=O)NCC2CNC(=O)C2)c1] | Method G using 3-[6-(2,3-dihydro-benzo[1,4]dioxin-5-yl)-2-methoxy-pyridin-3-ylamino]-benzoic acid and 4-aminomethyl-pyrrolidin-2-one; 16h; purified by prep HPLC | AnalpH2_MeOH_QC_V1: Rt: 7.94 min, m/z 475.1 [M + H]$^+$ AnalpH9_MeOH_QC_V1: Rt: 7.94 min, m/z 475.2 [M + H]$^+$ | 23.5 mg, 33%, White solid |
| Example 167 N-(1-Acetyl-piperidin-4-ylmethyl)-3-[6-(2,3-dihydro-benzo[1,4]dioxin-5-yl)-2-methoxy-pyridin-3-ylamino]-benzamide | 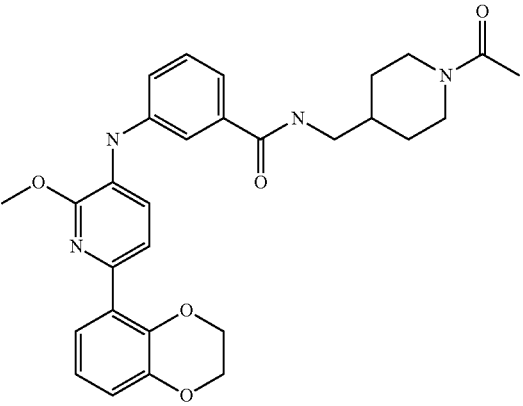 [SMILES: COc1nc(-c2cccc3c2OCCO3)ccc1Nc1cccc(C(=O)NCC2CCN(C(C)=O)CC2)c1] | Method G using 3-[6-(2,3-dihydro-benzo[1,4]dioxin-5-yl)-2-methoxy-pyridin-3-ylamino]-benzoic acid and 1-(4-aminomethyl-piperidin-1-yl)-ethanone; 16h; purified by prep HPLC | AnalpH2_MeOH_QC_V1: Rt: 8.17 min, m/z 517.3 [M + H]$^+$ AnalpH9_MeOH_QC_V1: Rt: 8.19 min, m/z 517.3 [M + H]$^+$ | 30 mg, 40%, White solid |
| Example 168 3-[6-(2,3-Dihydro-benzo[1,4]dioxin-5-yl)-2-methoxy-pyridin-3-ylamino]-N-(6-fluoro-pyridin-2-ylmethyl)-benzamide | 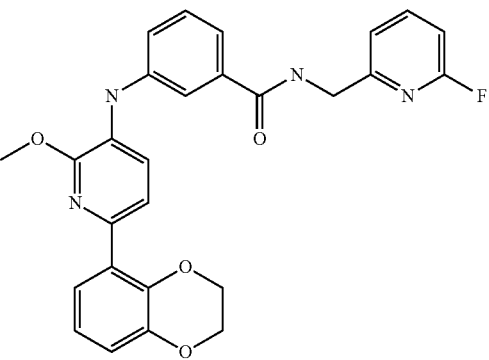 [SMILES: COc1nc(-c2cccc3c2OCCO3)ccc1Nc1cccc(C(=O)NCc2cccc(F)n2)c1] | Method G using 3-[6-(2,3-dihydro-benzo[1,4]dioxin-5-yl)-2-methoxy-pyridin-3-ylamino]-benzoic acid and (6-fluoropyridin-2-yl)methanamine dihydrochloride; 16h; purified by prep HPLC | AnalpH2_MeOH_QC_V1: Rt: 8.38 min, m/z 487.3 [M + H]+ AnalpH9_MeOH_QC_V1: Rt: 8.39 min, m/z 487.2 [M + H]+ | 29.1 mg, 40%, White solid |
| Example 181 N-(1-Benzyl-piperidin-4-ylmethyl)-3-[6-(2,3-dihydro-benzo[1,4]dioxin-5-yl)-2-methoxy-pyridin-3-ylamino]-benzamide | 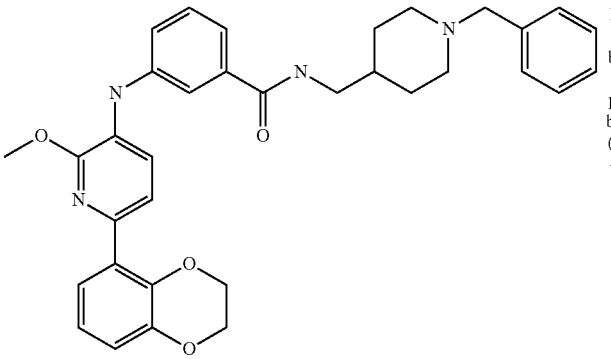 | Method G using 3-[6-(2,3-dihydro-benzo[1,4]dioxin-5-yl)-2-methoxy-pyridin-3-ylamino]-benzoic acid and C-(1-benzyl-piperidin-4-yl)-methylamine; 16h; purified by prep HPLC | AnalpH2_MeOH_QC_V1: Rt: 6.66 min, m/z 565.3 [M + H]$^+$ AnalpH9_MeOH_QC_V1: Rt: 8.93 min, m/z 565.3 [M + H]$^+$ 1H-NMR (400 MHz, DMSO-D6) δ 8.33 (t, J = 5.7 Hz, 1H), 7.81 (s, 1H), 7.60-7.38 (m, 4H), 7.32-7.13 (m, 8H), 6.94-6.72 (m, 2H), 4.33-4.19 (m, 4H), 3.94 (s, 3H), 3.38 (s, 2H), 3.11-3.03 (m, 2H), 2.82-2.68 (m, 2H), | 35.5 mg, 42%, White solid |

-continued

| Compound | Method | Analytical data | Mass, % yield, state |
|---|---|---|---|
| | | 1.94-1.73 (m, 2H), 1.69-1.37 (m, 3H), 1.21-1.04 (m, 2H) | |
| Example 182 3-[6-(2,3-Dihydro-benzo[1,4]dioxin-5-yl)-2-methoxy-pyridin-3-ylamino]-N-(2-oxo-piperidin-4-ylmethyl)-benzamide 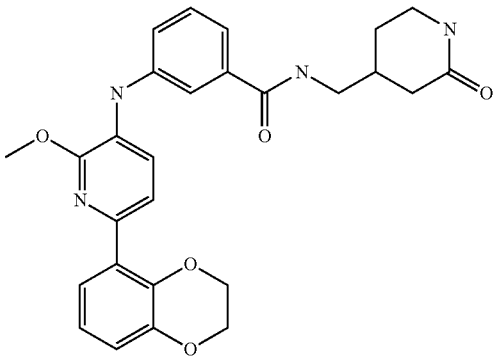 [SMILES: COc1nc(-c2cccc3c2OCCO3)ccc1Nc1cccc(C(=O)NCC2CCNC(=O)C2)c1] | Method G using 3-[6-(2,3-dihydro-benzo[1,4]dioxin-5-yl)-2-methoxy-pyridin-3-ylamino]-benzoic acid and 4-aminomethyl-piperidin-2-one; 16h; purified by prep HPLC | AnalpH2_MeOH_QC_V1: Rt: 7.99 min, m/z 489.1 [M + H]$^+$ AnalpH9_MeOH_QC_V1: Rt: 7.98 min, m/z 489.2 [M + H]$^+$ | 37 mg, 51%, White solid |
| Example 183 3-[6-(2,3-Dihydro-benzo[1,4]dioxin-5-yl)-2-methoxy-pyridin-3-ylamino]-N-(1H-pyrazol-4-ylmethyl)-benzamide 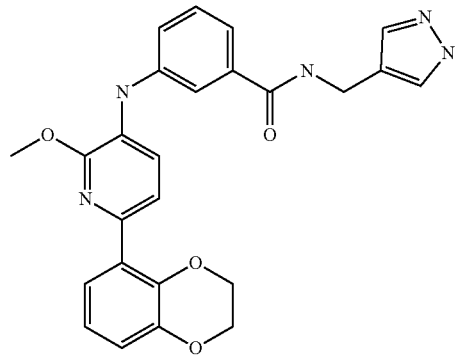 [SMILES: COc1nc(-c2cccc3c2OCCO3)ccc1Nc1cccc(C(=O)NCc2cn[nH]c2)c1] | Method G using 3-[6-(2,3-dihydro-benzo[1,4]dioxin-5-yl)-2-methoxy-pyridin-3-ylamino]-benzoic acid and 4-aminomethyl-1H-pyrazole hydrochloride; 16h; purified by prep HPLC | AnalpH2_MeOH_QC_V1: Rt: 8.00 min, m/z 458.2 [M + H]$^+$ AnalpH9_MeOH_QC_V1: Rt: 8.01 min, m/z 458.2 [M + H]$^+$ | 18.4 mg, 27%, White solid |
| 4-({3-[6-(2,3-Dihydro-benzo[1,4]dioxin-5-yl)-2-methoxy-pyridin-3-ylamino]-benzoyl-amino}-methyl)-piperidine-1-carboxylic acid tert-butyl ester 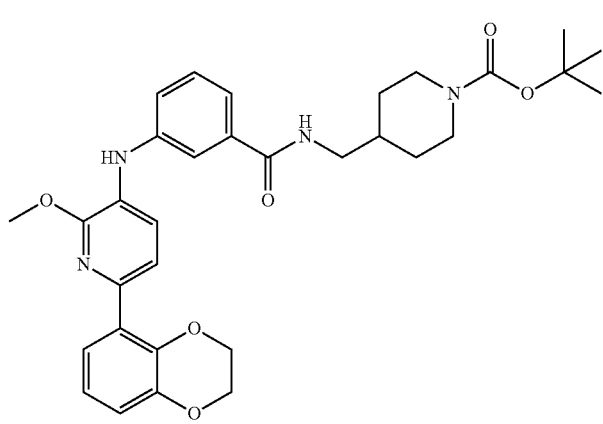 [SMILES: COc1nc(-c2cccc3c2OCCO3)ccc1Nc1cccc(C(=O)NCC2CCN(C(=O)OC(C)(C)C)CC2)c1] | Method G using 3-[6-(2,3-dihydro-benzo[1,4]dioxin-5-yl)-2-methoxy-pyridin-3-ylamino]-benzoic acid and 4-aminomethyl-piperidine-1-carboxylic acid tert-butyl ester; 16h. The crude material was used without further purification. | AnalpH2_MeOH_4min: Rt: 3.49 min, m/z 575.3 [M + H]$^+$ | 144 mg, Yellow gum |

Example 158: Synthesis of 4-[6-(2,3-Dihydro-benzo[1,4]dioxin-5-yl)-2-methoxy-pyridin-3-ylamino]-N-(1-methyl-piperidin-4-ylmethyl)-benzamide using General Method H

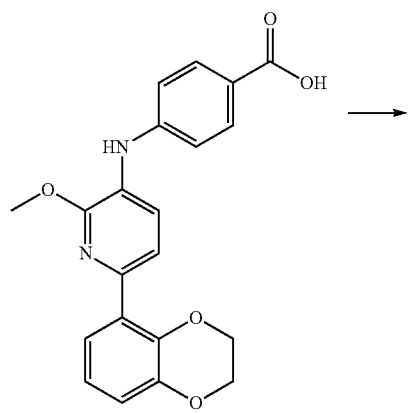

→

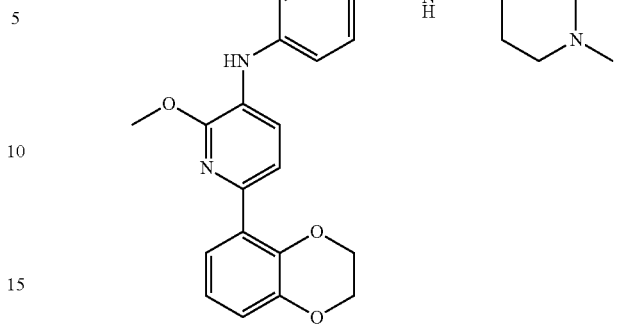

To a solution of C-(1-methyl-piperidin-4-yl)-methylamine (17 mg, 0.13 mmol, 1.1 eq), HATU (50 mg, 0.131 mmol, 1.1 eq) and 4-[6-(2,3-dihydro-benzo[1,4]dioxin-5-yl)-2-methoxy-pyridin-3-ylamino]-benzoic acid (45 mg, 0.12 mmol, 1.0 eq) in anhydrous DMF (1 mL) was added triethylamine (20 UL, 0.13 mmol, 1.1 eq) and the reaction mixture was stirred at RT for 72 h. The reaction mixture was purified directly by prep HPLC followed by column chromatography to give 4-[6-(2,3-dihydro-benzo[1,4]dioxin-5-yl)-2-methoxy-pyridin-3-ylamino]-N-(1-methyl-piperidin-4-ylmethyl)-benzamide (9.7 mg, 0.020 mmol, 17%) as a yellow solid.

AnalpH2_MeOH_QC_V1: Rt: 6.26 min, m/z 489.3 [M+H]$^+$

AnalpH9_MeOH_QC_V1: Rt: 8.05 min, m/z 489.3 [M+H]$^+$

The following compounds were made using general procedure H:

| Compound | Method | Analytical data | Mass, % yield, state |
|---|---|---|---|
| Example 174 4-[6-(2,3-Dihydro-benzo[1,4]dioxin-5-yl)-2-methoxy-pyridin-3-ylamino]-N-(6-methyl-pyridin-2-ylmethyl)-benzamide 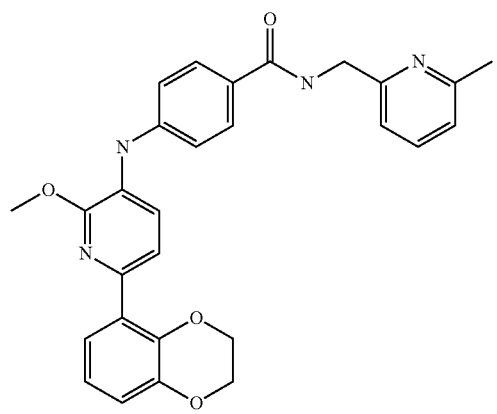 | Method H using 4-[6-(2,3-dihydro-benzo[1,4]dioxin-5-yl)-2-methoxy-pyridin-3-ylamino]-benzoic acid and C-(6-methyl-pyridin-2-yl)-methylamine; 16h; purified by column chromatography followed by prep HPLC | AnalpH2_MeOH_QC_V1: Rt: 7.18 min, m/z 483.3 [M + H]$^+$ AnalpH9_MeOH_QC_V1: Rt: 8.44 min, m/z 483.3 [M + H]$^+$ | 28 mg, 45%, Yellow solid |

-continued

| Compound | | Method | Analytical data | Mass, % yield, state |
|---|---|---|---|---|
| Example 175<br>4-[6-(2,3-Dihydro-benzo[1,4]dioxin-5-yl)-2-methoxy-pyridin-3-ylamino]-N-pyridin-3-ylmethyl-benzamide | 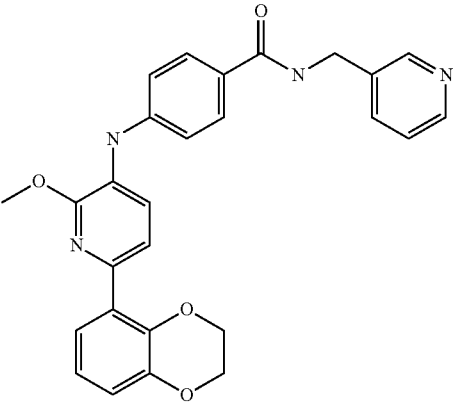 [SMILES: COc1nc(-c2cccc3c2OCCO3)ccc1Nc1ccc(C(=O)NCc2cccnc2)cc1] | Method H using 4-[6-(2,3-dihydro-benzo[1,4]dioxin-5-yl)-2-methoxy-pyridin-3-ylamino]-benzoic acid and C-pyridin-3-yl-methylamine; 16h; purified by column chromatography followed by prep HPLC | AnalpH2_MeOH_QC_V1: Rt: 7.25 min, m/z 469.3 [M + H]$^+$<br>AnalpH9_MeOH_QC_V1: Rt: 8.17 min, m/z 469.3 [M + H]$^+$ | 24 mg, 39%, Yellow solid |
| Example 176<br>4-[6-(2,3-Dihydro-benzo[1,4]dioxin-5-yl)-2-methoxy-pyridin-3-ylamino]-N-(6-fluoro-pyridin-2-ylmethyl)-benzamide | 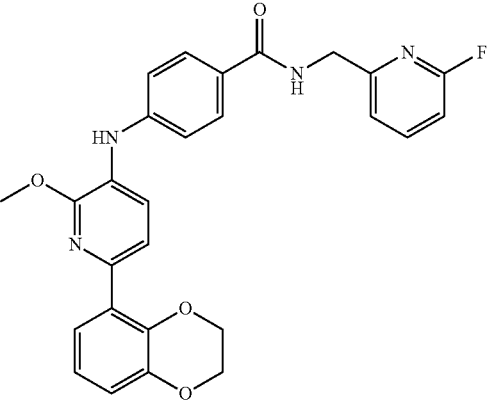 [SMILES: COc1nc(-c2cccc3c2OCCO3)ccc1Nc1ccc(C(=O)NCc2cccc(F)n2)cc1] | Method H using 4-[6-(2,3-dihydro-benzo[1,4]dioxin-5-yl)-2-methoxy-pyridin-3-ylamino]-benzoic acid and C-(6-fluoro-pyridin-2-yl)-methylamine; 16h; purified by column chromatography followed by prep HPLC | AnalpH2_MeOH_QC_V1: Rt: 8.31 min, m/z 487.3 [M + H]$^+$<br>AnalpH9_MeOH_QC_V1: Rt: 8.32 min, m/z 487.2 [M + H]$^+$ | 29 mg, 46%, white solid |
| Example 177<br>4-({4-[6-(2,3-Dihydro-benzo[1,4]dioxin-5-yl)-2-methoxy-pyridin-3-ylamino]-benzoyl-amino}-methyl)-piperidine-1-carboxylic acid tert-butyl ester | 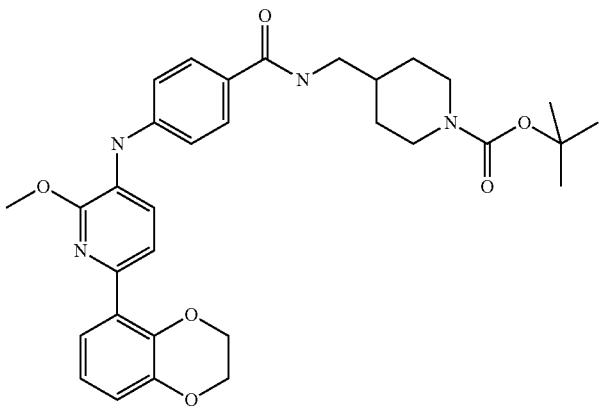 [SMILES: COc1nc(-c2cccc3c2OCCO3)ccc1Nc1ccc(C(=O)NCC2CCN(C(=O)OC(C)(C)C)CC2)cc1] | Method H using 4-[6-(2,3-dihydro-benzo[1,4]dioxin-5-yl)-2-methoxy-pyridin-3-ylamino]-benzoic acid and 4-aminomethyl-piperidine-1-carboxylic acid tert-butyl ester; 16h; purified by column chromatography followed by prep HPLC | AnalpH2_MeOH_QC_V1: Rt: 8.84 min, m/z 575.3 [M + H]$^+$<br>AnalpH9_MeOH_QC_V1: Rt: 8.86 min, m/z 575.3 [M + H]$^+$ | 36 mg, 48%, white solid |

-continued

| Compound | | Method | Analytical data | Mass, % yield, state |
|---|---|---|---|---|
| Example 185 N-(1-Benzyl-piperidin-4-ylmethyl)-4-[6-(2,3-dihydro-benzo[1,4]dioxin-5-yl)-2-methoxy-pyridin-3-ylamino]-benzamide | 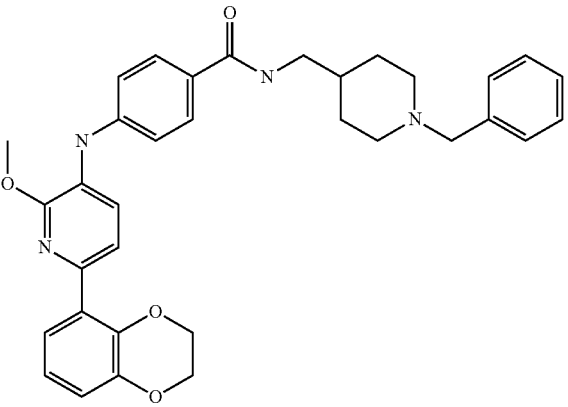 [SMILES: COc1nc(-c2cccc3c2OCCO3)ccc1Nc1ccc(C(=O)NCC2CCN(Cc3ccccc3)CC2)cc1] | Method H using 4-[6-(2,3-dihydro-benzo[1,4]dioxin-5-yl)-2-methoxy-pyridin-3-ylamino]-benzoic acid and C-(1-benzyl-piperidin-4-yl)-methylamine; 16h; purified by prep HPLC | AnalpH2_MeOH_QC_V1: Rt: 6.54 min, m/z 565.3 [M + H]⁺ AnalpH9_MeOH_QC_V1: Rt: 8.87 min, m/z 565.3 [M + H]⁺ | 23 mg, 31%, white solid |
| Example 196 4-[6-(2,3-Dihydro-benzo[1,4]dioxin-5-yl)-2-methoxy-pyridin-3-ylamino]-N-(2-oxo-piperidin-4-ylmethyl)-benzamide | 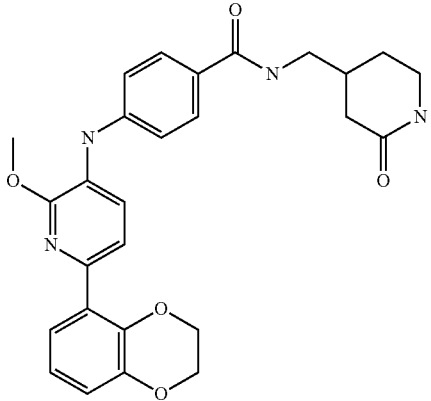 [SMILES: COc1nc(-c2cccc3c2OCCO3)ccc1Nc1ccc(C(=O)NCC2CCNC(=O)C2)cc1] | Method H using 4-[6-(2,3-dihydro-benzo[1,4]dioxin-5-yl)-2-methoxy-pyridin-3-ylamino]-benzoic acid and 4-aminomethyl-piperidin-2-one; 3h; purified by prep HPLC | AnalpH2_MeOH_QC_V1: Rt: 7.96 min, m/z 489.0 [M + H]⁺ AnalpH9_MeOH_QC_V1: Rt: 7.95 min, m/z 489.0 [M + H]⁺ | 36 mg, 62%, white solid |
| Example 197 2-{4-[6-(2,3-Dihydro-benzo[1,4]dioxin-5-yl)-2-methoxy-pyridin-3-ylamino]-phenyl}-N-(1-methyl-piperidin-4-ylmethyl)-acetamide | 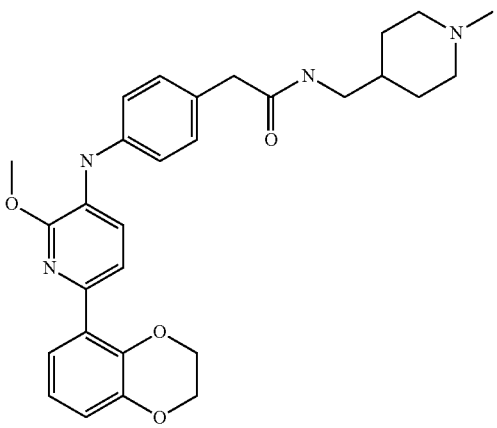 [SMILES: COc1nc(-c2cccc3c2OCCO3)ccc1Nc1ccc(CC(=O)NCC2CCN(C)CC2)cc1] | Method H using {4-[6-(2,3-dihydro-benzo[1,4]dioxin-5-yl)-2-methoxy-pyridin-3-ylamino]-phenyl}-acetic acid and C-(1-methyl-piperidin-4-yl)-methylamine; 16h; purified by prep HPLC | AnalpH2_MeOH_QC_V1: Rt: 6.38 min, m/z 503.3 [M + H]⁺ AnalpH9_MeOH_QC_V1: Rt: 8.17 min, m/z 503.3 [M + H]⁺ | 10.1 mg, 24%, white solid |

-continued

| | Compound | Method | Analytical data | Mass, % yield, state |
|---|---|---|---|---|
| Example 198 2-{4-[6-(2,3-Dihydro-benzo[1,4]dioxin-5-yl)-2-methoxy-pyridin-3-ylamino]-phenyl}-1-(4-methyl-piperazin-1-yl)-ethanone | | Method H using {4-[6-(2,3-dihydro-benzo[1,4]dioxin-5-yl)-2-methoxy-pyridin-3-ylamino]-phenyl}-acetic acid and 1-methyl-piperazine; 16h; purified by prep HPLC | AnalpH2_MeOH_QC_V1: Rt: 6.26 min, m/z 475.3 [M + H]$^+$ AnalpH9_MeOH_QC_V1: Rt: 8.39 min, m/z 475.3 [M + H]$^+$ | 7.3 mg, 19%, Off white solid |
| Example 202 2-{3-[6-(2,3-Dihydro-benzo[1,4]dioxin-5-yl)-2-methoxy-pyridin-3-ylamino]-phenyl}-N-(1-methyl-piperidin-4-ylmethyl)-acetamide | | Method H using {3-[6-(2,3-dihydro-benzo[1,4]dioxin-5-yl)-2-methoxy-pyridin-3-ylamino]-phenyl}-acetic acid and C-(1-methyl-piperidin-4-yl)-methylamine; 16h; purified by prep HPLC | AnalpH2_MeOH_QC_V1: Rt: 6.32 min, m/z 503.4 [M + H]$^+$ AnalpH9_MeOH_QC_V1: Rt: 8.16 min, m/z 503.5 [M + H]$^+$ | 8.0 mg, 16%, Off white solid |
| Example 203 2-{3-[6-(2,3-Dihydro-benzo[1,4]dioxin-5-yl)-2-methoxy-pyridin-3-ylamino]-phenyl}-N-(1-methyl-piperidin-4-yl)-acetamide | | Method H using {3-[6-(2,3-dihydro-benzo[1,4]dioxin-5-yl)-2-methoxy-pyridin-3-ylamino]-phenyl}-acetic acid and 1-methyl-piperidin-4-ylamine; 16h; purified by prep HPLC | AnalpH2_MeOH_QC_V1: Rt: 6.31 min, m/z 489.4 [M + H]$^+$ AnalpH9_MeOH_QC_V1: Rt: 8.35 min, m/z 489.4 [M + H]$^+$ | 8.5 mg, 18%, white solid |
| Example 204 2-{3-[6-(2,3-Dihydro-benzo[1,4]dioxin-5-yl)-2-methoxy-pyridin-3-ylamino]-phenyl}-1-(4-methyl-piperazin-1-yl)-ethanone | | Method H using {3-[6-(2,3-dihydro-benzo[1,4]dioxin-5-yl)-2-methoxy-pyridin-3-ylamino]-phenyl}-acetic acid and 1-methyl-piperazine; 16h; purified by prep HPLC | AnalpH2_MeOH_QC_V1: Rt: 6.23 min, m/z 475.4 [M + H]$^+$ AnalpH9_MeOH_QC_V1: Rt: 8.37 min, m/z 475.4 [M+H]$^+$ | 9.0 mg, 20%, white solid |

-continued

| Compound | | Method | Analytical data | Mass, % yield, state |
|---|---|---|---|---|
| Example 205 2-{3-[6-(2,3-Dihydro-benzo[1,4]dioxin-5-yl)-2-methoxy-pyridin-3-ylamino]-phenyl}-N-(2-oxo-piperidin-4-yl)-acetamide | 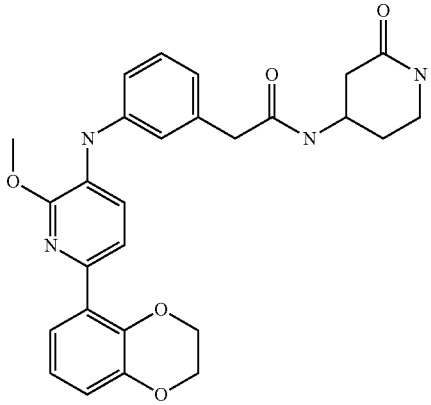 [SMILES: COc1nc(-c2cccc3c2OCCO3)ccc1Nc1cccc(CC(=O)NC2CCNC(=O)C2)c1] | Method H using {3-[6-(2,3-dihydro-benzo[1,4]dioxin-5-yl)-2-methoxy-pyridin-3-ylamino]-phenyl}-acetic acid and 4-amino-piperidin-2-one; 16h; purified by prep HPLC | AnalpH2_MeOH_QC_V1: Rt: 8.02 min, m/z 489.3 [M + H]$^+$ AnalpH9_MeOH_QC_V1: Rt: 8.03 min, m/z 489.3 [M + H]$^+$ | 6.0 mg, 13%, white solid |
| Example 206 2-{3-[6-(2,3-Dihydro-benzo[1,4]dioxin-5-yl)-2-methoxy-pyridin-3-ylamino]-phenyl}-N-(6-oxo-piperidin-3-yl)-acetamide | 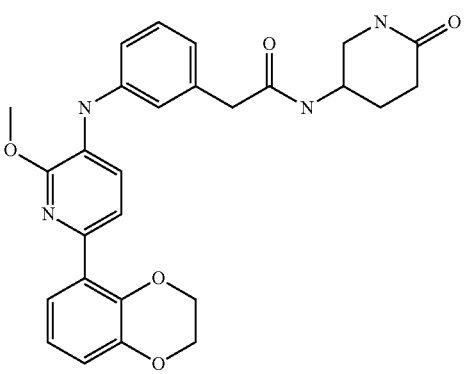 [SMILES: COc1nc(-c2cccc3c2OCCO3)ccc1Nc1cccc(CC(=O)NC2CCC(=O)NC2)c1] | Method H using {3-[6-(2,3-dihydro-benzo[1,4]dioxin-5-yl)-2-methoxy-pyridin-3-ylamino]-phenyl}-acetic acid and 5-aminopiperidin-2-one hydrochloride; 16h; purified by prep HPLC | AnalpH2_MeOH_QC_V1: Rt: 8.02 min, m/z 489.3 [M + H]$^+$ AnalpH9_MeOH_QC_V1: Rt: 8.03 min, m/z 489.3 [M + H]$^+$ | 6.1 mg, 13%, white solid |

The following compounds were prepared using general procedure F:

| Compound | | Method | Analytical data | Mass, % yield, state |
|---|---|---|---|---|
| Example 150 2-[6-(2,3-Dihydro-benzo[1,4]dioxin-5-yl)-2-methoxy-pyridin-3-ylamino]-N-piperidin-4-ylmethyl-benzamide | 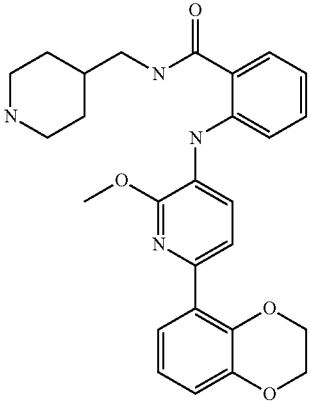 [SMILES: COc1nc(-c2cccc3c2OCCO3)ccc1Nc1ccccc1C(=O)NCC1CCNCC1] | using 4-({2-[6-(2,3-dihydro-benzo[1,4]dioxin-5-yl)-2-methoxy-pyridin-3-ylamino]-benzoylamino}-methyl)-piperidine-1-carboxylic acid tert-butyl ester and general method F; purified by prep HPLC | AnalpH2_MeOH_QC_V1: Rt: 6.34 min, m/z 475.2 [M + H]+ AnalpH9_MeOH_QC_V1: Rt: 7.45 min, m/z 475.2 [M + H]+ | 20.3 mg, 18%, Off white solid |

| Compound | | Method | Analytical data | Mass, % yield, state |
|---|---|---|---|---|
| Example 179<br>4-[6-(2,3-Dihydro-benzo[1,4]dioxin-5-yl)-2-methoxy-pyridin-3-ylamino]-N-piperidin-4-ylmethyl-benzamide | | using 4-({4-[6-(2,3-dihydro-benzo[1,4]dioxin-5-yl)-2-methoxy-pyridin-3-ylamino]-benzoylamino}-methyl)-piperidine-1-carboxylic acid tert-butyl ester and general method F; purified by prep HPLC | AnalpH2_MeOH_QC_V1: Rt: 6.05 min, m/z 475.3 [M + H]+<br>AnalpH9_MeOH_QC_V1: Rt: 7.67 min, m/z 475.3 [M + H]+ | 9.0 mg, 22%, yellow solid |
| Example 180<br>3-[6-(2,3-Dihydro-benzo[1,4]dioxin-5-yl)-2-methoxy-pyridin-3-ylamino]-N-piperidin-4-ylmethyl-benzamide | | using 4-({3-[6-(2,3-dihydro-benzo[1,4]dioxin-5-yl)-2-methoxy-pyridin-3-ylamino]-benzoylamino}-methyl)-piperidine-1-carboxylic acid tert-butyl ester and general method F with workup D; purified by prep HPLC | AnalpH2_MeOH_QC_V1: Rt: 6.29 min, m/z 475.3 [M + H]+<br>AnalpH9_MeOH_QC_V1: Rt: 7.39 min, m/z 475.3 [M + H]+ | 30 mg, 40%, Off white solid |

Synthesis of {4-[6-(2,3-Dihydro-benzo[1,4]dioxin-5-yl)-2-methoxy-pyridin-3-ylamino]-phenyl}-methanol

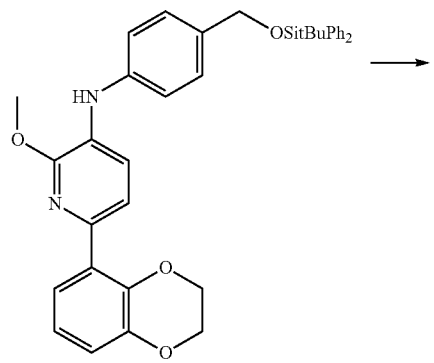

-continued

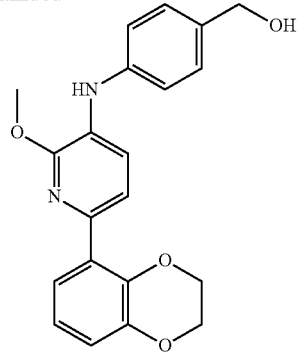

To a stirred solution of [4-(tert-butyl-diphenyl-silanyloxymethyl)-phenyl]-[6-(2,3-dihydro-benzo[1,4]dioxin-5-yl)-2-methoxy-pyridin-3-yl]-amine (0.99 g, 1.65 mmol) in anhydrous THF (7.5 mL) at 0° C. was added TBAF (2.5 mL, 2.50 mmol, 1M solution in THF) and the reaction mixture was allowed to warm to room temperature and then stirred for 1 h. The mixture was concentrated to approx. ¼ of the volume and partitioned between DCM and water. The organic layer was separated and the aqueous layer extracted with DCM. The combined organic layers were washed with brine, dried (MgSO₄) and concentrated under reduced pressure. The crude product was purified by column chromatography on silica gel eluting with 0-70% EtOAc/iso-hexane to afford {4-[6-(2,3-dihydro-benzo[1,4]dioxin-5-yl)-2-methoxy-pyridin-3-ylamino]-phenyl}-methanol (0.45 g, 1.23 mmol, 74.0%) as an orange gum. AnalpH2_MeOH_4 min, Rt: 3.33 min; m/z 365.3 [M+H]+

Synthesis of 4-[6-(2,3-Dihydro-benzo[1,4]dioxin-5-yl)-2-methoxy-pyridin-3-ylamino]-benzaldehyde

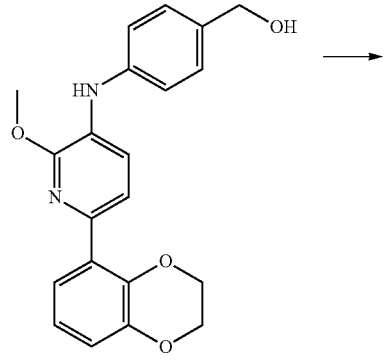

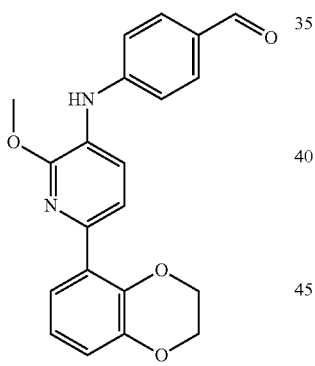

To a stirred solution of {4-[6-(2,3-dihydro-benzo[1,4]dioxin-5-yl)-2-methoxy-pyridin-3-ylamino]-phenyl}-methanol (0.45 g, 1.23 mmol) in anhydrous DCM (20 mL) at 0° C. was added Dess-Martin periodinane (0.64 g, 1.50 mmol) and the reaction mixture was stirred at 0° C. for 1 h, allowed to warm to room temperature, and then stirred for 16 h. The reaction was quenched with a mixture sat. aq. NaHCO₃ solution and 10% aq. Na₂S₂O₃ solution (1:1) and the organic layer was separated. The aqueous layer was extracted with DCM. The combined organic layers were washed with brine, dried (MgSO₄) and concentrated under reduced pressure. The crude product was purified by column chromatography on silica gel eluting with 0-50% EtOAc/iso-hexane to afford 4-[6-(2,3-dihydro-benzo[1,4]dioxin-5-yl)-2-methoxy-pyridin-3-ylamino]-benzaldehyde (0.24 g, 0.66 mmol, 54%) as a red gum. AnalpH2_MeOH_4 min, Rt: 3.41 min; m/z 363.3 [M+H]+

Synthesis of {3-[6-(2,3-Dihydro-benzo[1,4]dioxin-5-yl)-2-methoxy-pyridin-3-ylamino]-phenyl}-methanol

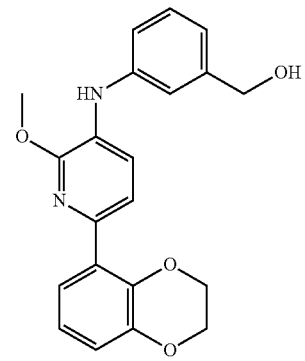

To a stirred solution of [3-(tert-butyl-diphenyl-silanyloxymethyl)-phenyl]-[6-(2,3-dihydro-benzo[1,4]dioxin-5-yl)-2-methoxy-pyridin-3-yl]-amine (0.32 g, 0.53 mmol) in anhydrous THF (3.5 mL) was added TBAF (0.80 mL, 0.80 mmol, 1M solution in THF) and the reaction mixture was stirred at room temperature for 3 h. The mixture was partitioned between DCM and water, the organic layer was separated and the aqueous layer extracted with DCM. The combined organic layers were washed with brine, dried (MgSO₄) and concentrated under reduced pressure. The crude product was purified by column chromatography on silica gel eluting with 0-60% EtOAc/iso-hexane to afford {3-[6-(2,3-dihydro-benzo[1,4]dioxin-5-yl)-2-methoxy-pyridin-3-ylamino]-phenyl}-methanol (0.15 g, 0.41 mmol, 78.0%) as an off white solid.

AnalpH2_MeOH_4 min, Rt: 3.34 min; m/z 365.2 [M+H]+

Synthesis of 3-[6-(2,3-Dihydro-benzo[1,4]dioxin-5-yl)-2-methoxy-pyridin-3-ylamino]-benzaldehyde

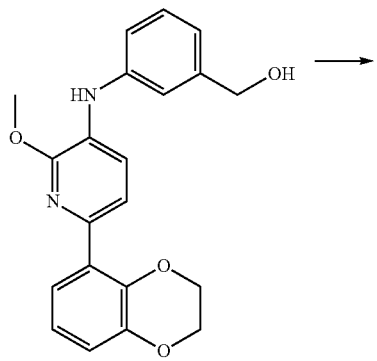

→

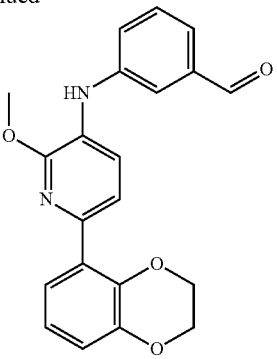

To a stirred solution of {3-[6-(2,3-dihydro-benzo[1,4]dioxin-5-yl)-2-methoxy-pyridin-3-ylamino]-phenyl}-methanol (655 mg, 1.80 mmol) in anhydrous DCM (5 mL) at 0° C. was added Dess-Martin periodinane (848 mg, 2.0 mmol) and the reaction mixture was stirred at 0° C. for 30 min. The reaction was quenched with sat. aq. NaHCO₃ solution and the organic layer was separated. The aqueous layer was extracted with DCM, and the combined organic layers were dried (phase separator) and concentrated under reduced pressure. The crude product was purified by column chromatography on silica gel eluting with 0-50% EtOAc/iso-hexane to afford 3-[6-(2,3-dihydro-benzo[1,4]dioxin-5-yl)-2-methoxy-pyridin-3-ylamino]-benzaldehyde (300 mg, 0.83 mmol, 46%) as a brown solid.

AnalpH2_MeOH_4 min, Rt: 3.36 min; m/z 363.2 [M+H]⁺

The following compounds were made using analogous procedure to General Procedure E1

| Compound | Method | Analytical data | Mass, % yield, state |
|---|---|---|---|
| 3-({4-[4-(2,3-Dihydro-benzo[1,4]dioxin-5-yl)-phenylamino]-benzylamino}-methyl)-morpholine-4-carboxylic acid tert-butyl ester | Using 4-(aminomethyl)-N-(4-(2,3-dihydrobenzo[b][1,4]-dioxin-5-yl)phenyl)aniline and tert-butyl 3-formylmorpholine-4-carboxylate, general method E; purified by column chromatography. | AnalpH2_MeOH_4 min: Rt: 2.53 min, m/z 532 [M + H]+ | 100 mg, 69% Yellow oil |

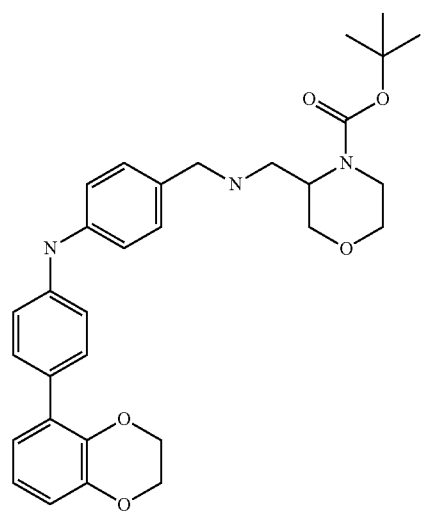

| Compound | | Method | Analytical data | Mass, % yield, state |
|---|---|---|---|---|
| 3-({4-[6-(2,3-Dihydro-benzo[1,4]dioxin-5-yl)-pyridazin-3-ylamino]-benzylamino}-methyl)-morpholine-4-carboxylic acid tert-butyl ester | 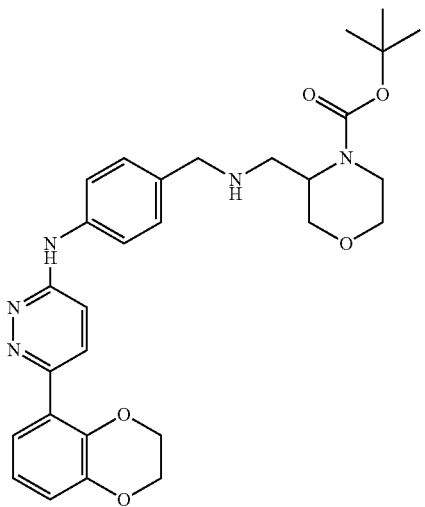 [SMILES: CC(C)(C)OC(=O)N1CCOCC1CNCc1ccc(Nc2ccc(-c3cccc4c3OCCO4)nn2)cc1] | Using (4-aminomethyl-phenyl)-[6-(2,3-dihydro-benzo[1,4]dioxin-5-yl)-pyridazin-3-yl]-amine and tert-butyl 3-formylmorpholine-4-carboxylate, general method E; purified by column chromatography. | AnalpH2_MeOH_4 min: Rt: 2.21 min, m/z 534.3 [M + H]+ | 75 mg, 30% |
| 3-({4-[5-(2,3-Dihydro-benzo[1,4]dioxin-5-yl)-pyrazin-2-ylamino]-benzylamino}-methyl)-morpholine-4-carboxylic acid tert-butyl ester | 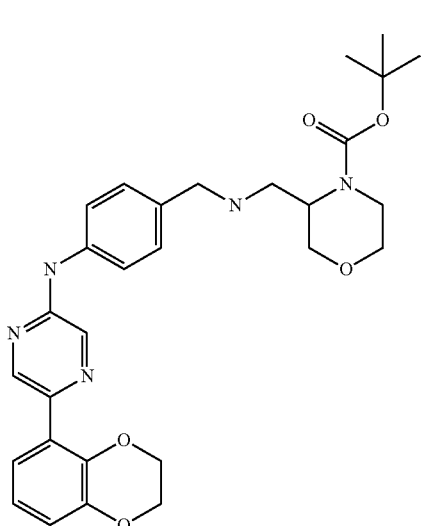 | Using (4-aminomethyl-phenyl)-[5-(2,3-dihydro-benzo[1,4]dioxin-5-yl)-pyrazin-2-yl]-amine and tert-butyl 3-formylmorpholine-4-carboxylate, general method E; purified by prep HPLC. | AnalpH2_MeOH_4 min: Rt: 2.42 min, m/z 534.3 [M + H]⁺ | Yellow oil. Product used directly in subsequent reaction |
| Example 170 4-({4-[6-(2,3-Dihydro-benzo[1,4]dioxin-5-yl)-2-methoxy-pyridin-3-ylamino]-benzylamino}-methyl)-1H-pyridin-2-one | 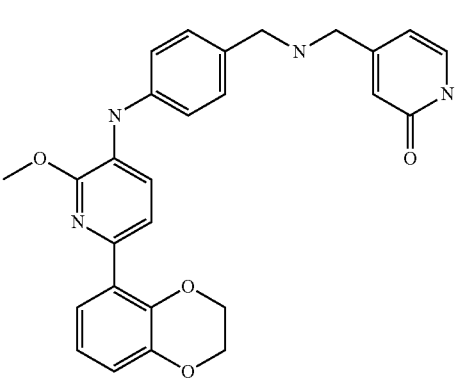 | Using 4-[6-(2,3-dihydro-benzo[1,4]dioxin-5-yl)-2-methoxy-pyridin-3-ylamino]-benzaldehyde and 4-aminomethyl-1H-pyridin-2-one, general method E; purified by prep HPLC. | AnalpH2_MeOH_QC_V1: Rt: 6.00 min, m/z 471.3 [M + H]⁺ AnalpH9_MeOH_QC_V1: Rt: 8.21 min, m/z 471.3 [M + H]⁺ | 9 mg, 20% White solid |

-continued

| Compound | | Method | Analytical data | Mass, % yield, state |
|---|---|---|---|---|
| Example 171 4-({4-[6-(2,3-Dihydro-benzo[1,4]dioxin-5-yl)-2-methoxy-pyridin-3-ylamino]-benzylamino}-methyl)-piperidine-1-carboxylic acid tert-butyl ester | 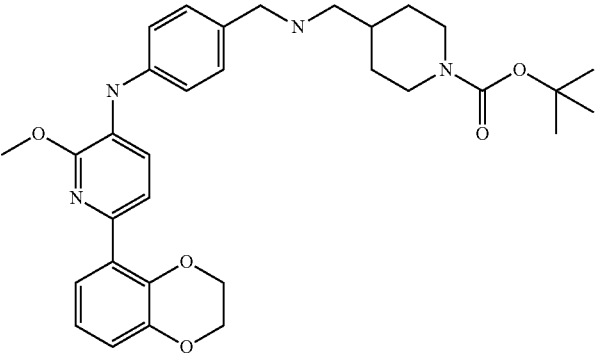 | Using 4-[6-(2,3-dihydro-benzo[1,4]dioxin-5-yl)-2-methoxy-pyridin-3-ylamino]-benzaldehyde and 4-aminomethyl-piperidine-1-carboxylic acid tert-butyl ester, general method E; purified by column chromatography. | AnalpH2_MeOH_QC_V1: Rt: 6.75 min, m/z 561.3 [M + H]+ AnalpH2_MeOH_QC_V1: Rt: 9.32 min, m/z 561.3 [M + H]+ | 34 mg, 74%, Off white solid |
| Example 172 5-({4-[6-(2,3-Dihydro-benzo[1,4]dioxin-5-yl)-2-methoxy-pyridin-3-ylamino]-benzylamino}-methyl)-piperidin-2-one | 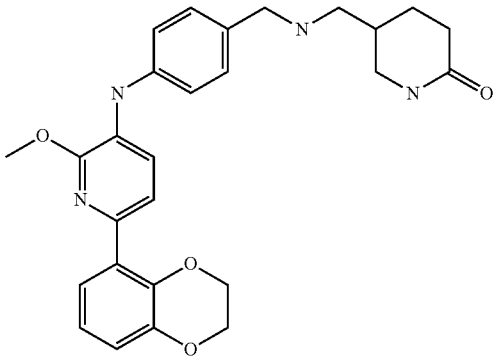 | Using 4-[6-(2,3-dihydro-benzo[1,4]dioxin-5-yl)-2-methoxy-pyridin-3-ylamino]-benzaldehyde and 5-aminomethyl-piperidin-2-one, general method E; purified by prep HPLC. | AnalpH2_MeOH_QC_V1: Rt: 6.03 min, m/z 475.3 [M + H]+ AnalpH9_MeOH_QC_V1: Rt: 8.15 min, m/z 475.3 [M + H]+ | 7 mg, 16%, white solid |
| Example 173 4-({4-[6-(2,3-Dihydro-benzo[1,4]dioxin-5-yl)-2-methoxy-pyridin-3-ylamino]-benzylamino}-methyl)-pyrrolidin-2-one | 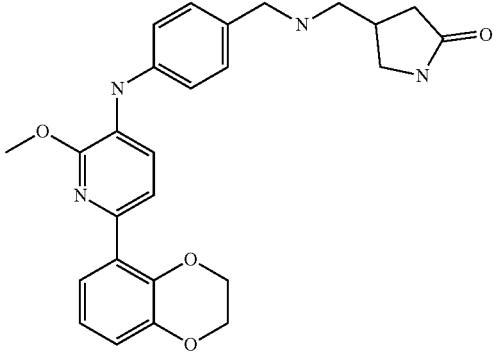 | Using 4-[6-(2,3-dihydro-benzo[1,4]dioxin-5-yl)-2-methoxy-pyridin-3-ylamino]-benzaldehyde and 4-aminomethyl-pyrrolidin-2-one, general method E; purified by prep HPLC. | AnalpH2_MeOH_QC_V1: Rt: 6.01 min, m/z 461.3 [M + H]+ AnalpH9_MeOH_QC_V1: Rt: 8.08 min, m/z 461.3 [M + H]+ | 10 mg, 23%, White solid |
| Example 186 [6-(2,3-Dihydro-benzo[1,4]dioxin-5-yl)-2-methoxy-pyridin-3-yl]-(4-{[(1-methyl-piperidin-4-ylmethyl)-amino]-methyl}-phenyl)-amine | 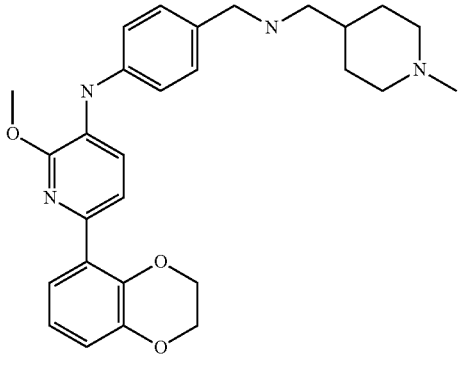 | Using 4-[6-(2,3-dihydro-benzo[1,4]dioxin-5-yl)-2-methoxy-pyridin-3-ylamino]-benzaldehyde and C-(1-methyl-piperidin-4-yl)-methylamine, general method E; purified by prep HPLC. | AnalpH2_MeOH_QC_V1: Rt: 4.92 min, m/z 475.2 [M + H]+ AnalpH9_MeOH_QC_V1: Rt: 8.15 min, m/z 475.2 [M + H]+ | 9 mg, 31%, Off white solid |

-continued

| Compound | | Method | Analytical data | Mass, % yield, state |
|---|---|---|---|---|
| Example 187 (4-{[(1-Benzyl-piperidin-4-ylmethyl)-amino]-methyl}-phenyl)-[6-(2,3-dihydro-benzo[1,4]dioxin-5-yl)-2-methoxy-pyridin-3-yl]-amine | 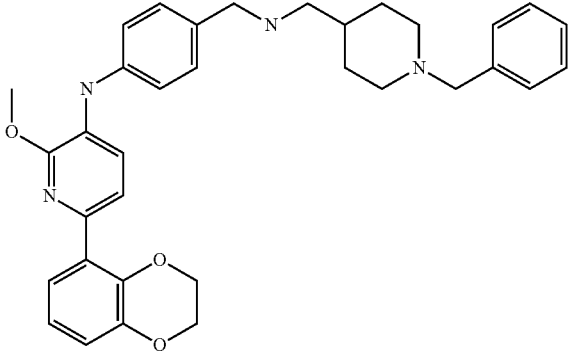 | Using 4-[6-(2,3-dihydro-benzo[1,4]dioxin-5-yl)-2-methoxy-pyridin-3-ylamino]-benzaldehyde and C-(1-benzyl-piperidin-4-yl)-methylamine, general method E; purified by prep HPLC. | AnalpH2_MeOH_QC_V1: Rt: 5.39 min, m/z 551.1 [M + H]+ AnalpH9_MeOH_QC_V1: Rt: 8.93 min, m/z 551.2 [M + H]+ | 8 mg, 24%, Off white solid |
| Example 188 [6-(2,3-Dihydro-benzo[1,4]dioxin-5-yl)-2-methoxy-pyridin-3-yl]-(4-{[(6-fluoro-pyridin-2-ylmethyl)-amino]-methyl}-phenyl)-amine | 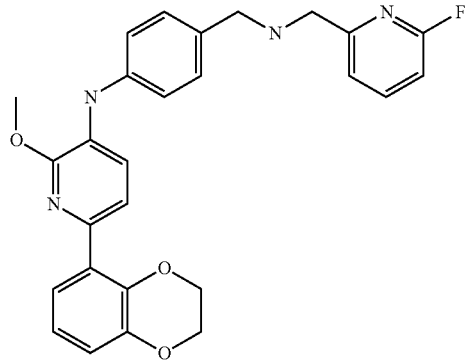 | Using 4-[6-(2,3-dihydro-benzo[1,4]dioxin-5-yl)-2-methoxy-pyridin-3-ylamino]-benzaldehyde and C-(6-fluoro-pyridin-2-yl)-methylamine, general method E; purified by prep HPLC. | AnalpH2_MeOH_QC_V1: Rt: 6.62 min, m/z 473.2 [M + H]+ AnalpH9_MeOH_QC_V1: Rt: 8.73 min, m/z 473.1 [M + H]+ | 9 mg, 31%, Off white solid |
| Example 189 [6-(2,3-Dihydro-benzo[1,4]dioxin-5-yl)-2-methoxy-pyridin-3-yl]-(3-{[(1-methyl-piperidin-4-ylmethyl)-amino]-methyl}-phenyl)-amine | 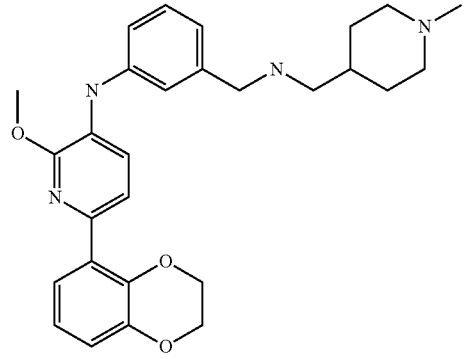 | Using 3-[6-(2,3-dihydro-benzo[1,4]dioxin-5-yl)-2-methoxy-pyridin-3-ylamino]-benzaldehyde and C-(1-methyl-piperidin-4-yl)-methylamine, general method E; purified by prep HPLC. | AnalpH2_MeOH_QC_V1: Rt: 5.03 min, m/z 475.2 [M + H]+ AnalpH9_MeOH_QC_V1: Rt: 8.29 min, m/z 475.3 [M + H]+ | 17 mg, 33%, Off white solid |
| Example 190 (3-{[(1-Benzyl-piperidin-4-ylmethyl)-amino]-methyl}-phenyl)-[6-(2,3-dihydro-benzo[1,4]dioxin-5-yl)-2-methoxy-pyridin-3-yl]-amine | 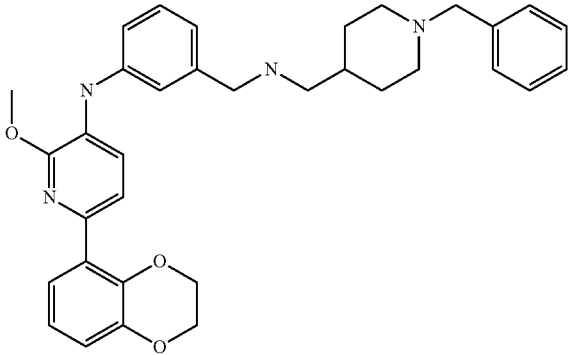 | Using 3-[6-(2,3-dihydro-benzo[1,4]dioxin-5-yl)-2-methoxy-pyridin-3-ylamino]-benzaldehyde and C-(1-benzyl-piperidin-4-yl)-methylamine, general method E; purified by prep HPLC. | AnalpH2_MeOH_QC_V1: Rt: 5.28 min, m/z 551.3 [M + H]+ AnalpH9_MeOH_QC_V1: Rt: 9.07 min, m/z 551.3 [M + H]+ | 32 mg, 53%, Off white solid |

-continued

| Compound | | Method | Analytical data | Mass, % yield, state |
|---|---|---|---|---|
| Example 191 1-[4-({3-[6-(2,3-Dihydro-benzo[1,4]dioxin-5-yl)-2-methoxy-pyridin-3-ylamino]-benzylamino}-methyl)-piperidin-1-yl]-ethanone | 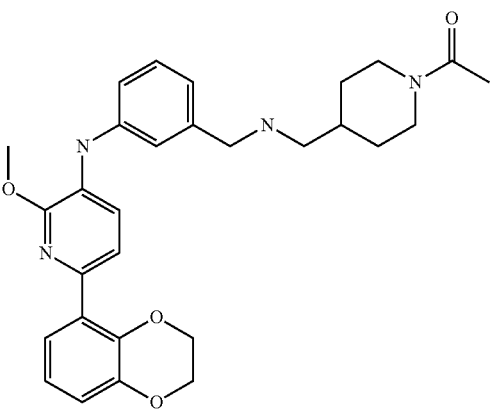 | Using 3-[6-(2,3-dihydro-benzo[1,4]dioxin-5-yl)-2-methoxy-pyridin-3-ylamino]-benzaldehyde and 1-(4-aminomethyl-piperidin-1-yl)-ethanone, general method E; purified by prep HPLC. | AnalpH2_MeOH_QC_V1: Rt: 6.20 min, m/z 503.2 [M + H]+ AnalpH9_MeOH_QC_V1: Rt: 8.37 min, m/z 503.3 [M + H]+ | 26.0 mg, 47% Off white solid |
| Example 192 5-({3-[6-(2,3-Dihydro-benzo[1,4]dioxin-5-yl)-2-methoxy-pyridin-3-ylamino]-benzylamino}-methyl)-pyrrolidin-2-one | 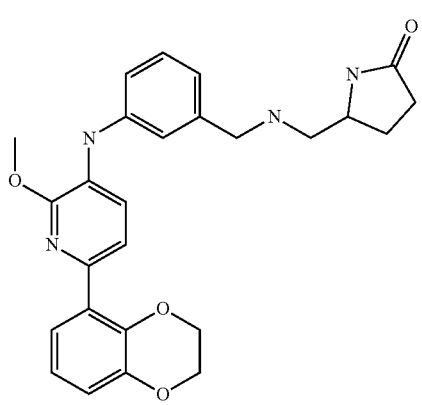 | Using 3-[6-(2,3-dihydro-benzo[1,4]dioxin-5-yl)-2-methoxy-pyridin-3-ylamino]-benzaldehyde and 5-aminomethyl-pyrrolidin-2-one, general method E; purified by prep HPLC. | AnalpH2_MeOH_QC_V1: Rt: 6.02 min, m/z 461.2 [M + H]+ AnalpH9_MeOH_QC_V1: Rt: 8.35 min, m/z 461.1 [M + H]+ | 9.5 mg, 19% Off white solid |
| Example 193 4-({3-[6-(2,3-Dihydro-benzo[1,4]dioxin-5-yl)-2-methoxy-pyridin-3-ylamino]-benzylamino}-methyl)-1H-pyridin-2-one | 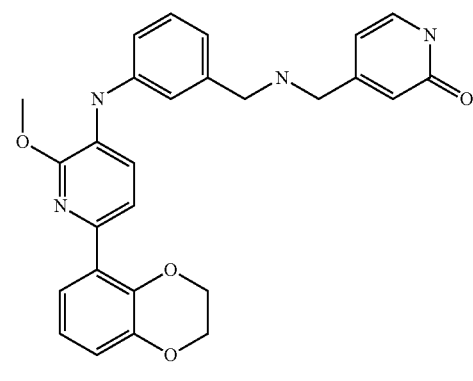 | Using 3-[6-(2,3-dihydro-benzo[1,4]dioxin-5-yl)-2-methoxy-pyridin-3-ylamino]-benzaldehyde and 4-aminomethyl-1H-pyridin-2-one, general method E; purified by prep HPLC. | AnalpH2_MeOH_QC_V1: Rt: 6.08 min, m/z 471.1 [M + H]+ AnalpH9_MeOH_QC_V1: Rt: 8.29 min, m/z 471.2 [M + H]+ | 18 mg, 35% Off white solid |
| Example 194 4-({3-[6-(2,3-Dihydro-benzo[1,4]dioxin-5-yl)-2-methoxy-pyridin-3-ylamino]-benzylamino}-methyl)-piperidin-2-one | 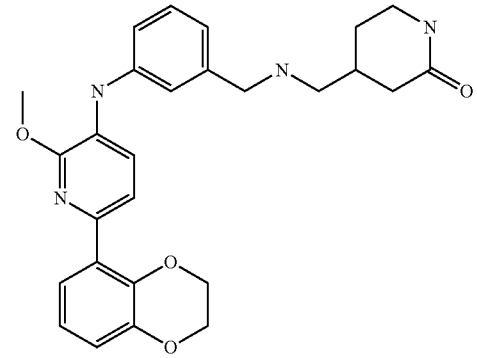 | Using 3-[6-(2,3-dihydro-benzo[1,4]dioxin-5-yl)-2-methoxy-pyridin-3-ylamino]-benzaldehyde and 4-aminomethyl-piperidin-2-one, general method E; purified by prep HPLC. | AnalpH2_MeOH_QC_V1: Rt: 6.07 min, m/z 475.1 [M + H]+ AnalpH9_MeOH_QC_V1: Rt: 8.26 min, m/z 475.2 [M + H]+ | 18 mg, 34% Off white solid |

| Compound | | Method | Analytical data | Mass, % yield, state |
|---|---|---|---|---|
| Example 195<br>5-({3-[6-(2,3-Dihydro-benzo[1,4]dioxin-5-yl)-2-methoxy-pyridin-3-ylamino]-benzylamino}-methyl)-piperidin-2-one | 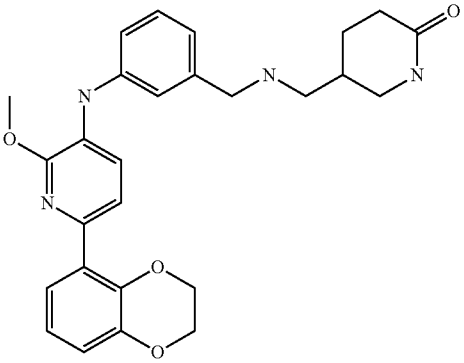 | Using 3-[6-(2,3-dihydro-benzo[1,4]dioxin-5-yl)-2-methoxy-pyridin-3-ylamino]-benzaldehyde and 5-aminomethyl-piperidin-2-one, general method E; purified by prep HPLC. | AnalpH2_MeOH_QC_V1: Rt: 6.07 min, m/z 475.1 [M + H]+ AnalpH9_MeOH_QC_V1: Rt: 8.29 min, m/z 475.1 [M + H]+ | 9.1 mg, 17% Off white solid |
| Example 199<br>[6-(2,3-Dihydro-benzo[1,4]dioxin-5-yl)-2-methoxy-pyridin-3-yl]-[4-(4-pyridin-3-ylmethyl-piperazin-1-ylmethyl)-phenyl]-amine | 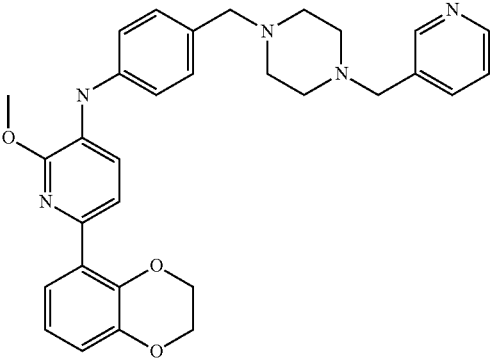 | Using 4-[6-(2,3-Dihydro-benzo[1,4]dioxin-5-yl)-2-methoxy-pyridin-3-ylamino]-benzaldehyde and 1-pyridin-3-ylmethyl-piperazine, general method E; purified by prep HPLC. | AnalpH2_MeOH_QC_V1: Rt: 5.75 min, m/z 524.3 [M + H]+ AnalpH9_MeOH_QC_V1: Rt: 8.91 min, m/z 524.3 [M + H]+ | 17.6 mg, 61% Off white solid |
| Example 200<br>1-{3-[6-(2,3-Dihydro-benzo[1,4]dioxin-5-yl)-2-methoxy-pyridin-3-ylamino]-benzyl}-piperidine-3-carboxylic acid amide | 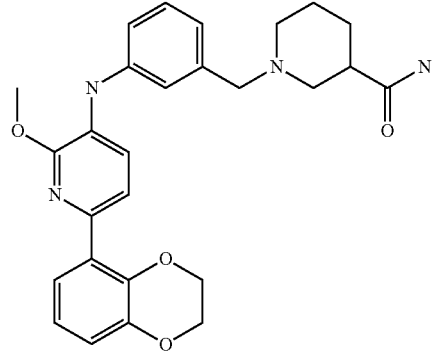 | Using 3-[6-(2,3-dihydro-benzo[1,4]dioxin-5-yl)-2-methoxy-pyridin-3-ylamino]-benzaldehyde and piperidine-3-carboxylic acid amide, general method E; purified by prep HPLC. | AnalpH2_MeOH_QC_V1: Rt: 6.17 min, m/z 475.3 [M + H]+ AnalpH9_MeOH_QC_V1: Rt: 8.65 min, m/z 475.3 [M + H]+ | 29.5 mg, 57% Off white solid |
| Example 201<br>4-({4-[6-(2,3-Dihydro-benzo[1,4]dioxin-5-yl)-2-methoxy-pyridin-3-ylamino]-benzylamino}-methyl)-piperidin-2-one | 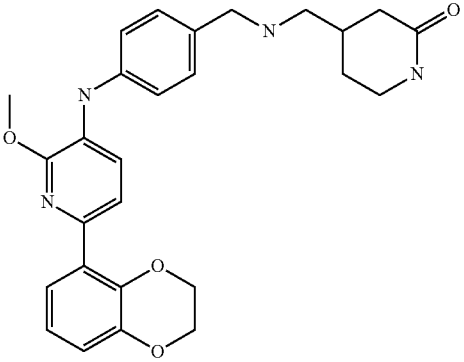 | Using 4-[6-(2,3-dihydro-benzo[1,4]dioxin-5-yl)-2-methoxy-pyridin-3-ylamino]-benzaldehyde and 4-aminomethyl-piperidin-2-one hydrochloride, general method E; purified by prep HPLC. | AnalpH2_MeOH_QC_V1: Rt: 6.06 min, m/z 475.3 [M + H]+ AnalpH9_MeOH_QC_V1: Rt: 8.12 min, m/z 475.3 [M + H]+ | 6.0 mg, 23% Off white solid |

-continued

| Compound | | Method | Analytical data | Mass, % yield, state |
|---|---|---|---|---|
| 4-{3-[6-(2,3-Dihydro-benzo[1,4]dioxin-5-yl)-2-methoxy-pyridin-3-ylamino]-benzyl}-piperazine-1-carboxylic acid tert-butyl ester | 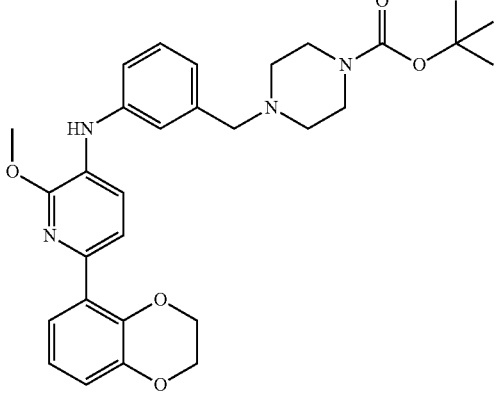 | Using 3-[6-(2,3-dihydro-benzo[1,4]dioxin-5-yl)-2-methoxy-pyridin-3-ylamino]-benzaldehyde and piperazine-1-carboxylic acid tert-butyl ester, general method E; purified by column chromatography. | AnalpH2_MeOH_4 min: Rt: 2.76 min, m/z 533.3 [M + H]+ | 94 mg, 64%, Brown oil |
| 4-(4-{3-[6-(2,3-Dihydro-benzo[1,4]dioxin-5-yl)-2-methoxy-pyridin-3-ylamino]-benzyl}-piperazin-1-ylmethyl)-pyrazole-1-carboxylic acid tert-butyl ester | 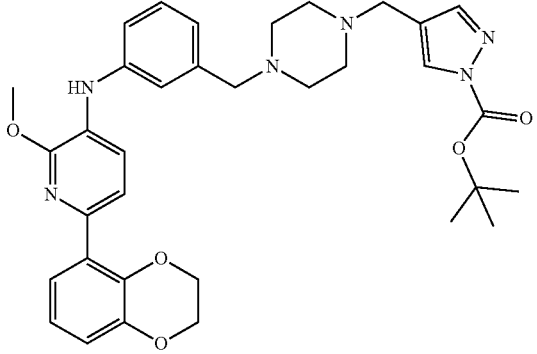 [SMILES: COc1nc(-c2cccc3c2OCCO3)ccc1Nc1cccc(CN2CCN(Cc3cnn(C(=O)OC(C)(C)C)c3)CC2)c1] | Using [6-(2,3-dihydro-benzo[1,4]dioxin-5-yl)-2-methoxy-pyridin-3-yl]-(3-piperazin-1-ylmethyl-phenyl)-amine and 4-formyl-pyrazole-1-carboxylic acid tert-butyl ester, general method E; purified by prep HPLC. | AnalpH2_MeOH_4 min: Rt: 2.64 min, m/z 613 [M + H]+ | 10 mg, 24%, colourless oil |
| Example 209 [6-(2,3-Dihydro-benzo[1,4]dioxin-5-yl)-2-methoxy-pyridin-3-yl]-(3-{[(1H-pyrazol-3-ylmethyl)-amino]-methyl}-phenyl)-amine | 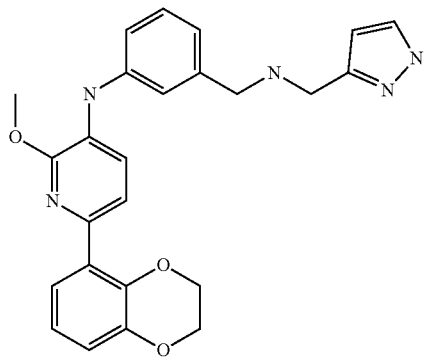 | Using (3-aminomethyl-phenyl)-[6-(2,3-dihydro-benzo[1,4]dioxin-5-yl)-2-methoxy-pyridin-3-yl]-amine and 1H-pyrazole-3-carbaldehyde, general method E; purified by prep HPLC. | AnalpH2_MeOH_QC_V1: Rt: 6.19 min, m/z 444.3 [M + H]+ AnalpH9_MeOH_QC_V1: Rt: 8.45 min, m/z 444.3 [M + H]+ | 3.1 mg, 5%, White solid |
| 4-({4-[6-(2,3-Dihydro-benzo[1,4]dioxin-5-yl)-2-methoxy-pyridin-3-ylamino]-benzylamino}-methyl)-pyrazole-1-carboxylic acid tert-butyl ester | 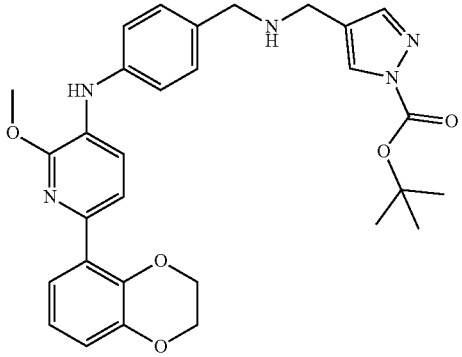 [SMILES: COc1nc(-c2cccc3c2OCCO3)ccc1Nc1ccc(CNCc2cnn(C(=O)OC(C)(C)C)c2)cc1] | Using (4-aminomethyl-phenyl)-[6-(2,3-dihydro-benzo[1,4]dioxin-5-yl)-2-methoxy-pyridin-3-yl]-amine and 4-aminomethyl-pyrazole-1-carboxylic acid tert-butyl ester, general method E; purified by prep HPLC. | AnalpH2_MeOH_4 min: Rt: 2.62 min, m/z 544.4 [M + H]+ | 65 mg, 75%, White solid |

The following compounds were prepared using general method F1.

| Compound | | Method | Analytical data | Mass, % yield, state |
|---|---|---|---|---|
| Example 151<br>4-(2,3-dihydrobenzo[b][1,4]dioxin-5-yl)-N-(4-(((morpholin-3-ylmethyl)amino)methyl)phenyl)aniline | 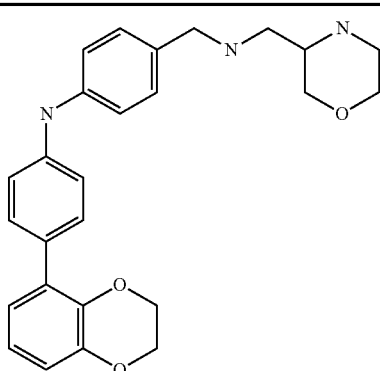 | using 3-({4-[4-(2,3-dihydro-benzo[1,4]dioxin-5-yl)-phenylamino]-benzylamino}-methyl)-morpholine-4-carboxylic acid tert-butyl ester and general method F1; purified by Prep HPLC | AnalpH2_MeOH_QC_V1: Rt: 4.70 min, m/z 432.2 [M + H]+<br>AnalpH9_MeOH_QC_V1: Rt: 7.70 min, m/z 432.2 [M + H]+ | 6.0 mg, 4%, Orange gum |
| Example 154<br>[6-(2,3-Dihydro-benzo[1,4]dioxin-5-yl)-pyridazin-3-yl]-(4-{[(morpholin-3-ylmethyl)-amino]-methyl}-phenyl)-amine | 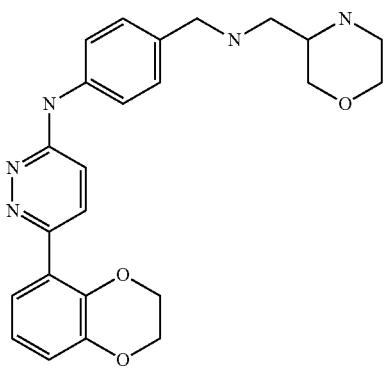 | using 3-({4-[6-(2,3-dihydro-benzo[1,4]dioxin-5-yl)-pyridazin-3-ylamino]-benzylamino}-methyl)-morpholine-4-carboxylic acid tert-butyl ester and general method F1; purified by prep HPLC | AnalpH2_MeOH_QC_V1: Rt: 3.45 min, m/z 434.3 [M + H]+<br>AnalpH9_MeOH_QC_V1: Rt: 6.90 min, m/z 434.3 [M + H]+ | 6.0 mg, 10% Off white solid |
| Example 155<br>[5-(2,3-Dihydro-benzo[1,4]dioxin-5-yl)-pyrazin-2-yl]-(4-{[(morpholin-3-ylmethyl)-amino]-methyl}-phenyl)-amine | 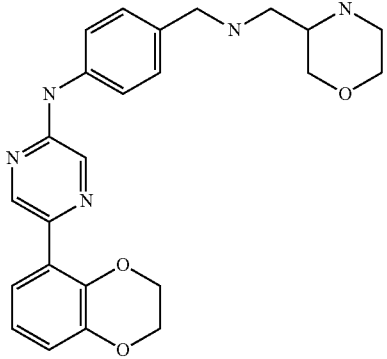 | using 3-({4-[5-(2,3-dihydro-benzo[1,4]dioxin-5-yl)-pyrazin-2-ylamino]-benzylamino}-methyl)-morpholine-4-carboxylic acid tert-butyl ester and general method F1; purified by prep HPLC | AnalpH2_MeOH_QC_V1: Rt: 4.17 min, m/z 434.2 [M + H]+<br>AnalpH9_MeOH_QC_V1: Rt: 7.34 min, m/z 434.3 [M + H]+ | 20 mg, 5% yellow solid |
| Example 178<br>[6-(2,3-Dihydro-benzo[1,4]dioxin-5-yl)-2-methoxy-pyridin-3-yl]-(4-{[(piperidin-4-ylmethyl)-amino]-methyl}-phenyl)-amine | 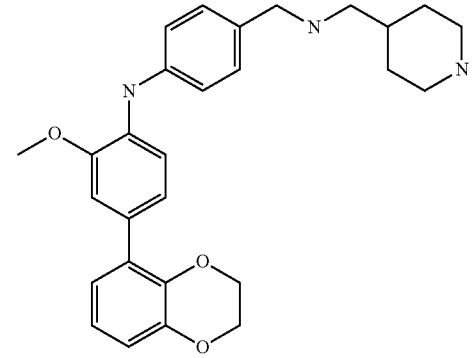 | using 4-({4-[6-(2,3-dihydro-benzo[1,4]dioxin-5-yl)-2-methoxy-pyridin-3-ylamino]-benzylamino}-methyl)-piperidine-1-carboxylic acid tert-butyl ester and general method F1; purified by prep HPLC | AnalpH2_MeOH_QC_V1: Rt: 4.86 min, m/z 461.3 [M + H]+<br>AnalpH9_MeOH_QC_V1: Rt: 8.02 min, m/z 461.2 [M + H]+ | 21 mg, Orange solid |

-continued

| Compound | | Method | Analytical data | Mass, % yield, state |
|---|---|---|---|---|
| Example 207 [6-(2,3-Dihydro-benzo[1,4]dioxin-5-yl)-2-methoxy-pyridin-3-yl]-(3-piperazin-1-ylmethyl-phenyl)-amine | 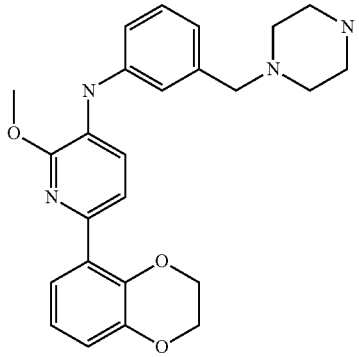 | using 4-{3-[6-(2,3-dihydro-benzo[1,4]dioxin-5-yl)-2-methoxy-pyridin-3-ylamino]-benzyl}-piperazine-1-carboxylic acid tert-butyl ester and general method F1; purified by column chromatography | AnalpH2_MeOH_QC_V1: Rt: 6.26 min, m/z 433.4 [M + H]+ AnalpH9_MeOH_QC_V1: Rt: 8.31 min, m/z 433.4 [M + H]+ | 10 mg, 100% White solid |
| Example 208 [6-(2,3-Dihydro-benzo[1,4]dioxin-5-yl)-2-methoxy-pyridin-3-yl]-{3-[4-(1H-pyrazol-4-ylmethyl)-piperazin-1-ylmethyl]-phenyl}-amine | 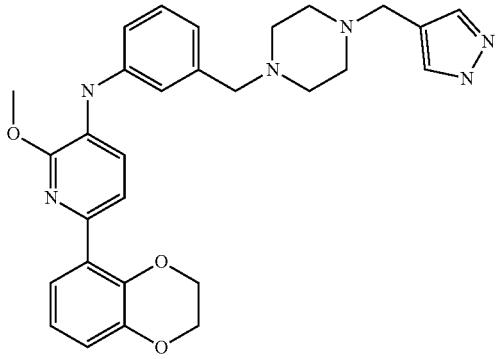 | using 4-({4-[6-(2,3-Dihydro-benzo[1,4]dioxin-5-yl)-2-methoxy-pyridin-3-ylamino]-benzylamino}-methyl)-piperidine-1-carboxylic acid tert-butyl ester and general method F1; purified by prep HPLC | AnalpH2_MeOH_QC_V1: Rt: 6.34 min, m/z 513.5 [M + H]+ AnalpH9_MeOH_QC_V1: Rt: 8.61 min, m/z 513.5 [M + H]+ | 8.0 mg, 92% White solid |

Synthesis of 3-[6-(2,3-Dihydro-benzo[1,4]dioxin-5-yl)-2-oxo-1,2-dihydro-pyridin-3-ylamino]-benzaldehyde

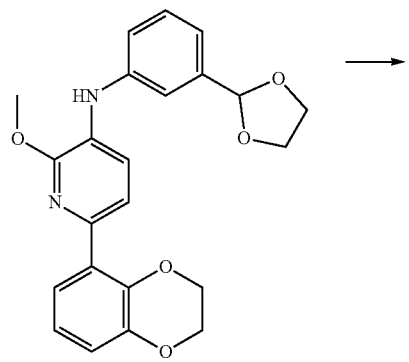

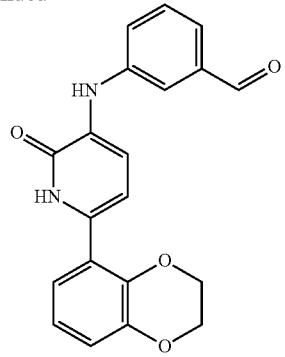

To a stirred solution of [6-(2,3-dihydro-benzo[1,4]dioxin-5-yl)-2-methoxy-pyridin-3-yl]-(3-[1,3]dioxolan-2-yl-phenyl)-amine (0.46 g, 1.1 mmol) in acetone (6 mL) and water (1.2 mL) was added p-toluenesulfonic acid monohydrate (210 mg, 1.1 mmol) and the reaction mixture was stirred at room temperature for 72 h and then at 40° C. for 4 h. The reaction mixture was concentrated under reduced pressure and the residue was dissolved in THF (10 mL) and 2M aq. HCl (5 mL) was added and the reaction stirred at room temperature for 16 h, then at 45° C. for 6 h, and then at reflux temperature for 24 h. The reaction was quenched with aq. K₂CO₃ solution and the aqueous layer was extracted with DCM. The combined organic layers were dried (MgSO₄) and concentrated under reduced pressure. The crude product was purified by column chromatography to afford 3-[6-(2,3-dihydro-benzo[1,4]dioxin-5-yl)-2-oxo-1,2-dihydro-pyridin-3-ylamino]-benzaldehyde (199 mg, 0.57 mmol, 52%) as a yellow foam.

AnalpH2_MeOH_4 min, Rt: 3.03 min; m/z 349.2 [M+H]⁺

Example 153: Synthesis of 6-(2,3-Dihydro-benzo[1,4]dioxin-5-yl)-3-(3-dimethylaminomethyl-phenylamino)-1H-pyridin-2-one

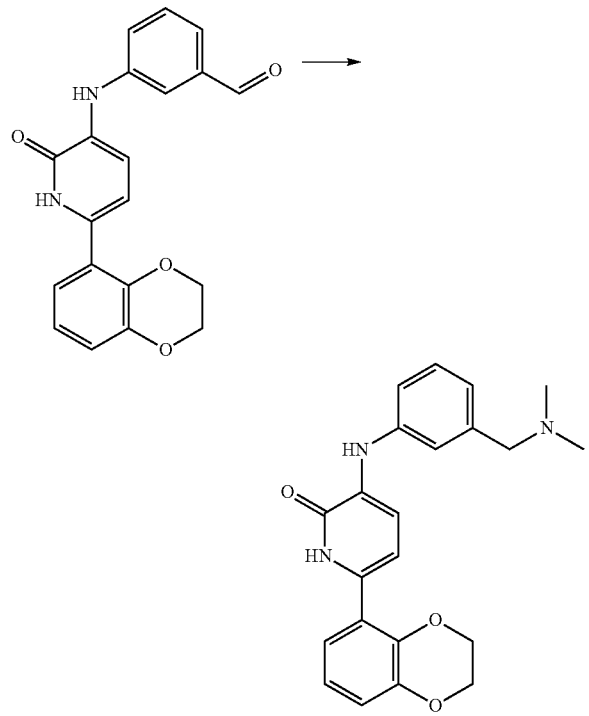

To a microwave vial containing [6-(2,3-dihydro-benzo[1,4]dioxin-5-yl)-2-methoxy-pyridin-3-yl]-(3-[1,3]dioxolan-2-yl-phenyl)-amine (109 mg, 0.31 mmol) was added 2M dimethylamine solution in methanol (1.5 mL, 1.55 mmol) and the reaction mixture heated at 100° C. for 1 h using a microwave reactor. The reaction mixture was cooled to 0° C. and sodium borohydride was added. The reaction mixture was allowed to warm to room temperature and stirred at room temperature for 72 h. The reaction was quenched with a few drops of acetic acid and concentrated under reduced pressure. The residue was partitioned between DCM and water and the organic layer separated. The aqueous layer was extracted with DCM and the combined organic layers were dried (MgSO₄) and concentrated under reduced pressure. The crude product was purified by prep HPLC to afford 6-(2,3-dihydro-benzo[1,4]dioxin-5-yl)-3-(3-dimethylaminomethyl-phenylamino)-1H-pyridin-2-one (39.3 mg, 0.10 mmol, 34%) as a pale yellow solid.

AnalpH2_MeOH_QC_V1: Rt: 5.22 min, m/z 378.2 [M+H]⁺

AnalpH9_MeOH_QC_V1: Rt: 7.91 min, m/z 378.2 [M+H]+

¹H-NMR (400 MHz, DMSO-d6) δ 11.61 (s, 1H), 7.65 (s, 1H), 7.26-7.07 (m, 4H), 6.96-6.77 (m, 4H), 6.27 (d, J=7.3 Hz, 1H), 4.48-4.12 (m, 4H), 3.34 (s, 2H), 2.14 (s, 6H)

Biological Activity

Protein Expression and Purification

For SPR assays pGEX-KRAS(G12V) plasmid was transformed into *E. coli* C41(DE3). Bacterial cells were cultured at 37° C. to an OD₆₀₀ of 0.6 and induced with IPTG (final 0.1 mM) at 18° C. over night. The GST fusion proteins were extracted from bacteria pellets after cell disruption in 140 mM NaCl, 2.7 mM KCl, 10 mM NaH₂PO₄, 1.8 mM KH₂PO₄, 1 mM EDTA, 2 mM MgCl₂ pH 7.4 and purified by glutathione-sepharose column chromatography (GE Healthcare), eluting with 50 mM Tris-HCl pH8.0, 10 mM reduced glutathione, 1 mM DTT, 2 mM MgCl₂. The eluted proteins were dialysed against 50 mM Tris-HCl pH8.0, 1 mM DTT, 2 mM MgCl₂ and concentrated to 10 mg/ml using a Biomax-30 ULTRAFREE-15 centrifugal filter device (Millipore). Purified KRAS protein was loaded with GPPNHP as described elsewhere (Pacold et al., 2000). Loaded protein was then purified by gel filtration on a HiLoad Superdex-75 HR column (GE Healthcare) in 1×PBS pH7.4, 5 mM MgCl₂ and concentrated for storage.

Protocol for KRas Small-Molecule Screening and Affinity Measurements by SPR

Protein Immobilization

To a previously immobilized CM5 chip (GE Healthcare BR-1005-30) with anti GST antibody via amine coupling method, GST in channel 1 and GST-human KRas166 (G12V) GPPNHP in channel 2 were immobilised. GST was immobilised between 2,000 and 5,000 Response units. KRAS166 (G12V) was immobilized between 10,000 to 15,000 Response Units.

Compound Screening

In a 96 well plate, compounds were diluted in 25 mM, 100 mM NaCl, 5 mM MgCl₂ and 5% DMSO Buffer to a final concentration of 100 uM. DCAI was used as positive control. Experiment also included a solvent correction curve for 5% DMSO. Screening and evaluation of the protein immobilization and the compounds screening was done accordingly to the BIACORE T200 control and evaluation software.

Calculations for how many response units are required for a 1:1 ratio of compound/protein interaction are shown below.

Protein immobilisation: 10,000 RU; average fragment 300 Da in size.

$R_{max} = (MWA/MWL) \times RL \times SM$

MWA is the molecular weight of the analyte in Da
MWL is the molecular weight of the ligand in Da
RL is the immobilization level in RU
SM is the molar stoichiometry (assume 1:1)
Rmax=300/47,500×10,000×1
Rmax=63 RU.

Cell Viability Assay protocols

Assay 1

Cells (A549 ATCC CCL-185) are cultured in Dulbecco's Modified Eagle's Medium plus 10% foetal calf serum and 2 mM L-glutamine at 37° C., 5% CO₂. Cells are plated onto white clear bottom 96-well plates (5000 cells/well in 200 μl media) and left to adhere overnight at 37° C., 5% CO₂. Next day, test compound (1 μl at 200× concentration in 100% DMSO) is added to give final test compound concentration 1× in 0.5% DMSO. After 48 h of incubation at 37° C., 5% CO₂, 20 μl CellTiter-Glo reagent (Promega G7572) is added into each well. Plates are incubated at room temperature with shaking for 30 min and then luminescence is read using a PheraStar plate reader. The concentration of compounds that decrease cell viability by 50% is calculated from dose response curves generated using Dotmatics data analysis software.

In the DLD1 cell assay, cells (ATCC CCL-221) are cultured in RPMI-1640 medium plus 10% foetal calf serum and 2 mM L-glutamine at 37° C., 5% $CO_2$.

In the H358 cell assay, cells (ATCC CRL-5807) are cultured in RPMI-1640 medium plus 10% foetal calf serum and 2 mM L-glutamine at 37° C., 5% $CO_2$.

Assay 2

Cancer cell lines were in seeded in ViewPlates-96 microplates (PerkinElmer). HT1080 cells at 7500 cells per well and cultured in DMEM, high glucose, GlutaMAX media containing 10% FBS at 37° C. in 5% CO atmosphere. Cells were cultured overnight and the compounds (dissolved in DMSO and diluted to 0.2% DMSO) were added to the cells at concentrations ranging from 0 to 20 μM. The cells were incubated under standard culture conditions for either 24, 48 or 72 h. Cell viability was as quantitated using the CellTiterGlo Luminescent Cell Viability Assay (Promega) according to the manufacturer's instructions to measure ATP generated by metabolically active cells. Luminescent signals were measured using an Envision 2103 Multilabel Microplate Reader (PerkinElmer). The luminescence signals obtained from the compound-treated cells were normalized against the signal for DMSO-only treated cells. The IC50 values, calculated from the 48 and 72 h CellTiterGlo data, were generated by non-linear regression using the software GraphPad Prism 7.00 for windows (GraphPad Inc).

| Example No. | Chemical Structure | SPR Response Units | Cell Viability (μM) H358 DLD-1 |
|---|---|---|---|
| 42 | 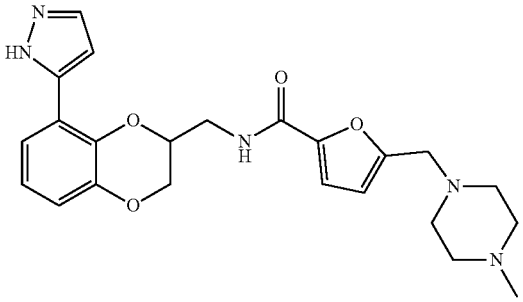 [SMILES: CN1CCN(Cc2ccc(C(=O)NCC3COc4cccc(-c5ccn[nH]5)c4O3)o2)CC1] | | 62 |
| 43 | 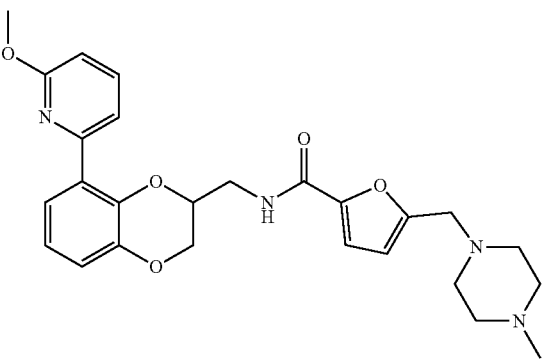 [SMILES: COc1cccc(-c2cccc3c2OC(CNC(=O)c2ccc(CN4CCN(C)CC4)o2)CO3)n1] | 105 | >100 19 |
| 52 | 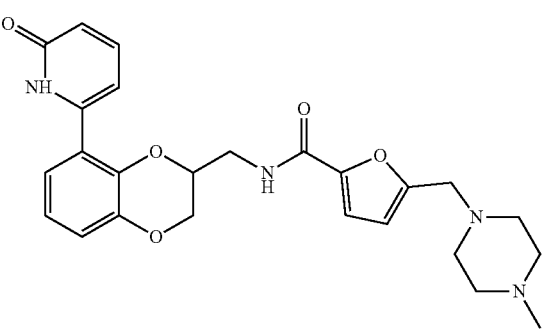 [SMILES: CN1CCN(Cc2ccc(C(=O)NCC3COc4cccc(-c5cccc(=O)[nH]5)c4O3)o2)CC1] | | 18 |

-continued

| Example No. | Chemical Structure | SPR Response Units | Cell Viability (μM) H358 DLD-1 |
|---|---|---|---|
| 45a | 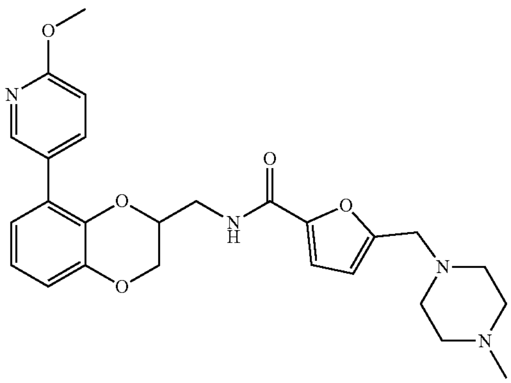 [SMILES: COc1ccc(-c2cccc3c2OC(CNC(=O)c2ccc(CN4CCN(C)CC4)o2)CO3)cn1] | 90 | |
| 39 | 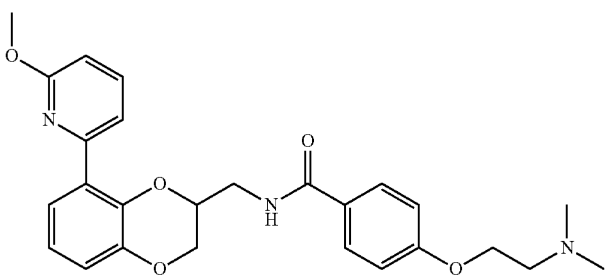 [SMILES: COc1cccc(-c2cccc3c2OC(CNC(=O)c2ccc(OCCN(C)C)cc2)CO3)n1] | 127 | 79<br>5 |
| 53 | 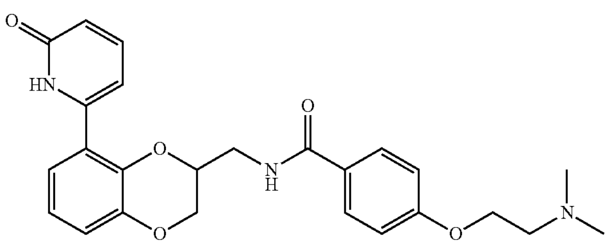 [SMILES: CN(C)CCOc1ccc(C(=O)NCC2COc3cccc(-c4cccc(=O)[nH]4)c3O2)cc1] | 52 | |
| 54 | 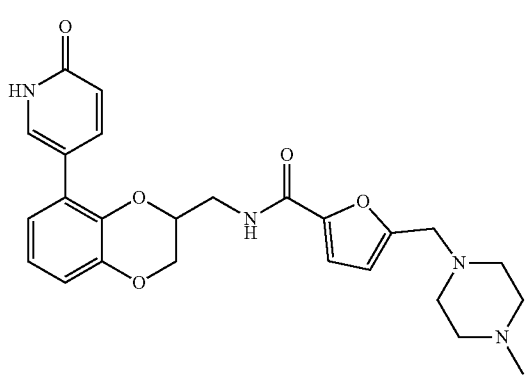 [SMILES: CN1CCN(Cc2ccc(C(=O)NCC3COc4cccc(-c5ccc(=O)[nH]c5)c4O3)o2)CC1] | 57 | |

-continued

| Example No. | Chemical Structure | SPR Response Units | Cell Viability (μM) H358 DLD-1 |
|---|---|---|---|
| 46 | 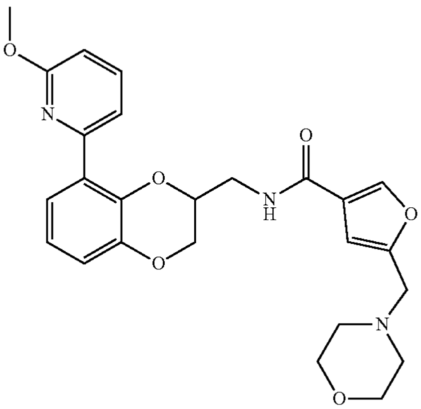 [SMILES: COc1cccc(-c2cccc3c2OC(CNC(=O)c2coc(CN4CCOCC4)c2)CO3)n1] | 148 | >100<br>>100 |
| 38 | 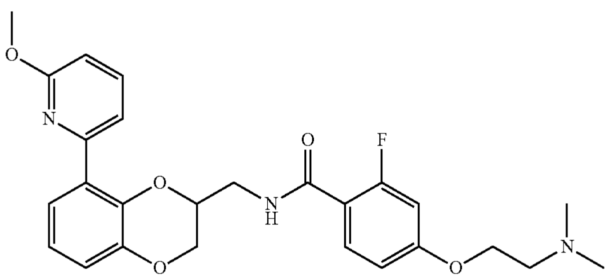 [SMILES: COc1cccc(-c2cccc3c2OC(CNC(=O)c2ccc(OCCN(C)C)cc2F)CO3)n1] | 335 | 58<br>3.6 |
| 137 | 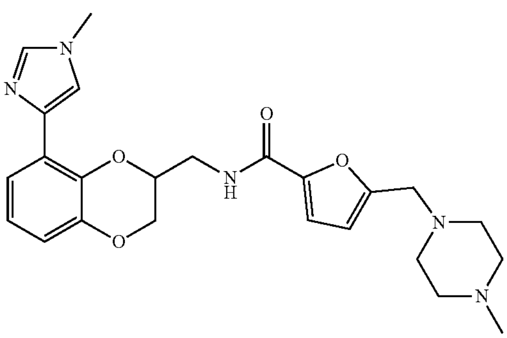 [SMILES: CN1CCN(Cc2ccc(C(=O)NCC3COc4cccc(-c5cn(C)cn5)c4O3)o2)CC1] | 50 | |
| 138 | 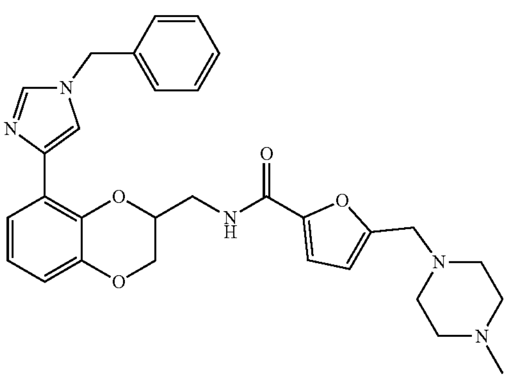 [SMILES: CN1CCN(Cc2ccc(C(=O)NCC3COc4cccc(-c5cn(Cc6ccccc6)cn5)c4O3)o2)CC1] | 238 | >100<br>18 |

| Example No. | Chemical Structure | SPR Response Units | Cell Viability (μM) H358 DLD-1 |
|---|---|---|---|
| 102 | 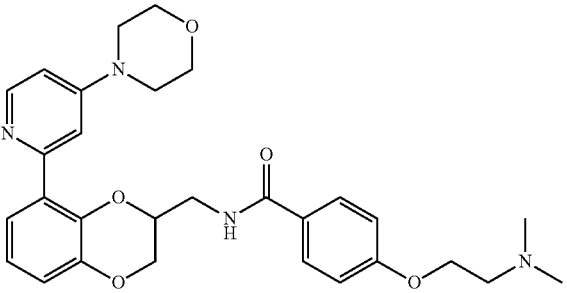 [SMILES: CN(C)CCOc1ccc(C(=O)NCC2COc3cccc(-c4cc(N5CCOCC5)ccn4)c3O2)cc1] | 126 | |
| 103 | 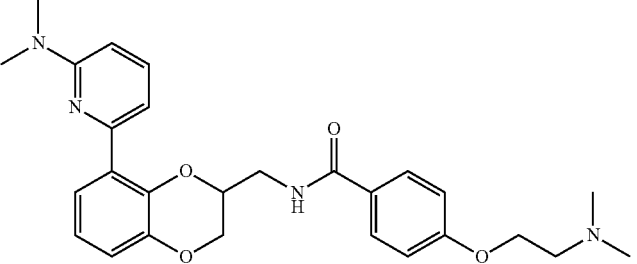 | 64 | |
| 104 | 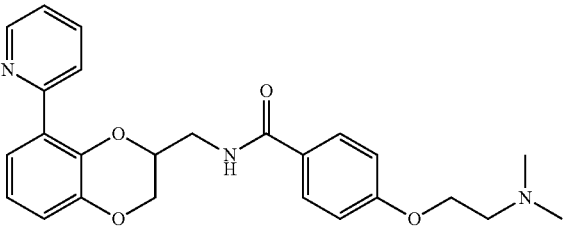 [SMILES: CN(C)CCOc1ccc(C(=O)NCC2COc3cccc(-c4ccccn4)c3O2)cc1] | 35 | |
| 40 | 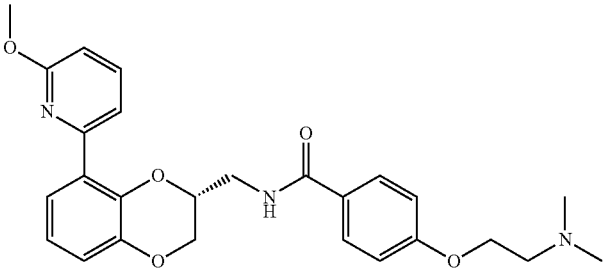 [SMILES: COc1cccc(-c2cccc3c2O[C@H](CNC(=O)c2ccc(OCCN(C)C)cc2)CO3)n1] | 58 | 52 12 |
| 105 | 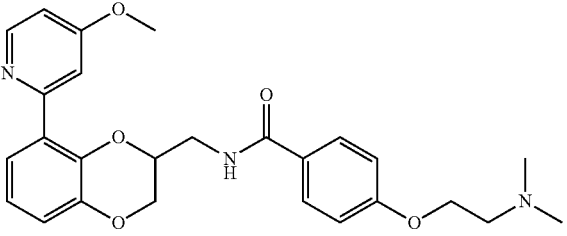 [SMILES: COc1ccnc(-c2cccc3c2OC(CNC(=O)c2ccc(OCCN(C)C)cc2)CO3)c1] | 27 | |

| Example No. | Chemical Structure | SPR Response Units | Cell Viability (μM) H358 DLD-1 |
|---|---|---|---|
| 44 | 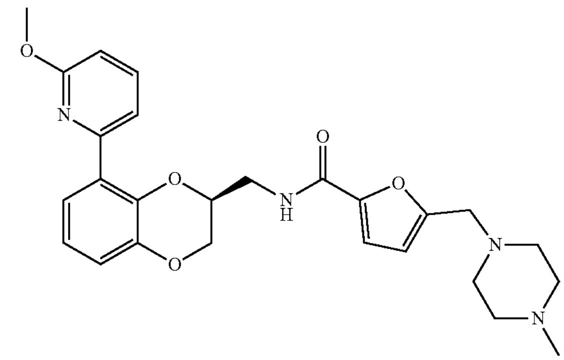 [SMILES: COc1cccc(-c2cccc3c2O[C@@H](CNC(=O)c2ccc(CN4CCN(C)CC4)o2)CO3)n1] | 42 | |
| 49 | 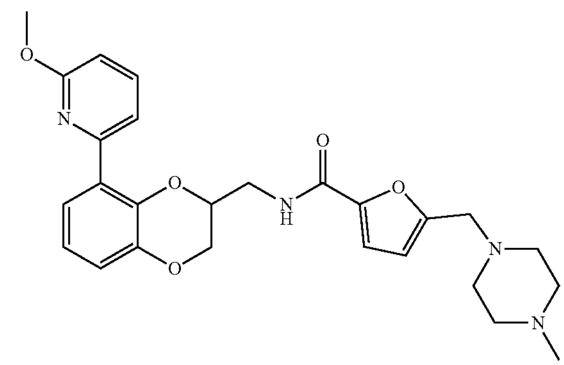 [SMILES: COc1cccc(-c2cccc3c2OC(CNC(=O)c2ccc(CN4CCN(C)CC4)o2)CO3)n1] | 37 | |
| 106 | 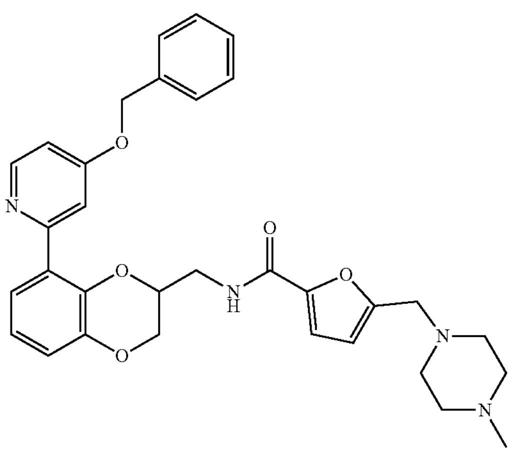 [SMILES: CN1CCN(Cc2ccc(C(=O)NCC3COc4cccc(-c5cc(OCc6ccccc6)ccn5)c4O3)o2)CC1] | 114 | 27<br>11 |
| 41 | 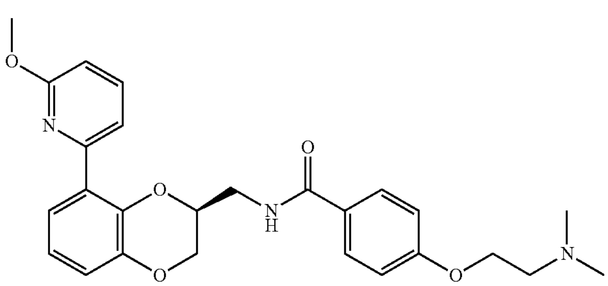 [SMILES: COc1cccc(-c2cccc3c2O[C@@H](CNC(=O)c2ccc(OCCN(C)C)cc2)CO3)n1] | 60 | 48<br>20 |

-continued

| Example No. | Chemical Structure | SPR Response Units | Cell Viability (μM) H358 DLD-1 |
|---|---|---|---|
| 45 | 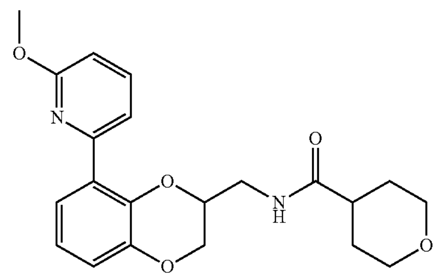 [SMILES: COc1cccc(-c2cccc3c2OC(CNC(=O)C2CCOCC2)CO3)n1] | 12 | |
| 51 | 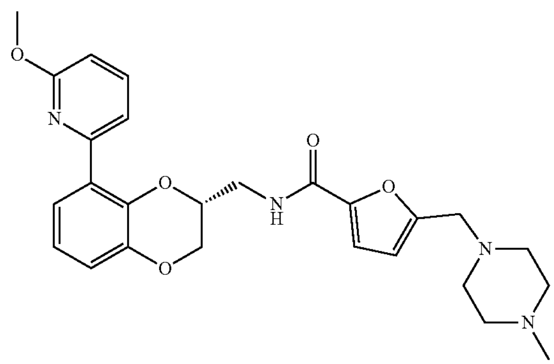 | 32 | |
| 107 | 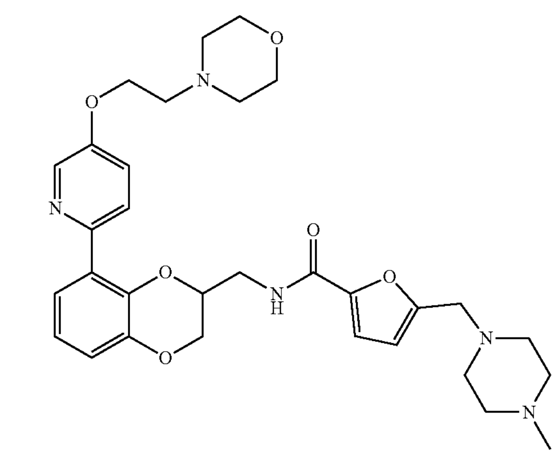 [SMILES: CN1CCN(Cc2ccc(C(=O)NCC3COc4cccc(-c5ccc(OCCN6CCOCC6)cn5)c4O3)o2)CC1] | 9 | |
| 50 | 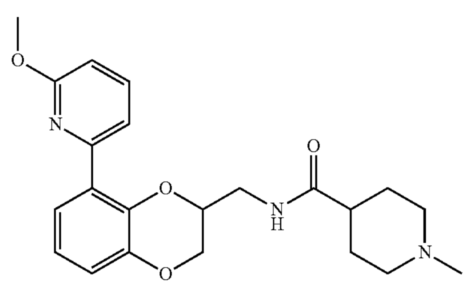 [SMILES: COc1cccc(-c2cccc3c2OC(CNC(=O)C2CCN(C)CC2)CO3)n1] | 14 | |

-continued

| Example No. | Chemical Structure | SPR Response Units | Cell Viability (μM) H358 DLD-1 |
|---|---|---|---|
| 47 | 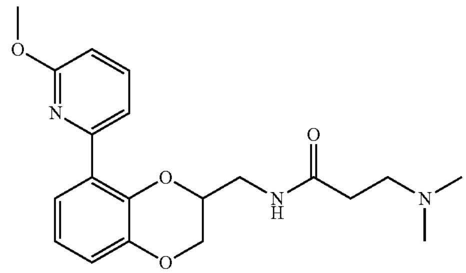 [SMILES: COc1cccc(-c2cccc3c2OC(CNC(=O)CCN(C)C)CO3)n1] | 16 | |
| 1 | 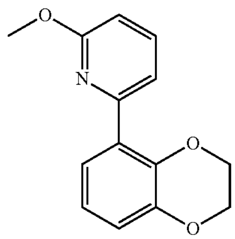 [SMILES: COc1cccc(-c2cccc3c2OCCO3)n1] | 10 | |
| 108 | 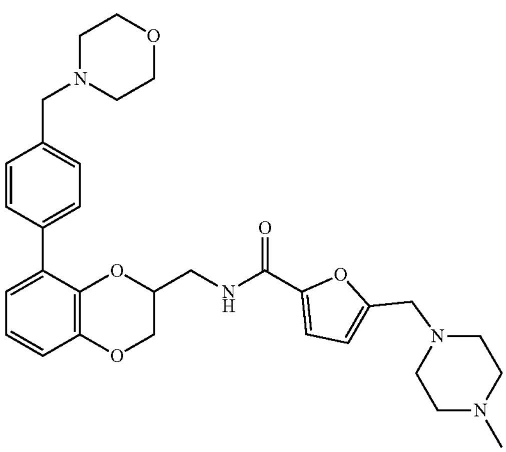 [SMILES: CN1CCN(Cc2ccc(C(=O)NCC3COc4cccc(-c5ccc(CN6CCOCC6)cc5)c4O3)o2)CC1] | 26 | |
| 109 | 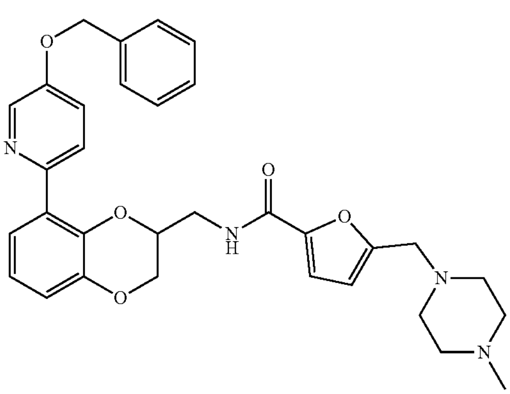 [SMILES: CN1CCN(Cc2ccc(C(=O)NCC3COc4cccc(-c5ccc(OCc6ccccc6)cn5)c4O3)o2)CC1] | 114 | >100 9 |

-continued

| Example No. | Chemical Structure | SPR Response Units | Cell Viability (μM) H358 DLD-1 |
|---|---|---|---|
| 82 | 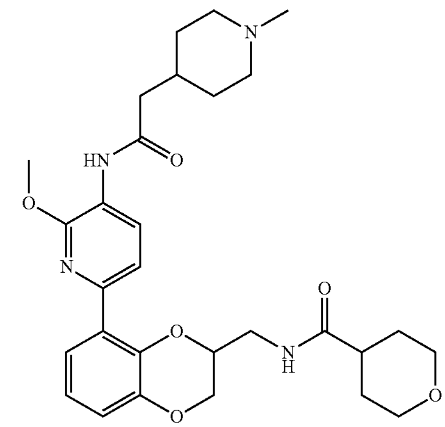 [SMILES: COc1nc(-c2cccc3c2OC(CNC(=O)C2CCOCC2)CO3)ccc1NC(=O)CC1CCN(C)CC1] | 12 | |
| 83 | 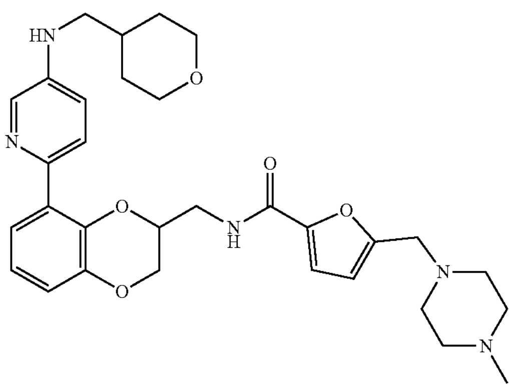 [SMILES: CN1CCN(Cc2ccc(C(=O)NCC3COc4cccc(-c5ccc(NCC6CCOCC6)cn5)c4O3)o2)CC1] | 16 | |
| 84 | 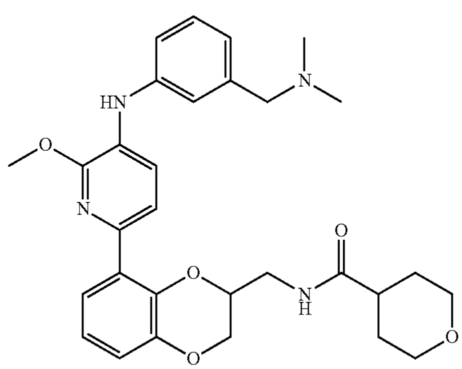 | 59 | 33<br>20 |
| 85 | 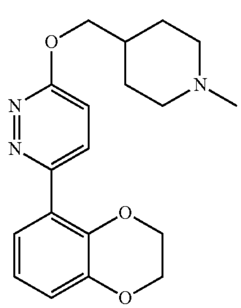 [SMILES: CN1CCC(COc2ccc(-c3cccc4c3OCCO4)nn2)CC1] | 20 | |

-continued
| Example No. | Chemical Structure | SPR Response Units | Cell Viability (μM) H358 DLD-1 |
|---|---|---|---|
| 86 | 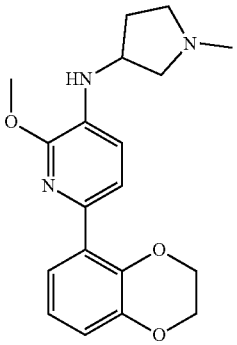 [SMILES: COc1nc(-c2cccc3c2OCCO3)ccc1NC1CCN(C)C1] | 17 | |
| 2 | 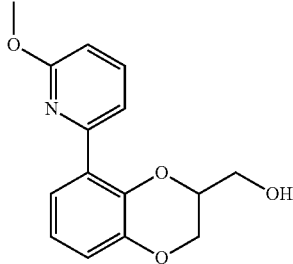 [SMILES: COc1cccc(-c2cccc3c2OC(CO)CO3)n1] | 17 | |
| 27 | 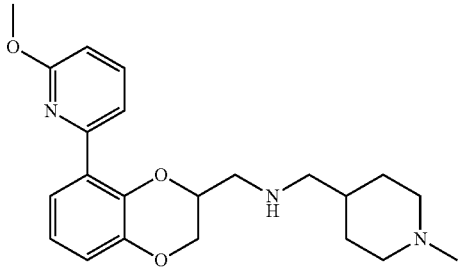 [SMILES: COc1cccc(-c2cccc3c2OC(CNCC2CCN(C)CC2)CO3)n1] | 58 | |
| 100 | 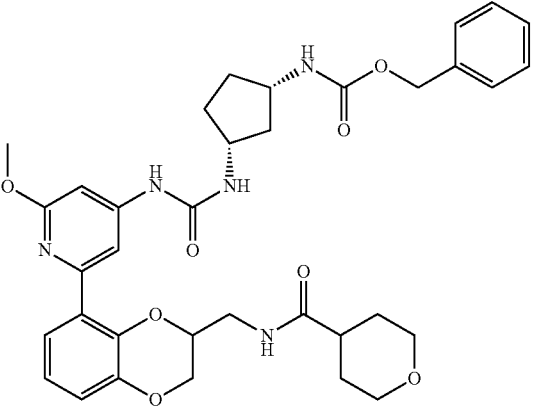 [SMILES: COc1cc(NC(=O)N[C@@H]2CC[C@H](NC(=O)OCc3ccccc3)C2)cc(-c2cccc3c2OC(CNC(=O)C2CCOCC2)CO3)n1] | 97 | 28 5 |

-continued

| Example No. | Chemical Structure | SPR Response Units | Cell Viability (μM) H358 DLD-1 |
|---|---|---|---|
| 87 | 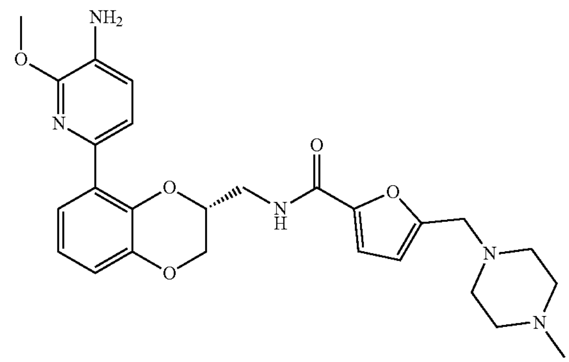 [SMILES: COc1nc(-c2cccc3c2O[C@H](CNC(=O)c2ccc(CN4CCN(C)CC4)o2)CO3)ccc1N] | | 56 |
| 28 | 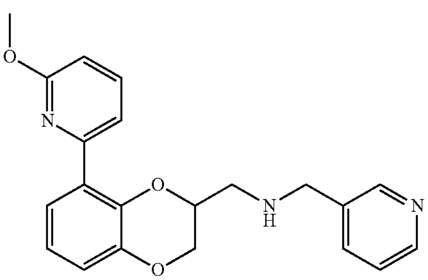 [SMILES: COc1cccc(-c2cccc3c2OC(CNCc2cccnc2)CO3)n1] | | 28 |
| 29 | 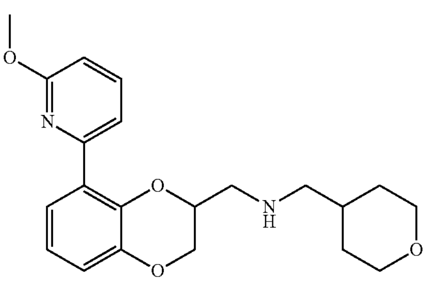 [SMILES: COc1cccc(-c2cccc3c2OC(CNCC2CCOCC2)CO3)n1] | | 14 |
| 29a | 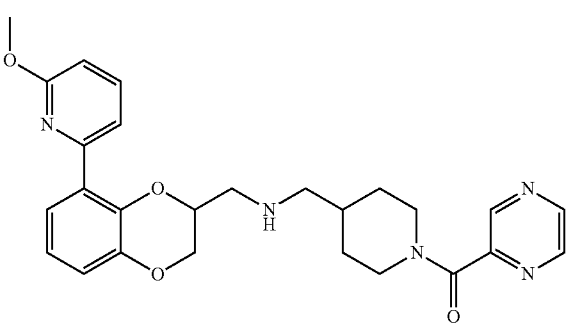 [SMILES: COc1cccc(-c2cccc3c2OC(CNCC2CCN(C(=O)c4cnccn4)CC2)CO3)n1] | | 26 |

-continued

| Example No. | Chemical Structure | SPR Response Units | Cell Viability (μM) H358 DLD-1 |
|---|---|---|---|
| 114 | 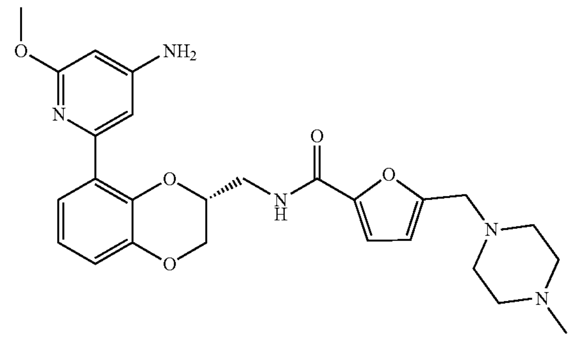 [SMILES: COc1cc(N)cc(-c2cccc3c2O[C@H](CNC(=O)c2ccc(CN4CCN(C)CC4)o2)CO3)n1] | | 23 |
| 131 | 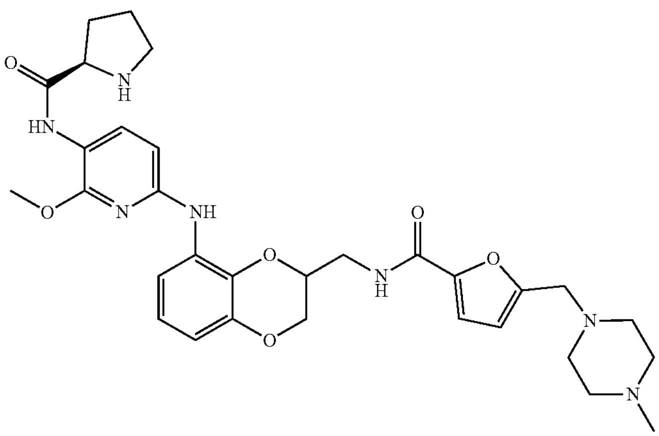 | | 40 |
| 110 | 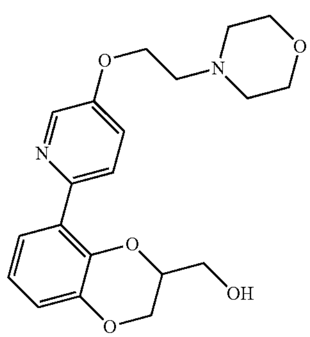 [SMILES: OCC1COc2cccc(-c3ccc(OCCN4CCOCC4)cn3)c2O1] | | 4.6 |
| 30 | 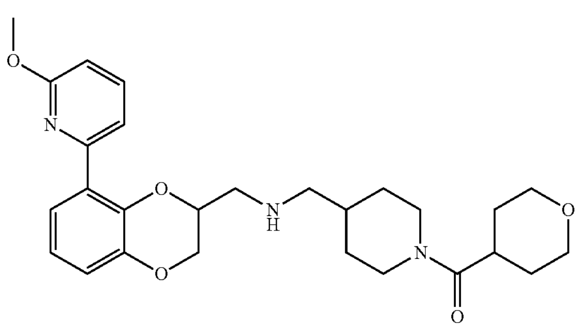 [SMILES: COc1cccc(-c2cccc3c2OC(CNCC2CCN(C(=O)C4CCOCC4)CC2)CO3)n1] | | 42 |

-continued

| Example No. | Chemical Structure | SPR Response Units | Cell Viability (μM) H358 DLD-1 |
|---|---|---|---|
| 31 | 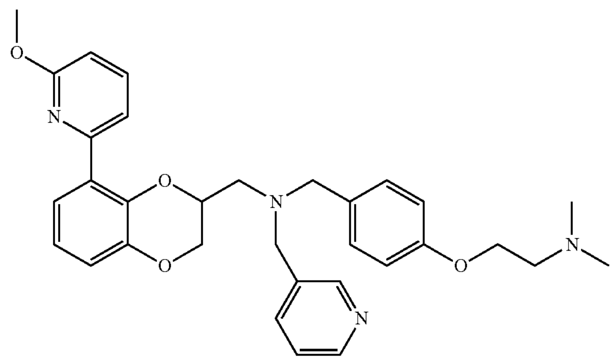 [SMILES: COc1cccc(-c2cccc3c2OC(CN(Cc2ccc(OCCN(C)C)cc2)Cc2cccnc2)CO3)n1] | 119 | 18 / 3 |
| 32 | 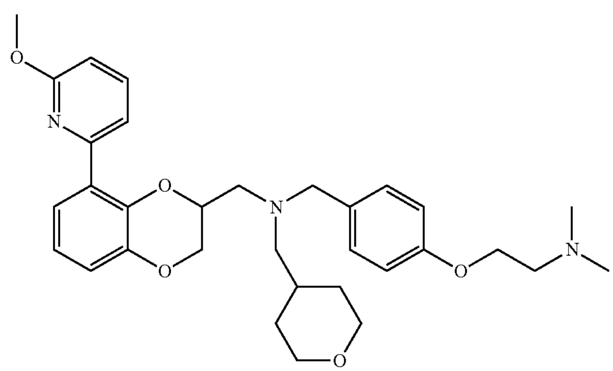 [SMILES: COc1cccc(-c2cccc3c2OC(CN(Cc2ccc(OCCN(C)C)cc2)CC2CCOCC2)CO3)n1] | 85 | 17 / 7 |
| 26 | 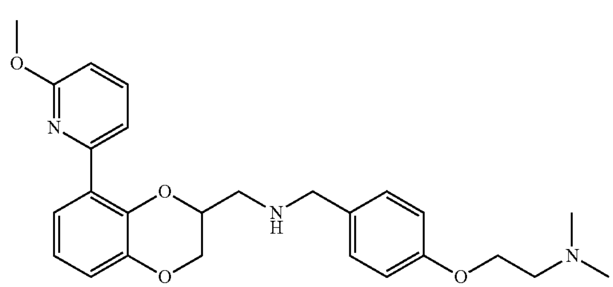 [SMILES: COc1cccc(-c2cccc3c2OC(CNCc2ccc(OCCN(C)C)cc2)CO3)n1] | 53 | 95 / 4 |
| 111 | 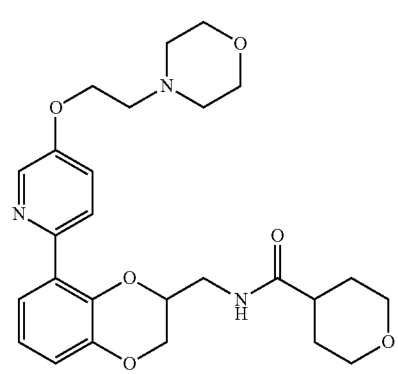 [SMILES: O=C(NCC1COc2cccc(-c3ccc(OCCN4CCOCC4)cn3)c2O1)C1CCOCC1] | 29 | |

-continued
| Example No. | Chemical Structure | SPR Response Units | Cell Viability (μM) H358 DLD-1 |
|---|---|---|---|
| 34 | 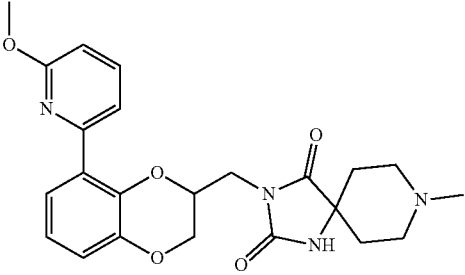 [SMILES: COc1cccc(-c2cccc3c2OC(CN2C(=O)NC4(CCN(C)CC4)C2=O)CO3)n1] | 37 | |
| 35 | 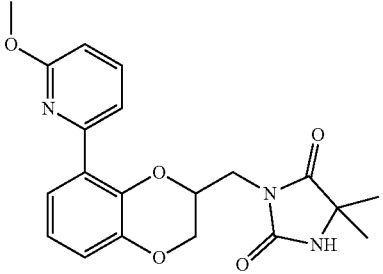 [SMILES: COc1cccc(-c2cccc3c2OC(CN2C(=O)NC(C)(C)C2=O)CO3)n1] | 33 | |
| 37 | 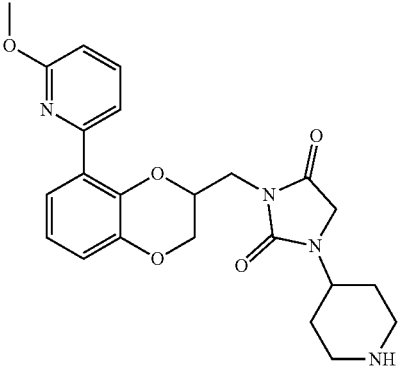 [SMILES: COc1cccc(-c2cccc3c2OC(CN2C(=O)CN(C4CCNCC4)C2=O)CO3)n1] | 31 | |
| 36 | 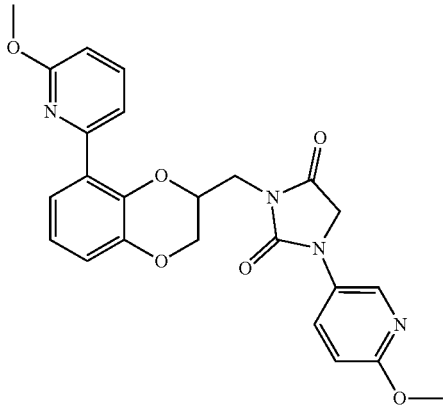 [SMILES: COc1ccc(N2CC(=O)N(CC3COc4cccc(-c5cccc(OC)n5)c4O3)C2=O)cn1] | 58 | |

| Example No. | Chemical Structure | SPR Response Units | Cell Viability (μM) H358 DLD-1 |
|---|---|---|---|
| 88 | 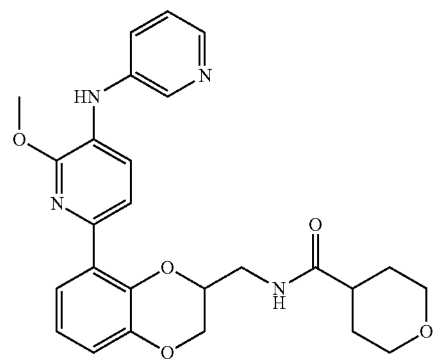 [SMILES: COc1nc(-c2cccc3c2OC(CNC(=O)C2CCOCC2)CO3)ccc1Nc1cccnc1] | 161 | |
| 135 | 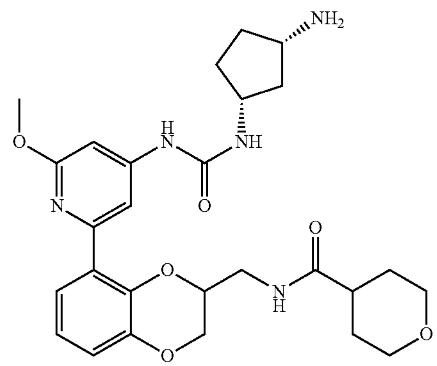 [SMILES: COc1cc(NC(=O)N[C@@H]2CC[C@H](N)C2)cc(-c2cccc3c2OC(CNC(=O)C2CCOCC2)CO3)n1] | 57 | |
| 48 | 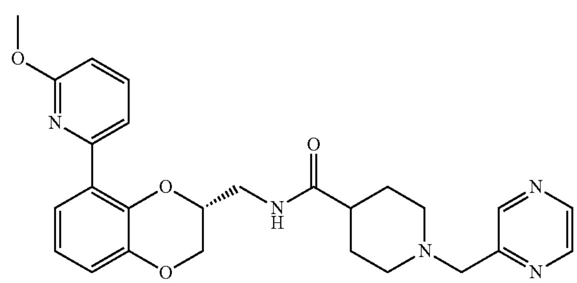 [SMILES: COc1cccc(-c2cccc3c2O[C@H](CNC(=O)C2CCN(Cc4cnccn4)CC2)CO3)n1] | 54 | |
| 89 | 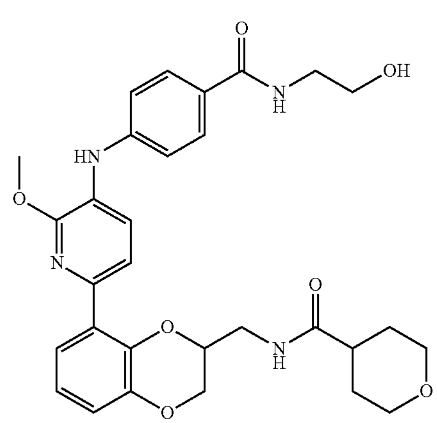 [SMILES: COc1nc(-c2cccc3c2OC(CNC(=O)C2CCOCC2)CO3)ccc1Nc1ccc(C(=O)NCCO)cc1] | 132 | |

-continued

| Example No. | Chemical Structure | SPR Response Units | Cell Viability (μM) H358 DLD-1 |
|---|---|---|---|
| 90 | 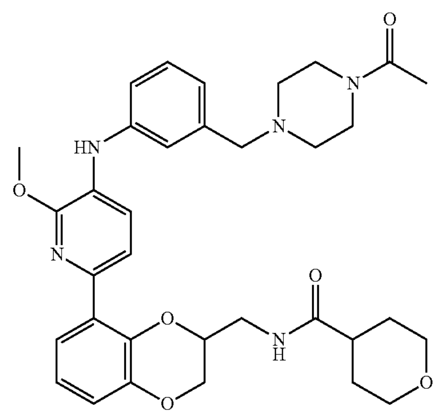 [SMILES: COc1nc(-c2cccc3c2OC(CNC(=O)C2CCOCC2)CO3)ccc1Nc1cccc(CN2CCN(C(C)=O)CC2)c1] | 140 | |
| 91 | 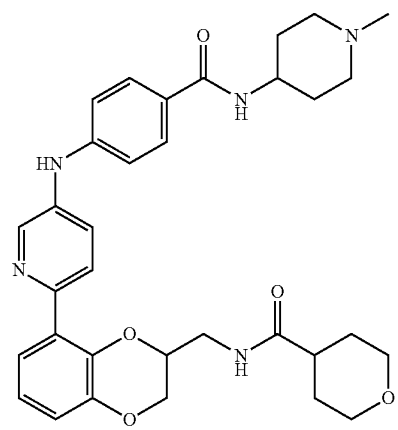 [SMILES: CN1CCC(NC(=O)c2ccc(Nc3ccc(-c4cccc5c4OC(CNC(=O)C4CCOCC4)CO5)nc3)cc2)CC1] | 66 | |
| 130 | 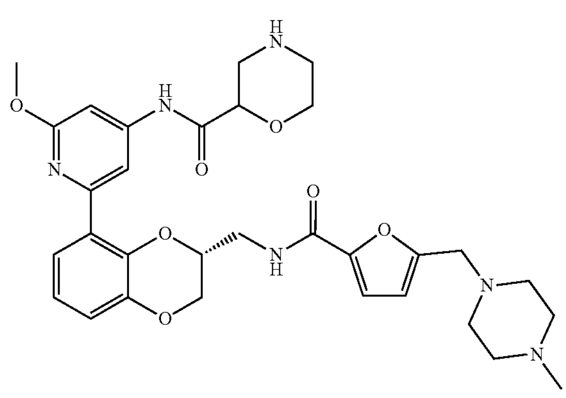 | 61 | 13.6<br>11.9 |

-continued

| Example No. | Chemical Structure | SPR Response Units | Cell Viability (μM) H358 DLD-1 |
|---|---|---|---|
| 112 | 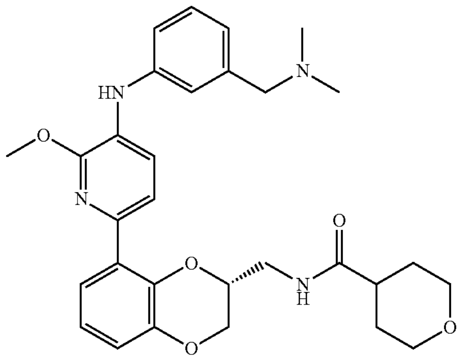 [SMILES: COc1nc(-c2cccc3c2O[C@H](CNC(=O)C2CCOCC2)CO3)ccc1Nc1cccc(CN(C)C)c1] | 90 | 18.8 16.3 |
| 92 | 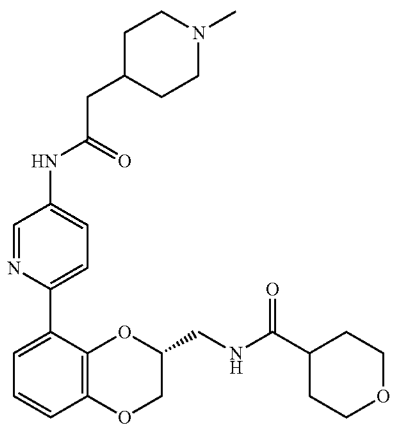 [SMILES: CN1CCC(CC(=O)Nc2ccc(-c3cccc4c3O[C@H](CNC(=O)C3CCOCC3)CO4)nc2)CC1] | 7 | |
| 113 | 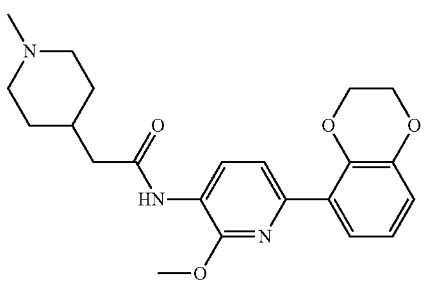 [SMILES: COc1nc(-c2cccc3c2OCCO3)ccc1NC(=O)CC1CCN(C)CC1] | 30 | |
| 93 | 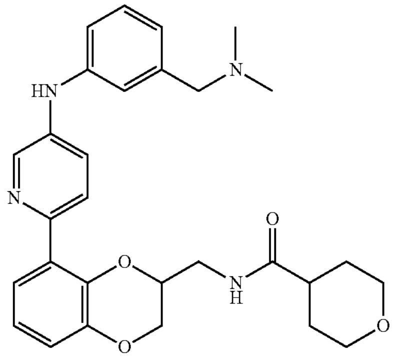 [SMILES: CN(C)Cc1cccc(Nc2ccc(-c3cccc4c3OC(CNC(=O)C3CCOCC3)CO4)nc2)c1] | 39 | |

| Example No. | Chemical Structure | SPR Response Units | Cell Viability (μM) H358 DLD-1 |
|---|---|---|---|
| 94 | 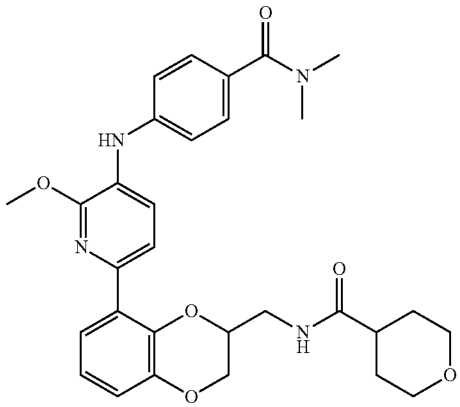 [SMILES: COc1nc(-c2cccc3c2OC(CNC(=O)C2CCOCC2)CO3)ccc1Nc1ccc(C(=O)N(C)C)cc1] | 111 | |
| 136 | 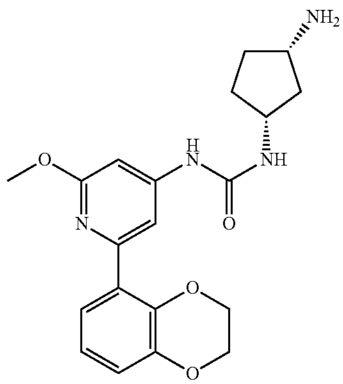 [SMILES: COc1cc(NC(=O)N[C@@H]2CC[C@H](N)C2)cc(-c2cccc3c2OCCO3)n1] | 75 | |
| 55 | 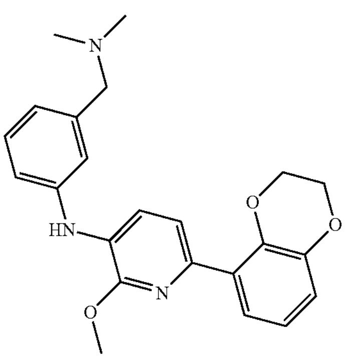 [SMILES: COc1nc(-c2cccc3c2OCCO3)ccc1Nc1cccc(CN(C)C)c1] | 130 | 8.0<br>9.2 |
| 141 | 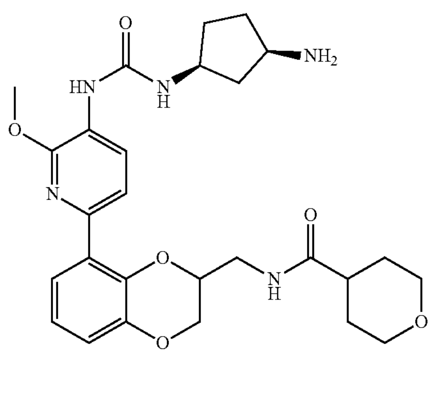 [SMILES: COc1nc(-c2cccc3c2OC(CNC(=O)C2CCOCC2)CO3)ccc1NC(=O)N[C@H]1CC[C@@H](N)C1] | 80 | |

-continued

| Example No. | Chemical Structure | SPR Response Units | Cell Viability (μM) H358 DLD-1 |
|---|---|---|---|
| 69 | 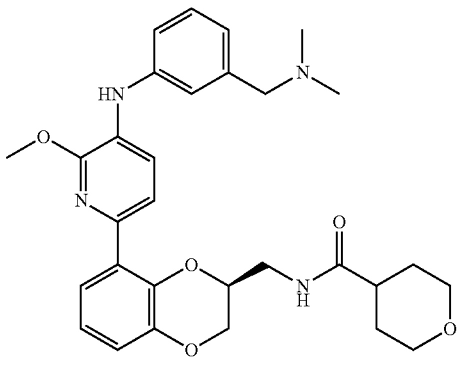 [SMILES: COc1nc(-c2cccc3c2O[C@@H](CNC(=O)C2CCOCC2)CO3)ccc1Nc1cccc(CN(C)C)c1] | 128 | 21<br>21.5 |
| 4 | 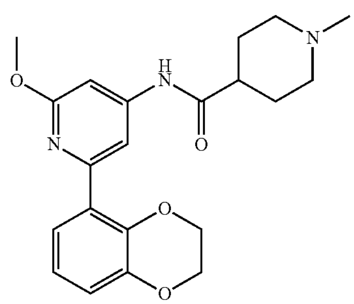 | 37 | |
| 17 | 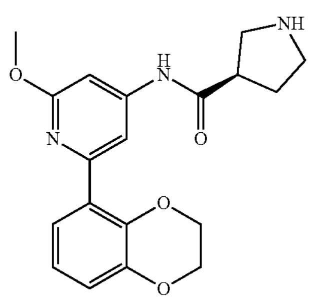 [SMILES: COc1cc(NC(=O)[C@@H]2CCNC2)cc(-c2cccc3c2OCCO3)n1] | 84 | |
| 56 | 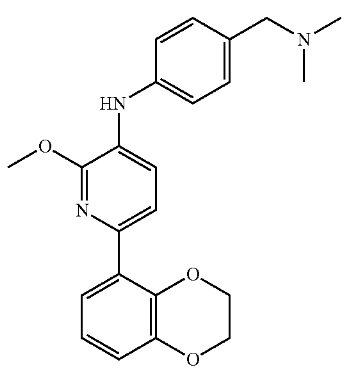 | 116 | 12<br>8<br>10 (HCT1080) |

| Example No. | Chemical Structure | SPR Response Units | Cell Viability (μM) H358 DLD-1 |
|---|---|---|---|
| 57 | 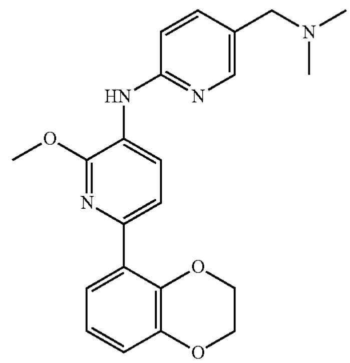 | 77 | 29<br>20.2 |
| 58 | 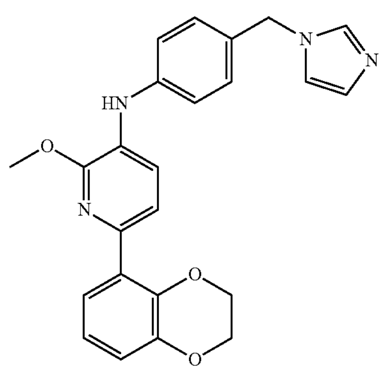 [SMILES: COc1nc(-c2cccc3c2OCCO3)ccc1Nc1ccc(Cn2ccnc2)cc1] | 269 | 19<br>16.2 |
| 3 | 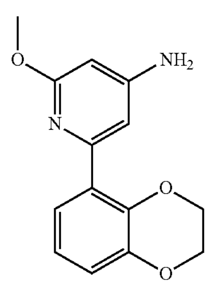 [SMILES: COc1cc(N)cc(-c2cccc3c2OCCO3)n1] | 16 | |
| 22 | 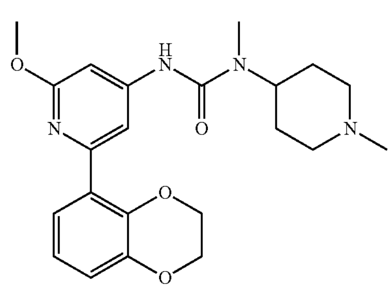 [SMILES: COc1cc(NC(=O)N(C)C2CCN(C)CC2)cc(-c2cccc3c2OCCO3)n1] | 55 | |

-continued

| Example No. | Chemical Structure | SPR Response Units | Cell Viability (μM) H358 DLD-1 |
|---|---|---|---|
| 23 | 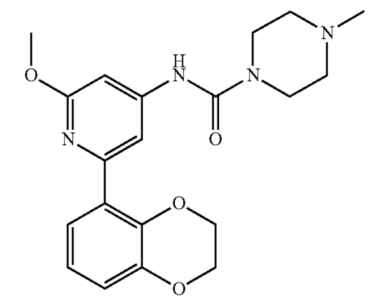 [SMILES: COc1cc(NC(=O)N2CCN(C)CC2)cc(-c2cccc3c2OCCO3)n1] | 58 | |
| 24 | 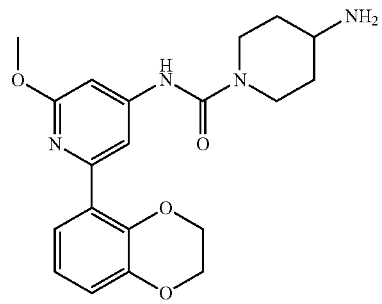 [SMILES: COc1cc(NC(=O)N2CCC(N)CC2)cc(-c2cccc3c2OCCO3)n1] | 60 | |
| 133 | 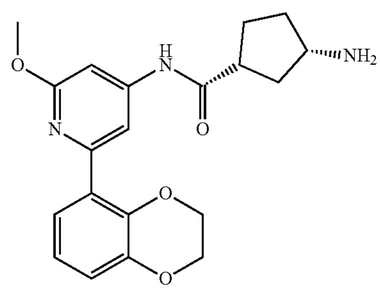 | 96 | |
| 140 | 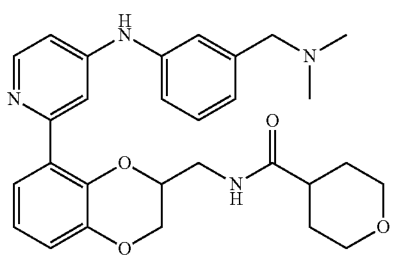 [SMILES: CN(C)Cc1cccc(Nc2ccnc(-c3cccc4c3OC(CNC(=O)C3CCOCC3)CO4)c2)c1] | 32 | |
| 142 | 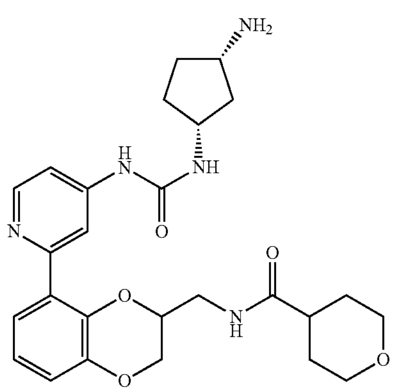 [SMILES: N[C@H]1CC[C@@H](NC(=O)Nc2ccnc(-c3cccc4c3OC(CNC(=O)C3CCOCC3)CO4)c2)C1] | 26 | |

-continued

| Example No. | Chemical Structure | SPR Response Units | Cell Viability (μM) H358 DLD-1 |
|---|---|---|---|
| 118 | 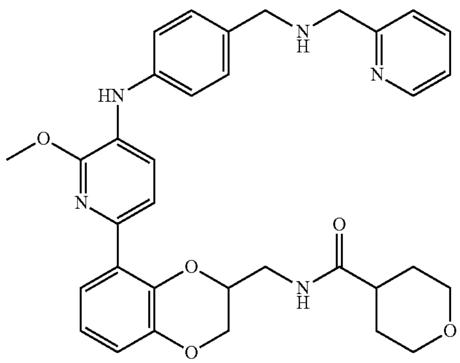 [SMILES: COc1nc(-c2cccc3c2OC(CNC(=O)C2CCOCC2)CO3)ccc1Nc1ccc(CNCc2ccccn2)cc1] | 291 | 12.8<br>11 |
| 119 | 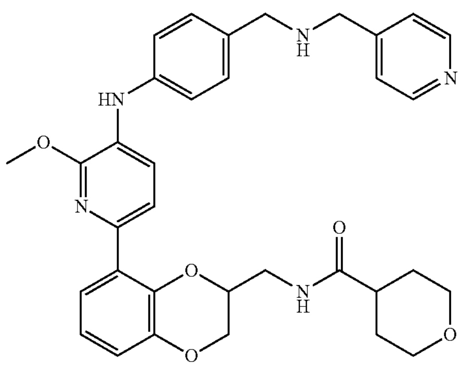 [SMILES: COc1nc(-c2cccc3c2OC(CNC(=O)C2CCOCC2)CO3)ccc1Nc1ccc(CNCc2ccncc2)cc1] | 349 | 10<br>11.2 |
| 120 | 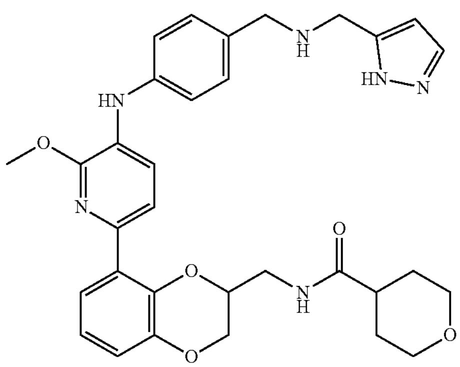 [SMILES: COc1nc(-c2cccc3c2OC(CNC(=O)C2CCOCC2)CO3)ccc1Nc1ccc(CNCc2ccn[nH]2)cc1] | 230 | 12.4<br>10.9 |
| 18 | 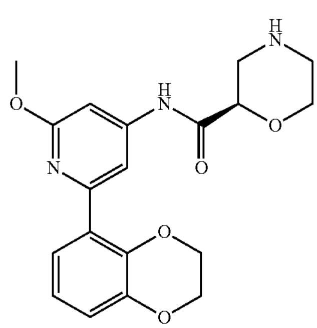 [SMILES: COc1cc(NC(=O)[C@H]2CNCCO2)cc(-c2cccc3c2OCCO3)n1] | 71 | |

-continued

| Example No. | Chemical Structure | SPR Response Units | Cell Viability (μM) H358 DLD-1 |
|---|---|---|---|
| 19 | 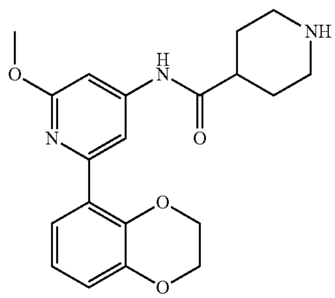 [SMILES: COc1cc(NC(=O)C2CCNCC2)cc(-c2cccc3c2OCCO3)n1] | 100 | |
| 20 | 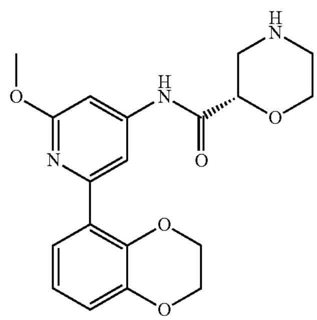 [SMILES: COc1cc(NC(=O)[C@@H]2CNCCO2)cc(-c2cccc3c2OCCO3)n1] | 80 | |
| 21 | 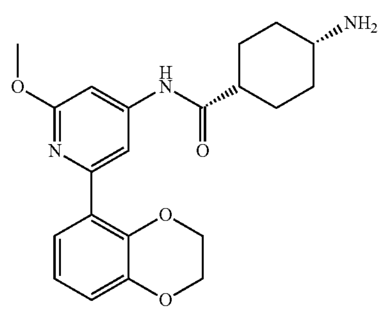 | 66 | |
| 127 | 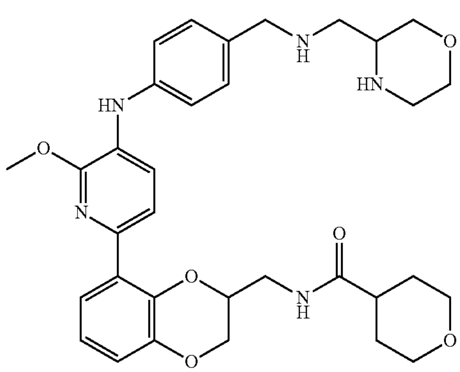 [SMILES: COc1nc(-c2cccc3c2OC(CNC(=O)C2CCOCC2)CO3)ccc1Nc1ccc(CNCC2COCCN2)cc1] | 205 | 16.9 18.9 |

| Example No. | Chemical Structure | SPR Response Units | Cell Viability (μM) H358 DLD-1 |
|---|---|---|---|
| 98 | 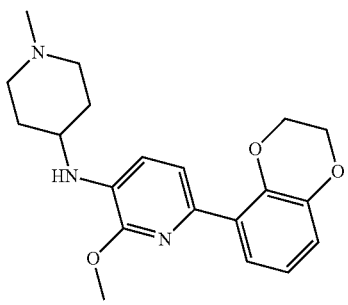 [SMILES: COc1nc(-c2cccc3c2OCCO3)ccc1NC1CCN(C)CC1] | 21 | |
| 99 | 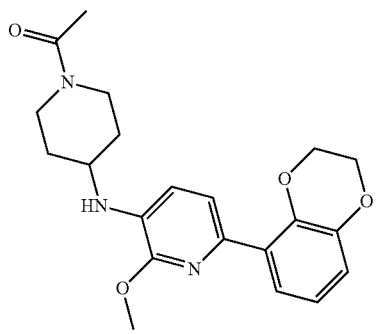 [SMILES: COc1nc(-c2cccc3c2OCCO3)ccc1NC1CCN(C(C)=O)CC1] | 33 | |
| 59 | 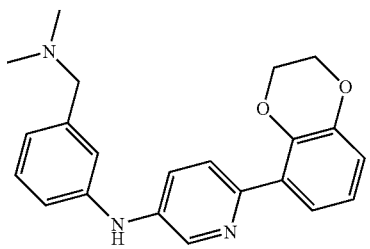 [SMILES: CN(C)Cc1cccc(Nc2ccc(-c3cccc4c3OCCO4)nc2)c1] | 79 | |
| 60 | 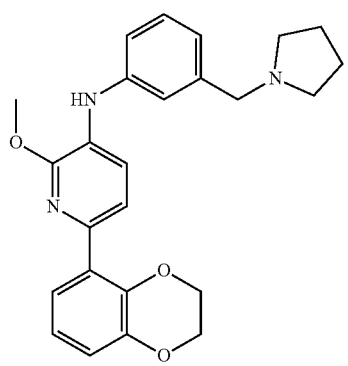 [SMILES: COc1nc(-c2cccc3c2OCCO3)ccc1Nc1cccc(CN2CCCC2)c1] | 108 | 11.4<br>7.5 |

-continued

| Example No. | Chemical Structure | SPR Response Units | Cell Viability (μM) H358 DLD-1 |
|---|---|---|---|
| 61 | 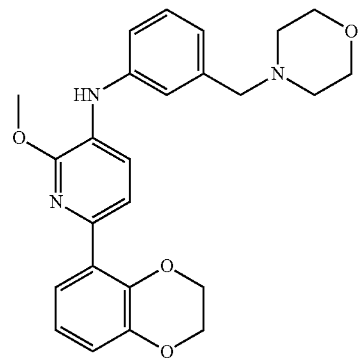 [SMILES: COc1nc(-c2cccc3c2OCCO3)ccc1Nc1cccc(CN2CCOCC2)c1] | 61 | 20.1 <br> 12.2 |
| 143 | 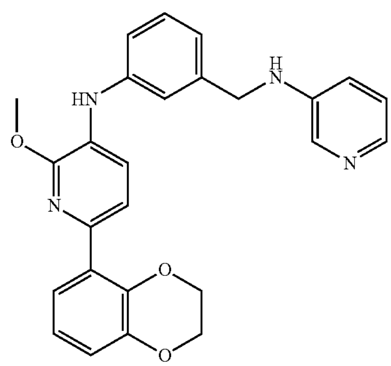 [SMILES: COc1nc(-c2cccc3c2OCCO3)ccc1Nc1cccc(CNc2cccnc2)c1] | 67 | 17.0 <br> 6.1 |
| 128 | 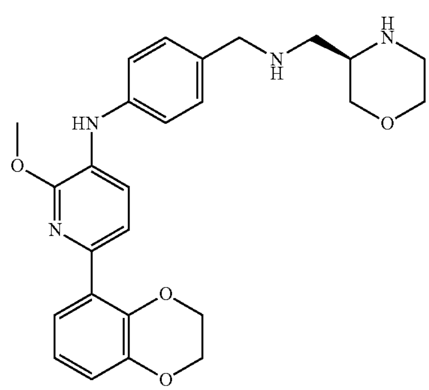 [SMILES: COc1nc(-c2cccc3c2OCCO3)ccc1Nc1ccc(CNC[C@@H]2COCCN2)cc1] | 99 | 6.7 <br> 9.5 |
| 129 | 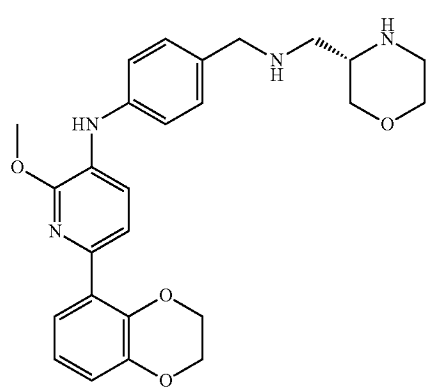 [SMILES: COc1nc(-c2cccc3c2OCCO3)ccc1Nc1ccc(CNC[C@H]2COCCN2)cc1] | 92 | 6.5 <br> 10.2 |

-continued
| Example No. | Chemical Structure | SPR Response Units | Cell Viability (μM) H358 DLD-1 |
|---|---|---|---|
| 62 | 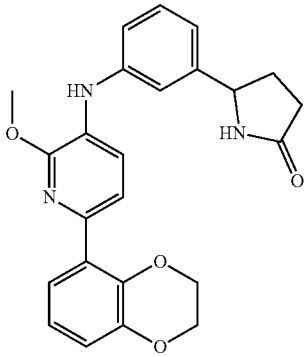 [SMILES: COc1nc(-c2cccc3c2OCCO3)ccc1Nc1cccc(C2CCC(=O)N2)c1] | 72 | 8.6<br>13.7 |
| 79 | 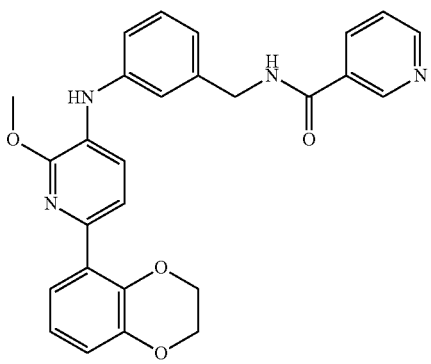 | 47 | 18.0<br>16.5 |
| 80 | 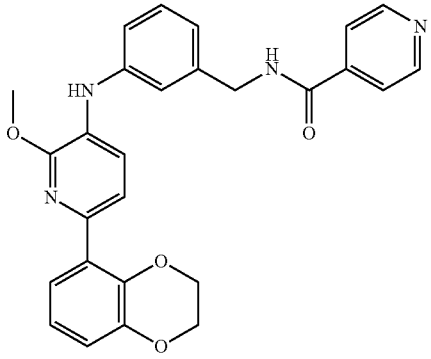 [SMILES: COc1nc(-c2cccc3c2OCCO3)ccc1Nc1cccc(CNC(=O)c2ccncc2)c1] | 51 | 16.5<br>13.4 |
| 81 | 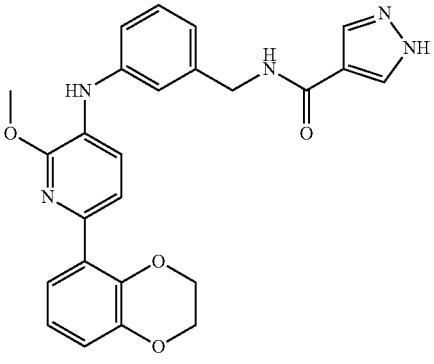 [SMILES: COc1nc(-c2cccc3c2OCCO3)ccc1Nc1cccc(CNC(=O)c2cn[nH]c2)c1] | 109 | |

-continued

| Example No. | Chemical Structure | SPR Response Units | Cell Viability (μM) H358 DLD-1 |
|---|---|---|---|
| 126 | 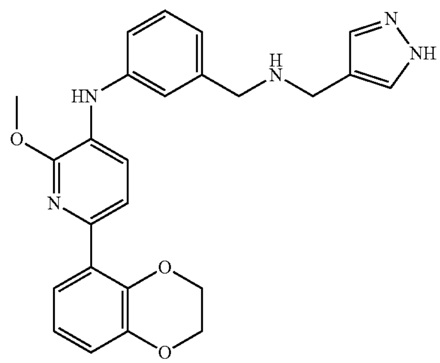 [SMILES: COc1nc(-c2cccc3c2OCCO3)ccc1Nc1cccc(CNCc2cn[nH]c2)c1] | 210 | 5.4<br>5.3 |
| 74 | 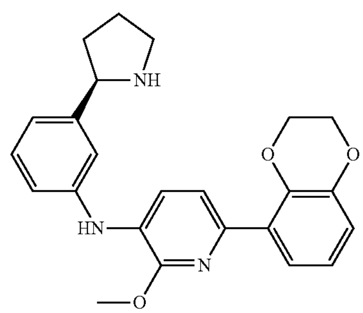 [SMILES: COc1nc(-c2cccc3c2OCCO3)ccc1Nc1cccc([C@H]2CCCN2)c1] | 110 | 3.11<br>6.0 |
| 75 | 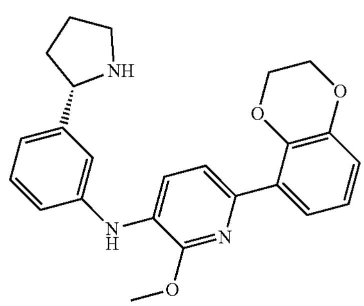 [SMILES: COc1nc(-c2cccc3c2OCCO3)ccc1Nc1cccc([C@@H]2CCCN2)c1] | 112 | 2.6<br>4.0 |
| 70 | 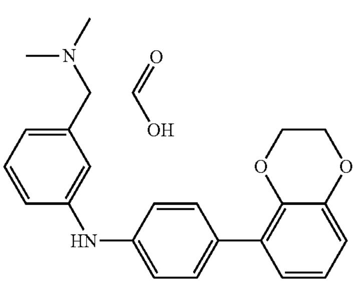 | 86 | 8.6<br>10.6 |

-continued

| Example No. | Chemical Structure | SPR Response Units | Cell Viability (μM) H358 DLD-1 |
|---|---|---|---|
| 72 | 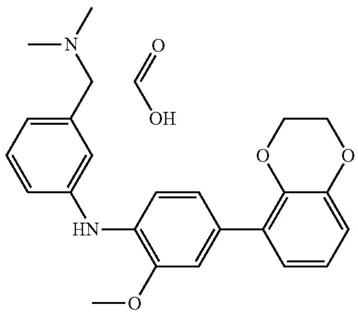 | 56 | 15.3 / 15.4 |
| 71 | 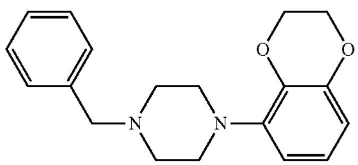 [SMILES: c1ccc(CN2CCN(c3cccc4c3OCCO4)CC2)cc1] | 14 | |
| 67a | 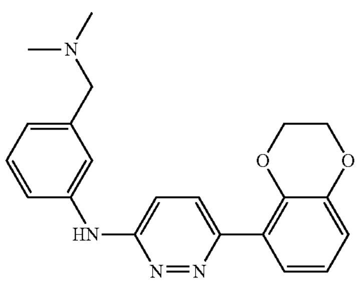 [SMILES: CN(C)Cc1cccc(Nc2ccc(-c3cccc4c3OCCO4)nn2)c1] | 31 | |
| 132 | 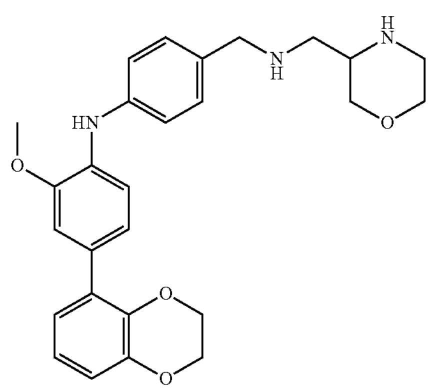 | 204 | 12.7 / 11.0 |
| 68 | 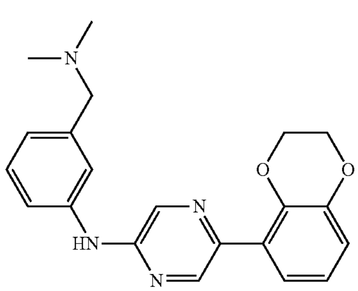 [SMILES: CN(C)Cc1cccc(Nc2cnc(-c3cccc4c3OCCO4)cn2)c1] | 81 | 21.1 / 19.3 |

-continued
| Example No. | Chemical Structure | SPR Response Units | Cell Viability (μM) H358 DLD-1 |
|---|---|---|---|
| 150 | 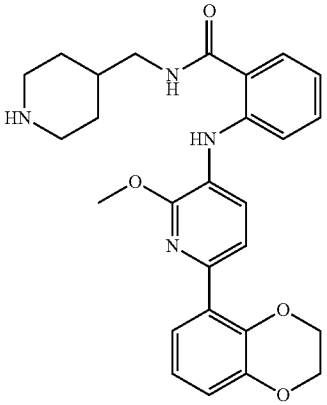 [SMILES: COc1nc(-c2cccc3c2OCCO3)ccc1Nc1ccccc1C(=O)NCC1CCNCC1] | ND | 12<br>2.5 |
| 151 | 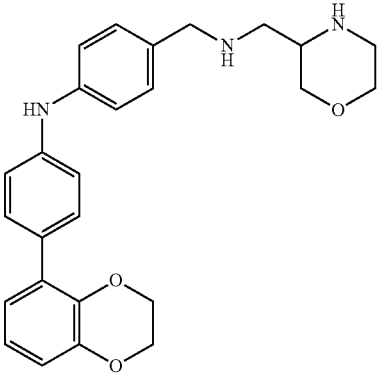 [SMILES: c1cc2c(c(-c3ccc(Nc4ccc(CNCC5COCCN5)cc4)cc3)c1)OCCO2] | 150 | 14.7<br>1.36 |
| 152 | 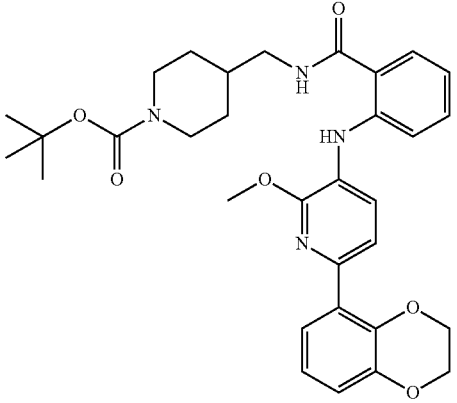 [SMILES: COc1nc(-c2cccc3c2OCCO3)ccc1Nc1ccccc1C(=O)NCC1CCN(C(=O)OC(C)(C)C)CC1] | 36 | |
| 153 | 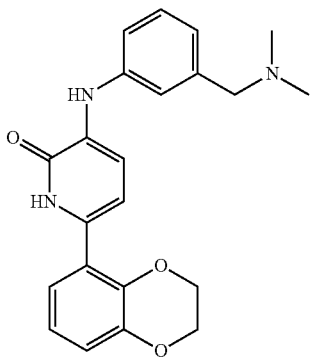 [SMILES: CN(C)Cc1cccc(Nc2ccc(-c3cccc4c3OCCO4)[nH]c2=O)c1] | 90 | 0.6<br>0.14 |

-continued
| Example No. | Chemical Structure | SPR Response Units | Cell Viability (μM) H358 DLD-1 |
|---|---|---|---|
| 154 | 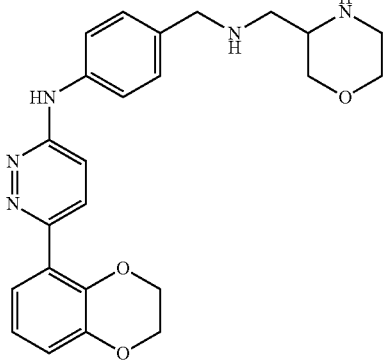 | 59 | |
| 155 | 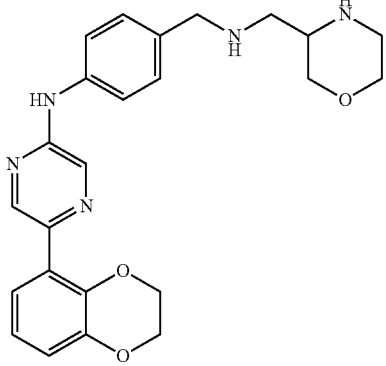 | 71 | 12.7<br>0.56 |
| 156 | 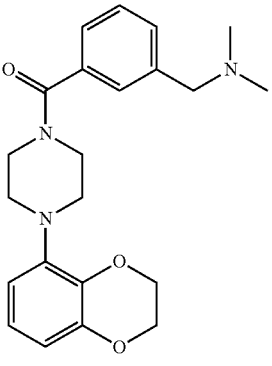 [SMILES: CN(C)Cc1cccc(C(=O)N2CCN(c3cccc4c3OCCO4)CC2)c1] | 5 | |
| 157 | 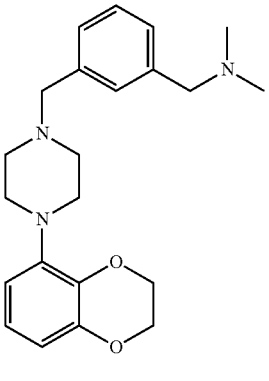 [SMILES: CN(C)Cc1cccc(CN2CCN(c3cccc4c3OCCO4)CC2)c1] | 7 | >150<br>>150 |

-continued

| Example No. | Chemical Structure | SPR Response Units | Cell Viability (μM) H358 DLD-1 |
|---|---|---|---|
| 158 | 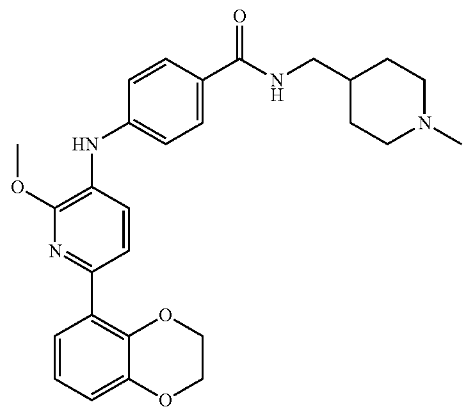 | 269 | 20.6<br>3.5 |
| 159 | 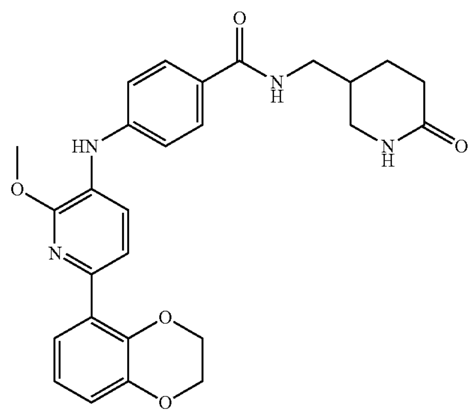 [SMILES: COc1nc(-c2cccc3c2OCCO3)ccc1Nc1ccc(C(=O)NCC2CCC(=O)NC2)cc1] | 122 | 24.7<br>14.1 |
| 160 | 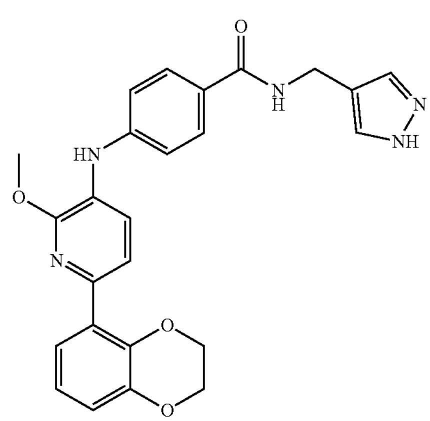 [SMILES: COc1nc(-c2cccc3c2OCCO3)ccc1Nc1ccc(C(=O)NCc2cn[nH]c2)cc1] | 89 | 20.7<br>11.0 |

| Example No. | Chemical Structure | SPR Response Units | Cell Viability (μM) H358 DLD-1 |
|---|---|---|---|
| 161 | 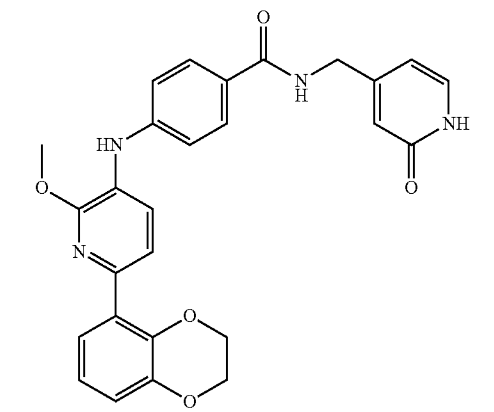 [SMILES: COc1nc(-c2cccc3c2OCCO3)ccc1Nc1ccc(C(=O)NCc2cc[nH]c(=O)c2)cc1] | 16 | |
| 162 | 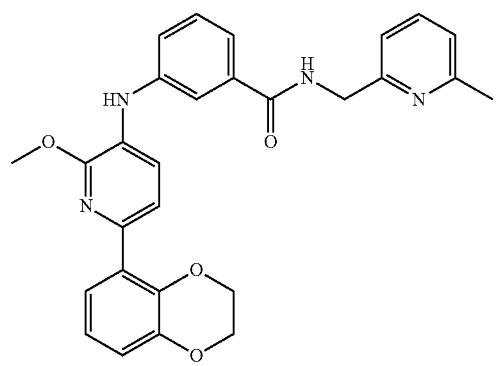 | 36 | 27.9 3.9 |
| 163 | 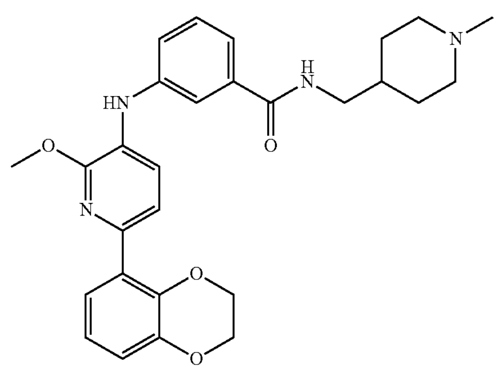 | 192 | 8.9 0.74 |
| 164 | 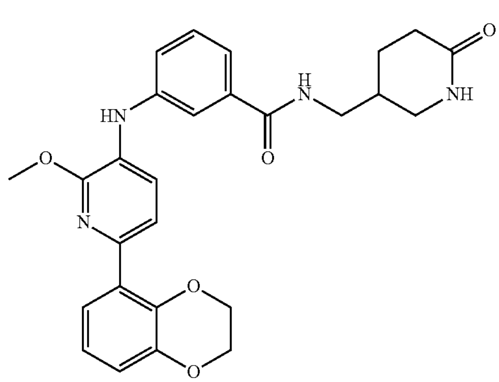 [SMILES: COc1nc(-c2cccc3c2OCCO3)ccc1Nc1cccc(C(=O)NCC2CCC(=O)NC2)c1] | 136 | 25.9 4.8 |

-continued

| Example No. | Chemical Structure | SPR Response Units | Cell Viability (μM) H358 DLD-1 |
|---|---|---|---|
| 165 | 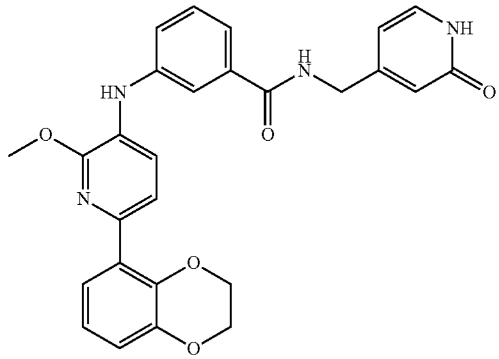 [SMILES: COc1nc(-c2cccc3c2OCCO3)ccc1Nc1cccc(C(=O)NCc2cc[nH]c(=O)c2)c1] | 114 | 18.3<br>11.1 |
| 166 | 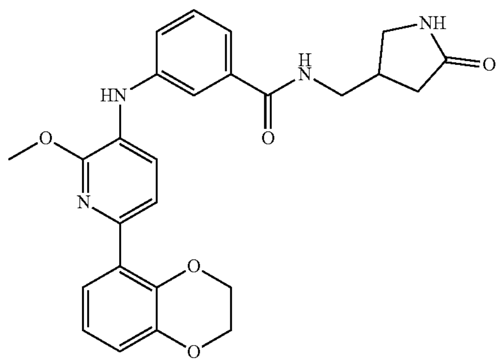 [SMILES: COc1nc(-c2cccc3c2OCCO3)ccc1Nc1cccc(C(=O)NCC2CNC(=O)C2)c1] | 133 | 20.5<br>8.3 |
| 167 | 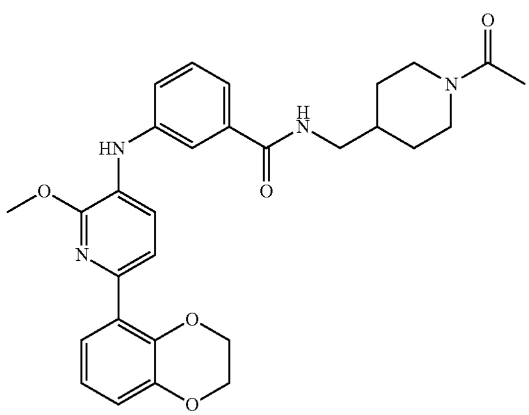 [SMILES: COc1nc(-c2cccc3c2OCCO3)ccc1Nc1cccc(C(=O)NCC2CCN(C(C)=O)CC2)c1] | 73 | 15.8<br>3.5 |
| 168 | 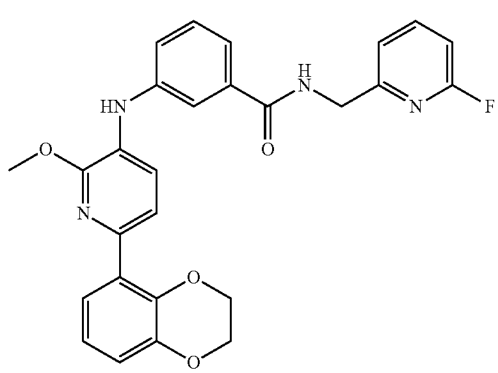 [SMILES: COc1nc(-c2cccc3c2OCCO3)ccc1Nc1cccc(C(=O)NCc2cccc(F)n2)c1] | 23 | |

-continued
| Example No. | Chemical Structure | SPR Response Units | Cell Viability (μM) H358 DLD-1 |
|---|---|---|---|
| 169 | 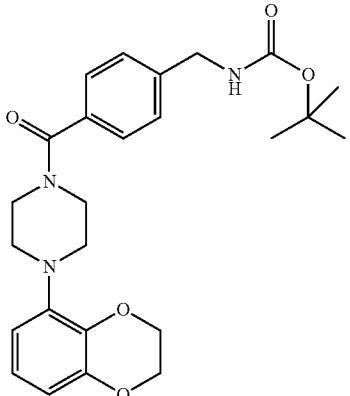 | 25 | |
| 170 | 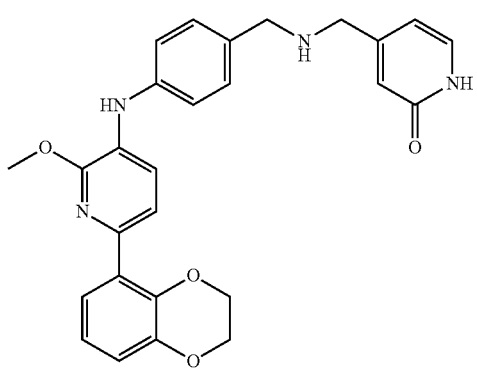 [SMILES: COc1nc(-c2cccc3c2OCCO3)ccc1Nc1ccc(CNCc2cc[nH]c(=O)c2)cc1] | 284 | 13.6<br>2.0 |
| 171 | 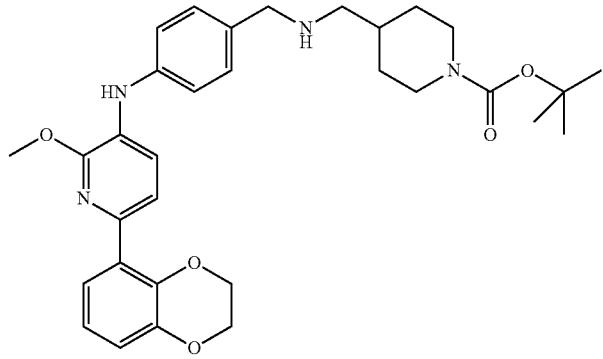 [SMILES: COc1nc(-c2cccc3c2OCCO3)ccc1Nc1ccc(CNCC2CCN(C(=O)OC(C)(C)C)CC2)cc1] | 30 | 6.6<br>0.14 |
| 172 | 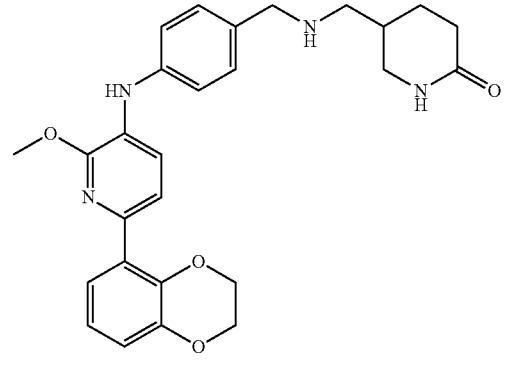 [SMILES: COc1nc(-c2cccc3c2OCCO3)ccc1Nc1ccc(CNCC2CCC(=O)NC2)cc1] | 174 | 23.3<br>4.7 |

-continued

| Example No. | Chemical Structure | SPR Response Units | Cell Viability (μM) H358 DLD-1 |
|---|---|---|---|
| 173 | 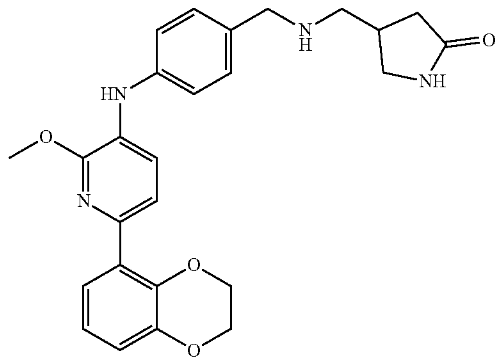 [SMILES: COc1nc(-c2cccc3c2OCCO3)ccc1Nc1ccc(CNCC2CNC(=O)C2)cc1] | 147 | 7.4<br>4.0 |
| 174 | 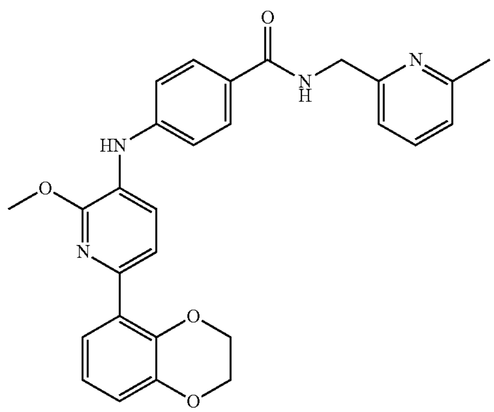 | 43 | |
| 175 | 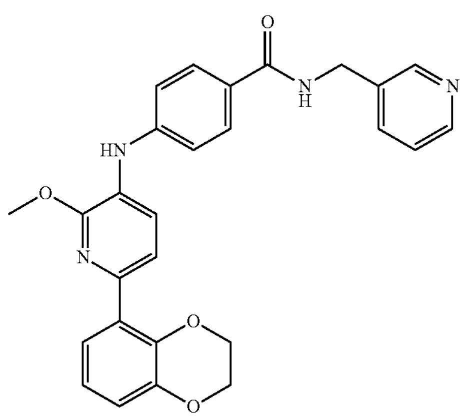 [SMILES: COc1nc(-c2cccc3c2OCCO3)ccc1Nc1ccc(C(=O)NCc2cccnc2)cc1] | 63 | 15.8<br>8.2 |

| Example No. | Chemical Structure | SPR Response Units | Cell Viability (μM) H358 DLD-1 |
|---|---|---|---|
| 176 | 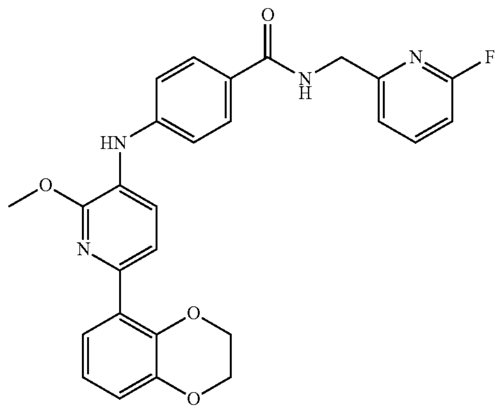 [SMILES: COc1nc(-c2cccc3c2OCCO3)ccc1Nc1ccc(C(=O)NCc2cccc(F)n2)cc1] | ND | |
| 177 | 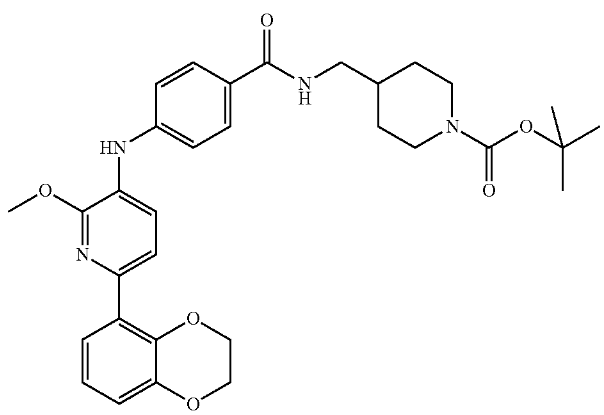 [SMILES: COc1nc(-c2cccc3c2OCCO3)ccc1Nc1ccc(C(=O)NCC2CCN(C(=O)OC(C)(C)C)CC2)cc1] | ND | |
| 178 | 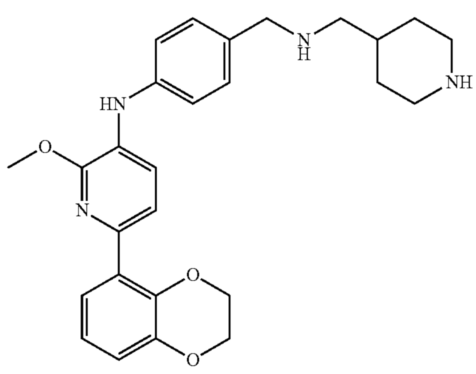 [SMILES: COc1nc(-c2cccc3c2OCCO3)ccc1Nc1ccc(CNCC2CCNCC2)cc1] | 150 | 1.8<br>0.27 |

-continued
| Example No. | Chemical Structure | SPR Response Units | Cell Viability (μM) H358 DLD-1 |
|---|---|---|---|
| 179 | 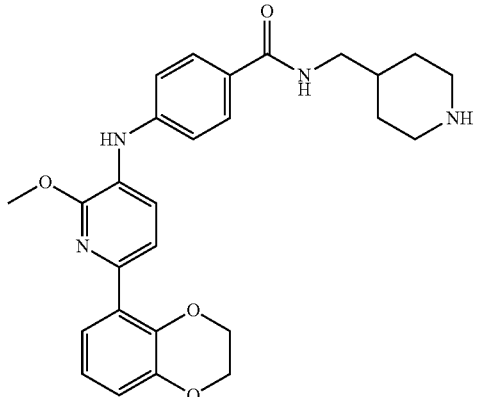 [SMILES: COc1nc(-c2cccc3c2OCCO3)ccc1Nc1ccc(C(=O)NCC2CCNCC2)cc1] | 162 | 7.5<br>0.39 |
| 180 | 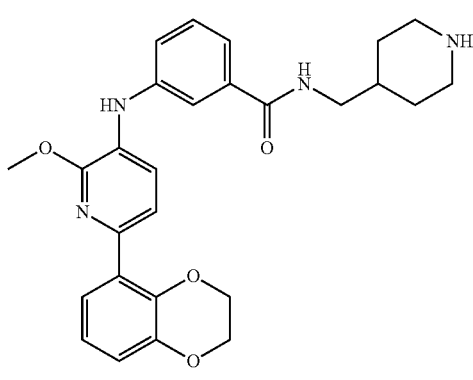 [SMILES: COc1nc(-c2cccc3c2OCCO3)ccc1Nc1cccc(C(=O)NCC2CCNCC2)c1] | 197 | 8.6<br>0.65 |
| 181 | 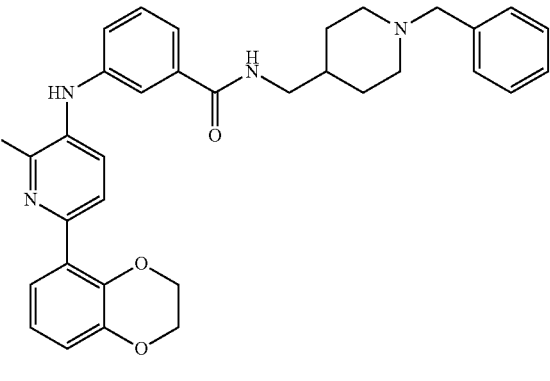 | 149 | 4.3<br>1.8 |
| 182 | 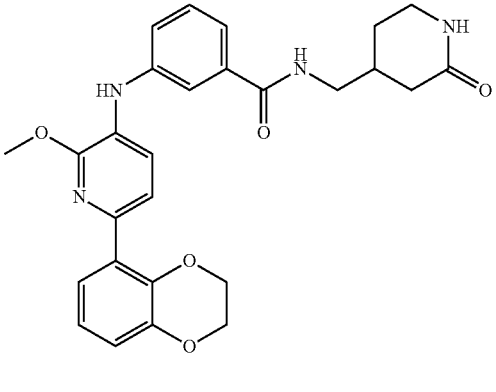 [SMILES: COc1nc(-c2cccc3c2OCCO3)ccc1Nc1cccc(C(=O)NCC2CCNC(=O)C2)c1] | 198 | 27.0<br>11.3 |

-continued

| Example No. | Chemical Structure | SPR Response Units | Cell Viability (μM) H358 DLD-1 |
|---|---|---|---|
| 183 | 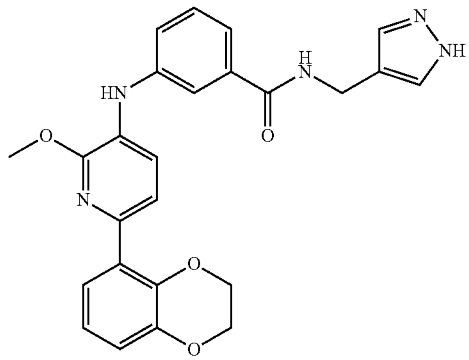 [SMILES: COc1nc(-c2cccc3c2OCCO3)ccc1Nc1cccc(C(=O)NCc2cn[nH]c2)c1] | TBD | 15.5 8.4 |
| 184 | 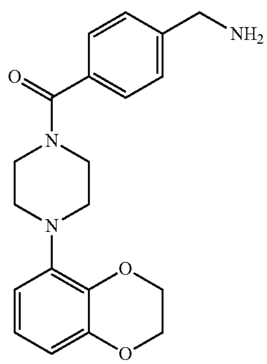 [SMILES: NCc1ccc(C(=O)N2CCN(c3cccc4c3OCCO4)CC2)cc1] | 10 | 3.6 1.2 |
| 185 | 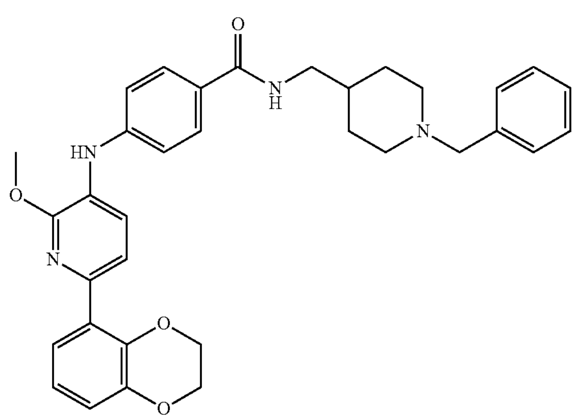 [SMILES: COc1nc(-c2cccc3c2OCCO3)ccc1Nc1ccc(C(=O)NCC2CCN(Cc3ccccc3)CC2)cc1] | 122 | 2.4 1.2 |
| 186 | 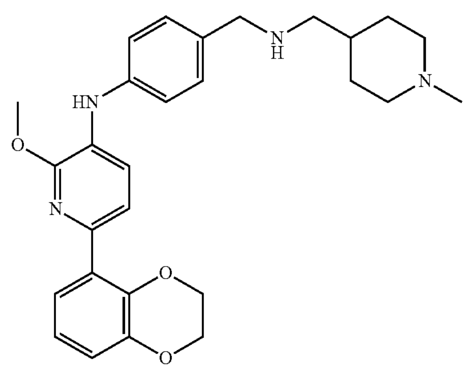 | 636 | 2.4 0.3 |

| Example No. | Chemical Structure | SPR Response Units | Cell Viability (μM) H358 DLD-1 |
|---|---|---|---|
| 187 | 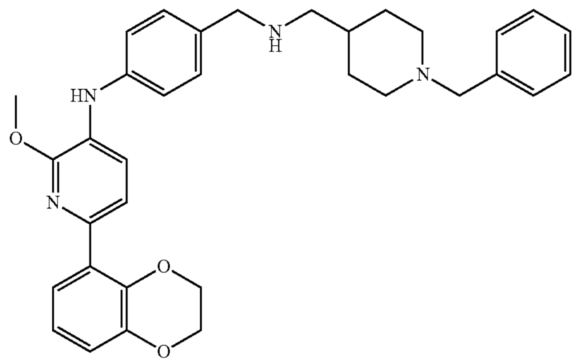 | 916 | 25.9<br>2.2 |
| 188 | 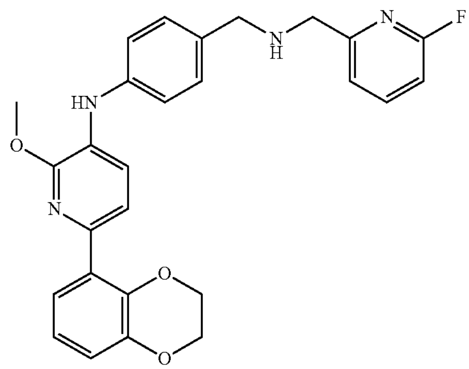 [SMILES: COc1nc(-c2cccc3c2OCCO3)ccc1Nc1ccc(CNCc2cccc(F)n2)cc1] | 103 | 27.4<br>49.5 |
| 189 | 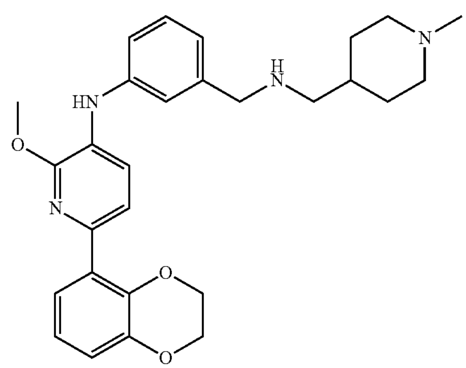 | 552 | 44.9<br>1.4 |
| 190 | 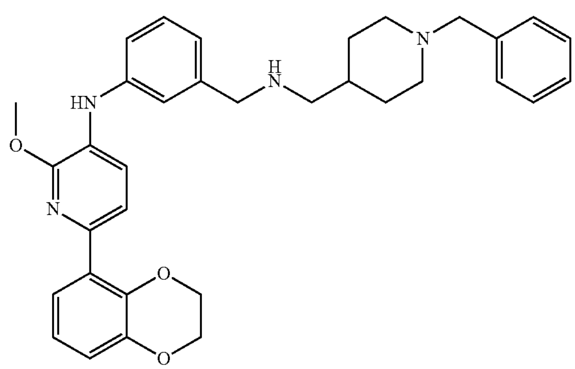 | 665 | 8.6<br>1.6 |

-continued

| Example No. | Chemical Structure | SPR Response Units | Cell Viability (μM) H358 DLD-1 |
|---|---|---|---|
| 191 | 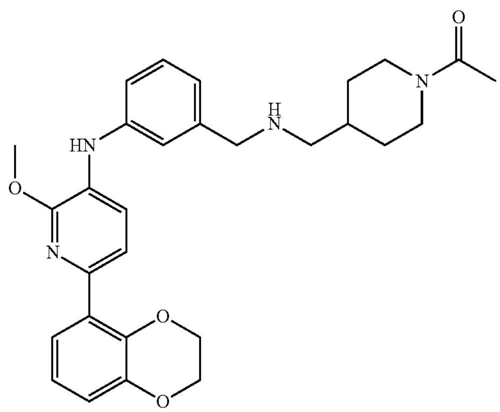 [SMILES: COc1nc(-c2cccc3c2OCCO3)ccc1Nc1cccc(CNCC2CCN(C(C)=O)CC2)c1] | 327 | 91.8<br>7.9 |
| 192 | 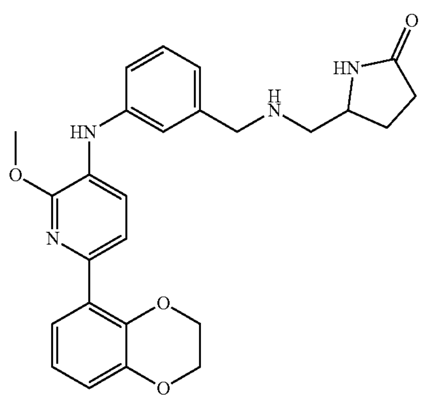 [SMILES: COc1nc(-c2cccc3c2OCCO3)ccc1Nc1cccc(CNCC2CCC(=O)N2)c1] | 321 | >150<br>11.4 |
| 193 | 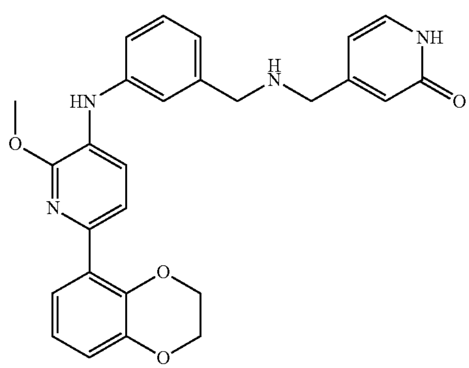 [SMILES: COc1nc(-c2cccc3c2OCCO3)ccc1Nc1cccc(CNCc2cc[nH]c(=O)c2)c1] | 388 | 52.5<br>14.8 |
| 194 | 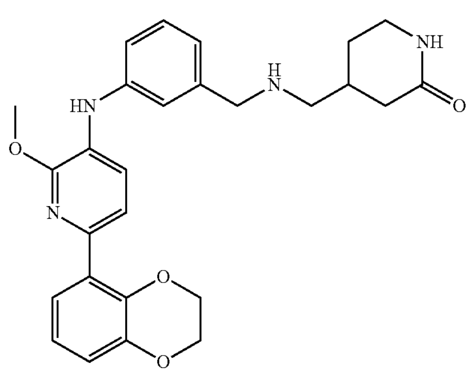 [SMILES: COc1nc(-c2cccc3c2OCCO3)ccc1Nc1cccc(CNCC2CCNC(=O)C2)c1] | 359 | >150<br>11.2 |

-continued

| Example No. | Chemical Structure | SPR Response Units | Cell Viability (μM) H358 DLD-1 |
|---|---|---|---|
| 195 | 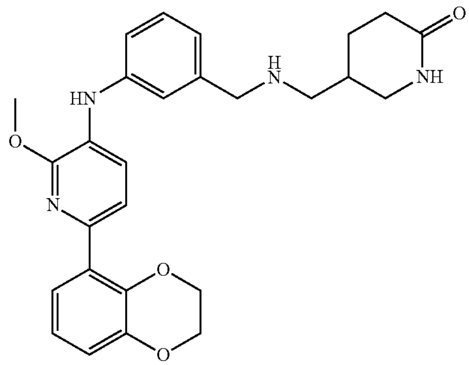 [SMILES: COc1nc(-c2cccc3c2OCCO3)ccc1Nc1cccc(CNCC2CCC(=O)NC2)c1] | 176 | 13.0<br>3.8 |
| 196 | 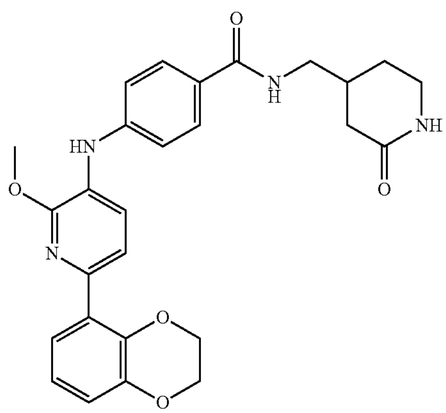 [SMILES: COc1nc(-c2cccc3c2OCCO3)ccc1Nc1ccc(C(=O)NCC2CCNC(=O)C2)cc1] | 194 | 30.6<br>7.2 |
| 197 | 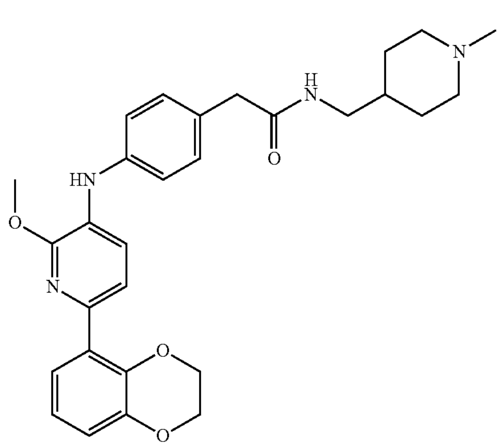 [SMILES: COc1nc(-c2cccc3c2OCCO3)ccc1Nc1ccc(CC(=O)NCC2CCN(C)CC2)cc1] | 453 | >150<br>15.9 |

-continued

| Example No. | Chemical Structure | SPR Response Units | Cell Viability (μM) H358 DLD-1 |
|---|---|---|---|
| 198 | 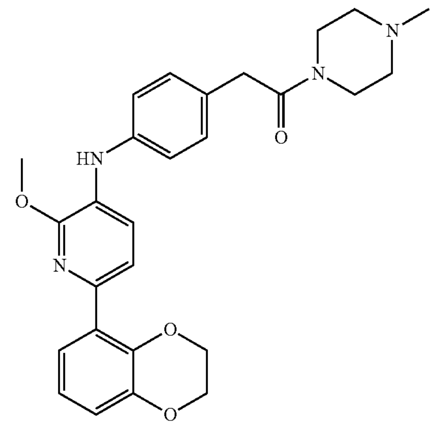 [SMILES: COc1nc(-c2cccc3c2OCCO3)ccc1Nc1ccc(CC(=O)N2CCN(C)CC2)cc1] | 330 | 1.57<br>21.8 |
| 199 | 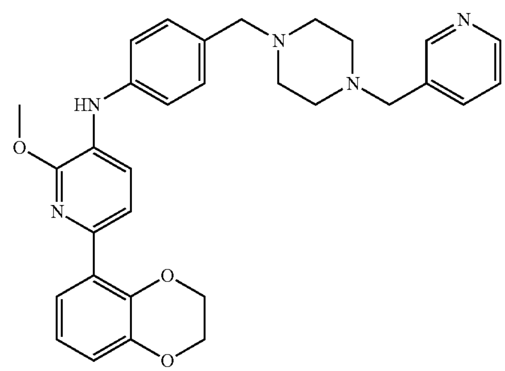 | 93 | 24.2<br>6.5 |
| 200 | 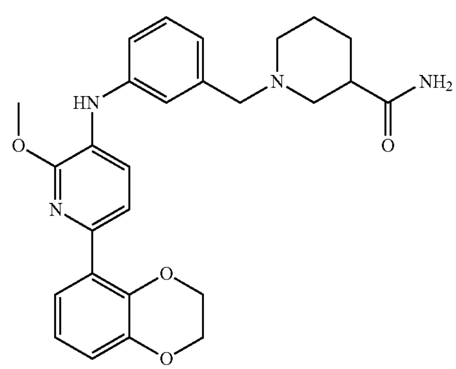 [SMILES: COc1nc(-c2cccc3c2OCCO3)ccc1Nc1cccc(CN2CCCC(C(N)=O)C2)c1] | 424 | 1.5<br>8.6 |
| 201 | 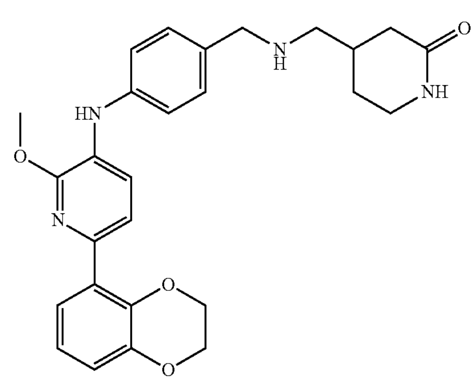 [SMILES: COc1nc(-c2cccc3c2OCCO3)ccc1Nc1ccc(CNCC2CCNC(=O)C2)cc1] | 209 | 6.8<br>10.5 |

-continued

| Example No. | Chemical Structure | SPR Response Units | Cell Viability (µM) H358 DLD-1 |
|---|---|---|---|
| 202 | 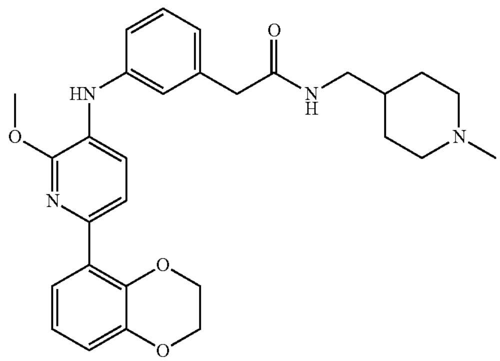 [SMILES: COc1nc(-c2cccc3c2OCCO3)ccc1Nc1cccc(CC(=O)NCC2CCN(C)CC2)c1] | 387 | 17.5<br>10.5 |
| 203 | 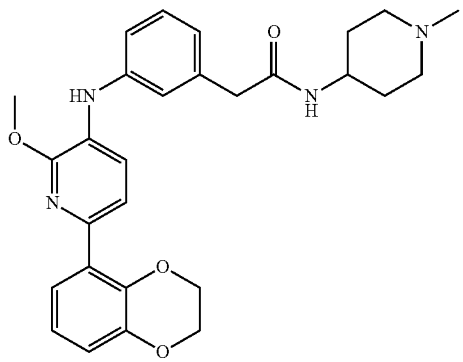 | 339 | 33.7<br>12.2 |
| 204 | 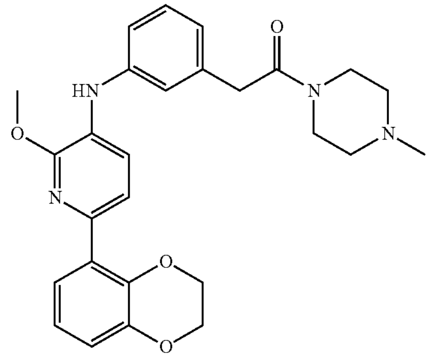 | 423 | 19.8<br>17.6 |
| 205 | 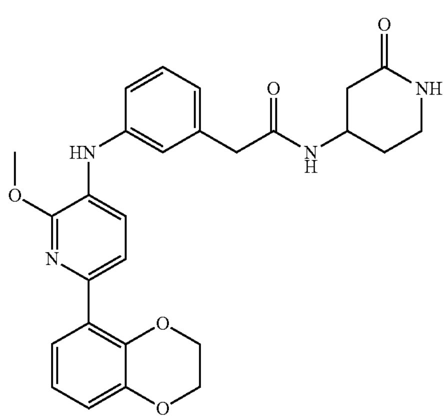 [SMILES: COc1nc(-c2cccc3c2OCCO3)ccc1Nc1cccc(CC(=O)NC2CCNC(=O)C2)c1] | 142 | 12.2<br>51.6 |

-continued
| Example No. | Chemical Structure | SPR Response Units | Cell Viability (μM) H358 DLD-1 |
|---|---|---|---|
| 206 | 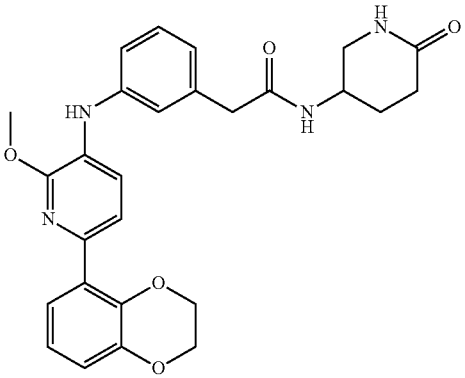 [SMILES: COc1nc(-c2cccc3c2OCCO3)ccc1Nc1cccc(CC(=O)NC2CCC(=O)NC2)c1] | 151 | 11<br>35.9 |
| 207 | 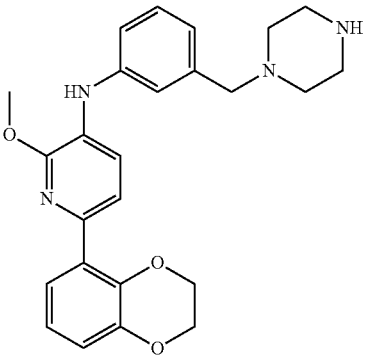 [SMILES: COc1nc(-c2cccc3c2OCCO3)ccc1Nc1cccc(CN2CCNCC2)c1] | 1189 | 5.8<br>22 |
| 208 | 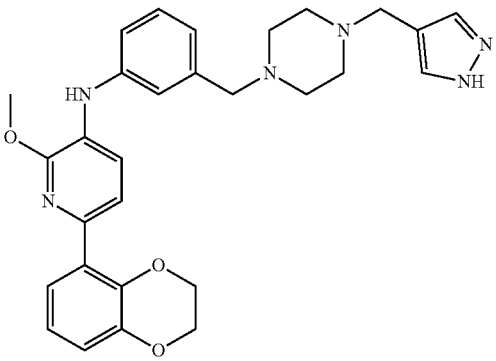 [SMILES: COc1nc(-c2cccc3c2OCCO3)ccc1Nc1cccc(CN2CCN(Cc3cn[nH]c3)CC2)c1] | 1266 | 17.4<br>5.8 |
| 209 | 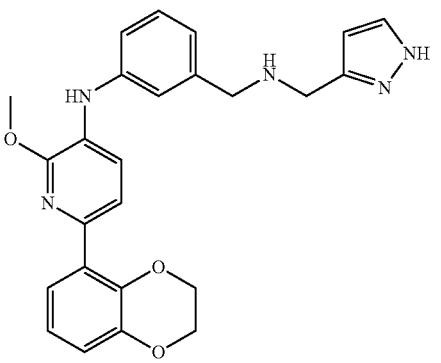 [SMILES: COc1nc(-c2cccc3c2OCCO3)ccc1Nc1cccc(CNCc2cc[nH]n2)c1] | 310 | 13.4<br>14.7 |

-continued

| Example No. | Chemical Structure | SPR Response Units | Cell Viability (μM) H358 DLD-1 |
|---|---|---|---|
| 210 | 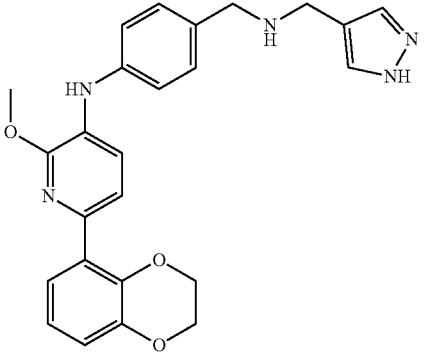 [SMILES: COc1nc(-c2cccc3c2OCCO3)ccc1Nc1ccc(CNCc2cn[nH]c2)cc1] | | |

BRET2 Cell Assay 650,000 HEK293T were seeded in each well of a 6 well plate. 24 hours later, cells were transfected with an appropriated BRET-based RAS biosensor (i.e. RAS-effector) using Lipofectamine 2000 transfection reagent (Thermo-Fisher). Cells were detached 24 hours later and washed with PBS and seeded in a white 96 well plate (clear bottom, PerkinElmer, cat #6005181) in OptiMEM no phenol red medium (Life Technologies) complemented with 4% FBS. Cells were left for 4 hours at 37° C. before adding compounds. Stock compounds were held at 10 mM in 100% DMSO and diluted in OptiMEM no red phenol+4% FBS to reach 10× the final concentration (2% DMSO for each concentration). The final concentrations in the cells were 0, 5, 10 and 20 UM (therefore the intermediate 10× concentrations were 0, 50, 100 and 200 μM. 10 μL of 10× compounds were added in each well of the 96 well plate to 0, 5, 10 and 20 UM final concentrations (with final 0.2% DMSO each). Quadruplicates were performed for each point. Cells were left for an additional 20 hours at 37° C. before the BRET2 signal reading directly after addition of Coelenterazine 400a substrate (10 UM final) to cells (Cayman Chemicals, cat #16157). BRET2 reading was carried out on an Envision instrument (2103 Multilabel Reader, PerkinElmer) with the BRET2 Dual Emission optical module (515 nm±30 and 410 nm±80; PerkinElmer).

Figure 1:
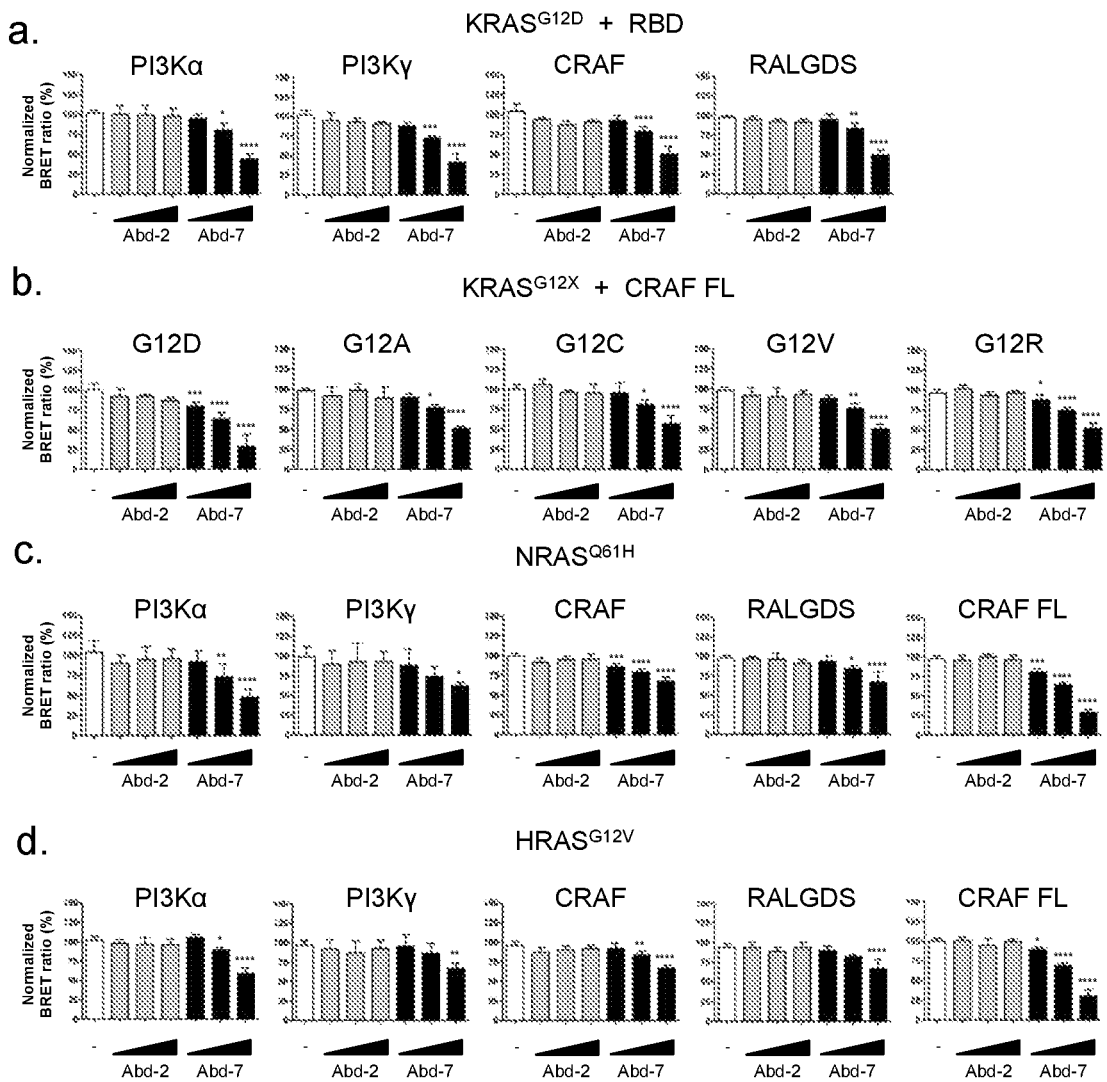
FIG. 1A, shows the effect of Abd-2 (Ref) and Abd-7 (compound 56) on KRASG12D interaction with PI3Kα, PI3Kγ, CRAF or RALGDS. The BRET signal is plotted as a % of control cells treated with DMSO only and dose response to 5, 10 and 20 UM of each compound.
FIG. 1B, shows the effect of Abd-2 (Ref) and Abd-7 (compound 56) on the BRET signal from interaction of KRASG12 mutants (Rluc8-KRASG12) and full length CRAF (GFP2-CRAF FL).
FIGS. 1C and D shows the effect of Abd-2 (ref) and Abd-7 (compound 56) on the interaction of NRASQ61H (panel c) and HRASG12V (panel d) with various RAS effectors domain and with full-length CRAF.
Figure 1:
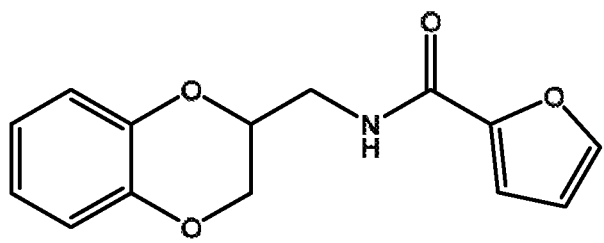

The ability of Example compound 56 to inhibit RAS-effector PPI using the above cell-based RAS-effector BRET2 assay was investigated. This assay comprises transfection of HEK293T cells with plasmids to express BRET donor (fusions of either K, N or HRAS, including a carboxy-terminal farnesylation signal tetrapeptide, with Renilla luciferase variant 8, Rluc8) and acceptor molecules (fusions of effector proteins with $GFP^2$) and permits the assessment of inhibitors of RAS-effector interaction. We determined the effect of compound 56 (labelled Abd-7) on the interaction of $KRAS^{G12D}$ and with PI3Kα and PI3Kγ, CRAF RAS-binding domain (RBD) and RALGDS RAS-associating domain (RA) compared with the low affinity Reference Compound Abd-2 FIG. 1a). Abd-2 has no effect on the BRET signal over a range of 5 to 20 μM while Abd-7/compound 56 reduces the BRET signal at 5, 10 and 20 μM for all of the RAS-effector PPIs tested. A similar inhibitory effect of Abd-7/compound 56, but not Abd-2, was observed using five different glycine 12 mutations of KRAS interacting with the full length CRAF-GFP2 fusion (FIG. 1b). Finally, we tested the efficacy of Abd-7, compared to Abd-2, in the BRET assays using other RAS family members, either NRASQ61H or HRASG12V, interacting with PI3Kα and PI3Kγ, CRAF-RBD or full length CRAF and RALGDS-RBD (respectively, FIGS. 1c and d). Abd-7/compound 56 interferes with all mutant RAS family member PPIs in this transfection assay.

The ability of Example compound 72 to inhibit RAS-effector PPI using the above cell-based RAS-effector BRET2 assay was also investigated. HEK293T cells were transiently transfected with BRET pairs and, after 24 hours to allow protein expression, the cells were seeded in 96 well plates. The compounds were added at different concentrations (5, 10 and 20 UM) and incubated on cells for a further 20 hours before the BRET reading. For each assay, the donor protein was $RLuc8-KRAS^{G12D}$ and the acceptor proteins were PI3Kγ RBD-$GFP^2$, PI3Kγ RBD-$GFP^2$, CRAF RBD-$GFP^2$ or RALGDS RA-$GFP^2$. A dose response reduction in BRET signal for the assays was observed with compound 72 but not with the Abd-2 indicating that only compound 72 interferes with the RAS-effector PPI (FIG. 2C).

Further, the efficacy of the RAS-binding compounds Abd-2 and compound 72 in binding to NRAS and HRAS using a BRET assay in which the RAS protein donors were co-expressed with either PI3K, CRAF or RALGDS acceptors (FIGS. 2A and B). While the low affinity Abd-2 compound does not interfere with the BRET signal in any of the NRAS and HRAS BRET assays using either effector RBDs (FIGS. 2A and B), compound 72 disturbs the BRET2 signal in dose response manner in all these RAS interactions. Therefore, the BRET-based RAS biosensors characterization of compound 72 shows this compound as a pan-RAS-effector interactions inhibitor that binds KRAS, NRAS and HRAS.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise paragraphed. No language in the specification should be construed as indicating any non-paragraphed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the paragraphs appended hereto as permitted by applicable law.

REFERENCES

Vetter I R, Wittinghofer A (2001) The guanine nucleotide-binding switch in three dimensions. Science 294: 1299-1304;

Downward J (2003) Targeting RAS signalling pathways in cancer therapy. Nat Rev Cancer 3: 11-22;

Marshall C J (1995) Specificity of receptor tyrosine kinase signalling: transient versus sustained extracellular signal-regulated kinase activation. Cell 80: 179-185;

Kolch W (2005) Coordinating ERK/MAPK signalling through scaffolds and inhibitors. Nat Rev Mol Cell Biol 6: 827-837;

GonzaleGarcia A, Pritchard C A, Paterson H F, Mavria G, Stamp G, Marshall C J (200 5) RalGDS is required for tumor formation in a model of skin carcinogenesis. Cancer Cell 7: 219-226;

Rangarajan A, Hong S J, Gifford A, Weinberg R A (2004) Species- and cell type-specific requirements for cellular transformation. Cancer Cell 6: 171-183;

Adjei A A (2001) Blocking oncogenic Ras signalling for cancer therapy. J Natl Cancer Inst93: 1062-1074;

Mendelsohn J, Baselga J (2000) The EGF receptor family as targets for cancer therapy. Oncogene 19: 6550-6565;

Johnson L, Mercer K, Greenbaum D, Bronson R T, Crowley D, Tuveson D A, Jacks T (2001) Somatic activation of the K-ras oncogene causes early onset lung cancer in mice. Nature 410: 1111-1116;

Chin L, Tam A, Pomerantz J, Wong M, Holash J, Bardeesy N, Shen Q, O'Hagan R, P antginis J, Zhou H, Horner II J W, Cordon-Cardo C, Yancopoulos G D, DePinho R A (1999) Essential role for oncogenic Ras in tumour maintenance. Nature 400: 468-472;

Fisher G H, Wellen S L, Klimstra D, Lenczowski J M, Tichelaar J W, Lizak M J, Whitsett J A, Koretsky A, Varmus H E (2001) Induction and apoptotic regression of lung adenocarcinomas by regulation of a K-Ras transgene in the presence and absence of tumor suppressor genes. Genes Dev 15: 3249-3262;

Friday B B, Adjei A A (2005) K-ras as a target for cancer therapy. Biochim Biophys Acta1756: 127-144;

Cattaneo A, Biocca S (1997) Intracellular Antibodies: Development and Applications. Springer: New York, USA;

Visintin M, Tse E, Axelson H, Rabbitts T H, Cattaneo A (1999) Selection of antibodies for intracellular function using a two-hybrid in vivo system. Proc Natl Acad Sci USA 96:11723-11728

Tse E, Lobato M N, Forster A, Tanaka T, Chung G T Y, Rabbitts T H (2002) Intracellula r antibody capture technology: application to selection of single chain Fv recognising the BCR-ABL oncogenic protein. J Mol Biol 317: 85-94;

Tanaka T, Rabbitts T H (2003) Intrabodies based on intracellular capture frameworks that bind the RAS protein with high affinity and impair oncogenic transformation. EMBO J., 22: 1025-1035;

Tanaka T, Lobato M N, Rabbitts T H (2003) Single domain intracellular antibodies: a minimal fragment for direct in vivo selection of antigen-specific intrabodies. J Mol Biol., 331: 1109-1120;

Tanaka et al., (2007) Tumour prevention by a single antibody domain targeting the interaction of signal transduction proteins with RAS; EMBO J., 26, 3250-3259

Blundell T L, Sibanda B L, Montalvao R W, Brewerton S, Chelliah V, Worth C L, Harmer N J, Davies O, Burke D (2006) Structural biology and bioinformatics in drug design: opportunities and challenges for target identification and lead discovery. Philos Trans R Soc Lond B Biol Sci 361: 413-423

The invention claimed is:
1. A compound of Formula (Ia), or a salt or solvate thereof:

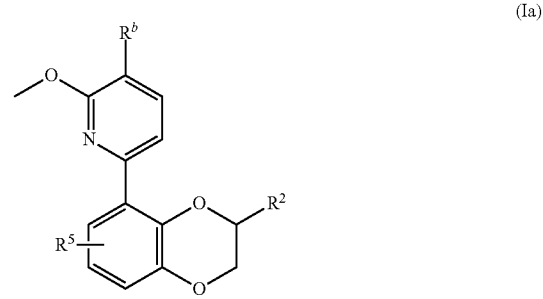

(Ia)

wherein
$R^5$ is selected from hydrogen, hydroxyl, halogen, CN, $C_{1-6}$ haloalkyl, $C_{1-6}$ haloalkoxy, O—$C_{1-6}$ alkyl and $C_{1-6}$ alkyl optionally substituted by one or more $R^a$;

$R^a$ is independently selected from hydroxyl, halogen, $C_{1-6}$ alkyl, CN, $C_{1-6}$ haloalkyl, $C_{1-6}$ haloalkoxy, $C_{3-6}$ cycloalkyl, 3-10 membered heterocycloalkyl, wherein said $C_{1-6}$ alkyl, $C_{3-6}$ cycloalkyl and 3-10 membered heterocycloalkyl are optionally substituted with one or more groups selected from hydroxyl, halogen, CN, $NR^cR^d$, $C_{1-6}$ haloalkyl, $C_{3-6}$ cycloalkyl, $C_{1-6}$ alkyl and O—$C_{1-6}$ alkyl;

$R^b$ is selected from hydroxyl, =O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-10 membered heterocycloalkyl, —C(=O)$R^d$, —C(=O)O$R^d$, —C(=O)N$R^cR^d$, —C(O)C(=O)$R^d$, —N$R^cR^d$, —$NR^cC(=O)R^d$, —$NR^cC(=O)OR^d$, —$NR^cC(=O)NR^cR^d$, —$NR^cS(=O)_2R^d$, —$NR^cS(=O)_2NR^cR^d$, —O$R^d$, —S$R^d$, —OC(=O)$R^d$, —OC(=O)N$R^cR^d$, —OC(=O)O$R^d$, —S(=O)$_2R^d$, —S(=O)$R^d$, —OS(=O)$R^d$, —OS(=O)$_2R^d$, —OS(=O)$_2OR^d$, —S(=O)N$R^cR^d$, —OS(=O)$_2NR^cR^d$, —S(=O)$_2NR^cR^d$ and a group of Formula II; wherein said $C_{3-6}$ cycloalkyl, $C_{1-6}$ alkyl, and 3-10 membered heterocycloalkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $C_{1-6}$ alkyl, and O—$C_{1-6}$ alkyl;

and wherein in Formula II:

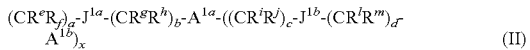
(II)

$R^e$, $R^f$, $R^g$, $R^h$, $R^i$, $R^j$, $R^l$, and $R^m$ are independently selected from hydrogen and $C_{1-6}$ alkyl;

$a$, $b$, $c$ and $d$ are independently selected from 0, 1, 2, 3 and 4, and $x$ is selected from 0 and 1;

$J^{1a}$ is selected from a direct bond, O, S, $CH_2$, C(O), C(O)$NR^{s1}$, $NR^{s1}$C(O), $NR^{s1}$C(O)$NR^{s1}$, $NR^{s1}$C(O)O, OC(O)$NR^{s1}$ and $NR^{s1}$; where $R^{s1}$ is selected from hydrogen and $C_{1-6}$ alkyl;

$J^{1b}$ is selected from a direct bond, O, S, $CH_2$, C(O), C(O)$NR^{s1}$, $NR^{s1}$C(O), $NR^{s1}$C(O)$NR^{s1}$, $NR^{s1}$C(O)O, OC(O)$NR^{s1}$ and $NR^{s1}$; where $R^{s1}$ is selected from hydrogen and $C_{1-6}$ alkyl;

$A^{1a}$ is selected from $C_{3-11}$cycloalkyl optionally substituted by one or more $R^k$, $C_{6-11}$ aryl optionally substituted by one or more $R^k$, 3-15 membered heterocycloalkyl optionally substituted by one or more $R^k$, 5-15 membered heteroaryl optionally substituted by one or more $R^k$;

$A^{1b}$ is selected from $C_{3-11}$cycloalkyl optionally substituted by one or more $R^r$, $C_{6-11}$ aryl optionally substituted by one or more $R^r$, 3-15 membered heterocycloalkyl optionally substituted by one or more $R^r$, 5-15 membered heteroaryl optionally substituted by one or more $R^r$;

$R^k$ and $R^r$ are independently selected from hydrogen, hydroxyl, =O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-10 membered heterocycloalkyl, phenyl, benzyl, alkylheterocycloalkyl, alkylheteroaryl, —C(=O)$R^d$, —C(=O)O$R^d$, —C(=O)$NR^cR^d$, —C(O)C(=O)$R^d$, —$NR^cR^d$, —$NR^c$C(=O)$R^d$, —$NR^c$C(=O)O$R^d$, —$NR^c$C(=O)$NR^cR^d$, —$NR^c$S(=O)$_2R^d$, —$NR^c$S(=O)$_2NR^cR^d$, —O$R^d$, —S$R^d$, —OC(=O)$R^d$, —OC(=O)$NR^cR^d$, —OC(=O)O$R^d$, —S(=O)$_2R^d$, —S(=O)$R^d$, —OS(=O)$R^d$, —OS(=O)$_2R^d$, —OS(=O)$_2OR^d$, —S(=O)$NR^cR^d$, —OS(=O)$_2NR^cR^d$, —S(=O)$_2NR^cR^d$; where said $C_{3-6}$ cycloalkyl, $C_{1-6}$ alkyl, 3-10 membered heterocycloalkyl, phenyl, benzyl, alkylheterocycloalkyl, alkylheteroaryl, and O—$C_{1-6}$ alkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^cR^d$, $C_{1-6}$ alkyl, O—$C_{1-6}$ alkyl, and phenyl;

$R^2$ is selected from hydrogen, halogen, hydroxyl, —CN, —C(=O)$R^d$, —C(=O)O$R^d$, —C(=O)$NR^cR^d$, —C(O)C(=O)$R^d$, —$NR^cR^d$, —$NR^c$C(=O)$R^d$, —$NR^c$C(=O)O$R^d$, —$NR^c$C(=O)$NR^cR^d$, —$NR^c$S(=O)$_2R^d$, —$NR^c$S(=O)$_2NR^cR^d$, —O$R^d$, —S$R^d$—OC(=O)$R^d$, —OC(=O)$NR^cR^d$, —OC(=O)O$R^d$, —S(=O)$R^d$, —S(=O)$_2R^d$, —OS(=O)$R^d$, —OS(=O)$_2R^d$, —OS(=O)$_2OR^d$, —S(=O)$NR^cR^d$, —OS(=O)$_2NR^cR^d$, —S(=O)$_2NR^cR^d$, $C_{1-10}$ haloalkyl, $C_{1-10}$alkyl optionally substituted by one or more $R^n$, $C_{2-6}$alkenyl optionally substituted by one or more $R^n$, $C_{2-6}$alkynyl optionally substituted by one or more $R^n$, or a group of Formula III

(III)

wherein $R^n$ is independently selected from hydroxyl, =O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-10 membered heterocycloalkyl, —C(=O)$R^d$, —C(=O)O$R^d$, —C(=O)$NR^cR^d$, —C(O)C(=O)$R^d$, —$NR^cR^d$, —$NR^c$C(=O)$R^d$, —$NR^c$C(=O)O$R^d$, —$NR^c$C(=O)$NR^cR^d$, —$NR^c$S(=O)$_2R^d$, —$NR^c$S(=O)$_2NR^cR^d$, —O$R^d$, —S$R^d$, —OC(=O)$R^d$, —OC(=O)$NR^cR^d$, —OC(=O)O$R^d$, —S(=O)$_2R^d$, —S(=O)$R^d$, —OS(=O)$R^d$, —OS(=O)$_2R^d$, —OS(=O)$_2OR^d$, —S(=O)$NR^cR^d$, —OS(=O)$_2NR^cR^d$ and —S(=O)$_2NR^cR^d$; where said $C_{3-6}$ cycloalkyl, $C_{1-6}$ alkyl, 3-10 membered heterocycloalkyl, $C_{1-6}$ alkyl and O—$C_{1-6}$ alkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^cR^d$, $C_{1-6}$ alkyl, and O—$C_{1-6}$ alkyl;

$R^p$ and $R^q$ are independently selected from hydrogen, $C_{1-6}$ alkyl, $C_{3-7}$cycloalkyl optionally substituted by one or more $R^a$, 5-6 membered ($C_{1-6}$alkyl)aryl optionally substituted by one or more $R^a$, 5-6 membered aryl optionally substituted by one or more $R^a$, ($C_{1-6}$alkyl)$C_{3-7}$ cycloalkyl optionally substituted by one or more $R^a$, 3-7 membered heterocycloalkyl optionally substituted by one or more $R^a$, 3-7 membered ($C_{1-6}$alkyl)heterocycloalkyl optionally substituted by one or more $R^a$, 5-6 membered heteroaryl optionally substituted by one or more $R^a$, and 5-6 membered ($C_{1-6}$alkyl)heteroaryl optionally substituted by one or more $R^a$;

$R^u$, $R^v$, $R^w$, $R^x$, $R^y$ and $R^z$ are independently selected from hydrogen and $C_{1-6}$ alkyl;

$f$, $g$, $h$, and $j$ are independently selected from 0, 1, 2, 3 and 4, and $y$ is selected from 0 and 1;

$J^{2a}$ is selected from a direct bond, O, S, C(O), $CH_2$, C(O)$NR^{s2}$, $NR^{s2}$C(O) and $NR^{s2}$; where $R^{s2}$ is selected from hydrogen, $C_{1-6}$ alkyl, $C_{3-7}$cycloalkyl optionally substituted by one or more $R^a$, 5-6 membered ($C_{1-6}$alkyl)aryl optionally substituted by one or more $R^a$, 5-6 membered aryl optionally substituted by one or more $R^a$, ($C_{1-6}$alkyl)$C_{3-7}$cycloalkyl optionally substituted by one or more $R^a$, 3-7 membered heterocycloalkyl optionally substituted by one or more $R^a$, 3-7 membered ($C_{1-6}$alkyl)heterocycloalkyl optionally substituted by one or more $R^a$, 5-6 membered heteroaryl optionally substituted by one or more $R^a$, and 5-6 membered ($C_{1-6}$alkyl)heteroaryl optionally substituted by one or more $R^a$;

$J^{2b}$ is selected from a direct bond, O, S, C(O), $CH_2$, C(O)$NR^{s2}$, $NR^{s2}$C(O) and $NR^{s2}$; where $R^{s2}$ is selected from hydrogen, $C_{1-6}$ alkyl, $C_{3-7}$cycloalkyl optionally substituted by one or more $R^a$, 5-6 membered ($C_{1-6}$alkyl)aryl optionally substituted by one or more $R^a$, 5-6 membered aryl optionally substituted by one or more $R^a$, ($C_{1-6}$alkyl)$C_{3-7}$cycloalkyl optionally substituted by one or more $R^a$, 3-7 membered heterocycloalkyl optionally substituted by one or more $R^a$, 3-7 membered ($C_{1-6}$alkyl)heterocycloalkyl optionally substituted by one or more $R^a$, 5-6 membered heteroaryl optionally substituted by one or more $R^a$, and 5-6 membered ($C_{1-6}$alkyl)heteroaryl optionally substituted by one or more $R^a$;

$A^{2a}$ is selected from $C_{3-11}$ cycloalkyl optionally substituted by one or more $R^t$, 3-15 membered heterocycloalkyl optionally substituted by one or more $R^t$, $C_{6-11}$ aryl optionally substituted by one or more $R^t$ and 5-15 membered heteroaryl optionally substituted by one or more $R^t$;

$A^{2b}$ is selected from $C_{3-11}$ cycloalkyl optionally substituted by one or more $R^t$, 3-15 membered heterocycloalkyl optionally substituted by one or more $R^t$, $C_{6-11}$ aryl optionally substituted by one or more $R^t$ and 5-15 membered heteroaryl optionally substituted by one or more $R^t$; and $R^t$ is selected from hydroxyl, =O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-10 membered heterocycloalkyl, —C(=O)$R^d$, —C(=O)O$R^d$, —C(=O)NR$^c$R$^d$, —C(O)C(=O)$R^d$, —NR$^c$R$^d$, —NR$^c$C(=O)$R^d$, —NR$^c$C(=O)O$R^d$, —NR$^c$C(=O)NR$^c$R$^d$, —NR$^c$S(=O)$_2$R$^d$, —NR$^c$S(=O)$_2$NR$^c$R$^d$, —O$R^d$, —S$R^d$, —OC(=O)$R^d$, —OC(=O)NR$^c$R$^d$, —OC(=O)O$R^d$, —S(=O)$_2$R$^d$, —S(=O)$R^d$, —OS(=O)$R^d$, —OS(=O)$_2$R$^d$, —OS(=O)$_2$O$R^d$, —S(=O)NR$^c$R$^d$, —OS(=O)$_2$NR$^c$R$^d$ and —S(=O)$_2$NR$^c$R$^d$; where said $C_{3-6}$ cycloalkyl, $C_{1-6}$ alkyl, 3-10 membered heterocycloalkyl, $C_{1-6}$ alkyl and O—$C_{1-6}$alkyl are optionally substituted with one or more groups selected from hydroxyl, halogen, =O, CN, $C_{1-6}$ haloalkyl, $C_{1-6}$ haloalkoxy, $C_{3-6}$ cycloalkyl, NR$^c$R$^d$, $C_{1-6}$ alkyl, and O—$C_{1-6}$ alkyl; wherein, each $R^c$ is independently selected from hydrogen, hydroxyl, halogen, CN, $C_{1-6}$ haloalkyl, $C_{3-6}$ cycloalkyl, $C_{1-6}$ alkyl and O—$C_{1-6}$ alkyl;

each $R^d$ is independently selected from hydrogen, hydroxyl, halogen, CN, $C_{1-6}$ haloalkyl, 3-10 membered heterocycloalkyl, $C_{3-6}$ cycloalkyl, $C_{1-6}$ alkyl, O—$C_{1-6}$ alkyl and $C_{6-11}$ aryl, wherein said $C_{1-6}$ alkyl, O—$C_{1-6}$ alkyl, $C_{6-11}$ aryl, 3-10 membered heterocycloalkyl and $C_{3-6}$ cycloalkyl are optionally substituted with one or more groups selected from hydroxyl, =O, halogen, CN, NH$_2$, NHMe, NMe$_2$, ($C_{1-6}$ haloalkyl, $C_{3-6}$ cycloalkyl, $C_{6-11}$ aryl, $C_{1-6}$ alkyl and O—$C_{1-6}$ alkyl; or $R^c$ and $R^d$, when attached to the same atom, together with the atom to which they are attached form a 3-10 membered ring, optionally containing one or more for heteroatoms selected from O, NH and S, and wherein said ring is optionally substituted with one or more $R^a$.

2. A compound according to claim 1, or a salt or solvate thereof, wherein $R^b$ is selected from hydroxyl, =O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-10 membered heterocycloalkyl, —NR$^c$R$^d$, and a group of Formula II.

3. A compound according to claim 1, or a salt or solvate thereof, wherein $R^b$ is selected from =O, $C_{1-6}$ alkyl, O—$C_{1-6}$ alkyl and —NR$^c$R$^d$.

4. A compound according to claim 1, or a salt or solvate thereof, wherein $R^b$ is a group of Formula II.

5. A compound according to claim 1, or a salt or solvate thereof, wherein the compound is of sub-Formula Ic:

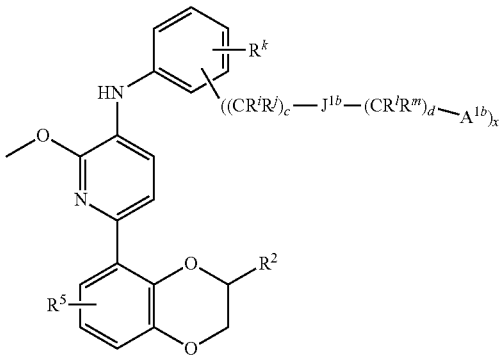

(Ic)

wherein $R^2$, $R^5$, $R^i$, $R^j$, $R^k$, $J^{1b}$, $R^l$, $R^m$, $A^{1b}$, c, d and x are defined in claim 1.

6. A compound according to claim 5, or a salt or solvate thereof, wherein $R^k$ is hydrogen and x is 1.

7. A compound according to claim 1, or a salt or solvate thereof, wherein $R^2$ is selected from hydrogen, $C_{1-10}$alkyl optionally substituted by one or more $R^n$ and or a group of Formula III.

8. A compound according to claim 1, or a salt or solvate thereof, wherein $R^2$ is selected from hydrogen or a group of Formula III.

9. A compound according to claim 1, or a salt or solvate thereof, wherein $R^5$ is selected from hydrogen, $C_{1-3}$ alkyl and halogen.

10. A compound, or a salt or solvate thereof, selected from the group consisting of:
- 2-(2,3-Dihydro-benzo[1,4]dioxin-5-yl)-6-methoxy-pyridine;
- [8-(6-Methoxy-pyridin-2-yl)-2,3-dihydro-benzo[1,4]dioxin-2-yl]-methanol;
- 2-(2,3-Dihydro-benzo[1,4]dioxin-5-yl)-6-methoxy-pyridin-4-ylamine;
- 1-Methyl-piperidine-4-carboxylic acid [2-(2,3-dihydro-benzo[1,4]dioxin-5-yl)-6-methoxy-pyridin-4-yl]-amide;
- 3-Chloro-6-(2,3-dihydro-benzo[1,4]dioxin-5-yl)-2-methoxy-pyridine;
- 5-Chloro-2-(2,3-dihydro-benzo[1,4]dioxin-5-yl)-pyridine;
- 5-(4-Chloro-3-methoxy-phenyl)-2,3-dihydro-benzo[1,4]dioxine;
- (R)-3-[2-(2,3-dihydro-benzo[1,4]dioxin-5-yl)-6-methoxy-pyridin-4-ylcarbamoyl]-pyrrolidine-1-carboxylic acid tert-butyl ester;
- (R)-2-[2-(2,3-Dihydro-benzo[1,4]dioxin-5-yl)-6-methoxy-pyridin-4-ylcarbamoyl]-morpholine-4-carboxylic acid tert-butyl ester;
- 4-[2-(2,3-Dihydro-benzo[1,4]dioxin-5-yl)-6-methoxy-pyridin-4-ylcarbamoyl]-piperidine-1-carboxylic acid tert-butyl ester;
- (S)-2-[2-(2,3-Dihydro-benzo[1,4]dioxin-5-yl)-6-methoxy-pyridin-4-ylcarbamoyl]-morpholine-4-carboxylic acid tert-butyl ester;
- 2-{2-methoxy-6-[(R)-3-({[5-(4-methyl-piperazin-1-ylmethyl)-furan-2-carbonyl]-amino}-methyl)-2,3-dihydro-benzo[1,4]dioxin-5-yl]-pyridin-4-ylcarbamoyl}-morpholine-4-carboxylic acid tert-butyl ester;
- tert-butyl N-[(1S,3R)-3-[[2-(2,3-dihydro-1,4-benzodioxin-5-yl)-6-methoxy-4-pyridyl]carbamoyl]cyclopentyl]carbamate;
- {4-[2-(2,3-Dihydro-benzo[1,4]dioxin-5-yl)-6-methoxy-pyridin-4-ylcarbamoyl]-cyclohexyl}-carbamic acid tert-butyl ester;
- (R)-Pyrrolidine-3-carboxylic acid [2-(2,3-dihydro-benzo[1,4]dioxin-5-yl)-6-methoxy-pyridin-4-yl]-amide;
- (R)-Morpholine-2-carboxylic acid [2-(2,3-dihydro-benzo[1,4]dioxin-5-yl)-6-methoxy-pyridin-4-yl]-amide;
- Piperidine-4-carboxylic acid [2-(2,3-dihydro-benzo[1,4]dioxin-5-yl)-6-methoxy-pyridin-4-yl]-amide;
- (S)-Morpholine-2-carboxylic acid [2-(2,3-dihydro-benzo[1,4]dioxin-5-yl)-6-methoxy-pyridin-4-yl]-amide;
- 4-Amino-cyclohexanecarboxylic acid [2-(2,3-dihydro-benzo[1,4]dioxin-5-yl)-6-methoxy-pyridin-4-yl]-amide;
- 3-[2-(2,3-Dihydro-benzo[1,4]dioxin-5-yl)-6-methoxy-pyridin-4-yl]-1-methyl-1-(1-methyl-piperidin-4-yl)-urea;

4-Methyl-piperazine-1-carboxylic acid [2-(2,3-dihydro-benzo[1,4]dioxin-5-yl)-6-methoxy-pyridin-4-yl]-amide;

4-Amino-piperidine-1-carboxylic acid [2-(2,3-dihydro-benzo[1,4]dioxin-5-yl)-6-methoxy-pyridin-4-yl]-amide;

5-(6-methoxy-2-pyridyl)-2,3-dihydro-1,4-benzodioxine-3-carbaldehyde;

{2-[4-({[8-(6-Methoxy-pyridin-2-yl)-2,3-dihydro-benzo[1,4]dioxin-2-ylmethyl]-amino}-methyl)-phenoxy]-ethyl}-dimethyl-amine;

[8-(6-Methoxy-pyridin-2-yl)-2,3-dihydro-benzo[1,4]dioxin-2-ylmethyl]-(1-methyl-piperidin-4-ylmethyl)-amine;

[8-(6-Methoxy-pyridin-2-yl)-2,3-dihydro-benzo[1,4]dioxin-2-ylmethyl]-pyridin-3-ylmethyl-amine;

[8-(6-Methoxy-pyridin-2-yl)-2,3-dihydro-benzo[1,4]dioxin-2-ylmethyl]-(tetrahydro-pyran-4-ylmethyl)-amine;

[4-({[8-(6-Methoxy-pyridin-2-yl)-2,3-dihydro-benzo[1,4]dioxin-2-ylmethyl]-amino}-methyl)-piperidin-1-yl]-pyrazin-2-yl-methanone;

[4-({[8-(6-Methoxy-pyridin-2-yl)-2,3-dihydro-benzo[1,4]dioxin-2-ylmethyl]-amino}-methyl)-piperidin-1-yl]-(tetrahydro-pyran-4-yl)-methanone;

{2-[4-({[8-(6-Methoxy-pyridin-2-yl)-2,3-dihydro-benzo[1,4]dioxin-2-ylmethyl]-pyridin-3-ylmethyl-amino}-methyl)-phenoxy]-ethyl}-dimethyl-amine;

2-(4-{[[8-(6-Methoxy-pyridin-2-yl)-2,3-dihydro-benzo[1,4]dioxin-2-ylmethyl]-(tetrahydro-pyran-4-ylmethyl)-amino]-methyl}-phenoxy)-ethyl]-dimethyl-amine;

toluene-4-sulfonic acid 8-(6-methoxy-pyridin-2-yl)-2,3-dihydro-benzo[1,4]dioxin-2-ylmethyl ester;

3-[8-(6-Methoxy-pyridin-2-yl)-2,3-dihydro-benzo[1,4]dioxin-2-ylmethyl]-8-methyl-1,3,8-triaza-spiro[4.5]decane-2,4-dione;

3-[8-(6-Methoxy-pyridin-2-yl)-2,3-dihydro-benzo[1,4]dioxin-2-ylmethyl]-5,5-dimethyl-imidazolidine-2,4-dione;

1-(6-Methoxy-pyridin-3-yl)-3-[8-(6-methoxy-pyridin-2-yl)-2,3-dihydro-benzo[1,4]dioxin-2-ylmethyl]-imidazolidine-2,4-dione;

3-[8-(6-Methoxy-pyridin-2-yl)-2,3-dihydro-benzo[1,4]dioxin-2-ylmethyl]-1-piperidin-4-yl-imidazolidine-2,4-dione;

4-(2-Dimethylamino-ethoxy)-2-fluoro-N-[8-(6-methoxy-pyridin-2-yl)-2,3-dihydro-benzo[1,4]dioxin-2-ylmethyl]-benzamide;

4-(2-Dimethylamino-ethoxy)-N-[8-(6-methoxy-pyridin-2-yl)-2,3-dihydro-benzo[1,4]dioxin-2-ylmethyl]-benzamide;

4-(2-Dimethylamino-ethoxy)-N—[(R)-8-(6-methoxy-pyridin-2-yl)-2,3-dihydro-benzo[1,4]dioxin-2-ylmethyl]-benzamide;

4-(2-Dimethylamino-ethoxy)-N—[(S)-8-(6-methoxy-pyridin-2-yl)-2,3-dihydrobenzo[1,4]dioxin-2-ylmethyl]-benzamide;

5-(4-Methyl-piperazin-1-ylmethyl)-furan-2-carboxylic acid [8-(2H-pyrazol-3-yl)-2,3-dihydro-benzo[1,4]dioxin-2-ylmethyl]-amide;

5-(4-Methyl-piperazin-1-ylmethyl)-furan-2-carboxylic acid [8-(6-methoxy-pyridin-2-yl)-2,3-dihydro-benzo[1,4]dioxin-2-ylmethyl]-amide;

5-(4-Methyl-piperazin-1-ylmethyl)-furan-2-carboxylic acid [(S)-8-(6-methoxy-pyridin-2-yl)-2,3-dihydro-benzo[1,4]dioxin-2-ylmethyl]-amide;

Tetrahydro-pyran-4-carboxylic acid [8-(6-methoxy-pyridin-2-yl)-2,3-dihydro-benzo[1,4]dioxin-2-ylmethyl]-amide;

5-(4-Methyl-piperazin-1-ylmethyl)-furan-2-carboxylic acid [8-(6-methoxy-pyridin-3-yl)-2,3-dihydro-benzo[1,4]dioxin-2-ylmethyl]-amide;

5-Morpholin-4-ylmethyl-furan-3-carboxylic acid [8-(6-methoxy-pyridin-2-yl)-2,3-dihydro-benzo[1,4]dioxin-2-ylmethyl]-amide;

3-Dimethylamino-N-[8-(6-methoxy-pyridin-2-yl)-2,3-dihydro-benzo[1,4]dioxin-2-ylmethyl]-propionamide;

1-Pyrazin-2-ylmethyl-piperidine-4-carboxylic acid [(R)-8-(6-methoxy-pyridin-2-yl)-2,3-dihydro-benzo[1,4]dioxin-2-ylmethyl]-amide;

5-(4-Methyl-piperazin-1-ylmethyl)-oxazole-2-carboxylic acid [8-(6-methoxy-pyridin-2-yl)-2,3-dihydro-benzo[1,4]dioxin-2-ylmethyl]-amide;

1-Methyl-piperidine-4-carboxylic acid [8-(6-methoxy-pyridin-2-yl)-2,3-dihydro-benzo[1,4]dioxin-2-ylmethyl]-amide;

5-(4-Methyl-piperazin-1-ylmethyl)-furan-2-carboxylic acid [(R)-8-(6-methoxy-pyridin-2-yl)-2,3-dihydro-benzo[1,4]dioxin-2-ylmethyl]-amide;

5-(4-Methyl-piperazin-1-ylmethyl)-furan-2-carboxylic acid [8-(6-oxo-1,6-dihydro-pyridin-2-yl)-2,3-dihydro-benzo[1,4]dioxin-2-ylmethyl]-amide;

4-(2-dimethylamino-ethoxy)-N-[8-(6-oxo-1,6-dihydro-pyridin-2-yl)-2,3-dihydro-benzo[1,4]dioxin-2-ylmethyl]-benzamide;

5-(4-methyl-piperazin-1-ylmethyl)-furan-2-carboxylic acid [8-(6-oxo-1,6-dihydro-pyridin-3-yl)-2,3-dihydro-benzo[1,4]dioxin-2-ylmethyl]-amide;

[6-(2,3-dihydro-benzo[1,4]dioxin-5-yl)-2-methoxy-pyridin-3-yl]-(3-dimethylaminomethyl-phenyl)-amine;

[6-(2,3-Dihydro-benzo[1,4]dioxin-5-yl)-2-methoxy-pyridin-3-yl]-(4-dimethylaminomethyl-phenyl)-amine;

[6-(2,3-Dihydro-benzo[1,4]dioxin-5-yl)-2-methoxy-pyridin-3-yl]-(5-dimethylaminomethyl-pyridin-2-yl)-amine;

[6-(2,3-Dihydro-benzo[1,4]dioxin-5-yl)-2-methoxy-pyridin-3-yl]-(4-imidazol-1-ylmethyl-phenyl)-amine;

[6-(2,3-Dihydro-benzo[1,4]dioxin-5-yl)-pyridin-3-yl]-(3-dimethylaminomethyl-phenyl)-amine;

[6-(2,3-Dihydro-benzo[1,4]dioxin-5-yl)-2-methoxy-pyridin-3-yl]-(3-pyrrolidin-1-ylmethyl-phenyl)-amine;

[6-(2,3-Dihydro-benzo[1,4]dioxin-5-yl)-2-methoxy-pyridin-3-yl]-(3-morpholin-4-ylmethyl-phenyl)-amine;

5-{3-[6-(2,3-Dihydro-benzo[1,4]dioxin-5-yl)-2-methoxy-pyridin-3-ylamino]-phenyl}-pyrrolidin-2-one;

(R)-2-{3-[6-(2,3-Dihydro-benzo[1,4]dioxin-5-yl)-2-methoxy-pyridin-3-ylamino]-phenyl}-pyrrolidine-1-carboxylic acid tert-butyl ester;

(S)-2-{3-[6-(2,3-Dihydro-benzo[1,4]dioxin-5-yl)-2-methoxy-pyridin-3-ylamino]-phenyl}-pyrrolidine-1-carboxylic acid tert-butyl ester;

{4-[6-(2,3-Dihydro-benzo[1,4]dioxin-5-yl)-2-methoxy-pyridin-3-ylamino]-benzyl}-carbamic acid tert-butyl ester;

{3-[6-(2,3-Dihydro-benzo[1,4]dioxin-5-yl)-2-methoxy-pyridin-3-ylamino]-benzyl}-carbamic acid tert-butyl ester;

{3-[6-(2,3-Dihydro-benzo[1,4]dioxin-5-yl)-2-methoxy-pyridin-3-ylamino]-phenyl}-methanol;

[6-(2,3-Dihydro-benzo[1,4]dioxin-5-yl)-pyridazin-3-yl]-(3-dimethylaminomethyl-phenyl)-amine;

[5-(2,3-Dihydro-benzo[1,4]dioxin-5-yl)-pyrazin-2-yl]-(3-dimethylaminomethyl-phenyl)-amine;
Tetrahydro-pyran-4-carboxylic acid {(S)-8-[5-(3-dimethylaminomethyl-phenylamino)-6-methoxy-pyridin-2-yl]-2,3-dihydro-benzo[1,4]dioxin-2-ylmethyl}-amide;
[4-(2,3-Dihydro-benzo[1,4]dioxin-5-yl)-phenyl]-(3-dimethylaminomethyl-phenyl)-amine;
1-Benzyl-4-(2,3-dihydro-benzo[1,4]dioxin-5-yl)-piperazine;
[4-(2,3-Dihydro-benzo[1,4]dioxin-5-yl)-2-methoxy-phenyl]-(3-dimethylaminomethyl-phenyl)-amine;
{4-[4-(2,3-Dihydro-benzo[1,4]dioxin-5-yl)-2-methoxy-phenylamino]-benzyl}-carbamic acid tert-butyl ester;
[6-(2,3-Dihydro-benzo[1,4]dioxin-5-yl)-2-methoxy-pyridin-3-yl]-((R)-3-pyrrolidin-2-yl-phenyl)-amine;
[6-(2,3-Dihydro-benzo[1,4]dioxin-5-yl)-2-methoxy-pyridin-3-yl]-((S)-3-pyrrolidin-2-yl-phenyl)-amine;
(4-Aminomethyl-phenyl)-[6-(2,3-dihydro-benzo[1,4]dioxin-5-yl)-2-methoxy-pyridin-3-yl]-amine;
(3-Aminomethyl-phenyl)-[6-(2,3-dihydro-benzo[1,4]dioxin-5-yl)-2-methoxy-pyridin-3-yl]-amine;
(4-Aminomethyl-phenyl)-[4-(2,3-dihydro-benzo[1,4]dioxin-5-yl)-2-methoxy-phenyl]-amine;
N-{3-[6-(2,3-Dihydro-benzo[1,4]dioxin-5-yl)-2-methoxy-pyridin-3-ylamino]-benzyl}-nicotinamide;
N-{3-[6-(2,3-Dihydro-benzo[1,4]dioxin-5-yl)-2-methoxy-pyridin-3-ylamino]-benzyl}-isonicotinamide;
1H-Pyrazole-4-carboxylic acid 3-[6-(2,3-dihydro-benzo[1,4]dioxin-5-yl)-2-methoxy-pyridin-3-ylamino]-benzylamide;
Tetrahydro-pyran-4-carboxylic acid (8-{6-methoxy-5-[2-(1-methyl-piperidin-4-yl)-acetylamino]-pyridin-2-yl}-2,3-dihydro-benzo[1,4]dioxin-2-ylmethyl)-amide;
5-(4-Methyl-piperazin-1-ylmethyl)-furan-2-carboxylic acid (8-{5-[(tetrahydro-pyran-4-ylmethyl)-amino]-pyridin-2-yl}-2,3-dihydro-benzo[1,4]dioxin-2-ylmethyl)-amide;
Tetrahydro-pyran-4-carboxylic acid {8-[5-(3-dimethyl-aminomethyl-phenylamino)-6-methoxy-pyridin-2-yl]-2,3-dihydro-benzo[1,4]dioxin-2-ylmethyl}-amide;
3-(2,3-Dihydro-benzo[1,4]dioxin-5-yl)-6-(1-methyl-piperidin-4-ylmethoxy)-pyridazine;
[6-(2,3-Dihydro-benzo[1,4]dioxin-5-yl)-2-methoxy-pyridin-3-yl]-(1-methyl-pyrrolidin-3-yl)-amine;
5-(4-Methyl-piperazin-1-ylmethyl)-furan-2-carboxylic acid [(R)-8-(5-amino-6-methoxy-pyridin-2-yl)-2,3-dihydro-benzo[1,4]dioxin-2-ylmethyl]-amide;
Tetrahydro-pyran-4-carboxylic acid {8-[6-methoxy-5-(pyridin-3-ylamino)-pyridin-2-yl]-2,3-dihydro-benzo[1,4]dioxin-2-ylmethyl}-amide;
Tetrahydro-pyran-4-carboxylic acid (8-{5-[4-(2-hydroxy-ethylcarbamoyl)-phenylamino]-6-methoxy-pyridin-2-yl}-2,3-dihydro-benzo[1,4]dioxin-2-ylmethyl)-amide;
Tetrahydro-pyran-4-carboxylic acid (8-{5-[3-(4-acetyl-piperazin-1-ylmethyl)-phenylamino]-6-methoxy-pyridin-2-yl}-2,3-dihydro-benzo[1,4]dioxin-2-ylmethyl)-amide;
Tetrahydro-pyran-4-carboxylic acid (8-{5-[4-(1-methyl-piperidin-4-ylcarbamoyl)-phenylamino]-pyridin-2-yl}-2,3-dihydro-benzo[1,4]dioxin-2-ylmethyl)-amide;
Tetrahydro-pyran-4-carboxylic acid ((R)-8-{5-[2-(1-methyl-piperidin-4-yl)-acetylamino]-pyridin-2-yl}-2,3-dihydro-benzo[1,4]dioxin-2-ylmethyl)-amide;
Tetrahydro-pyran-4-carboxylic acid {8-[5-(3-dimethyl-aminomethyl-phenylamino)-pyridin-2-yl]-2,3-dihydro-benzo[1,4]dioxin-2-ylmethyl}-amide;
Tetrahydro-pyran-4-carboxylic acid {8-[5-(4-dimethyl-carbamoyl-phenylamino)-6-methoxy-pyridin-2-yl]-2,3-dihydro-benzo[1,4]dioxin-2-ylmethyl}-amide;
((1R,3S)-3-{3-[2-Methoxy-6-(3-{[(tetrahydro-pyran-4-carbonyl)-amino]-methyl}-2,3-dihydro-benzo[1,4]dioxin-5-yl)-pyridin-3-yl]-ureido}-cyclopentyl)-carbamic acid tert-butyl ester;
((1S,3R)-3-{3-[2-(3-{[(Tetrahydro-pyran-4-carbonyl)-amino]-methyl}-2,3-dihydro-benzo[1,4]dioxin-5-yl)-pyridin-4-yl]-ureido}-cyclopentyl)-carbamic acid tert-butyl ester;
tetrahydro-pyran-4-carboxylic acid [8-(4-chloro-pyridin-2-yl)-2,3-dihydro-benzo[1,4]dioxin-2-ylmethyl]-amide;
[6-(2,3-Dihydro-benzo[1,4]dioxin-5-yl)-2-methoxy-pyridin-3-yl]-(1-methyl-piperidin-4-yl)-amine;
1-{4-[6-(2,3-Dihydro-benzo[1,4]dioxin-5-yl)-2-methoxy-pyridin-3-ylamino]-piperidin-1-yl}-ethanone;
((1S,3R)-3-{3-[2-Methoxy-6-(3-{[(tetrahydro-pyran-4-carbonyl)-amino]-methyl}-2,3-dihydro-benzo[1,4]dioxin-5-yl)-pyridin-4-yl]-ureido}-cyclopentyl)-carbamic acid benzyl ester;
((1S,3R)-3-{3-[2-(2,3-Dihydro-benzo[1,4]dioxin-5-yl)-6-methoxy-pyridin-4-yl]-ureido}-cyclopentyl)-carbamic acid benzyl ester;
4-(2-Dimethylamino-ethoxy)-N-[8-(4-morpholin-4-yl-pyridin-2-yl)-2,3-dihydro-benzo[1,4]dioxin-2-ylmethyl]-benzamide;
4-(2-Dimethylamino-ethoxy)-N-[8-(6-dimethylamino-pyridin-2-yl)-2,3-dihydro-benzo[1,4]dioxin-2-ylmethyl]-benzamide;
4-(2-Dimethylamino-ethoxy)-N-(8-pyridin-2-yl-2,3-dihydro-benzo[1,4]dioxin-2-ylmethyl)-benzamide;
4-(2-Dimethylamino-ethoxy)-N-[8-(4-methoxy-pyridin-2-yl)-2,3-dihydro-benzo[1,4]dioxin-2-ylmethyl]-benzamide;
5-(4-Methyl-piperazin-1-ylmethyl)-furan-2-carboxylic acid [8-(4-benzyloxy-pyridin-2-yl)-2,3-dihydro-benzo[1,4]dioxin-2-ylmethyl]-amide;
5-(4-methyl-piperazin-1-ylmethyl)-furan-2-carboxylic acid {8-[5-(2-morpholin-4-yl-ethoxy)-pyridin-2-yl]-2,3-dihydro-benzo[1,4]dioxin-2-ylmethyl}-amide;
5-(4-Methyl-piperazin-1-ylmethyl)-furan-2-carboxylic acid [8-(4-morpholin-4-ylmethyl-phenyl)-2,3-dihydro-benzo[1,4]dioxin-2-ylmethyl]-amide;
5-(4-Methyl-piperazin-1-ylmethyl)-furan-2-carboxylic acid [8-(5-benzyloxy-pyridin-2-yl)-2,3-dihydro-benzo[1,4]dioxin-2-ylmethyl]-amide;
{8-[5-(2-Morpholin-4-yl-ethoxy)-pyridin-2-yl]-2,3-dihydro-benzo[1,4]dioxin-2-yl}-methanol;
Tetrahydro-pyran-4-carboxylic acid {8-[5-(2-morpholin-4-yl-ethoxy)-pyridin-2-yl]-2,3-dihydro-benzo[1,4]dioxin-2-ylmethyl}-amide;
Tetrahydro-pyran-4-carboxylic acid {(R)-8-[5-(3-dimethylaminomethyl-phenylamino)-6-methoxy-pyridin-2-yl]-2,3-dihydro-benzo[1,4]dioxin-2-ylmethyl}-amide;
N-[6-(2,3-Dihydro-benzo[1,4]dioxin-5-yl)-2-methoxy-pyridin-3-yl]-2-(1-methyl-piperidin-4-yl)-acetamide;
5-(4-Methyl-piperazin-1-ylmethyl)-furan-2-carboxylic acid [(R)-8-(4-amino-6-methoxy-pyridin-2-yl)-2,3-dihydro-benzo[1,4]dioxin-2-ylmethyl]-amide;
Tetrahydro-pyran-4-carboxylic acid [(S)-8-(5-chloro-6-methoxy-pyridin-2-yl)-2,3-dihydro-benzo[1,4]dioxin-2-ylmethyl]-amide;

{4-[2-Methoxy-6-(3-{[(tetrahydro-pyran-4-carbonyl)-amino]-methyl}-2,3-dihydro-benzo[1,4]dioxin-5-yl)-pyridin-3-ylamino]-benzyl}-carbamic acid tert-butyl ester;

tetrahydro-pyran-4-carboxylic acid {8-[5-(4-aminomethyl-phenylamino)-6-methoxy-pyridin-2-yl]-2,3-dihydro-benzo[1,4]dioxin-2-ylmethyl}-amide;

Tetrahydro-pyran-4-carboxylic acid {8-[6-methoxy-5-(4-{[(pyridin-2-ylmethyl)-amino]-methyl}-phenylamino)-pyridin-2-yl]-2,3-dihydro-benzo[1,4]dioxin-2-ylmethyl}-amide;

Tetrahydro-pyran-4-carboxylic acid {8-[6-methoxy-5-(4-{[(pyridin-4-ylmethyl)-amino]-methyl}-phenylamino)-pyridin-2-yl]-2,3-dihydro-benzo[1,4]dioxin-2-ylmethyl}-amide;

Tetrahydro-pyran-4-carboxylic acid {8-[6-methoxy-5-(4-{[(2H-pyrazol-3-ylmethyl)-amino]-methyl}-phenylamino)-pyridin-2-yl]-2,3-dihydro-benzo[1,4]dioxin-2-ylmethyl}-amide;

3-({4-[2-Methoxy-6-(3-{[(tetrahydro-pyran-4-carbonyl)-amino]-methyl}-2,3-dihydro-benzo[1,4]dioxin-5-yl)-pyridin-3-ylamino]-benzylamino}-methyl)-morpholine-4-carboxylic acid tert-butyl ester;

(R)-3-({4-[6-(2,3-Dihydro-benzo[1,4]dioxin-5-yl)-2-methoxy-pyridin-3-ylamino]-benzylamino}-methyl)-morpholine-4-carboxylic acid tert-butyl ester;

(S)-3-({4-[6-(2,3-Dihydro-benzo[1,4]dioxin-5-yl)-2-methoxy-pyridin-3-ylamino]-benzylamino}-methyl)-morpholine-4-carboxylic acid tert-butyl ester;

4-({3-[6-(2,3-Dihydro-benzo[1,4]dioxin-5-yl)-2-methoxy-pyridin-3-ylamino]-benzylamino}-methyl)-pyrazole-1-carboxylic acid tert-butyl ester;

3-({4-[4-(2,3-Dihydro-benzo[1,4]dioxin-5-yl)-2-methoxy-phenylamino]-benzylamino}-methyl)-morpholine-4-carboxylic acid tert-butyl ester;

[6-(2,3-Dihydro-benzo[1,4]dioxin-5-yl)-2-methoxy-pyridin-3-yl]-(3-{[(1H-pyrazol-4-ylmethyl)-amino]-methyl}-phenyl)-amine;

Tetrahydro-pyran-4-carboxylic acid {8-[6-methoxy-5-(4-{[(morpholin-3-ylmethyl)-amino]-methyl}-phenylamino)-pyridin-2-yl]-2,3-dihydro-benzo[1,4]dioxin-2-ylmethyl}-amide;

[6-(2,3-Dihydro-benzo[1,4]dioxin-5-yl)-2-methoxy-pyridin-3-yl]-(4-{[((R)-1-morpholin-3-ylmethyl)-amino]-methyl}-phenyl)-amine;

[6-(2,3-Dihydro-benzo[1,4]dioxin-5-yl)-2-methoxy-pyridin-3-yl]-(4-{[((S)-1-morpholin-3-ylmethyl)-amino]-methyl}-phenyl)-amine;

Morpholine-2-carboxylic acid {2-methoxy-6-[(R)-3-({[5-(4-methyl-piperazin-1-ylmethyl)-furan-2-carbonyl]-amino}-methyl)-2,3-dihydro-benzo[1,4]dioxin-5-yl]-pyridin-4-yl}-amide;

(R)-Pyrrolidine-2-carboxylic acid {2-methoxy-6-[3-({[5-(4-methyl-piperazin-1-ylmethyl)-furan-2-carbonyl]-amino}-methyl)-2,3-dihydro-benzo[1,4]dioxin-5-ylamino]-pyridin-3-yl}-amide;

[4-(2,3-Dihydro-benzo[1,4]dioxin-5-yl)-2-methoxy-phenyl]-(4-{[(morpholin-3-ylmethyl)-amino]-methyl}-phenyl)-amine;

(1R,3S)-3-Amino-cyclopentanecarboxylic acid [2-(2,3-dihydro-benzo[1,4]dioxin-5-yl)-6-methoxy-pyridin-4-yl]-amide;

(R)-2-{2-Methoxy-6-[3-({[5-(4-methyl-piperazin-1-ylmethyl)-furan-2-carbonyl]-amino}-methyl)-2,3-dihydro-benzo[1,4]dioxin-5-ylamino]-pyridin-3-ylcarbamoyl}-pyrrolidine-1-carboxylic acid tert-butyl ester;

Tetrahydro-pyran-4-carboxylic acid [3-(3-{4-[3-((1R,3S)-3-amino-cyclopentyl)-ureido]-6-methoxy-pyridin-2-yl}-2-hydroxy-phenoxy)-propyl]-amide;

1-((1R,3S)-3-Amino-cyclopentyl)-3-[2-(2,3-dihydro-benzo[1,4]dioxin-5-yl)-6-methoxy-pyridin-4-yl]-urea;

5-(4-Methyl-piperazin-1-ylmethyl)-furan-2-carboxylic acid [8-(1-methyl-1H-imidazol-4-yl)-2,3-dihydro-benzo[1,4]dioxin-2-ylmethyl]-amide;

5-(4-Methyl-piperazin-1-ylmethyl)-furan-2-carboxylic acid [8-(1-benzyl-1H-imidazol-4-yl)-2,3-dihydro-benzo[1,4]dioxin-2-ylmethyl]-amide;

5-(4-Chloro-phenyl)-2,3-dihydro-benzo[1,4]dioxine;

tetrahydro-pyran-4-carboxylic acid {8-[4-(3-dimethyl-aminomethyl-phenylamino)-pyridin-2-yl]-2,3-dihydro-benzo[1,4]dioxin-2-ylmethyl}-amide;

tetrahydro-pyran-4-carboxylic acid (8-{5-[3-((1S,3R)-3-amino-cyclopentyl)-ureido]-6-methoxy-pyridin-2-yl}-2,3-dihydro-benzo[1,4]dioxin-2-ylmethyl)-amide; and tetrahydro-pyran-4-carboxylic acid (8-{4-[3-((1R,3S)-3-amino-cyclopentyl)-ureido]-pyridin-2-yl}-2,3-dihydro-benzo[1,4]dioxin-2-ylmethyl)-amide.

11. A pharmaceutical composition comprising a compound according to claim 1 or a pharmaceutically acceptable salt or solvate thereof, and one or more pharmaceutically acceptable excipients.

12. A method of treating a proliferative disorder in a patient in need of such treatment, said method comprising administering to said patient a therapeutically effective amount of a compound according to claim 1, or a pharmaceutically acceptable salt or solvate thereof.

13. A method of treating cancer in a patient in need of such treatment, said method comprising administering to said patient a therapeutically effective amount of a compound according to claim 1, or a pharmaceutically acceptable salt or solvate thereof.

14. A method of inhibiting cell proliferation in vitro or in vivo, said method comprising contacting a cell with an effective amount of a compound according claim 1, or a pharmaceutically acceptable salt or solvate thereof.

15. A method of inhibiting a RAS-effector protein-protein interaction in vitro or in vivo, said method comprising contacting a cell with an effective amount of a compound according to claim 1, or a pharmaceutically acceptable salt or solvate thereof.

16. A combination comprising a compound according to claim 1 and a further therapeutically active agent.

* * * * *